United States Patent [19]
Sato et al.

[11] Patent Number: 5,861,429
[45] Date of Patent: Jan. 19, 1999

[54] 13-SUBSTITUTED MILBEMYCIN 5-OXIME DERIVATIVES, THEIR PREPARATION AND THEIR USE AGAINST INSECTS AND OTHER PESTS

[75] Inventors: Kazuo Sato, Shiga-ken; Akio Saito; Toshimitsu Toyama, both of Tokyo, all of Japan

[73] Assignee: Sankyo Company, Limited, Tokyo, Japan

[21] Appl. No.: 723,835

[22] Filed: Sep. 30, 1996

[30] Foreign Application Priority Data

Sep. 29, 1995 [JP] Japan .................... 7-252965

[51] Int. Cl.⁶ .................... A61K 31/335; A61K 31/38; A61K 31/505; A61K 31/425
[52] U.S. Cl. .................... 514/450; 514/183; 514/274; 514/338; 514/321; 514/369; 514/376; 514/422; 514/444; 549/264; 549/60; 544/316; 548/187; 548/229; 548/526; 548/952; 546/197; 546/281.7; 546/283.1
[58] Field of Search .................... 549/264, 60; 514/450, 514/183, 274, 321, 338, 369, 376, 422, 444; 544/316; 546/281.7, 283.1, 197; 548/187, 229, 526, 952

[56] References Cited

U.S. PATENT DOCUMENTS 3,950,360 4/1976 Aoki et al. .................... 424/279
4,171,314 10/1979 Chabala et al. .................... 424/279

(List continued on next page.)

FOREIGN PATENT DOCUMENTS 0 246 739 11/1987 European Pat. Off. .
0 675 133 10/1995 European Pat. Off. .
WO 96/16064 5/1996 WIPO .

OTHER PUBLICATIONS

Database WPI, Section Ch, Week 9627, Derwent Publications Ltd., London, GB; Class B02, AN 96-268520, XP002020775, 9 616 064 (Sankyo Co Ltd), 30 May 1966 of WO 96 16064 A (Sankyo Company Ltd) 30 May 1996.

*Primary Examiner*—Amelia Owens
*Attorney, Agent, or Firm*—Frishauf, Holtz, Goodman, Langer & Chick, P.C.

[57] ABSTRACT

Compounds of formula (I):

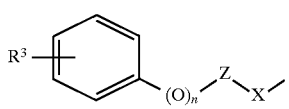

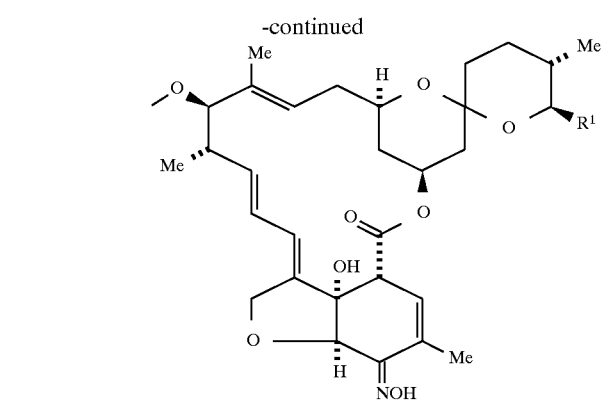

wherein: $R^1$ is methyl, ethyl, isopropyl or sec-butyl; X is carbonyl or methylene; Z is $=C=(R^2)_2$ or $=C=(CH_2)_m$, in which $R^2$ is alkyl, and m is integer of from 2 to 5); n is 0 or 1; $R^3$ is nitro, amino, alkylamino, dialkylamino, alkoxy, alkoxyalkoxy, or a group (iii), (iv), (v), (vi), (vii), (viii) or (ix):

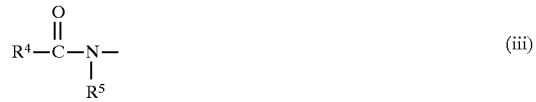

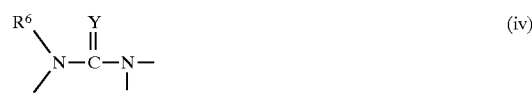

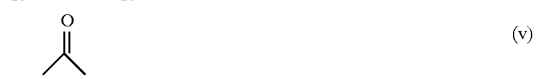

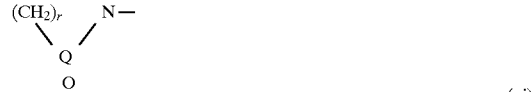

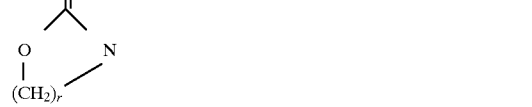

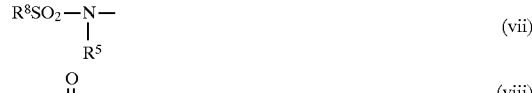

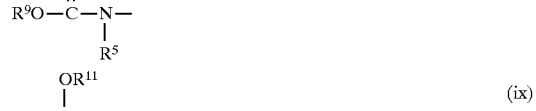

, wherein: $R^4$ represents: alkyl; substituted alkyl; cycloalkyl having from 3 to 6 carbon atoms; substituted cycloalkyl; alkenyl; alkynyl; carbocyclic aryl; or heterocyclic; $R^5$ is hydrogen atom or alkyl; $R^6$ represents: hydrogen; alkyl; or cycloalkyl; $R^7$ represents: alkyl; cycloalkyl; carbocyclic aryl; or aralkyl; or $R^6$ and $R^7$, together with the nitrogen atom to which they are attached, are fused to form heterocyclic ring; Y is oxygen or sulfur; r is 1, 2 or 3; Q is methylene or carbonyl; $R^8$ is: alkyl or carbocyclic aryl; $R^9$ is: alkyl; cycloalkyl; carbocyclic aryl; or aralkyl; $R^{10}$ is heterocyclic; and $R^{11}$ is aLkyl; have valuable acaricidal, insecticidal and anthelmintic activities.

83 Claims, No Drawings

U.S. PATENT DOCUMENTS

| | | | |
|---|---|---|---|
| 4,173,571 | 11/1979 | Chabala et al. | 424/279 |
| 4,201,861 | 5/1980 | Mrozik et al. | 536/17 A |
| 4,203,976 | 5/1980 | Fisher et al. | 424/180 |
| 4,206,205 | 6/1980 | Mrozik et al. | 424/180 |
| 4,289,760 | 9/1981 | Mrozik et al. | 424/181 |
| 4,346,171 | 8/1982 | Takiguchi et al. | 435/119 |
| 4,423,209 | 12/1983 | Mrozik | 536/7.1 |
| 4,457,920 | 7/1984 | Mrozik | 424/180 |
| 4,547,491 | 10/1985 | Mrozik et al. | 514/30 |
| 4,547,520 | 10/1985 | Ide et al. | 514/450 |
| 4,579,864 | 4/1986 | Linn et al. | 514/450 |
| 4,945,105 | 7/1990 | Sato et al. | 514/450 |
| 4,963,582 | 10/1990 | Sato et al. | 514/450 |
| 5,276,033 | 1/1994 | Yanai et al. | 514/241 |
| 5,428,034 | 6/1995 | Morisawa et al. | 514/232.8 |

13-SUBSTITUTED MILBEMYCIN 5-OXIME DERIVATIVES, THEIR PREPARATION AND THEIR USE AGAINST INSECTS AND OTHER PESTS

BACKGROUND TO THE INVENTION

The present invention relates to a series of new 13-substituted milbemycin 5-oxime derivatives which have valuable acaricidal, insecticidal and anthelmintic activities. The invention also provides methods and compositions for using these compounds as well as processes for their preparation.

There are several classes of known compounds with a structure based on a 16-membered macrolide ring, which are obtained by fermentation of various microorganisms or semi-synthetically by chemical derivatization of such natural fermentation products, and which exhibit acaricidal, insecticidal, anthelmintic and antiparasitic activities. The milbemycins and avermectins are examples of two such classes of known compounds, but others exist and are normally identified in the prior art by different names or code numbers. The namers for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion, a standardized system of nomenclature will be used herein, which follows the normal rules for naming derivatives of organic compounds as recommended by the International Union of Pure and Applied Chemistry (IUPAC), Organic Chemistry Division, Commission on Nomenclature of Organic Chemistry, and which is based on the hypothetical parent compound hereby defined as "milbemycin", which is that compound represented by the following formula (A):

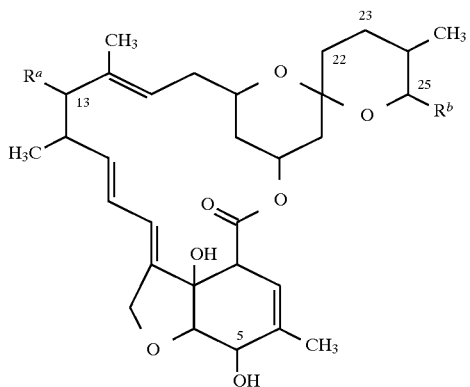

(A)

wherein $R^a$ and $R^b$ both represent hydrogen atoms.

For the avoidance of doubt, the above formula (A) also shows the numbering of positions of the macrolide ring system applied to those positions of most relevance to the compounds of the present invention.

The naturally produced inilbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (A) in which $R^a$ at position 13 is a hydrogen atom and $R^b$ at position 25 is a methyl group, an ethyl group or an isopropyl group, these compounds being designated as milbemycin $A_3$, milbemycin $A_4$ and milbemycin D, respectively. The milbemycin analog having a hydrogen atom at position 13 and substituted at position 25 with a sec-butyl group was disclosed in U.S. Pat. No. 4,173,571, where it was known as "13-deoxy-22,23-dihydroavermectin $B_{1a}$ aglycone".

Subsequently, various derivatives of the original milbemycins and avermectins have been prepared and their activities investigated. For example, 5-esterified milbemycins have been disclosed in U.S. Pat. No. 4,201,861, Pat. No. 4,206,205, Pat. No. 4,173,571, Pat. No. 4,171,314, Pat. No. 4,203,976, Pat. No. 4,289,760, Pat. No. 4,457,920, Pat. No. 4,579,864 and Pat. No. 4,547,491, in European Patent Publications No. 8184, No. 102,721, No. 115,930, No. 180,539 and No. 184,989 and in Japanese Patent Applications Kokai (i.e. as laid open to public inspection) No. 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and in European Patent Publication No. 203 832.

Milbemycins having an ester bond at the 13-position are of particular relevance to the present invention and a number of compounds in which the 13-hydroxy group in the compounds of the above formula (A) has been esterified is disclosed in Japanese Patent Kokai Application No. Sho 61-180787, which describes esters of a variety of carboxylic acids such as the alkanoic acids. Other milbemycin derivatives having an ester bond at the 13-position are described in Japanese Patent Kokai Application No. Hei 1-104078. In this document there are disclosed compounds in which the carboxylic acid moiety has a side chain, such as an alkyl group, at the α-position of the carboxylic acid group.

The closest prior art to the present invention is thought by us to be represented by U.S. Pat. No. 4,963,582 (equivalent to European Patent No. 246 739), which discloses a series of 13-ester derivatives. These, however, differ from the compounds of the present invention in the nature of the group at the 13-position.

The various classes of milbemycin-related macrolide compounds referred to above are all disclosed as having one or more types of activity as antibiotic, anthelmintic, ectoparasiticidal, acaricidal or other pesticidal agents. However, there is still a continuing need to provide such agents with improved activity against one or more classes of agricultural and horticultural pests.

It has now been discovered that the activity of such milbemycin-related derivatives can be improved by appropriately selecting the combination of substituents on the macrolide ring system, especially the substituents at position 13. In particular, it has now been found that the activity of the compounds can be improved upon by appropriate selection of certain highly specific ester groups at the 13 position, as specified below. In general, the compounds of the present invention tend to have a better pesticidal activity than do the compounds of the prior art, and many of the compounds of the present invention have a very substantially better activity. The compounds of the present invention are, in particular, substantially more active than those of the prior art, including U.S. Pat. No. 4,963,582, especially against fleas.

BRIEF SUMMARY OF INVENTION

Accordingly, it is an object of the present invention to provide such macrolide compounds which may have improved activity.

It is another object of the invention to provide methods for preparing such compounds.

It is a still further object of the invention to provide pesticidal compositions and methods using the said compounds.

Other objects and advantages will become apparent as the description proceeds.

The present invention thus provides compounds of formula (I):

(I)

wherein:
$R^1$ represents a methyl group, an ethyl group, an isopropyl group or a sec-butyl group:

X represents a carbonyl group or a methylene group:

Z represents a group of formula (i) or (ii):

$$=C=(R^2)_2 \quad (i)$$

$$=C=(CH_2)_m \quad (ii)$$

in which $R^2$ represents an alkyl group having from 1 to 3 carbon atoms, and m represents an integer of from 2 to 5;

n is 0 or 1;

$R^3$ represents a nitro group, an amino group, a ($C_1$–$C_4$ alkyl)amino group, a di($C_1$–$C_4$ alkyl)amino group, an alkoxy group having from 1 to 4 carbon atoms, a ($C_1$–$C_3$ alkoxy)-($C_2$–$C_3$ alkoxy) group, or a group of formula (iii), (iv), (v), (vi), (vii), (viii) or (ix):

$$R^4-\overset{O}{\underset{\|}{C}}-\underset{R^5}{\overset{|}{N}}- \quad (iii)$$

(iv)

(v)

-continued (vi)

$$R^8SO_2-\underset{R^5}{\overset{|}{N}}- \quad (vii)$$

$$R^9O-\overset{O}{\underset{\|}{C}}-\underset{R^5}{\overset{|}{N}}- \quad (viii)$$

(ix)

wherein:
$R^4$ represents: an alkyl group having from 1 to 6 carbon atoms; a substituted alkyl group which has from 1 to 6 carbon atoms and which is substituted by at least one substituent selected from the group consisting of substituents α, defined below; a cycloalkyl group having from 3 to 6 carbon atoms; a cycloalkyl group which has from 3 to 10 carbon atoms and which is substituted by at least one substituent selected from the group consisting of substituents β, defined below; an alkenyl group having from 2 to 6 carbon atoms; an alkynyl group having from 2 to 6 carbon atoms; a carbocyclic aryl group which has from 6 to 14 ring carbon atoms and which is unsubstituted or which is substituted by at least one substituent selected from the group consisting of substituents γ, defined below; or a heterocyclic group having from 3 to 6 ring atoms, of which at least one is a heteroatom selected from the group consisting of nitrogen, oxygen and sulfiur hetero-atoms, said heterocyclic group being unsubstituted or being substituted by at least one substituent selected from the group consisting of substituents γ, defmed below, and oxygen atoms (to form an oxo group);

$R^5$ represents a hydrogen atom or an alkyl group having from 1 to 4 carbon atoms;

$R^6$ represents: a hydrogen atom; an alkyl group having from 1 to 6 carbon atoms; or a cycloalkyl group having from 3 to 6 carbon atoms;

$R^7$ represents: an alkyl group having from 1 to 6 carbon atoms; a cycloalkyl group having from 3 to 6 carbon atoms; a carbocyclic aryl group which has from 6 to 14 ring carbon atoms which is unsubstituted or which is substituted by at least one substituent selected from the group consisting of substituents γ, defined below; or an aralkyl group in which the aryl part is carbocyclic and has from 6 to 10 ring carbon atoms and the alkyl part has from 1 to 4 carbon atoms; or $R^6$ and $R^7$, together with the nitrogen atom to which they are attached, are fused to form a heterocyclic ring having from 3 to 6 ring atoms;

Y represents an oxygen atom or a sulfur atom; r is 1, 2 or 3;

Q represents a methylene group or a carbonyl group;

$R^8$ represents: an alkyl group having from 1 to 4 carbon atoms or a carbocyclic aryl group which has from 6 to 10 ring carbon atoms and which is unsubstituted or which is substituted by at least one substituent selected from the group consisting of substituents γ, defined below;

$R^9$ represents: an alkyl group having from 1 to 6 carbon atoms; a cycloalkyl group having from 3 to 6 carbon atoms; a carbocyclic aryl group which has from 6 to 10 ring carbon atoms and which is unsubstituted or which is substituted by at least one substituent selected from the group consisting of substituents γ, defined below; or an aralkyl group in which the aryl part is carbocyclic and has from 6 to 10 ring carbon atoms and the alkyl part has from 1 to 4 carbon atoms;

$R^{10}$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents δ, defined below, and oxygen atoms (to form an oxo group);

$R^{11}$ represents an alkyl group having from 1 to 3 carbon atoms;

substituents α are selected from the group consisting of: halogen atoms; cyano groups; alkoxy groups having from 1 to 4 carbon atoms; alkylthio groups having from 1 to 4 carbon atoms; alkylsulfonyl groups having from 1 to 4 carbon atoms; alkanoyloxy groups having from 2 to 5 carbon atoms; alkoxycarbonyl groups having from 2 to 5 carbon atoms; carbocyclic aryloxy groups which have from 6 to 10 ring carbon atoms; carbocyclic arylthio groups which have from 6 to 10 ring carbon atoms; carbocyclic arylsulfonyl groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 5 carbon atoms; alkoxycarbonylamino groups having from 2 to 5 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has from 1 to 4 carbon atoms; carbocyclic aryl groups which have from 6 to 10 ring carbon atoms which are unsubstituted or which are substituted by at least one substituent selected from the group consisting of substituents γ; groups $R^h$, where $R^h$ represents a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents γ, defined below, and oxygen atoms (to form an oxo group); groups of formula $R^h$—S—, where $R^h$ is as defined above; alkanoyl groups having from 2 to 5 carbon atoms; and aralkyloxycarbonylamino groups in which the aryl part is carbocyclid and has from 6 to 10 ring carbon atoms and the alkyl part has from 1 to 4 carbonatoms;

substituents β are selected from the group consisting of halogen atoms, alkoxy groups having from 1 to 4 carbon atoms, and alkanoyloxy groups having from 2 to 5 carbon atoms;

substituents γ are selected from the group consisting of: halogen atoms; hydroxy groups; cyano groups; nitro groups; alkyl groups having from 1 to 4 carbon atoms; alkoxy groups having from 1 to 4 carbon atoms; and alkoxycarbonyl groups having from 2 to 5 carbon atoms;

substituents δ are selected from the group consisting of amino groups, alkanoylamino groups having from 2 to 5 carbon atoms, haloalkanoylamino groups having from 2 to 5 carbon atoms, and alkoxycarbonylamino groups having from 2 to 6 carbon atoms;

and salts thereof.

The invention still further provides an anthelmintic, acaricidal and insecticidal composition comprising an anthelmintic, acaricidal and insecticidal compound in admixture with an agriculturally or horticulturally acceptable carrier or diluent, wherein said compound is selected from the group consisting of compounds of formula (I) and salts thereof.

The invention still further provides a method of protecting plants and animals, which may be human or non-human, from damage by parasites selected from the group consisting of acarids, helminths and insects, which comprises applying an active compound to said plants or animals or to parts of or reproductive matter (e.g. seeds) of said plants or to a locus including said plants, said animals or parts of said plants or reproductive matter of said plants, wherein the active compound is selected from the group consisting of compounds of formula (I) and salts thereof.

DETAILED DESCRIPTION OF INVENTION

In the compounds of the present invention, $R^1$ may represent a methyl, ethyl, isopropyl or sec-butyl group. Of these, the methyl and ethyl groups are preferred, and the ethyl group is most preferred.

X represents a methylene or carbonyl group; of which the carbonyl group is preferred.

Where Z represents a group of formula >C=($R^2$)$_2$ and $R^2$ represents an alkyl group having from 1 to 3 carbon atoms, this may be a straight or branched chain group having from 1 to 3 carbon atoms, that is the methyl, ethyl, propyl and isopropyl groups, of which the methyl group is preferred.

Where Z represents a group of formula =C=($CH_2$)$_m$, m may represent an integer from 2 to 5, i.e. 2, 3, 4 or 5, and, in this case, Z represents a spiro-cycloalkyl group, specifically a cyclopropyl, cyclobutyl, cyclopentyl or cyclohexyl group, respectively. Of these, we particularly prefer the cyclopropyl and cyclobutyl groups.

Where $R^3$ represents a ($C_1$–$C_4$ alkyl)amino group, the alkyl part of this group may be a straight or branched chain group, and examples of such groups include the methylamino, ethylamino, propylamino, isopropylamino, butylamino, isobutylamino, sec-butylamino and t-butylamino groups, of which we prefer the methylamino, ethylamino, propylamino and butylamino groups, the methylamino group being most preferred.

Where $R^3$ represents a di($C_1$–$C_4$ alkyl)amino group, the two alkyl groups may be the same or different and may be straight or branched chain groups having from 1 to 4 carbon atoms. Examples of such groups include the dimethylamino, diethylamino, dipropylamino, diisopropylamino, dibutylamino, diisobutylamino, di-sec-butylamino, di-t-butylamino, N-methyl-N-ethylamino, N-methyl-N-propylamino, N-methyl-N-isopropylamino, N-methyl-N-butylamino, N-methyl-N-isobutylamino, N-methyl-N-secbutylamino, N-methyl-N-t-butylamino, N-ethyl-N-propylamino, N-ethyl-N-isopropylamino, N-ethyl-N-butylamino, N-ethyl-N-isobutylamino, N-ethyl-N-sec-butylamino, N-ethyl-N-t-butylamino, N-propyl-N-isopropylamino, N-propyl-N-butylamino, N-propyl-N-isobutylamino, N-propyl-N-sec-butylamino, N-propyl-N-t-butylamino, N-isopropyl-N-butylamino, N-isopropyl-N-isobutylamino, N-isopropyl-N-sec-butylamino, N-isopropyl-N-t-butylamino, N-butyl-N-isobutylamino, N-butyl-N-sec-butylamino, N-butyl-N-t-butylamino, N-isobutyl-N-sec-butylamino, N-isobutyl-N-t-butylamino and N-sec-butyl-N-t-butylamino, groups, of which we prefer those groups in which the two alkyl groups are the same, especially the dimethylamino, diethylamino, dipropylamino and dibutylamino groups, of which the dimethylamino and diethylamino groups are most preferred.

Where $R^3$ represents an alkoxy group having from 1 to 4 carbon atoms, this may be a straight or branched chain group having from 1 to 4 carbon atoms, that is the methoxy, ethoxy, propoxy, isopropoxy, butoxy, isobutoxy, sec-butoxy and t-butoxy groups, of which we prefer the methoxy, ethoxy, propoxy and butoxy groups, the methoxy and ethoxy groups being more preferred, and the methoxy group being most preferred.

Where $R^3$ represents a $(C_1-C_3$ alkoxy)-$(C_2-C_3$ alkoxy) group, each alkoxy group may be a straight or branched chain group having from 1 to 3, or 2 or 3, carbon atoms and may be selected from those alkoxy groups listed above. Examples of such alkoxyalkoxy groups include the 1-methoxyethoxy, 1-ethoxyethoxy, 1-propoxyethoxy, 1-isopropoxyethoxy, 1-butoxyethoxy, 1-isobutoxyethoxy, 1-sec-butoxyethoxy, 1-t-butoxyethoxy, 2-methoxyethoxy, 2-ethoxyethoxy, 2-propoxyethoxy, 2-isopropoxyethoxy, 2-butoxyethoxy, 2-isobutoxyethoxy, 2-sec-butoxyethoxy, 2-t-butoxyethoxy, 1-methoxypropoxy, 1-ethoxypropoxy, 1-propoxypropoxy, 1-isopropoxypropoxy, 1-butoxypropoxy, 1-isobutoxypropoxy, 1-sec-butoxypropoxy, 1-t-butoxypropoxy, 2-methoxypropoxy, 2-ethoxypropoxy, 2-propoxypropoxy, 2-isopropoxypropoxy, 2-butoxypropoxy, 2-isobutoxypropoxy, 2-sec-butoxypropoxy, 2-t-butoxypropoxy, 3-methoxypropoxy, 3-ethoxypropoxy, 3-propoxypropoxy, 3-isopropoxypropoxy, 3-butoxypropoxy, 3-isobutoxypropoxy, 3-sec-butoxypropoxy and 3-t-butoxypropoxy groups, of which the 2-methoxyethoxy, 2-ethoxyethoxy, 2-propoxyethoxy, 2-isopropoxyethoxy, 2-butoxyethoxy, 2-isobutoxyethoxy, 2-sec-butoxyethoxy and 2-t-butoxyethoxy groups are preferred, the 2-methoxyethoxy group being most preferred.

Where $R^3$ represents a group of formula (iii):

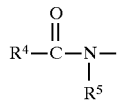

and $R^4$ represents an alkyl group having from 1 to 6 carbon atoms, this may be a straight or branched chain group having from 1 to 6 carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alyl groups having from 1 to 4 carbon atoms, preferably the methyl, ethyl, propyl, isopropyl, butyl and isobutyl groups, more preferably the methyl and ethyl groups, and most preferably the methyl group. The resulting groups of formula (iii) are alkanoylamino groups having from 2 to 7, preferably 2 or 3, carbon atoms, and thus those groups of formula (iii) in which, for example, $R^4$ represents a methyl or ethyl group are the acetylamino and propionylamino groups, respectively.

Where $R^3$ represents a group of formula (iii) and $R^4$ represents a substituted alkyl group which has from 1 to 6 carbon atoms and which is substituted by at least one substituent selected from the group consisting of substituents α, defined above, the alkyl group may be a straight or branched chain group having from 1 to 6 carbon atoms, and examples include those unsubstituted alkyl groups given above. Examples of the groups and atoms included in substituents α are given below. As explained above, the resulting group of formula (iii) is an alkanoylamino group having from 2 to 7 carbon atoms, which, in this case, is substituted by at least one substituent selected from the group consisting of substituents α. Specific examples of such alkanoylamino groups represented by $R^3$ include:

halogenated alkanoylamino groups having from 2 to 7 carbon atoms, especially halogenated acetylamino groups (such as the chloroacetylamino, dichloroacetylamino, trichloroacetylamino, bromoacetylamino, fluoroacetylamino, difluoroacetylamino and trifluoroacetylamino groups), halogenated propionylamino groups (such as the 3-chloropropionylamino, 3-dichloropropionylamino, 3-trichloropropionylamino and 3-trifluoropropionylamino groups), halogenated butyrylamino groups (such as the 4-chlorobutyrylamino, 4-dichlorobutyrylamino, 4-trichlorobutyrylamino and 4-trifluorobutyrylamino groups), halogenated pentanoylamino groups (such as the 5-chloropentanoylamino, 5-dichloropentanoylamino, 5-trichloropentanoylamino and 5-trifluoropentanoylamino groups), halogenated hexanoylamino groups (such as the 6-chlorohexanoylamino, 6-dichlorohexanoylamino, 6-trichlorohexanoylamino and 6-trifluorohexanoylamino groups), and halogenated heptanoylamino groups (such as the 7-chloroheptanoylamino, 7-dichloroheptanoylamino, 7-trichloroheptanoylamino and 7-trifluoroheptanoylamino groups); of these, we prefer the halogenated acetylamino groups, especially the chloroacetylamino, bromoacetylamino, difluoroacetylamino and trifluoroacetylamino groups);

cyano-substituted alkanoylamino groups having from 2 to 7 carbon atoms, especially cyano-substituted acetylamino groups, such as the cyanoacetylamino group, cyano-substituted propionylamino groups. such as the 3-cyanopropionylamino group, cyano-substituted butyrylamino groups, such as the 4-cyanobutyrylamino group, cyano-substituted pentanoylamino groups, such as the 5-cyanopentanoylamino group, cyano-substituted hexanoylamino groups, such as the 6-cyanohexanoylamino group, and cyano-substituted heptanoylamino groups, such as the 7-cyanoheptanoylamino groups; of these, we prefer the cyano-substituted acetylamino groups, especially the cyanoacetylamino group;

alkylthio-substituted alkanoylamino groups having from 2 to 7 carbon atoms, especially alkylthio-substituted acetylamino groups [such as the methylthioacetylamino, di(methylthio)acetylamino, tri (methylthio)acetylamino, propylthioacetylamino, ethylthioacetylamino, di(ethylthio)acetylamino and tri(ethylthio)acetylamino groups], alkylthio-substituted propionylamino groups [such as the 3-methylthiopropionylamino and 3-di(methylthio) propionylamino groups], alkylthio-substituted butyrylamino groups [such as the 4-methylthiobutyrylamino and 4-di(methylthio)butyrylamino groups], alkylthio-substituted pentanoylamino groups [such as the 5-methylthiopentanoylamino and 5-di(methylthio) pentanoylamino groups], alkylthio-substituted hexanoylamino groups [such as the 6-methylthiohexanoylamino and 6-di(methylthio) hexanoylamino groups], and alkylthio-substituted heptanoylamino groups [such as the 7-methylthioheptanoylamino and 7-di(methylthio) heptanoylamino groups]; of these, we prefer the alkylthio-substituted acetylamino groups, especially the methylthioacetylamino, propylthioacetylamino and di(ethylthio)acetylamino groups;

alkylsulfonyl-substituted alkanoylamino groups having from 2 to 7 carbon atoms, especially alkylsulfonyl-substituted acetylamino groups [such as the methylsulfonylacetylamino, di(methylsulfonyl) acetylamino, tri(methyl-sulfonyl)acetylamino, propylsulfonylacetylamino, ethylsulfonylacetylamino, di(ethylsulfonyl)acetylamino and tri(ethylsulfonyl) acetylamino groups], alkylsulfonyl-substituted propionylamino groups [such as the 3-methylsulfonylpropionylamino and 3-di(methylsulfonyl)propionylamino groups], alkylsulfonyl-substituted butyrylamino groups [such as the 4-methylsulfonylbutyrylamino and 4-di(methylsulfonyl)butyrylamino groups], alkylsulfonyl-substituted pentanoylamino groups [such as the 5-methylsulfonylpentanoylamino and 5-di(methylsulfonyl)pentanoylamino groups], alkylsulfonyl-substituted hexanoylamino groups [such as the 6-methylsulfonylhexanoylamino and 6-di(methylsulfonyl)hexanoylamino groups], and alkylsulfonyl-substituted heptanoylamino groups [such as the 7-methylsulfonylheptanoylamino and 7-di(methylsulfonyl)heptanoylamino groups]; of these, we prefer the alkylsulfonyl-substituted acetylamino groups, especially the methylsulfonylacetylamino, propylsulfonylacetylamino and di(ethylsulfonyl) acetylamino groups;

alkanoyloxy-substituted alkanoylamino groups having from 2 to 7 carbon atoms, especially alkanoyloxy-substituted acetylamino groups (such as the acetoxyacetylamino, propionyloxyacetylamino and butyryloxyacetylamino groups), alkanoyloxy-substituted propionylamino groups (such as the 3-acetoxypropionylamino group), alkanoyloxy-substituted butyrylamino groups (such as the 4-acetoxybutyrylamino group), alkanoyloxy-substituted pentanoylamino groups (such as the 5-acetoxypentanoylamino group), alkanoyloxy-substituted hexanoylamino groups (such as the 6-acetoxyhexanoylamino group), and alkanoyloxy-substituted heptanoylamino groups (such as the 7-acetoxyheptanoylamino group); of these, we prefer the alkanoyloxy-substituted acetylamino groups, especially the acetoxyacetylamino, propionyloxyacetylamino and 3-acetoxypropionylamino groups;

alkoxycarbonyl-substituted alkanoylamino groups having from 2 to 7 carbon atoms, especially alkoxycarbonyl-substituted acetylamino groups [such as the methoxycarbonylacetylamino, propoxycarbonylacetylamino and ethoxycarbonylacetylamino groups], alkoxycarbonyl-substituted propionylamino groups [such as the 3-methoxycarbonylpropionylamino group], alkoxycarbonyl-substituted butyrylamino groups [such as the 4-methoxycarbonylbutyrylamino group], alkoxycarbonyl-substituted pentanoylamino groups [such as the 5-methoxycarbonylpentanoylamino group], alkoxycarbonyl-substituted hexanoylamino groups [such as the 6-methoxycarbonylhexanoylamino group], and alkoxycarbonyl-substituted heptanoylamino groups [such as the 7-methoxycarbonylheptanoylamino group]; of these, we prefer the alkoxycarbonyl-substituted propionylamino groups, especially the methoxycarbonylpropionylamino group;

aryloxy-substituted alkanoylamino groups having from 2 to 7 carbon atoms, especially aryloxy-substituted acetylamino groups, such as the phenoxyacetylamino group, aryloxy-substituted propionylamino groups. such as the 3-phenoxypropionylamino group, aryloxy-substituted butyrylamino groups, such as the 4-phenoxybutyrylamino group, aryloxy-substituted pentanoylamino groups, such as the 5-phenoxypentanoylamino group, aryloxy-substituted hexanoylamino groups, such as the 6-phenoxyhexanoylamino group, and aryloxy-substituted heptanoylamino groups, such as the 7-phenoxyheptanoylamino groups; of these, we prefer the aryloxy-substituted acetylamino groups, especially the phenoxyacetylamino group;

arylthio-substituted alkanoylamino groups having from 2 to 7 carbon atoms, especially arylthio-substituted acetylamino groups, such as the phenylthioacetylamino group, arylthio-substituted propionylamino groups. such as the 3-phenylthiopropionylamino group, arylthio-substituted butyrylamino groups, such as the 4-phenylthiobutyrylamino group, arylthio-substituted pentanoylamino groups, such as the 5-phenylthiopentanoylamino group, arylthio-substituted hexanoylamino groups, such as the 6-phenylthiohexanoylamino group, and arylthio-substituted heptanoylamino groups, such as the 7-phenylthioheptanoylamino groups; of these, we prefer the arylthiosubstituted acetylamino groups, especially the phenylthioacetylamino group;

arylsulfonyl-substituted alkanoylamino groups having from 2 to 7 carbon atoms, especially arylsulfonyl-substituted acetylamino groups, such as the phenylsulfonylacetylamino group, arylsulfonyl-substituted propionylamino groups. such as the 3-phenylsulfonylpropionylamino group, arylsulfonyl-substituted butyrylamino groups, such as the 4-phenylsulfonylbutyrylamino group, arylsulfonyl-substituted pentanoylamino groups, such as the 5-phenylsulfonylpentanoylamino group, arylsulfonyl-substituted hexanoylamino groups, such as the 6-phenylsulfonylhexanoylamino group, and arylsulfonyl-substituted heptanoylamino groups, such as the 7-phenylsulfonylheptanoylamino groups; of these, we prefer the arylsulfonyl-substituted acetylamino groups, especially the phenylsulfonylacetylamino group; amino-substituted alkanoylamino groups having from2 to 7 carbon atoms, especially: amino-substituted acetylamino groups, such as the aminoacetylamino group; amino-substituted propionylamino groups, such as the 2-aminopropionylamino and 3-aminopropionylamino groups; amino-substituted butyrylamino groups, such as the 2-aminobutyrylamino, 3-aminobutyrylamino and 4-aminobutyrylamino groups; amino-substituted methylpropionylamino groups, such as the 3-amino-3-methylpropionylamino and 2-amino-2-methylpropionylamino groups; amino-substituted pentanoylamino groups, such as the 2-aminopentanoylamino, 3-aminopentanoylamino, 4-aminopentanoylamino and 5-aminopentanoylamino groups; amino-substituted methylbutyrylamino groups, such as the 2-amino-3-methylbutyrylamino and 2-amino-2-methylbutyrylamino groups; amino-substituted hexanoylamino groups, such as the 2-aminohexanoylamino, 3-aminohexanoylamino, 4-aminohexanoylamino, 5-aminohexanoylamino and 6-aminohexanoylamino groups; amino-substituted methylpentanoylamino groups, such as the 2-amino-3-methylpentanoylamino and 2-amino-4-methylpentanoylamino groups; amino-substituted dimethylbutyrylamino groups, such as the 2-amino-3,3-dimethylbutyrylamino group; and amino-substituted heptanoylamino groups, such as the 2-aminoheptanoylamino and 7-aminoheptanoylamino groups; of these, we prefer the amino-substituted acetylamino groups, preferably the aminoacetylamino, 2-aminopropionylamino, 3-aminopropionylamino, 2-amino-2-methylpropionylamino, 2-amino-3-methylbutyrylamino, 2-amino-3,3-dimethylbutyrylamino and 2-amino-4-methylpentanoylamino groups; more preferably the aminoacetyl-amino, 2-aminopropionylamino, 3-aminopropionylamino, 2-amino-2-methylpropionylamino and 2-amino-3-methylbutyrylamino groups; and most preferably the aminoacetylamino, 2-aminopropionylamino and 3-aminopropionyl groups;

($C_2$–$C_5$ alkanoyl) amino-substituted $C_2$–$C_7$ alkanoylamino groups, especially: substituted acetylamino groups, such as the (N-acetylamino)acetylamino, (N-butyrylamino)acetylamino and (N-valerylamino)acetylamino groups; substituted propionylamino groups, such as the 3-(N-acetylamino)propionylamino, 3-(N-butyrylamino)propionylamino and 3-(N-valerylamino)propionylamino groups; substituted butyrylamino groups, such as the 4-(N-acetylamino)butyrylamino, 4-(N-butyrylamino)butyrylamino and 4-(N-valerylamino)butyrylamino groups; substituted valerylamino groups, such as the 5-(N-acetylamino)valerylamino, 5-(N-butyrylamino)valerylamino and 5-(N-valerylamino)valerylamino groups; of these, the (N-acetylamino)acetylamino group is preferred;

N-($C_2$–$C_5$ alkanoyl)-N-($C_1$–$C_3$ alkyl)amino-substituted alkanoylamino groups in which the alkanoylamino part has from 2 to 7 carbon atoms, especially: substituted acetylamino groups, such as the (N-methyl-N-acetylamino)acetylamino, (N-ethyl-N-acetylamino)acetylamino, (N-propyl-N-acetylamino)acetylamino, (N-methyl-N-butyrylamino)acetylamino, (N-ethyl-N-butyrylamino)acetylamino, (N-propyl-N-butyrylamino)acetylamino, (N-methyl-N-valerylamino)acetylamino, (N-ethyl-N-valerylamino)acetylamino and (N-propyl-N-valerylamino)acetylamino groups; substituted propionylamino groups, such as the 3-(N-methyl-N-acetylamino)propionylamino, 3-(N-ethyl-N-acetylamino) propionylamino, 3-(N-propyl-N-acetylamino)-propionylamino, 3-(N-methyl-N-butyrylamino)propionylamino, 3-(N-ethyl-N-butyrylamino)propionylamino, 3-(N-propyl-N-butyrylamino)propionylamino, 3-(N-methyl-N-valerylamino)propionylamino, 3-(N-ethyl-N-valerylamino)propionylamino and 3-(N-propyl-N-valerylamino)propionylamino groups; substituted butyrylamino groups, such as the 4-(N-methyl-N-acetylamino)butyrylamino, 4-(N-ethyl-N-acetylamino)butyrylamino, 4-(N-propyl-N-acetylamino)butyrylamino, 4-(N-methyl-N-butyrylamino)butyrylamino, 4-(N-ethyl-N-butyrylamino)butyrylamino, 4-(N-propyl-N-butyrylamino)butyrylamino, 4-(N-methyl-N-valerylamino)butyrylamino, 4-(N-ethyl-N-valerylamino)butyrylamino and 4-(N-propyl-N-valerylamino)butyrylamino groups; and substituted valerylamino groups, such as the 5-(N-methyl-N-acetylamino)valerylamino, 5-(N-ethyl-N-acetylamino)valerylamino, 5-(N-propyl-N-acetylamino)valerylamino, 5-(N-methyl-N-butyryl-amino)valerylamino, 5-(N-ethyl-N-butyrylamino)valerylamino, 5-(N-propyl-N-butyrylamino)valerylamino, 5-(N-methyl-N-valerylamino)valerylamino, 5-(N-ethyl-N-valerylamino)valerylamino and 5-(N-propyl-N-valerylamino)valerylamino groups; of these, the (N-methyl-N-acetylamino)acetylamino group is preferred;

($C_2$–$C_5$ haloalkanoyl) amino-substituted $C_2$–$C_7$ alkanoylamino groups, in which the alkanoyl groups may be as exemplified above and the halogen atoms may be chlorine, bromine, fluorine or iodine, especially: haloalkanoylamino-substituted acetylamino groups, such as the (N-chloroacetylamino)acetylamino, (N-dichloroacetylamino)acetylamino, (N-trichloroacetylamino)acetylamino, (N-fluoroacetylamino)acetylamino, (N-difluoroacetylamino)acetylamino, (N-trifluoroacetylamino)acetylamino, (N-bromoacetylamino)acetylamino, (N-iodoacetylamino)acetylamino, (N-4-chlorobutyrylamino)acetylamino, (N-4-fluorobutyrylamino)acetylamino and (N-5-fluorovalerylamino)acetylamino groups; haloalkanoylamino-substituted propionylamino groups, such as the (N-chloroacetylamino)propionylamino, (N-dichloroacetylamino)propionylamino, (N-trichloroacetylamino)propionylamino, (N-fluoroacetylamino)propionylamino, (N-difluoroacetylamino)propionylamino, (N-trifluoroacetylamino)propionylamino, (N-bromoacetylamino)propionylamino, (N-iodoacetylamino)propionylamino, (N-4-chlorobutyrylamino)propionylamino, (N-4-fluorobutyrylamino)propionylamino and (N-5-fluorovalerylamino)propionylamino groups; haloalkanoylamino-substituted butyrylamino groups, such as the(N-chloroacetylamino)butyrylamino, (N-dichloroacetylamino)butyrylamino, (N-trichloroacetylamino)butyrylamino, (N-fluoroacetylamino)butyrylamino, (N-difluoroacetylamino)butyrylamino, (N-trifluoroacetylamino)butyrylamino, (N-bromoacetylamino)butyrylamino, (N-iodoacetylamino)butyrylamino, (N-4-chlorobutyrylamino)butyrylamino, (N-4- fluorobutyrylamino)butyrylamino and (N-5-fluorovalerylamino)butyrylamino groups; and haloalkenoylamino-substituted valerylamino groups, such as the (N-chloroacetylamino)valerylamino, (N-dichloroacetylamino)valerylamino, (N-trichloroacetylamino)valerylamino, (N-fluoroacetylamino)valerylamino, N-difluoroacetylamino)valerylamino, (N-trifluoroacetylamino)valerylamino, (N-bromoacetylamino)valerylamino, (N-iodoacetylamino)valerylamino, (N-4-chlorobutyrylamino)valerylamino, (N-4-fluorobutyrylamino)valerylamino and (N-5-fluorovalerylamino)valerylamino groups; of these, the (N-chloroacetylamino)acetylamino group is preferred; alkoxycarbonylamino-substituted alkanoylaamino groups in which the alkoxycarbonyl part has from 2 to 5 carbon atoms and the alkanoylamino part has from 2 to 7 carbon atoms, especially alkoxycarbonylamino-substituted acetylamino groups [such as the methoxycarbonylaminoacetylamino, ethoxycarbonylaminoacetylamino, propoxycarbonylaminoacetylamino, isopropoxycarbonylaminoacetylamino, butoxycarbonylaminoacetylamino and t-butoxycarbonylaminoacetylamino groups], alkoxycarbonylamino-substituted propionylamino groups [such as the 2-methoxycarbonylaminopropionylamino, 3-methoxycarbonylaminopropionylamino, 2-ethoxycarbonylaminopropionylamino, 3-ethoxycarbonylaminopropionylamino, 2-propoxycarbonylaminopropionylamino, 3-propoxycarbonylaminopropionylamino, 2-isopropoxycarbonylaminopropionylamino, 3-isopropoxycarbonylaminopropionylamino, 2-butoxycarbonylaminopropionylamino, 3-butoxycarbonylaminopropionylamino, 2-t-butoxycarbonylaminopropionylamino and 3-t-butoxycarbonylaminopropionylamino groups], alkoxycarbonylamino-substituted butyrylamino groups [such as the 2-methoxycarbonylaminobutyrylamino, 4-methoxycarbonylaminobutyrylamino, 2-ethoxycarbonylaminobutyrylamino and 4-ethoxycarbonylaminobutyrylamino groups], alkoxycarbonylamino-substituted isobutyrylamino groups [such as the 2-methoxycarbonylamino-2-methylpropionylamino, 2-ethoxycarbonylamino-2-methylpropionylamino, 2-propoxycarbonylamino-2-methylpropionylamino, 2-isopropoxycarbonylamino-2-methylpropionylamino, 2-butoxycarbonylamino-2-methylpropionylamino and 2-t-butoxyearbonylamino-2-methylpropionylamino groups], alkoxycarbonylamirio-substituted pentanoylamino groups [such as the 5-methoxycarbonylaminopentanoylamino and 5-ethoxycarbonylaminopentanoylamino groups], alkoxycarbonylamino-substituted 4-methylpentanoylamino groups [such as the 2-methoxycarbonylamino-4-methylpentanoylamino and 2-ethoxycarbonylamino-4-methylpentanoylamino groups], alkoxycarbonylamino-substituted isovalerylamino groups [such as the 2-methoxycarbonylamino-3-methylbutyrylamino and 2-ethoxycarbonylamino-3-methylbutyrylamino groups], alkoxycarbonylamino-substituted hexanoylamino groups [such as the 6-methoxycarbonylaminohexanoylamino group], alkoxycarbonylamino-substituted 3,3-dimethylbutyrylamino groups [such as the 2-methoxycarbonylamino-3,3-dimethylbutyrylamino and 2-ethoxycarbonylamino-3,3-dimethylbutyrylamino groups], and alkoxycarbonylamino-substituted heptanoylamino groups [such as the 7-methoxycarbonylaminoheptanoylamino group]; of these, we prefer the alkoxycarbonylamino-substituted acetylamino, propionylamino, butyrylamino, isobutyrylamino, isovalerylamino, 4-methylpentanoylamino and 3,3-dimethylbutyrylamino groups, especially the methoxycarbonylaminoacetylamino, ethoxycarbonylaminoacetylamino, t-butoxycarbonylaminoacetylamino, 2-methoxycarbonylaminopropionylamino, 3-methoxycarbonylaminopropionylamino, 2-methoxycarbonylaminobutyrylamino, 2-methoxycarbonylamino-2-methylpropionylamino, 2-methoxycarbonylamino-3-methylbutyrylamino, 2-methoxycarbonylamino-4-methylpentanoylamino and 2-methoxycarbonylamino-3,3-dimethylbutyrylamino groups;

N-($C_2$–$C_5$ alkoxycarbonyl)-N-($C_1$–$C_3$ alkyl)amino-substituted alkanoylamino groups, especially N-alkoxycarbonyl-N-alkylamino-substituted acetylamino groups [such as the (N-methoxycarbonyl-N-methylamino)acetylamino, (N-ethoxycarbonyl-N-methylamino)acetylamino, (N-propoxycarbonyl-N-methylamino)acetylamino, (N-isopropoxycarbonyl-N-methylamino)acetylamino, (N-butoxycarbonyl-N-methylamino)acetylamino and (N-t-butoxycarbonyl-N-methylamino)acetylanino groups], N-alkoxycarbonyl-N-alkylamino-substituted propionylamino groups [such as the 2-(N-methoxycarbonyl-N-methylamino)propionylamino, 3-(N-methoxycarbonyl-N-methylamino)propionylamino, 2-(N-ethoxycarbonyl-N-methylamino)propionylamino, 3-N-ethoxycarbonyl-N-methylamino)propionylamino, 2-(N-propoxycarbonyl-N-methylamino)propionylamino, 3-(N-propoxycarbonyl-N-methylamino) propionylamino, 2-(N-isopropoxycarbonyl-N-methylamino)propionylamino, 3-(N-isopropoxycarbonyl-N-methylamino)propionylamino, 2-(N-butoxycarbonyl-N-methylamino) propionylamino, 3-(N-butoxycarbonyl-N-methylamino)propionylamino, 2-(N-t-butoxycarbonyl-N-methylamino)propionylamino and 3-(N-t-butoxycarbonyl-N-methylamino)propionylamino groups], N-alkoxycarbonyl-N-alkylamino-substituted butyrylamino groups [such as the 2-(N-methoxycarbonyl-N-methylamino)butyrylamino, 4-(N-methoxycarbonyl-N-methylamino)butyrylamino, 2-(N-ethoxycarbonyl-N-methylamino)butyrylamino and 4-(N-ethoxycarbonyl-N-methylamino) butyrylamino groups], N-alkoxycarbonyl-N-alkylamino-substituted isobutyrylamino groups [such as the 2-(N-methoxycarbonyl-N-methylamino)-2-methylpropionylamino, 2-(N-ethoxycarbonyl-N-methylamino)-2-methylpropionylamino, 2-(N-propoxycarbonyl-N-methylamino)-2-methylpropionylamino, 2-(N-isopropoxycarbonyl-N-methylamino)-2-methylpropionylamino, 2-(N-butoxycarbonyl-N-methylamino)-2-methylpropionylamino and 2-(N-t-butoxycarbonyl-N-methylamino)-2-methylpropionylamino groups], N-alkoxycarbonyl-N-alkylamino-substituted pentanoylamino groups [such as the 5-(N-methoxycarbonyl-N-methylamino)pentanoylamino and 5-(N-ethoxycarbonyl-N-methylamino)pentanoylamino groups], N-alkoxycarbonyl-N-alkylamino-substituted 4-methylpentanoylamino groups [such as the 2-(N-methoxycarbonyl-N-methylamino)-4-methylpentanoylamino and 2-(N-ethoxycarbonyl-N-methylamino)-4-methylpentanoylamino groups], N-alkoxycarbonyl-N-alkylamino-substituted isovalerylamino groups [such as the 2-(N-methoxycarbonyl-N-methylamino)amino-3-methylbutyrylamino and 2-(N-ethoxycarbonyl-N-methylamino)-3-methylbutyrylamino groups], N-alkoxycarbonyl-N-alkylamino-substituted hexanoylamino groups [such as the 6-(N-methoxycarbonyl-N-methylamino)hexanoylamino group], N-alkoxycarbonyl-N-alkylamino-substituted 3,3-dimethylbutyrylamino groups [such as the 2-(N-methoxycarbonyl-N-methylamino)-3,3-dimethylbutyrylamino and 2-(N-ethoxycarbonyl-N-methylamino)-3,3-dimethylbutyrylamino groups], and N-alkoxycarbonyl-N-alkylamino-substituted heptanoylamino groups [such as the 7-(N-methoxycarbonyl-N-methylamino)aminoheptanoylamino group]; of these, we prefer the N-alkoxycarbonyl-N-methylamino-substituted acetylamino, propionylamino and butyrylamino groups, especially the N-methoxycarbonyl-N-methylaminoacetylamino group;

haloalkoxycarbonylamino-substituted alkanoylamino groups in which the haloalkoxycarbonyl part has from 2 to 5 carbon atoms, the alkanoylamino part has from 2 to 7 carbon atoms, and the halogen atom is preferably chlorine, bromine, fluorine or iodine, more preferably chlorine or fluorine, especially haloalkoxycarbonylamino-substituted acetylamino groups [such as the chloromethoxycarbonylaminoacetylamino, trichloromethoxycarbonylaminoacetylamino, 2,2,2-trifluoroethoxycarbonylaminoacetylamino, 3-bromopropoxycarbonylaminoacetylamino and 4-chlorobutoxycarbonylaminoacetylamino groups], haloalkoxycarbonylamino-substituted propionylamino groups [such as the 2-chloromethoxycarbonylaminopropionylamino, 2-trichloromethoxycarbonylaminopropionylamino, 3-chloromethoxycarbonylaminopropionylamino, 3-trichloromethoxycarbonylaminopropionylamino, 2-(2,2,2-trifluoroethoxycarbonylamino)propionylamino, 3-(2,2,2-trifluoroethoxycarbonylamino)propionylamino, 2-(3-bromopropoxycarbonylamino)propionylamino, 3-(3-bromopropoxycarbonylamino)propionylamino, 2-(4-chlorobutoxycarbonylamino)propionylamino and 3-(4-chlorobutoxycarbonylamino)propionylamino groups], haloalkoxycarbonylamino-substituted butyrylamino groups [such as the 2-chloromethoxycarbonylaminobutyrylamino, 4-chloromethoxycarbonylaminobutyrylamino, 2-(2,2,2-trifluoroethoxycarbonylamino)butyrylamino and 4-(2,2,2-trifluoroethoxycarbonylamino)butyrylamino groups], haloalkoxycarbonylamino-substituted isobutyrylamine groups [such as the 2-chloromethoxycarbonylamino-2-methylpropionylamino, 2-(2,2,2-trifluoroethoxycarbonylamino)-2-methylpropionylamino, 2-(3-bromopropoxycarbonylamino)-2-methylpropionylamino and 2-(4-chlorobutoxycarbonylamino)-2-methylpropionylamino groups], haloalkoxycarbonylamino-substituted pentanoylamino groups [such as the 5-chloromethoxycarbonylaminopentanoylamino and 5-(2,2,2-trifluoroethoxycarbonylamino)pentanoylamino groups], haloalkoxycarbonylamino-substituted 4-methylpentanoylamino groups [such as the 2-chloromethoxycarbonylamino-4-methylpentanoylamino and 2-(2,2,2-trifluoroethoxycarbonylamino)-4-methylpentanoylamino groups], haloalkoxycarbonylamino-substituted isovalerylamino groups [such as the 2-chloromethoxycarbonylamino-3-methylbutyrylamino and 2-(2,2,2-trifluoroethoxycarbonylamino)-3-methylbutyrylamino groups], haloalkoxycarbonylamino-substituted hexanoylamino groups [such as the 6-chloromethoxycarbonylaminohexanoylamino group], haloalkoxycarbonylamino-substituted 3,3-dimethylbutyrylamino groups [such as the 2-chloromethoxycarbonylamino-3,3-dimethylbutyrylamino and 2-(2,2,2-trifluoroethoxycarbonylamino)-3,3-dimethylbutyrylamino groups], and haloalkoxycarbonylamino-substituted heptanoylamino groups [such as the 7-chloromethoxycarbonylaminoheptanoylamino group]; of these, we prefer the haloalkoxycarbonylamino-substituted acetylamino, propionylamino, butyrylamino, isobutyrylamino, isovalerylamino, 4-methylpentanoylamino and 3,3-dimethylbutyrylamino groups, especially the chloromethoxycarbonylaminoacetylamino, 2,2,2-trifluoroethoxycarbonylaminoacetylamino, 2-chloromethoxycarbonylaminopropionylamino, 3-chloromethoxycarbonylaminopropionylamino, 2-chloromethoxycarbonylaminobutyrylamino, 2-chloromethoxycarbonylamino-2-methylpropionylamino, 2-chloromethoxycarbonylamino-3-methylbutyrylamino, 2-chloromethoxycarbonylamino-4-methylpentanoylamino and 2-chloromethoxycarbonylamino-3,3-dimethylbutyrylamino grouaps; carbocyclic arylcarbonylamino-substituted alkanoylamino groups in which the alkanoylamino part has from 2 to 7 carbon atoms, and the aryl part has from 6 to 10 ring carbon atoms (such aryl groups include the phenyl, 1-naphthyl and 2-naphthyl groups), for example the benzoylaminoacetylamino, 3-benzoylaminopropionylamino, 4-benzoylaminobutyrylamino, 5-benzoylaminopentanoylamino, 6-benzoylaminohexanoylamino, 7-benzoylaminoheptanoylamino and naphthoylaminoacetylamino groups; aralkylcarbonylamino-substituted alkanoylamino groups in which the alkanoylamino part has from 2 to 7 carbon atoms, the aryl part is carbocyclic and has from 6 to 10 ring carbon atoms and the alkyl part has from 1 to 4 carbon atoms (such aralkyl groups include the benzyl, phenethyl, 3-phenylpropionyl and 4-phenylbutyryl groups), for example the phenylacetylaminoacetylamino, 3-phenylpropionylaminoacetylamino, 4-phenylbutyrylaminoacetylamino and 5-phenylpentanoylaminoacetylamino groups;

carbocyclic aryl-substituted alkanoylamino groups in which the alkanoylamino part has from 2 to 7 carbon atoms and the aryl part has from 6 to 10 ring carbon atoms which are unsubstituted or which are substituted by at least one substituent selected from the group consisting of substituents γ, for example the phenylacetylamino, 4-nitrophenylacetylamino, 4-fluorophenylacetylamino, 4-chlorophenylacetylamino, 4-methylphenylacetylamino, 4-ethylphenylacetylamino, 4-trifluoromethylphenylacetylamino, 4-aminomethylphenylacetylamino, 3-nitrophenylacetylamino, 3-fluorophenylacetylamino, 3-chlorophenylacetylamino, 3-methylphenylacetylamino, 3-ethylphenylacetylamino, 3-trifluoromethylphenylacetylamino, 3-aminomethylphenylacetylamino and 1-naphthylacetylamino groups;

alkanoylamino groups substituted by a group $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ, and oxygen atoms (to form an oxo group), for example the 2-oxo-1-azetidinylacetylamino, 2-oxo-1-piperidylacetylamino, 2,6-dioxo-1-piperidylacetylamino, pyrimidylacetylamino, pyridylacetylamino, 2-oxo-1-pyrrolidinylacetylamino, 2,5-dioxo-1-pyrrolidinylacetylamino, thiazolidinylacetylamino, thienylacetylamino, thiazolylacetylamino and 2-oxo-1,3-oxazolin-3-ylacetylamino groups;

alkanoylamino groups substituted by a group of formula $R^h$—S—, where $R^h$ is as defined above, for example the 2-pyrimidylacetylamino, 2-pyridylacetylamino, 2-thiazolidinylacetylamino groups; alkanoylamino groups substituted by an alkanoyl group having from 2 to 5 carbon atoms, for example the acetylacetylamino, propionylacetylamino, butyrylacetylamino, pivaloylacetylamino, 3-acetylpropionylamino, 3-propionylpropionylamino, 3-butyrylpropionylamino, 3-pivaloylpropionylamino, 4-acetylbutyrylamino, 4-propionylbutyrylamino, 4-butyrylbutyrylamino and 4-pivaloylbutyrylamino groups; and alkanoylamino groups substituted by an aralkyloxycarbonylamino group in which the aryl part is carbocyclic and has from 6 to 10 ring carbon atoms and the alkyl part has from 1 to 4 carbon atoms, for example the benzyloxycarbonylaminoacetylamino, phenethyloxycarbonylaminoacetylamino, 3-phenylpropyloxycarbonylaminoacetylamino, 4-phenylbutyloxycarbonylaminoacetylamino and 5-phenylpentyloxycarbonylaminoacetylamino groups.

Where $R^3$ represents a group of formula (iii) and $R^4$ represents a cycloalkyl group having from 3 to 6 carbon atoms, this group is a cycloalkylcarbonylamino group. Examples of such groups include the cyclopropanecarbonylamino, cyclobutanecarbonylamino, cyclopentanecarbonylamino, cyclohexanecarbonylamino, N-methyl-N-cyclopropanecarbonylamino, N-methyl-N-cyclobutanecarbonylamino, N-methyl-N-cyclopentanecarbonylamino, N-methyl-N-cyclohexanecarbonylamino, N-ethyl-N-cyclopropanecarbonylamino, N-ethyl-N-cyclobutanecarbonylamino, N-ethyl-N-cyclopentanecarbonylamino, N-ethyl-N-cyclohexanecarbonylamino, N-propyl-N-cyclopropanecarbonylamino, N-propyl-N-cyclobutanecarbonylamino, N-propyl-N-cyclopentanecarbonylamino and N-propyl-N-cyclohexanecarbonylamino groups.

Where $R^3$ represents a group of formula (iii) and $R^4$ represents a cycloalkyl group which has from 3 to 10 carbon atoms and which is substituted by at least one substituent selected from the group consisting of substituents β, defined above, the unsubstituted cycloalkyl group may be a monocyclic or polycyclic, e.g. bicyclic, ring system, for example, a cyclopropyl, cyclobutyl, cyclopentyl, cyclohexyl, cycloheptyl, cyclooctyl, norbornyl, norpinanyl, bornyl or menthyl group. Examples of the group of formula (iii) include the 1-aminocyclobutane-1-carbonyl, 1-aminocyclopentane-1-carbonyl, 1-aminocyclohexane-1-carbonyl, 2-chlorocyclobutane-1-carbonyl, 2-chlorocyclopentane-1-carbonyl, 2-chlorocyclohexane-1-carbonyl, 2-fluorocyclobutane-1-carbonyl, 2-fluorocyclopentane-1-carbonyl, 2-fluorocyclohexane-1-carbonyl, 2-methoxycyclobutane-1-carbonyl, 2-methoxycyclopentane-1-carbonyl, 2-methoxycyclohexane-1-carbonyl, 2-ethoxycyclobutane-1-carbonyl, 2-ethoxycyclopentane-1-carbonyl, 2-ethoxycyclohexane-1-carbonyl, 2-acetoxycyclobutane-1-carbonyl, 2-acetoxycyclopentane-1-carbonyl, 2-acetoxycyclohexane-1-carbonyl, 2-propionyloxycyclobutane-1-carbonyl, 2-propionyloxycyclopentane-1-carbonyl and 2-propionyloxycyclohexane-1-carbonyl groups.

Where $R^3$ represents a group of formula (iii) and $R^4$ represents an alkenyl group having from 2 to 6 carbon atoms, the alkenyl group may be a straight or branched chain group having from 2 to 6, preferably 3 or 4, carbon atoms, and examples of such alkenyl groups include the vinyl, allyl, methallyl, 1-propenyl, isopropenyl, 1-butenyl, 2-butenyl, 3-butenyl, 1-pentenyl, 2-pentenyl, 3-pentenyl and 4-pentenyl groups, of which the vinyl, allyl, methallyl, 1-propenyl, isopropenyl and butenyl groups are preferred. Preferred examples of the group of formula (iii) represented by $R^3$ include the acryloylamino, crotonoylamino, isocrotonoylamino, 3-butenoylamino, 2-pentenoylamino, 4-pentenoylamino, 2-hexenoylamino and 5-hexenoylamino groups, of which the acryloylamino, crotonoylamino and isocrotonoylamino groups are most preferred.

Where $R^3$ represents a group of formula (iii) and $R^4$ represents an alkynyl group having from 2 to 6 carbon atoms, the alkynyl group may be a straight or branched chain group having from 2 to 6, preferably 3 or 4, carbon atoms, and examples of such alkynyl groups include the ethynyl, propargyl (2-propynyl), 1-propynyl, 1-butynyl, 2-butynyl, 3-butynyl, 1-pentynyl, 2-pentynyl, 3-pentynyl and 4-pentynyl groups, of which the ethynyl, propynyl and butynyl groups are preferred. Preferred examples of the group of formula (iii) represented by $R^3$ include the propioloyl, 3-butynoylamino, 2-pentynoylamino, 4-pentynoylamino, 2-hexynoylamino and 5-hexynoylamino groups, of which the propioloyl group is most preferred.

Where $R^3$ represents a group of formula (iii) and $R^4$ represents a carbocyclic aryl group which has from 6 to 14 ring carbon atoms and which is unsubstituted or which is substituted by at least one substituent selected from the group consisting of substituents γ, defined above, the substituents γ are as exemplified separately below. Examples of such groups of formula (iii) include the benzoylamino, 1-naphthoylamino, 2-naphthoylamino, 1-fluorenecarbonylamino, 1-phenanthrenecarbonylamino, 1-anthracenecarbonylamino, 2-fluorobenzoylamino, 3-fluorobenzoylamino, 4-fluorobenzoylamino, 2-chlorobenzoylamino, 3-chlorobenzoylamino, 4-chrorobenzoylamino, 2-methylbenzoylamino, 3-methylbenzoylamino, 4-methylbenzoylamino, 2-ethylbenzoylamino, 3-ethylbenzoylamino, 4-ethylbenzoylamino, 2-propylbenzoylamino, 3-propylbenzoylamino, 4-propylbenzoylamino, 2-isopropylbenzoylamino, 3-isopropylbenzoylamino, 4-isopropylbenzoyl, amino, 2-butylbenzoylamino, 3-butylbenzoylamino, 4-butylbenzoylamino, 2-t-butylbenzoylamino, 3-t-butylbenzoylamino, 4-t-butylbenzoylaminlo, 2-methoxybenzoylamino, 3-methoxybenzoylamino, 4-methoxybenzoylamino, 3,4-dimethoxybenzoylamino, 2-ethoxybenzoylamino, 3-ethoxybenzoylamino, 4-ethoxybenzoylamino, 2-propoxybenzoylamino, 3-propoxybenzoylamino, 4-propoxybenzoylamino, 2-isopropoxybenzoylamino, 3-isopropoxybenzoylamino, 4-isopropoxybenzoylamino, 2-butoxybenzoylamino, 3-butoxybenzoylamino, 4-butoxybenzoylamino, 2-t-butoxybenzoylamino, 3-t-butoxybenzoylamino, 4-t-butoxybenzoylamino, 2-nitrobenzoylamino, 3-nitrobenzoylamino, 4-nitrobenzoylamino, 2-aminobenzoylamino, 3-aminobenzoylamino and 4-aminobenzoylamino groups, of which the benzoylamino, 2-fluorobenzoylamino, 3-fluorobenzoylamino, 4-fluorobenzoylamino, 3-chlorobenzoylamino, 4-chlorobenzoylamino, 3-methoxybenzoylamino, 4-methoxybenzoylamino, 3,4-dimethoxybenzoylamino, 4-t-butylbenzoylamino, 3-nitrobenzoylamino and 4-nitrobenzoylamino groups are preferred.

Where $R^3$ represents a group of formula (iii) and $R^4$ represents a heterocyclic group having from 3 to 6 ring atoms, of which at least one is a heteroatom selected from the group consisting of nitrogen, oxygen and sulfur heteroatoms, the heterocyclic group is unsubstituted or is substituted by at least one substituent selected from the group consisting of substituents γ, defined above, and oxygen atoms (to form an oxo group). Examples of such heterocyclic groups include the flryl, lactam, piperidyl, pyrimidyl, pyrrolidinyl, thiazolidinyl, thienyl and thiazolyl groups which may be substituted or unsubstituted. Specific examples of groups of formula (iii) include the 2-faroylamino, 3-furoylamino, 5-γ-lactamcarbonylamino, 2-piperidinecarbonylamino, 3-piperidinecarbonylamino, 4-piperidinecarbonylamino, 1-methoxycarbonyl-4-piperidinecarbonylamino, 1-ethoxycarbonyl-4-piperidinecarbonylamino, 2-pyrimidinecarbonylamino, 3-pyrimidinecarbonylamino, 3-pyridinecarbonylamino, 4-pyridinecarbionylamino, 3-pyrrolidinecarbonylamino, 1-methoxycarbonyl-2-pyrrolidininecarbonylamino, 1-ethoxycarbonyl-2-pyrrolidinecarbonylamino, 3-thiazolidinecarbonylamino, 4-thiazolidinecarbonylamino, 3-methoxycarbonyl-4-thiazolidinecarbonylamino, 3-ethoxycarbonyl-4-thiazolidinecarbonylamino, 2-thienyl and 3-thienyl groups, of which the 2-furoylamino, γ-lactamcarbonylamino, 1-methoxycarbonyl-4-piperidinecarbonylamino, 3-pyridinecarbonylamino, 4-pyridinecarbonylamino, 1-methoxycarbonyl-2-pyrrolidininecarbonylamino, 1-ethoxycarbonyl-2-pyrrolidinecarbonylamino, 3-methoxycarbonyl-4-thiazolidinecarbonylamino and 2-thienyl groups are particularly preferred.

Where $R^3$ represents a group of formula (iii), (iv), (vii), (viii) or (ix), and $R^5$ represents an alkyl group, this may be a straight or branched chain alkyl group having from 1 to 4, preferably 1 or 2, carbon atoms, and examples include the methyl, ethyl, propyl, isopropyl, butyl, isobutyl and t-butyl groups. Of these, we most prefer the methyl group.

Where $R^3$ represents a group of formula (iv) and $R^6$ represents an alkyl group, this may be a straight or branched chain group having from 1 to 6, preferably from 1 to 5, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

Where $R^3$ represents a group of formula (iv) and $R^6$ represents a cycloalkyl group, this has from 3 to 6 carbon atoms, and examples include the cyclopropyl, cyclobutyl, cyclopentyl and cyclohexyl groups;

Where $R^3$ represents a group of formula (iv) and $R^7$ represents an alkyl or cycloalkyl group, these may be any of the groups exemplified above in relation to $R^6$.

Where $R^3$ represents a group of formula (iv) and $R^7$ represents an aryl group, this is a carbocyclic aryl group which has from 6 to 14 ring carbon atoms and which is unsubstituted or which is substituted by at least one substituent selected from the group consisting of substituents γ, defined-above and exemplified below. Examples of such aryl groups include the phenyl, 1-naphthyl, 2-naphthyl, 1-fluorenyl, 1-phenanthrenyl, 1-anthracenyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-t-butylphenyl, 3-t-butylphenyl, 4-t-butylphenyl, 2-methoxyphenyl, 3-methoxyphenyl, 4-methoxyphenyl, 3,4-dimethoxyphenyl, 2-ethoxyphenyl, 3-ethoxyphenyl, 4-ethoxyphenyl, 2-propoxyphenyl, 3-propoxyphenyl, 4-propoxyphenyl, 2-isopropoxyphenyl, 3-isopropoxyphenyl, 4-isopropoxyphenyl, 2-butoxyphenyl, 3-butoxyphenyl, 4-butoxyphenyl, 2-t-butoxyphenyl, 3-t-butoxyphenyl, 4-t-butoxyphenyl, 2-nitrophenyl, 3-nitrophenyl, 4-nitrophenyl, 2-aminophenyl, 3-aminophenyl and 4-aminophenyl groups, of which the phenyl, 2-fluorophenyl, 3-fluorophenyl, 4-fluorophenyl, 3-chlorophenyl, 4-chlorophenyl, 3-methoxyphenyl, 4-methoxyphenyl, 3,4-dimethoxyphenyl, 4-t-butylphenyl, 3-nitrophenyl and 4-nitrophenyl groups are preferred.

Where $R^3$ represents a group of formula (iv) and $R^6$ and $R^7$, together with the nitrogen atom to which they are attached, are fused to form a heterocyclic ring having from 3 to 6 ring atoms, this may be any of the nitrogen-containing heterocyclic groups included among the groups exemplified in relation to $R^4$, above, preferably a 1-pyrrolidinyl group.

Where $R^3$ represents a group of formula (vii), (viii) or (ix), and $R^8$ represents an alkyl group, this may be a straight or branched chain alkyl group having from 1 to 4, preferably 1 or 2, carbon atoms, and examples include the methyl, ethyl, propyl, isopropyl, butyl, isobutyl and t-butyl groups. Of these, we most prefer the methyl group.

Where $R^3$ represents a group of formula (vii), (viii) or (ix), and $R^8$ represents an aryl group, this is a carbocyclic aryl group which has from 6 to 10 ring carbon atoms and which is unsubstituted or which is substituted by at least one substituent selected from the group consisting of substituents γ, defined above and exemplified below. Examples of such aryl groups include the phenyl, 1-ntaphthyl, 2-naphthyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-t-butylphenyl, 3-t-butylphenyl, 4-t-butylphenyl, 2-methoxyphenyl, 3-methoxyphenyl, 4-methoxyphenyl, 3,4-dimethoxyphenyl, 2-ethoxyphenyl, 3-ethoxyphenyl, 4-ethoxyphenyl, 2-propoxyphenyl, 3-propoxyphenyl, 4-propoxyphenyl, 2-isopropoxyphenyl, 3-isopropoxyphenyl, 4-isopropoxyphenyl, 2-butoxyphenyl, 3-butoxyphenyl, 4-butoxyphenyl, 2-t-butoxyphenyl, 3-t-butoxyphenyl, 4-t-butoxyphenyl, 2-nitrophenyl, 3-nitrophenyl, 4-nitrophenyl, 2-aminophenyl, 3-aminophenyl and 4-aminophenyl groups, of which the phenyl, 2-fluorophenyl, 3-fluorophenyl, 4-fluorophenyl, 3-chlorophenyl, 4-chlorophenyl, 3-methoxyphenyl, 4-methoxyphenyl, 3,4-dimethoxyphenyl, 4-t-butylphenyl, 3-nitrophenyl and 4-nitrophenyl groups are preferred.

Where $R^3$ represents a group of formula (viii), and $R^9$ represents an alkyl or aryl group, this may be any of those defined and exemplified above in relation to $R^8$.

Where $R^3$ represents a group of formula (viii), and $R^9$ represents a cycloalkyl group, this may be any of those defined and exemplified above in relation to $R^6$.

Where $R^3$ represents a group of formula (viii), and $R^9$ represents an aralkyl group, the aryl part is carbocyclic and has from 6 to 10 ring carbon atoms and the alkyl part has from 1 to 4 carbon atoms, the alkyl and aryl parts of this group may each independently be as defined and exemplified above in relation to $R^8$. Specific examples of such aralkyl groups include the benzyl, 1-phenylethyl, 2-phenylethyl (phenethyl), 3-phenylpropyl, 2-phenylpropyl, 4-phenylbutyl, 2-phenylbutyl, 1-naphthylmethyl and 2-naphthylmethyl groups. These groups may be substituted or unsubstituted, and, if substituted, the substituent or substituents is or are selected from the group consisting of substituents γ, defined above anid exemplified below. Examples of the substituted groups include the 2-fluorobenzyl, 3-fluorobenzyl, 4-fluorobenzyl, 2-chlorobenzyl, 3-chlorobenzyl, 4-chlorobenzyl, 2-methylbenzyl, 3-methylbenzyl, 4-methylbenzyl, 2-ethylbenzyl, 3-ethylbenzyl, 4-ethylbenzyl, 2-propylbenzyl, 3-propylbenzyl, 4-propylbenzyl, 2-isopropylbenzyl, 3-isopropylbenzyl, 4-isopropylbenzyl, 2-butylbenzyl, 3-butylbenzyl, 4-butylbenzyl, 2-t-butylbenzyl, 3-t-butylbenzyl, 4-t-butylbenzyl, 2-methoxybenzyl, 3-methoxybenzyl, 4-methoxybenzyl, 3,4-dimethoxybenzyl, 2-ethoxybenzyl, 3-ethoxybenzyl, 4-ethoxybenzyl, 2-propoxybenzyl, 3-propoxybenzyl, 4-propoxybenzyl, 2-isopropoxybenzyl, 3-isopropoxybenzyl, 4-isopropoxybenzyl, 2-butoxybenzyl, 3-butoxybenzyl, 4-butoxybenzyl, 2-t-butoxybenzyl, 3-t-butoxybenzyl, 4-t-butoxybenzyl, 2-nitrobenzyl, 3-nitrobenzyl, 4-nitrobenzyl, 2-aminobenzyl, 3-aminobenzyl and 4-aminobenzyl groups.

Where $R^3$ represents a group of formula (ix), and $R^{10}$ represents a heterocyclic group, this may be any of the heterocyclic groups included among the groups exemplified in relation to $R^4$, above, preferably a 2-chloroacetylamino-4-thiazolyl, 2-methoxycarbonylamino-4-thiazolyl or 2-thienyl group.

Where $R^3$ represents a group of formula (ix), and $R^{10}$ represents an alkyl group, this may be a straight or branched chain alkyl group having from 1 to 3 carbon atoms, and examples include the methyl, ethyl, propyl and isopropyl groups. Of these, we prefer the methyl group.

Substituents α include:

halogen atoms, such as the fluorine, chlorine, bromine or iodine atoms, of which we prefer the fluorine and chlorine atoms;

cyano groups;

alkoxy groups having from 1 to 4 carbon atoms, such as the methoxy, ethoxy, propoxy, isopropoxy, butoxy, isobutoxy, sec-butoxy and t-butoxy groups, most preferably the methoxy group;

alkylthio groups having from 1 to 4 carbon atoms, such as the methylthio, ethylthio, propylthio, isopropylthio, butylthio, isobutylthio, sec-butylthio and t-butylthio groups, most preferably the methylthio group;

alkylsulfonyl groups having from 1 to 4 carbon atoms, such as the methylsulfonyl, ethylsulfonyl, propylsulfonyl, isopropylsulfonyl, butylsulfonyl, isobutylsulfonyl, sec-butylsulfonyl and t-butylsulfonyl groups, most preferably the methylsulfonyl group;

alkanoyloxy groups having from 2 to 5 carbon atoms, such as the acetoxy, propionyloxy, butyryloxy, isobutyryloxy, valeryloxy, isovaleryloxy and pivaloyloxy groups, of which the acetoxy group is preferred;

alkoxycarbonyl groups having from 2 to 5 carbon atoms, such as the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, most preferably the methoxycarbonyl group;

carbocyclic aryloxy groups which have from 6 to 10 ring carbon atoms, such as the phenoxy, 1-naphthyloxy and 2-naphthyloxy groups, of which we prefer the phenoxy group;

carbocyclic arylthio groups which have from 6 to 10 ring carbon atoms, such as the phenylthio, 1-naphthylthio and 2-naphthylthio groups, of which we prefer the phenylthio group;

carbocyclic arylsulfonyl groups which have from 6 to 10 ring carbon atoms, such as the phenylsulfonyl, 1-naphthylsulfonyl and 2-naphthylsulfonyl groups, of which we prefer the phenylsulfonyl group;

amino groups;

alkanoylamino groups having from 2 to 5 carbon atoms, such as the acetylamino, propionylamino, butyrylamino, isobutyrylamino, valerylamino, isovalerylamino and pivaloylamino groups, of which the acetylamino group is preferred;

N-($C_2$–$C_5$ alkanoyl)-N-($C_1$–$C_3$ alkyl)amino groups, such as the N-acetyl-N-methylamino, N-propionyl-N-methylamino, N-butyryl-N-methylamino, N-isobutyryl-N-methylamino, N-valeryl-N-methylamino, N-isovaleryl-N-methylamino, N-pivaloyl-N-methylamino, N-acetyl-N-ethylamino, N-propionyl-N-ethylamino, N-butyryl-N-ethylamino, N-isobutyryl-N-ethylamino, N-valeryl-N-ethylamino, N-isovaleryl-N-ethylamino, N-pivaloyl-N-ethylamino, N-acetyl-N-propylamino, N-propionyl-N-propylamino, N-butyryl-N-propylanino, N-isobutyryl-N-propylamino, N-valeryl-N-propylamino, N-isovaleryl-N-propylamino, N-pivaloyl-N-propylamino, N-acetyl-N-isopropylamino, N-propionyl-N-isopropylamino, N-butyryl-N-isopropylamino, N-isobutyryl-N-isopropylamino, N-valeryl-N-isopropylamino, N-isovaleryl-N-isopropylamino and N-pivaloyl-N-isopropylamino groups, of which the N-methyl-N-acetylamino group is preferred;

haloalkanoylamino groups having from 2 to 5 carbon atoms, such as the chloroacetylamino, dichloroacetylamino, trichloroacetylamino, fluoroacetylamino, difluoroacetylamino, trifluoroacetylamino, bromoacetylamino, iodoacetylamino, 4-chlorobutyrylamino, 4-fluorobutyrylamino and 5-fluorovalerylamino groups, of these, the chloroacetylamino group is preferred;

alkoxycarbonylamino groups having from 2 to 5 carbon atoms, such as the methoxycarbonylamino, ethoxycarbonylamino, propoxycarbonylamino, isopropoxycarbonylamino, butoxycarbonylamino, isobutoxycarbonylamino, sec-butoxycarbonylamino and t-butoxycarbonylamino groups, most preferably the methoxycarbonylamino group;

N-($C_2$–$C_5$ alkoxycarbonyl)-N-($C_1$–$C_3$ alkyl)amino groups, such as the N-methoxycarbonyl-N-methylamino, N-ethoxycarbonyl-N-methylamino, N-propoxycarbonyl-N-methylamino, N-isopropoxycarbonyl-N-methylamino, N-butoxycarbonyl-N-methylamino, N-isobutoxycarbonyl-N-methylamino, N-sec-butoxycarbonyl-N-methylamino, N-t-butoxycarbonyl-N-methylamino, N-methoxycarbonyl-N-ethylamino, N-ethoxycarbonyl-N-ethylamino, N-propoxycarbonyl-N-ethylamino, N-isopropoxycarbonyl-N-ethylamino, N-butoxycarbonyl-N-ethylamino, N-isobutoxycarbonyl-N-ethylamino, N-sec-butoxycarbonyl-N-ethylamino, N-t-butoxycarbonyl-N-ethylamino, N-methoxycarbonyl-N-propylamino, N-ethoxycarbonyl-N-propylamino, N-propoxycarbonyl-N-propylamino, N-isopropoxycarbonyl-N-propylamino, N-butoxycarbonyl-N-propylamino, N-isobutoxycarbonyl-N-propylamino, N-sec-butoxycarbonyl-N-propylamino, N-t-butoxycarbonyl-N-propylamino, N-methoxycarbonyl-N-isopropylamino, N-ethoxycarbonyl-N-isopropylamino, N-propoxycarbonyl-N-isopropylamino, N-isopropoxycarbonyl-N-isopropylamino, N-butoxycarbonyl-N-isopropylamino, N-isobutoxycarbonyl-N-isopropylamino, N-sec-butoxycarbonyl-N-isopropylamino and N-t-butoxycarbonyl-N-isopropylamino groups, most preferably the N-methoxycarbonyl-N-methylamino group;

haloalkoxycarbonylamino groups having from 2 to 5 carbon atoms, such as the chloromethoxycarbonylamino, dichloromethoxycarbonylamino, trichloromethoxycarbonylamino, fluoromethoxycarbonylamino, difluoromethoxycarbonylamino, trifluoromethoxycarbonylamino, fluoromethoxycarbonylamino, difluoromethoxycarbonylamino, trifluoromethoxycarbonylamino, bromomethoxycarbonylamino, iodomethoxycarbonylamino, 2-chloroethoxycarbonylamino, 2-fluoroethoxycarbonylamino, 2-bromoethoxycarbonylamino, 2-iodoethoxycarbonylamino, 2,2,2-trifluoroethoxycarbonylamino, 2,2,2-trichloroethoxycarbonylamino, 3-fluoropropoxycarbonylamino, 3-chloropropoxycarbonylamino, 3-bromopropoxycarbonylamino, 3-iodopropoxycarbonylamino, 4-chlorobutoxyparbonylamino and 5-chloropentyloxycarbonylamino groups, of which we prefer the chloromethoxycarbonylamino and 2,2,2-trifluoroethoxycarbonylamino groups;

carbocyclic arylcarbonylamino groups in which the aryl part has from 6 to 10 ring carbon atoms, such as the benzoylamino, 1-naphthoylamino and 2-naphthoylamino groups, of which we prefer the benzoylamino group;

aralkylcarbonylamino groups in which the aryl part is carbocyclic and has from 6 to 10 ring carbon atoms and the alkyl part has from 1 to 4 carbon atoms, such as the phenylacetylamino, 2-phenylpropionylamino, 3-phenylpropionylamino, 4-phenylbutyrylamino, 3-phenylbutyrylamino, 4-phenylvalerylamino, 2-phenylvalerylamino, 1-naphthylacetylamino and 2-naphthylacetylamino groups, of which we prefer the phenylacetylamino group;

carbocyclic aryl groups which have from 6 to 10 ring carbon atoms which are unsubstituted or which are substituted by at least one substituent selected from the group consisting of substituents γ, such as the phenyl, 1-naphthyl, 2-naphthyl, 2-fluorophenyl, 3-fluorophenyl, 4-fluorophenyl, 2-chlorophenyl, 3-chlorophenyl, 4-chlorophenyl, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-butylphenyl, 3-butylphenyl, 4-butylphenyl, 2-t-butylphenyl, 3-t-butylphenyl, 4-t-butylphenyl, 2-methoxyphenyl, 3-methoxyphenyl, 4-methoxyphenyl, 3,4-dimethoxyphenyl, 2-ethoxyphenyl, 3-ethoxyphenyl, 4-ethoxyphenyl, 2-propoxyphenyl, 3-propoxyphenyl, 4-propoxyphenyl, 2-isopropoxyphenyl, 3-isopropoxyphenyl, 4-isopropoxyphenyl, 2-butoxyphenyl, 3-butoxyphenyl, 4-butoxyphenyl, 2-t-butoxyphenyl, 3-t-butoxyphenyl, 4-t-butoxyphenyl, 2-nitrophenyl, 3-nitrophenyl, 4-nitrophenyl, 2-aminophenyl, 3-aminophenyl and 4-aminophenyl groups, of which the phenyl, 2-fluorophenyl, 3-fluorophenyl, 4-fluorophenyl, 3-chlorophenyl, 4-chlorophenyl, 3-methoxyphenyl, 4-methoxyphenyl, 3,4-dimethoxyphenyl, 4-t-butylphenyl, 3-nitrophenyl and 4-nitrophenyl groups are preferred;

groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ, and oxygen atoms (to form an oxo group), such as the 2-oxo-1-azetidinyl, 2-oxo- 1-piperidyl, 2,6-dioxo-1-piperidyl, pyrimidyl, pyridyl, 2-oxo-1-pyrrolidinyl, 2,5-dioxo-1-pyrrolidinyl, thiazolidinyl, thienyl, thiazolyl and 2-oxo-1,3-oxazolin-3-yl groups;

groups of formula $R^h$—S—, where $R^h$ is as defined above, such as the 2-oxo-1-azetidinylthio, 2-oxo-1-piperidylthio, 2,6-dioxo-1-piperidylthio, pyrimidylthio, pyridylthio, 2-oxo-1-pyrrolidinylthio, 2,5-dioxo-1-pyrrolidinylthio, thiazolidinylthio, thienylthio, thiazolylthio and 2-oxo-1,3-oxazolin-3-ylthio groups, of which the 2-pyrimidylthio, 2-pyridylthio and 2-thiazolidinylthio groups are preferred;

alkanoyl groups having from 2 to 5 carbon atoms, such as the acetyl, propionyl, butyryl, isobutyryl, valeryl, isovaleryl and pivaloyl groups, of which the acetyl group is preferred;

and aralkyloxycarbonylamino groups in which the aryl part is carbocyclic and has from 6 to 10 ring carbon atoms and the alkyl part has from 1 to 4 carbon atoms, such as the benzyloxycarbonylamino, phenethyloxycarbonylamino, 3-phenylpropyloxycarbonylamino, 4-phenylbutyloxycarbonylamino and 5-phenylpentyloxycarbonylamino groups.

Examples of groups which may be included in substituents β are:

halogen atoms, such as the fluorine, chlorine, bromine or iodne atoms, of which we prefer the fluorine and chlorine atoms;

alkoxy groups having from 1 to 4 carbon atoms, such as the methoxy, ethoxy, propoxy, isopropoxy, butoxy, isobutoxy, sec-butoxy and t-butoxy groups, most preferably the methoxy group; and alkanoyloxy groups having from 2 to 5 carbon atoms acetoxy, propionyloxy, butyryloxy, isobutyryloxy, valeryloxy, isovaleryloxy and pivaloyloxy groups, of which the acetoxy group is preferred.

Examples of groups which may be included in substituents γ are:

halogen atoms, such as the fluorine, chlorine, bromine or iodine atoms, of which we prefer the fluorine and chlorine atoms;

hydroxy groups;

cyano groups;

nitro groups;

alkyl groups having from 1 to 4 carbon atoms, such as the methyl, ethyl, propyl, isopropyl, butyl, isobutyl, sec-butyl and t-butyl groups, most preferably the methyl group;

alkoxy groups having from 1 to 4 carbon atoms, such as the methoxy, ethoxy, propoxy, isopropoxy, butoxy, isobutoxy, sec-butoxy and t-butoxy groups, most preferably the methoxy group;

and alkoxycarbonyl groups having a total of from 2 to 5 carbon atoms (i.e. the alkoxy part has from 1 to 4 carbon atoms), such as the methoxycarbonyl, ethoxycarbonyl, propoxycarbonyl, isopropoxycarbonyl, butoxycarbonyl, isobutoxycarbonyl, sec-butoxycarbonyl and t-butoxycarbonyl groups, most preferably the methoxycarbonyl group.

Examples of groups which may be included in substituents δ are:

amino groups;

alkanoylamino groups having from 2 to 5 carbon atoms, such as the acetylamino, propionylamino, butyrylamino, isobutyrylamino, valerylamino, isovalerylamino and pivaloylamino groups, of which the acetylamino group is preferred;

haloalkanoylamino groups having from 2 to 5 carbon atoms, such as the chloroacetylamino, dichloroacetylamino, trichloroacetylamino, fluoroacetylamino, difluoroacetylamino, trifluoroacetylamino, bromoacetylamino, iodoacetylamino, 4-chlorobutyrylamino, 4-fluorobutyrylamino and 5-fluorovalerylamino groups, of these, the chloroacetylamino group is preferred; and alkoxycarbonylamino groups having from 2 to 6 carbon atoms, such as the methoxycarbonylamino, ethoxycarbonylamino, propoxycarbonylamino, isopropoxycarbonylamino, butoxycarbonylamino, isobutoxycarbonylamino, sec-butoxycarbonylamino, t-butoxycarbonylamino and pentyloxycarbonylamino groups, most preferably the methoxycarbonylamino group.

In general above, where substituents are referred to, there is no particular limitation on the number of substituents, except such as may be imposed by the number of substitutable positions and possibly by steric constraints. However, in general, where the group is substituted, from 1 to 3 substituents are preferred, 0, 1 or 2 substituents being more preferred, and 0 or 1 being still more preferred.

The compounds of the present invention-may contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques. In particular, the compounds of the present invention can exist in the α- or β-configuration with respect to the stereochemistry of the 13-position of the milbemycin skeleton. Although all such isomers and mixtures thereof form a part of the present invention, the preferred configuration is the β-configuration.

Preferred classes of compounds of the present invention are those compounds of formula (I) in which:

(A). Z represents a group of formula (i) and $R^2$ represents a methyl or ethyl group. or (A'). Z represents a group of formula (ii) and m is 2, 3 or 4.

(B). n is 0.

(C). $R^3$ represents an amino group, a ($C_1$–$C_3$ alkyl)amino group, a di($C_1$–$C_3$ alkyl)amino group, an alkoxy group having from 1 to 3 carbon atoms, or a group of formula (iii), (iv), (v), (vi) or (vii):

(iii)

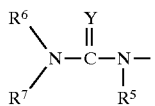
(iv)

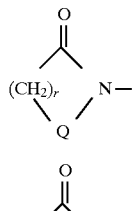
(v)

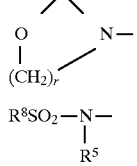
(vi)

$R^8SO_2-N-$
$\quad\quad\quad |$
$\quad\quad\quad R^5$
(vii)

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms;

$R^5$ represents a hydrogen atom or an alkyl group having from 1 to 3 carbon atoms;

$R^6$ represents: a hydrogen atom; or an alkyl group having from 1 to 4 carbon atoms;

$R^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the alkyl part has 1 or 2 carbon atoms; or $R^6$ and $R^7$, together with the nitrogen atom to which they are attached, are fused to form a heterocyclic ring having 5 or 6 ring atoms;

Y represents oxygen atom or sulfur atom;

r is 1, 2 or 3;

Q represents a methylene group or a carbonyl group;

$R^8$ represents: an alkyl group having from 1 to 4 carbon atoms or a carbocyclic aryl group which has from 6 to 10 ring carbon atoms which is unsubstituted or which is substituted by at least one substituent selected from the group consisting of substituents $\gamma^1$, defined below;

substituents $\alpha^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents $\gamma^1$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms; groups of formula $R^h$—S—, where $R^h$ is as defined above; and alkanoyl groups having from 2 to 5 carbon atoms;

substituents $\gamma^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

Of these, we particularly prefer those compounds of formula (1) and salts thereof in which Z is as defined in (A) or (A') above, and $R^3$ is as defined in (C) above, and especially those in which Z is as defined in (A) or (A') above, $R^3$ is as defined in (C) above, and n is as defined in (B) above.

More preferred classes of compounds of the present invention are those compounds of formula (I) in which:

(D). $R^1$ represents a methyl or ethyl group.

(E). Z represents a group of formula (i) and $R^2$ represents a methyl group.

(E'). Z represents a group of formula (ii) and m is 2 or 4.

(F). $R^3$ represents an amino group, a methylamino group, an ethylamino group, an alkoxy group having from 1 to 3 carbon atoms, or a group of formula (iii), (v) or (vi):

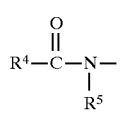
(iii)

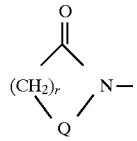
(v)

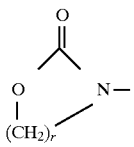

wherein:
$R^4$ represents: an alkyl group having from 1 to 4 carbon atoms; a substituted alkyl group which has from 1 to 3 carbon atoms and which is substituted by at least one substituent selected from the group consisting of substituents α, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $γ^1$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $γ^1$, defined below, and oxygen atoms;

r is 1, 2 or 3;

Q represents a methylene group or a carbonyl group;

substituents $α^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms, N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $γ^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $γ^2$, defined below, and oxygen atoms; and groups of formula $R^h$—S—, where $R^h$ is as defined above;

substituents $γ^2$ are selected from the group consisting of: halogen atoms; cyano groups; nitro groups; methyl groups; ethyl groups; methoxy groups; and alkoxycarbonyl groups having 2 or 3 carbon atoms.

Of these, we particularly prefer those compounds of formula (I) and salts thereof in which $R^1$ is as defined in (D) above, Z is as defined in (E) or (E') above, and $R^3$ is as defined in (F) above, and especially those in which $R^1$ is as defined in (D) above, Z is as defined in (E) or (E') above, $R^3$ is as defined in (F) above, and n is as defined in (B) above.

Still more preferred classes of compounds of the present invention are those compounds of formula (I) in which:

(G). $R^1$ represents an ethyl group.

(H). $R^3$ represents an amino group, a methylamino group, an ethylamino group, or a group of formula (iii) or (vi):

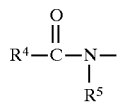

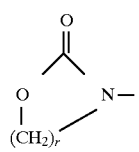

wherein:
$R^4$ represents: an alkyl group having from 1 to 4 carbon atoms; a substituted alkyl group which has from 1 to 3 carbon atoms and which is substituted by at least one substituent selected from the group consisting of substituents $α^3$, defined below; a cycloalkyl group having 5 or 6 carbon atoms; a phenyl group which is unsubstituted or which is substituted by at least one substituent selected from the group consisting of substituents $γ^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $γ^3$, defined below;

r is 2;

Q represents a methylene group or a carbonyl group;

substituents $α^3$ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents $γ^2$ are selected from the group consisting of: halogen atoms; cyano groups; nitro groups; methyl groups; ethyl groups; methoxy groups; and ethoxy groups.

Of these, we particularly prefer those compounds of formula (I) and salts thereof in which $R^1$ is as defined in (G) above, Z is as definpd in (E) or (E') above, and $R^3$ is as defined in (H) above, and especially those in which $R^1$ is as defined in (G) above, Z is as defined in (E) or (E') above, $R^3$ is as defined in (H) above, and n is as defined in (B) above.

Examples of certain compounds of the present invention are those compounds of formula (I):

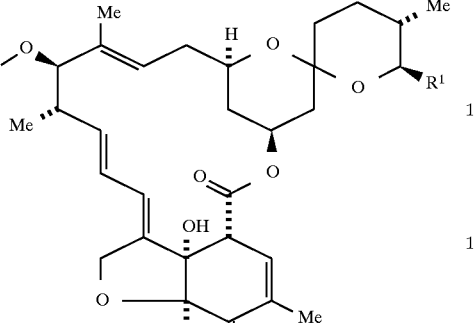

in which the substituents are as defined in Table 1. In the Table, the following abbreviations are used:

| | |
|---|---|
| Ac | acetyl |
| Azt | azetidinyl |
| Bu | butyl |
| cBu | cyclobutyl |
| iBu | isobutyl |
| sBu | sec-butyl |
| tBu | t-butyl |
| Bz | benzyl |
| Et | ethyl |
| Fur | furyl |
| Hx | hexyl |
| cHx | cyclohexyl |
| Isox | isoxazolyl |
| Lac | lactum, i.e. 5-γ-Lac is |

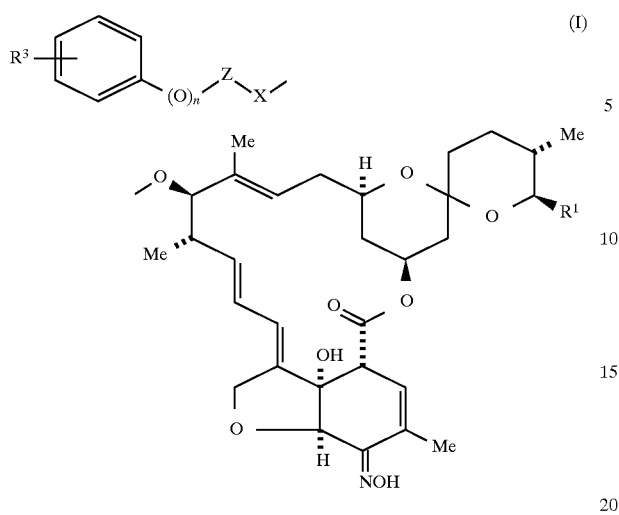

| | |
|---|---|
| Me | methyl |
| Ph | phenyl |
| Pip | piperidyl |
| Pn | pentyl |
| cPn | cyclopentyl |
| Pr | propyl |
| cPr | cyclopropyl |
| iPr | isopropyl |
| Pym | pyrimidyl |
| Pyr | pyridyl |
| Pyrd | pyrrolidinyl |
| Thdn | thiazolidinyl |
| Thi | thienyl |
| Thiz | thiazolyl |

TABLE 1

| Cpd. No. | $R^1$ | Z | n | X | $R^3$ |
|---|---|---|---|---|---|
| 1 | Et | =C(Me)$_2$ | 1 | C = O | 4-NO$_2$ |
| 2 | Et | =C(Me)$_2$ | 0 | C = O | 4-NO$_2$ |
| 3 | Et | =C(Me)$_2$ | 0 | C = O | 3-NO$_2$ |
| 4 | Et | =C(Me)$_2$ | 0 | C = O | 2-NO$_2$ |
| 5 | Et | =C(Me)$_2$ | 1 | C = O | 4-NH$_2$ |
| 6 | Et | =C(Me)$_2$ | 0 | C = O | 4-NH$_2$ |
| 7 | Et | =C(Me)$_2$ | 0 | C = O | 3-NH$_2$ |
| 8 | Et | =C(Me)$_2$ | 0 | C = O | 2-NH$_2$ |
| 9 | Et | =C(Me)$_2$ | 0 | C = O | 4-NHMe |
| 10 | Et | =C(Me)$_2$ | 0 | C = O | 4-NHEt |
| 11 | Et | =C(Me)$_2$ | 0 | C = O | 4-NHPr |
| 12 | Et | =C(Me)$_2$ | 0 | C = O | 4-NHBu |
| 13 | Et | =C(Me)$_2$ | 0 | C = O | 4-NMe$_2$ |
| 14 | Et | =C(Me)$_2$ | 0 | C = O | 4-NEt$_2$ |
| 15 | Et | =C(Me)$_2$ | 1 | C = O | 4-MeO |
| 16 | Et | =C(Me)$_2$ | 0 | C = O | 4-MeO |
| 17 | Et | =C(Me)$_2$ | 0 | C = O | 3-MeO |
| 18 | Et | =C(Me)$_2$ | 0 | C = O | 2-MeO |
| 19 | Et | =C(Me)$_2$ | 0 | C = O | 4-OEt |
| 20 | Et | =C(Me)$_2$ | 0 | C = O | 4-OPr |
| 21 | Et | =C(Me)$_2$ | 0 | C = O | 2-OiPr |
| 22 | Et | =C(Me)$_2$ | 0 | C = O | 4-OBu |
| 23 | Et | =C(Me)$_2$ | 0 | C = O | 4-OiBu |
| 24 | Et | =C(Me)$_2$ | 0 | C = O | 4-OCH$_2$CH$_2$OCH$_3$ |
| 25 | Et | =C(Me)$_2$ | 1 | C = O | 4-NHAc |
| 26 | Et | =C(Me)$_2$ | 0 | C = O | 4-NHAc |
| 27 | Me | =C(Me)$_2$ | 0 | C = O | 4-NHAc |
| 28 | Et | =C(Me)$_2$ | 0 | C = O | 4-N(Me)Ac |
| 29 | Et | =C(Me)$_2$ | 0 | C = O | 4-N(Et)Ac |
| 30 | Et | =C(Me)$_2$ | 0 | C = O | 4-N(Pr)Ac |
| 31 | Et | =C(Me)$_2$ | 0 | C = O | 4-N(Bu)Ac |
| 32 | Et | =C(Me)$_2$ | 0 | C = O | 3-NHAc |
| 33 | Et | =C(Me)$_2$ | 0 | C = O | 4-NHCOEt |

TABLE 1-continued

| Cpd. No. | R¹ | Z | n | X | R³ |
|---|---|---|---|---|---|
| 34 | Et | =C(Me)₂ | 0 | C = O | 4-NHCOPr |
| 35 | Et | =C(Me)₂ | 0 | C = O | 4-NHCOiPr |
| 36 | Et | =C(Me)₂ | 0 | C = O | 4-NHCOBu |
| 37 | Et | =C(Me)₂ | 0 | C = O | 4-NHCOiBu |
| 38 | Et | =C(Me)₂ | 0 | C = O | 4-NHCOtBu |
| 39 | Et | =C(Me)₂ | 0 | C = O | 4-NHCOcPr |
| 40 | Et | =C(Me)₂ | 0 | C = O | 4-NHCOcBu |
| 41 | Et | =C(Me)₂ | 0 | C = O | 4-NHCOcPn |
| 42 | Et | =C(Me)₂ | 0 | C = O | 4-NHCOcHx |
| 43 | Et | =C(Me)₂ | 0 | C = O | 4-NHCOCH₂Br |
| 44 | Et | =C(Me)₂ | 0 | C = O | 4-NHCOCF₃ |
| 45 | Et | =C(Me)₂ | 0 | C = O | 4-NHCOCHF₂ |
| 46 | Et | =C(Me)₂ | 0 | C = O | 4-NHCOCH₂CN |
| 47 | Et | =C(Me)₂ | 0 | C = O | 4-NHCOCH₂OMe |
| 48 | Et | =C(Me)₂ | 0 | C = O | 4-NHCOCH₂OEt |
| 49 | Et | =C(Me)₂ | 0 | C = O | 4-NHCOCH₂OAc |
| 50 | Et | =C(Me)₂ | 0 | C = O | 4-NHCOCH₂OCOPr |
| 51 | Et | =C(Me)₂ | 0 | C = O | 4-NHCOCH₂SMe |
| 52 | Et | =C(Me)₂ | 0 | C = O | 4-NHCOCH₂SO₂Me |
| 53 | Et | =C(Me)₂ | 0 | C = O | 4-NHCOCH₂SPh |
| 54 | Et | =C(Me)₂ | 0 | C = O | 4-NHCOCH₂S(2-Pym) |
| 55 | Et | =C(Me)₂ | 0 | C = O | 4-NHCOCH₂S(2-Pyr) |
| 56 | Et | =C(Me)₂ | 0 | C = O | 4-NHCOCH₂S(2-Thdn) |
| 57 | Et | =C(Me)₂ | 0 | C = O | 4-NHCOCH₂CH₂COMe |
| 58 | Et | =C(Me)₂ | 0 | C = O | 4-NHCOCH₂CH₂COOMe |
| 59 | Et | =C(Me)₂ | 0 | C = O | 4-NHCOCH=CHMe |
| 60 | Et | =C(Me)₂ | 0 | C = O | 4-NHCOC≡CH |
| 61 | Et | =C(Me)₂ | 0 | C = O | 4-NHCOCH₂(4-NO₂Ph) |
| 62 | Et | =C(Me)₂ | 0 | C = O | 4-NHCOCH₂(4-MeOPh) |
| 63 | Et | =C(Me)₂ | 0 | C = O | 4-NHCOPh |
| 64 | Et | =C(Me)₂ | 0 | C = O | 4-NHCO(2-FPh) |
| 65 | Et | =C(Me)₂ | 0 | C = O | 4-NHCO(3-FPh) |
| 66 | Et | =C(Me)₂ | 0 | C = O | 4-NHCO(4-FPh) |
| 67 | Et | =C(Me)₂ | 0 | C = O | 4-NHCO(4-ClPh) |
| 68 | Et | =C(Me)₂ | 0 | C = O | 4-NHCO(3-ClPh) |
| 69 | Et | =C(Me)₂ | 0 | C = O | 4-NHCO(4-MeOPh) |
| 70 | Et | =C(Me)₂ | 0 | C = O | 4-NHCO(3-MeOPh) |
| 71 | Et | =C(Me)₂ | 0 | C = O | 4-NHCO(3,4-di-MeOPh) |
| 72 | Et | =C(Me)₂ | 0 | C = O | 4-NHCO(4-tBuPh) |
| 73 | Et | =C(Me)₂ | 0 | C = O | 4-NHCO(4-NO₂Ph) |
| 74 | Et | =C(Me)₂ | 0 | C = O | 4-NHCO(3-NO₂Ph) |
| 75 | Et | =C(Me)₂ | 0 | C = O | 4-NHCO(3-Pyr) |
| 76 | Et | =C(Me)₂ | 0 | C = O | 4-NHCO(4-Pyr) |
| 77 | Et | =C(Me)₂ | 0 | C = O | 4-NHCO(2-Fur) |
| 78 | Et | =C(Me)₂ | 0 | C = O | 4-NHCO(2-Thi) |
| 79 | Et | =C(Me)₂ | 0 | C = O | 4-NHCOCH₂NH₂ |
| 80 | Et | =C(Me)₂ | 1 | C = O | 4-NHCOCH₂NHCOOMe |
| 81 | Et | =C(Me)₂ | 0 | C = O | 4-NHCOCH₂NHCOOMe |
| 82 | Et | =C(Me)₂ | 0 | C = O | 3-NHCOCH₂NHCOOMe |
| 83 | Et | =C(Me)₂ | 0 | C = O | 2-NHCOCH₂NHCOOMe |
| 84 | Me | =C(Me)₂ | 0 | C = O | 4-NHCOCH₂NHCOOMe |
| 85 | iPr | =C(Me)₂ | 0 | C = O | 4-NHCOCH₂NHCOOMe |
| 86 | sBu | =C(Me)₂ | 0 | C = O | 4-NHCOCH₂NHCOOMe |
| 87 | Et | =C(Me)₂ | 0 | C = O | 4-NHCOCH₂NHCOOEt |
| 88 | Et | =C(Me)₂ | 0 | C = O | 4-NHCOCH₂NHCOOCH₂CCl₃ |
| 89 | Et | =C(Me)₂ | 0 | C = O | 4-NHCOCH₂NHCOOtBu |
| 90 | Et | =C(Me)₂ | 0 | C = O | 4-NHCOCH₂NHCOOBz |
| 91 | Et | =C(Me)₂ | 0 | C = O | 4-NHCOCH₂NHAc |
| 92 | Me | =C(Me)₂ | 0 | C = O | 4-NHCOCH₂NHAc |
| 93 | Et | =C(Me)₂ | 0 | C = O | 3-NHCOCH₂NHAc |
| 94 | Et | =C(Me)₂ | 0 | C = O | 4-NHCOCH₂NHCOPh |
| 95 | Et | =C(Me)₂ | 0 | C = O | 4-NHCOCH₂N(Me)COOMe |
| 96 | Et | =C(Me)₂ | 0 | C = O | 4-N(Me)COCH₂NHCOOMe |
| 97 | Et | =C(Me)₂ | 0 | C = O | 4-NHCOCH(Me)NHCOOMe |
| 98 | Et | =C(Me)₂ | 0 | C = O | 4-NHCOCH₂NHCOEt |
| 99 | Et | =C(Me)₂ | 0 | C = O | 4-NHCOCH(Me)NHCOOEt |
| 100 | Et | =C(Me)₂ | 0 | C = O | 4-NHCOCH(Et)NHCOOMe |
| 101 | Et | =C(Me)₂ | 0 | C = O | 4-NHCOCH(iPr)NHCOOMe |
| 102 | Et | =C(Me)₂ | 0 | C = O | 4-NHCOCH(iBu)NHCOOMe |
| 103 | Et | =C(Me)₂ | 0 | C = O | 4-NHCOCH(tBu)NHCOOMe |
| 104 | Et | =C(Me)₂ | 0 | C = O | 4-NHCOCH(CH₂CH₂SMe)NHCOOMe |
| 105 | Et | =C(Me)₂ | 0 | C = O | 4-NHCOCH(CH₂SMe)NHCOOMe |
| 106 | Et | =C(Me)₂ | 0 | C = O | 4-NHCOCH(CH₂SEt)NHCOOMe |
| 107 | Et | =C(Me)₂ | 0 | C = O | 4-NHCOC(Me)₂NHCOOMe |
| 108 | Me | =C(Me)₂ | 0 | C = O | 4-NHCOC(Me)₂NHCOOMe |
| 109 | Et | =C(Me)₂ | 0 | C = O | 4-NHCOCH₂CH₂NH₂ |
| 110 | Et | =C(Me)₂ | 0 | C = O | 4-NHCOCH₂CH₂NHCOOMe |

TABLE 1-continued

| Cpd. No. | R¹ | Z | n | X | R³ |
|---|---|---|---|---|---|
| 111 | Et | =C(Me)₂ | 1 | C = 0 | 4-NHCO(1-COOMe-2-Pyrd) |
| 112 | Et | =C(Me)₂ | 0 | C = 0 | 4-NHCO(1-COOMe-2-Pyrd) |
| 113 | Me | =C(Me)₂ | 0 | C = 0 | 4-NHCO(1-COOMe-2-Pyrd) |
| 114 | Et | =C(Me)₂ | 0 | C = 0 | 4-NHCO(1-COOEt-2-Pyrd) |
| 115 | Et | =C(Me)₂ | 0 | C = 0 | 4-NHCO(1-COOMe-4-Pip) |
| 116 | Et | =C(Me)₂ | 0 | C = 0 | 4-NHCO(3-COOEt-4-Thdn) |
| 117 | Et | =C(Me)₂ | 0 | C = 0 | 4-NHCO(5-γ-Lac) |
| 118 | Et | =C(Me)₂ | 0 | C = 0 | 4-NHCOC(=NOMe)(2-NHCOCH₂Cl-4-Thiz) |
| 119 | Et | =C(Me)₂ | 0 | C = 0 | 4-NHCOC(=NOMe)(2-NHCOOMe-4-Thiz) |
| 120 | Et | =C(Me)₂ | 0 | C = 0 | 4-NHCOC(=NOMe)(2-Thi) |
| 121 | Et | =C(Me)₂ | 0 | C = 0 | 4-NHCOOMe |
| 122 | Me | =C(Me)₂ | 0 | C = 0 | 4-NHCOOMe |
| 123 | Et | =C(Me)₂ | 0 | C = 0 | 4-N(Me)COOMe |
| 124 | Et | =C(Me)₂ | 0 | C = 0 | 4-NHCOOEt |
| 125 | Et | =C(Me)₂ | 0 | C = 0 | 4-NHCOOPr |
| 126 | Et | =C(Me)₂ | 0 | C = 0 | 4-NHCOOiPr |
| 127 | Et | =C(Me)₂ | 0 | C = 0 | 4-NHCOOBu |
| 128 | Et | =C(Me)₂ | 0 | C = 0 | 4-NHCOOiBu |
| 129 | Et | =C(Me)₂ | 0 | C = 0 | 4-NHCOOcPr |
| 130 | Et | =C(Me)₂ | 0 | C = 0 | 4-NHCOOBz |
| 131 | Et | =C(Me)₂ | 0 | C = 0 | 4-NHCOOPh |
| 132 | Et | =C(Me)₂ | 0 | C = 0 | 4-NHCONHMe |
| 133 | Me | =C(Me)₂ | 0 | C = 0 | 4-NHCONHMe |
| 134 | Et | =C(Me)₂ | 0 | C = 0 | 3-NHCONHMe |
| 135 | Et | =C(Me)₂ | 0 | C = 0 | 4-NHCONHEt |
| 136 | Et | =C(Me)₂ | 0 | C = 0 | 4-NHCONHPr |
| 137 | Et | =C(Me)₂ | 0 | C = 0 | 4-NHCONHiPr |
| 138 | Et | =C(Me)₂ | 0 | C = 0 | 4-NHCONHBu |
| 139 | Et | =C(Me)₂ | 0 | C = 0 | 4-NHCONHtBu |
| 140 | Et | =C(Me)₂ | 0 | C = 0 | 4-NHCONHcHx |
| 141 | Et | =C(Me)₂ | 0 | C = 0 | 4-NHCONHBz |
| 142 | Et | =C(Me)₂ | 0 | C = 0 | 4-NHCONMe₂ |
| 143 | Et | =C(Me)₂ | 0 | C = 0 | 4-NHCO(1-Pyrd) |
| 144 | Et | =C(Me)₂ | 0 | C = 0 | 4-NHCONHPh |
| 145 | Et | =C(Me)₂ | 0 | C = 0 | 4-NHCSNHMe |
| 146 | Et | =C(Me)₂ | 0 | C = 0 | 4-NHCSNHEt |
| 147 | Et | =C(Me)₂ | 1 | C = 0 | 4-NHSO₂Me |
| 148 | Et | =C(Me)₂ | 0 | C = 0 | 4-NHSO₂Me |
| 149 | Me | =C(Me)₂ | 0 | C = 0 | 4-NHSO₂Me |
| 150 | Et | =C(Me)₂ | 0 | C = 0 | 3-NHSO₂Me |
| 151 | Et | =C(Me)₂ | 0 | C = 0 | 4-N(Me)SO₂Me |
| 152 | Et | =C(Me)₂ | 0 | C = 0 | 4-N(Et)SO₂Me |
| 153 | Et | =C(Me)₂ | 0 | C = 0 | 4-N(Pr)SO₂Me |
| 154 | Et | =C(Me)₂ | 0 | C = 0 | 4-N(Bu)SO₂Me |
| 155 | Et | =C(Me)₂ | 0 | C = 0 | 4-NHSO₂Et |
| 156 | Et | =C(Me)₂ | 0 | C = 0 | 4-NHSO₂Pr |
| 157 | Et | =C(Me)₂ | 0 | C = 0 | 4-NHSO₂Bu |
| 158 | Et | =C(Me)₂ | 0 | C = 0 | 4-NHSO₂Ph |
| 159 | Et | =C(Me)₂ | 0 | C = 0 | 4-NHSO₂(4-MePh) |
| 160 | Et | =C(Me)₂ | 0 | C = 0 | 4-(2-oxo-1-Azt) |
| 161 | Et | =C(Me)₂ | 0 | C = 0 | 4-(2-oxo-1-Pip) |
| 162 | Et | =C(Me)₂ | 0 | C = 0 | 4-(2,6-dioxo-1-Pip) |
| 163 | Et | =C(Me)₂ | 0 | C = 0 | 4-(2-oxo-1-Pyrd) |
| 164 | Et | =C(Me)₂ | 0 | C = 0 | 4-(2,5-dioxo-1-Pyrd) |
| 165 | Et | =C(Me)₂ | 0 | C = 0 | 4-(2-oxo-1,3-oxazolin-3-yl) |
| 166 | Et | =C(CH₂)₄ | 1 | C = 0 | 4-NO₂ |
| 167 | Et | =C(CH₂)₄ | 0 | C = 0 | 4-NO₂ |
| 168 | Et | =C(CH₂)₄ | 0 | C = 0 | 3-NO₂ |
| 169 | Et | =C(CH₂)₄ | 0 | C = 0 | 2-NO₂ |
| 170 | Et | =C(CH₂)₄ | 1 | C = 0 | 4-NH₂ |
| 171 | Et | =C(CH₂)₄ | 0 | C = 0 | 4-NH₂ |
| 172 | Et | =C(CH₂)₄ | 0 | C = 0 | 3-NH₂ |
| 173 | Et | =C(CH₂)₄ | 0 | C = 0 | 2-NH₂ |
| 174 | Et | =C(CH₂)₄ | 0 | C = 0 | 4-NHMe |
| 175 | Et | =C(CH₂)₄ | 0 | C = 0 | 4-NHEt |
| 176 | Et | =C(CH₂)₄ | 0 | C = 0 | 4-NHPr |
| 177 | Et | =C(CH₂)₄ | 0 | C = 0 | 4-NHBu |
| 178 | Et | =C(CH₂)₄ | 0 | C = 0 | 4-NMe₂ |
| 179 | Et | =C(CH₂)₄ | 0 | C = 0 | 4-NEt₂ |
| 180 | Et | =C(CH₂)₄ | 1 | C = 0 | 4-MeO |
| 181 | Et | =C(CH₂)₄ | 0 | C = 0 | 4-MeO |
| 182 | Et | =C(CH₂)₄ | 0 | C = 0 | 3-MeO |
| 183 | Et | =C(CH₂)₄ | 0 | C = 0 | 2-MeO |
| 184 | Et | =C(CH₂)₄ | 0 | C = 0 | 4-OEt |
| 185 | Et | =C(CH₂)₄ | 0 | C = 0 | 4-OPr |

TABLE 1-continued

| Cpd. No. | R¹ | Z | n | X | R³ |
|---|---|---|---|---|---|
| 186 | Et | =C(CH$_2$)$_4$ | 0 | C = 0 | 2-OiPr |
| 187 | Et | =C(CH$_2$)$_4$ | 0 | C = 0 | 4-OBu |
| 188 | Et | =C(CH$_2$)$_4$ | 0 | C = 0 | 4-OiBu |
| 189 | Et | =C(CH$_2$)$_4$ | 0 | C = 0 | 4-OCH$_2$CH$_2$OCH$_3$ |
| 190 | Et | =C(CH$_2$)$_4$ | 1 | C = 0 | 4-NHAc |
| 191 | Et | =C(CH$_2$)$_4$ | 0 | C = 0 | 4-NHAc |
| 192 | Me | =C(CH$_2$)$_4$ | 0 | C = 0 | 4-NHAc |
| 193 | Et | =C(CH$_2$)$_4$ | 0 | C = 0 | 4-N(Me)Ac |
| 194 | Et | =C(CH$_2$)$_4$ | 0 | C = 0 | 4-N(Et)Ac |
| 195 | Et | =C(CH$_2$)$_4$ | 0 | C = 0 | 4-N(Pr)Ac |
| 196 | Et | =C(CH$_2$)$_4$ | 0 | C = 0 | 4-N(Bu)Ac |
| 197 | Et | =C(CH$_2$)$_4$ | 0 | C = 0 | 3-NHAc |
| 198 | Et | =C(CH$_2$)$_4$ | 0 | C = 0 | 4-NHCOEt |
| 199 | Et | =C(CH$_2$)$_4$ | 0 | C = 0 | 4-NHCOPr |
| 200 | Et | =C(CH$_2$)$_4$ | 0 | C = 0 | 4-NHCOiPr |
| 201 | Et | =C(CH$_2$)$_4$ | 0 | C = 0 | 4-NHCOBu |
| 202 | Et | =C(CH$_2$)$_4$ | 0 | C = 0 | 4-NHCOiBu |
| 203 | Et | =C(CH$_2$)$_4$ | 0 | C = 0 | 4-NHCOtBu |
| 204 | Et | =C(CH$_2$)$_4$ | 0 | C = 0 | 4-NHCOcPr |
| 205 | Et | =C(CH$_2$)$_4$ | 0 | C = 0 | 4-NHCOcBu |
| 206 | Et | =C(CH$_2$)$_4$ | 0 | C = 0 | 4-NHCOcPn |
| 207 | Et | =C(CH$_2$)$_4$ | 0 | C = 0 | 4-NHCOcHx |
| 208 | Et | =C(CH$_2$)$_4$ | 0 | C = 0 | 4-NHCOCH$_2$Br |
| 209 | Et | =C(CH$_2$)$_4$ | 0 | C = 0 | 4-NHCOCF$_3$ |
| 210 | Et | =C(CH$_2$)$_4$ | 0 | C = 0 | 4-NHCOCHF$_2$ |
| 211 | Et | =C(CH$_2$)$_4$ | 0 | C = 0 | 4-NHCOCH$_2$CN |
| 212 | Et | =C(CH$_2$)$_4$ | 0 | C = 0 | 4-NHCOCH$_2$OMe |
| 213 | Et | =C(CH$_2$)$_4$ | 0 | C = 0 | 4-NHCOCH$_2$OEt |
| 214 | Et | =C(CH$_2$)$_4$ | 0 | C = 0 | 4-NHCOCH$_2$OAc |
| 215 | Et | =C(CH$_2$)$_4$ | 0 | C = 0 | 4-NHCOCH$_2$OCOPr |
| 216 | Et | =C(CH$_2$)$_4$ | 0 | C = 0 | 4-NHCOCH$_2$SMe |
| 217 | Et | =C(CH$_2$)$_4$ | 0 | C = 0 | 4-NHCOCH$_2$SO$_2$Ph |
| 218 | Et | =C(CH$_2$)$_4$ | 0 | C = 0 | 4-NHCOCH$_2$SPh |
| 219 | Et | =C(CH$_2$)$_4$ | 0 | C = 0 | 4-NHCOCH$_2$S(2-Pym) |
| 220 | Et | =C(CH$_2$)$_4$ | 0 | C = 0 | 4-NHCOCH$_2$S(2-Pyr) |
| 221 | Et | =C(CH$_2$)$_4$ | 0 | C = 0 | 4-NHCOCH$_2$S(2-Thdn) |
| 222 | Et | =C(CH$_2$)$_4$ | 0 | C = 0 | 4-NHCOCH$_2$CH$_2$COMe |
| 223 | Et | =C(CH$_2$)$_4$ | 0 | C = 0 | 4-NHCOCH$_2$CH$_2$COOMe |
| 224 | Et | =C(CH$_2$)$_4$ | 0 | C = 0 | 4-NHCOCH=CHMe |
| 225 | Et | =C(CH$_2$)$_4$ | 0 | C = 0 | 4-NHCOC≡CH |
| 226 | Et | =C(CH$_2$)$_4$ | 0 | C = 0 | 4-NHCOCH$_2$Ph |
| 227 | Et | =C(CH$_2$)$_4$ | 0 | C = 0 | 4-NHCOCH$_2$(4-NO$_2$Ph) |
| 228 | Et | =C(CH$_2$)$_4$ | 0 | C = 0 | 4-NHCOPh |
| 229 | Et | =C(CH$_2$)$_4$ | 0 | C = 0 | 4-NHCO(2-FPh) |
| 230 | Et | =C(CH$_2$)$_4$ | 0 | C = 0 | 4-NHCO(3-FPh) |
| 231 | Et | =C(CH$_2$)$_4$ | 0 | C = 0 | 4-NHCO(4-FPh) |
| 232 | Et | =C(CH$_2$)$_4$ | 0 | C = 0 | 4-NHCO(4-ClPh) |
| 233 | Et | =C(CH$_2$)$_4$ | 0 | C = 0 | 4-NHCO(3-ClPh) |
| 234 | Et | =C(CH$_2$)$_4$ | 0 | C = 0 | 4-NHCO(4-MeOPh) |
| 235 | Et | =C(CH$_2$)$_4$ | 0 | C = 0 | 4-NHCO(3-MeOPh) |
| 236 | Et | =C(CH$_2$)$_4$ | 0 | C = 0 | 4-NHCO(3,4-di-MeOPh) |
| 237 | Et | =C(CH$_2$)$_4$ | 0 | C = 0 | 4-NHCO(4-tBuPh) |
| 238 | Et | =C(CH$_2$)$_4$ | 0 | C = 0 | 4-NHCO(4-NO$_2$Ph) |
| 239 | Et | =C(CH$_2$)$_4$ | 0 | C = 0 | 4-NHCO(3-NO$_2$Ph) |
| 240 | Et | =C(CH$_2$)$_4$ | 0 | C = 0 | 4-NHCO(3-Pyr) |
| 241 | Et | =C(CH$_2$)$_4$ | 0 | C = 0 | 4-NHCO(4-Pyr) |
| 242 | Et | =C(CH$_2$)$_4$ | 0 | C = 0 | 4-NHCO(2-Fur) |
| 243 | Et | =C(CH$_2$)$_4$ | 0 | C = 0 | 4-NHCO(2-Thi) |
| 244 | Et | =C(CH$_2$)$_4$ | 0 | C = 0 | 4-NHCOCH$_2$NH$_2$ |
| 245 | Et | =C(CH$_2$)$_4$ | 1 | C = 0 | 4-NHCOCH$_2$NHCOOMe |
| 246 | Et | =C(CH$_2$)$_4$ | 0 | C = 0 | 4-NHCOCH$_2$NHCOOMe |
| 247 | Et | =C(CH$_2$)$_4$ | 0 | C = 0 | 3-NHCOCH$_2$NHCOOMe |
| 248 | Et | =C(CH$_2$)$_4$ | 0 | C = 0 | 2-NHCOCH$_2$NHCOOMe |
| 249 | Me | =C(CH$_2$)$_4$ | 0 | C = 0 | 4-NHCOCH$_2$NHCOOMe |
| 250 | iPr | =C(CH$_2$)$_4$ | 0 | C = 0 | 4-NHCOCH$_2$NHCOOMe |
| 251 | sBu | =C(CH$_2$)$_4$ | 0 | C = 0 | 4-NHCOCH$_2$NHCOOMe |
| 252 | Et | =C(CH$_2$)$_4$ | 0 | C = 0 | 4-NHCOCH$_2$NHCOOEt |
| 253 | Et | =C(CH$_2$)$_4$ | 0 | C = 0 | 4-NHCOCH$_2$NHCOOCH$_2$CCl$_3$ |
| 254 | Et | =C(CH$_2$)$_4$ | 0 | C = 0 | 4-NHCOCH$_2$NHCOOtBu |
| 255 | Et | =C(CH$_2$)$_4$ | 0 | C = 0 | 4-NHCOCH$_2$NHCOOBz |
| 256 | Et | =C(CH$_2$)$_4$ | 0 | C = 0 | 4-NHCOCH$_2$NHAc |
| 257 | Me | =C(CH$_2$)$_4$ | 0 | C = 0 | 4-NHCOCH$_2$NHAc |
| 258 | Et | =C(CH$_2$)$_4$ | 0 | C = 0 | 3-NHCOCH$_2$NHAc |
| 259 | Et | =C(CH$_2$)$_4$ | 0 | C = 0 | 4-NHCOCH$_2$NHCOPh |
| 260 | Et | =C(CH$_2$)$_4$ | 0 | C = 0 | 4-NHCOCH$_2$N(Me)COOMe |
| 261 | Et | =C(CH$_2$)$_4$ | 0 | C = 0 | 4-N(Me)COCH$_2$NHCOOMe |
| 262 | Et | =C(CH$_2$)$_4$ | 0 | C = 0 | 4-NHCOCH(Me)NHCOOMe |

TABLE 1-continued

| Cpd. No. | R¹ | Z | n | X | R³ |
|---|---|---|---|---|---|
| 263 | Et | =C(CH$_2$)$_4$ | 0 | C = 0 | 4-NHCOCH$_2$NHCOEt |
| 264 | Et | =C(CH$_2$)$_4$ | 0 | C = 0 | 4-NHCOCH(Me)NHCOOEt |
| 265 | Et | =C(CH$_2$)$_4$ | 0 | C = 0 | 4-NHCOCH(Et)NHCOOMe |
| 266 | Et | =C(CH$_2$)$_4$ | 0 | C = 0 | 4-NHCOCH(iPr)NHCOOMe |
| 267 | Et | =C(CH$_2$)$_4$ | 0 | C = 0 | 4-NHCOCH(iBu)NHCOOMe |
| 268 | Et | =C(CH$_2$)$_4$ | 0 | C = 0 | 4-NHCOCH(tBu)NHCOOMe |
| 269 | Et | =C(CH$_2$)$_4$ | 0 | C = 0 | 4-NHCOCH(CH$_2$CH$_2$SMe)NHCOOMe |
| 270 | Et | =C(CH$_2$)$_4$ | 0 | C = 0 | 4-NHCOCH(CH$_2$SMe)NHCOOMe |
| 271 | Et | =C(CH$_2$)$_4$ | 0 | C = 0 | 4-NHCOCH(CH$_2$SEt)NHCOOMe |
| 272 | Et | =C(CH$_2$)$_4$ | 0 | C = 0 | 4-NHCOC(Me)$_2$NHCOOMe |
| 273 | Me | =C(CH$_2$)$_4$ | 0 | C = 0 | 4-NHCOC(Me)$_2$NHCOOMe |
| 274 | Et | =C(CH$_2$)$_4$ | 0 | C = 0 | 4-NHCOCH$_2$CH$_2$NH$_2$ |
| 275 | Et | =C(CH$_2$)$_4$ | 0 | C = 0 | 4-NHCOCH$_2$CH$_2$NHCOOMe |
| 276 | Et | =C(CH$_2$)$_4$ | 1 | C = 0 | 4-NHCO(1-COOMe-2-Pyrd) |
| 277 | Et | =C(CH$_2$)$_4$ | 0 | C = 0 | 4-NHCO(1-COOMe-2-Pyrd) |
| 278 | Me | =C(CH$_2$)$_4$ | 0 | C = 0 | 4-NHCO(1-COOMe-2-Pyrd) |
| 279 | Et | =C(CH$_2$)$_4$ | 0 | C = 0 | 4-NHCO(1-COOEt-2-Pyrd) |
| 280 | Et | =C(CH$_2$)$_4$ | 0 | C = 0 | 4-NHCO(1-COOMe-4-Pip) |
| 281 | Et | =C(CH$_2$)$_4$ | 0 | C = 0 | 4-NHCO(3-COOEt-4-Thdn) |
| 282 | Et | =C(CH$_2$)$_4$ | 0 | C = 0 | 4-NHCO(5-γ-Lac) |
| 283 | Et | =C(CH$_2$)$_4$ | 0 | C = 0 | 4-NHCOC(=NOMe)(2-NHCOCH$_2$Cl-4-Thiz) |
| 284 | Et | =C(CH$_2$)$_4$ | 0 | C = 0 | 4-NHCOC(=NOMe)(2-NHCOOMe-4-Thiz) |
| 285 | Et | =C(CH$_2$)$_4$ | 0 | C = 0 | 4-NHCOC(=NOMe)(2-Thi) |
| 286 | Et | =C(CH$_2$)$_4$ | 0 | C = 0 | 4-NHCOOMe |
| 287 | Me | =C(CH$_2$)$_4$ | 0 | C = 0 | 4-NHCOOMe |
| 288 | Et | =C(CH$_2$)$_4$ | 0 | C = 0 | 3-NHCOOMe |
| 289 | Et | =C(CH$_2$)$_4$ | 0 | C = 0 | 4-NHCOOEt |
| 290 | Et | =C(CH$_2$)$_4$ | 0 | C = 0 | 4-NHCOOPr |
| 291 | Et | =C(CH$_2$)$_4$ | 0 | C = 0 | 4-NHCOOiPr |
| 292 | Et | =C(CH$_2$)$_4$ | 0 | C = 0 | 4-NHCOOBu |
| 293 | Et | =C(CH$_2$)$_4$ | 0 | C = 0 | 4-NHCOOiBu |
| 294 | Et | =C(CH$_2$)$_4$ | 0 | C = 0 | 4-NHCOOcPr |
| 295 | Et | =C(CH$_2$)$_4$ | 0 | C = 0 | 4-NHCOOBz |
| 296 | Et | =C(CH$_2$)$_4$ | 0 | C = 0 | 4-NHCOOPh |
| 297 | Et | =C(CH$_2$)$_4$ | 0 | C = 0 | 4-NHCONHMe |
| 298 | Me | =C(CH$_2$)$_4$ | 0 | C = 0 | 4-NHCONHMe |
| 299 | Et | =C(CH$_2$)$_4$ | 0 | C = 0 | 3-NHCONHMe |
| 300 | Et | =C(CH$_2$)$_4$ | 0 | C = 0 | 4-NHCONHEt |
| 301 | Et | =C(CH$_2$)$_4$ | 0 | C = 0 | 4-NHCONHPr |
| 302 | Et | =C(CH$_2$)$_4$ | 0 | C = 0 | 4-NHCONHiPr |
| 303 | Et | =C(CH$_2$)$_4$ | 0 | C = 0 | 4-NHCONHBu |
| 304 | Et | =C(CH$_2$)$_4$ | 0 | C = 0 | 4-NHCONHiBu |
| 305 | Et | =C(CH$_2$)$_4$ | 0 | C = 0 | 4-NHCONHcHx |
| 306 | Et | =C(CH$_2$)$_4$ | 0 | C = 0 | 4-NHCONHBz |
| 307 | Et | =C(CH$_2$)$_4$ | 0 | C = 0 | 4-NHCONMe$_2$ |
| 308 | Et | =C(CH$_2$)$_4$ | 0 | C = 0 | 4-NHCO(1-Pyrd) |
| 309 | Et | =C(CH$_2$)$_4$ | 0 | C = 0 | 4-NHCONHPh |
| 310 | Et | =C(CH$_2$)$_4$ | 0 | C = 0 | 4-NHCSNHMe |
| 311 | Et | =C(CH$_2$)$_4$ | 0 | C = 0 | 4-NHCSNHEt |
| 312 | Et | =C(CH$_2$)$_4$ | 1 | C = 0 | 4-NHSO$_2$Me |
| 313 | Et | =C(CH$_2$)$_4$ | 0 | C = 0 | 4-NHSO$_2$Me |
| 314 | Me | =C(CH$_2$)$_4$ | 0 | C = 0 | 4-NHSO$_2$Me |
| 315 | Et | =C(CH$_2$)$_4$ | 0 | C = 0 | 3-NHSO$_2$Me |
| 316 | Et | =C(CH$_2$)$_4$ | 0 | C = 0 | 4-N(Me)SO$_2$Me |
| 317 | Et | =C(CH$_2$)$_4$ | 0 | C = 0 | 4-N(Et)SO$_2$Me |
| 318 | Et | =C(CH$_2$)$_4$ | 0 | C = 0 | 4-N(Pr)SO$_2$Me |
| 319 | Et | =C(CH$_2$)$_4$ | 0 | C = 0 | 4-N(Bu)SO$_2$Me |
| 320 | Et | =C(CH$_2$)$_4$ | 0 | C = 0 | 4-NHSO$_2$Et |
| 321 | Et | =C(CH$_2$)$_4$ | 0 | C = 0 | 4-NHSO$_2$Pr |
| 322 | Et | =C(CH$_2$)$_4$ | 0 | C = 0 | 4-NHSO$_2$Bu |
| 323 | Et | =C(CH$_2$)$_4$ | 0 | C = 0 | 4-NHSO$_2$Ph |
| 324 | Et | =C(CH$_2$)$_4$ | 0 | C = 0 | 4-NHSO$_2$(4-MePh) |
| 325 | Et | =C(CH$_2$)$_4$ | 0 | C = 0 | 4-(2-oxo-1-Azt) |
| 326 | Et | =C(CH$_2$)$_4$ | 0 | C = 0 | 4-(2-oxo-1-Pip) |
| 327 | Et | =C(CH$_2$)$_4$ | 0 | C = 0 | 4-(2,6-dioxo-1-Pip) |
| 328 | Et | =C(CH$_2$)$_4$ | 0 | C = 0 | 4-(2-oxo-1-Pyrd) |
| 329 | Et | =C(CH$_2$)$_4$ | 0 | C = 0 | 4-(2,5-dioxo-1-Pyrd) |
| 330 | Et | =C(CH$_2$)$_4$ | 0 | C = 0 | 4-(2-oxo-1,3-oxazolin-3-yl) |
| 331 | Et | =C(Me)$_2$ | 0 | C = 0 | 4-NO$_2$ |
| 332 | Et | =C(Et)$_2$ | 0 | C = 0 | 4-NH$_2$ |
| 333 | Et | =C(Et)$_2$ | 0 | C = 0 | 4-NHMe |
| 334 | Et | =C(Et)$_2$ | 0 | C = 0 | 4-NMe$_2$ |
| 335 | Et | =C(Et)$_2$ | 0 | C = 0 | 4-MeO |
| 336 | Et | =C(Et)$_2$ | 0 | C = 0 | 4-NHAc |
| 337 | Et | =C(Et)$_2$ | 0 | C = 0 | 4-N(Me)Ac |

TABLE 1-continued

| Cpd. No. | R¹ | Z | n | X | R³ |
|---|---|---|---|---|---|
| 338 | Et | =C(Et)₂ | 0 | C=0 | 3-NHAc |
| 339 | Et | =C(Et)₂ | 0 | C=0 | 4-NHCOEt |
| 340 | Et | =C(Et)₂ | 0 | C=0 | 4-NHCOPr |
| 341 | Et | =C(Et)₂ | 0 | C=0 | 4-NHCOiPr |
| 342 | Et | =C(Et)₂ | 0 | C=0 | 4-NHCOBu |
| 343 | Et | =C(Et)₂ | 0 | C=0 | 4-NHCOcPr |
| 344 | Et | =C(Et)₂ | 0 | C=0 | 4-NHCOcBu |
| 345 | Et | =C(Et)₂ | 0 | C=0 | 4-NHCOcHx |
| 346 | Et | =C(Et)₂ | 0 | C=0 | 4-NHCOCF₃ |
| 347 | Et | =C(Et)₂ | 0 | C=0 | 4-NHCOCH₂CN |
| 348 | Et | =C(Et)₂ | 0 | C=0 | 4-NHCOCH₂OMe |
| 349 | Et | =C(Et)₂ | 0 | C=0 | 4-NHCOCH₂OEt |
| 350 | Et | =C(Et)₂ | 0 | C=0 | 4-NHCOCH₂OAc |
| 351 | Et | =C(Et)₂ | 0 | C=0 | 4-NHCOCH₂SMe |
| 352 | Et | =C(Et)₂ | 0 | C=0 | 4-NHCOPh |
| 353 | Et | =C(Et)₂ | 0 | C=0 | 4-NHCO(2-FPh) |
| 354 | Et | =C(Et)₂ | 0 | C=0 | 4-NHCO(3-FPh) |
| 355 | Et | =C(Et)₂ | 0 | C=0 | 4-NHCO(4-FPh) |
| 356 | Et | =C(Et)₂ | 0 | C=0 | 4-NHCO(4-ClPh) |
| 357 | Et | =C(Et)₂ | 0 | C=0 | 4-NHCO(3,4-di-MeOPh) |
| 358 | Et | =C(Et)₂ | 0 | C=0 | 4-NHCO(3-Pyr) |
| 359 | Et | =C(Et)₂ | 0 | C=0 | 4-NHCO(4-Pyr) |
| 360 | Et | =C(Et)₂ | 0 | C=0 | 4-NHCO(2-Fur) |
| 361 | Et | =C(Et)₂ | 0 | C=0 | 4-NHCO(2-Thi) |
| 362 | Et | =C(Et)₂ | 0 | C=0 | 4-NHCOCH₂NHCOOMe |
| 363 | Et | =C(Et)₂ | 0 | C=0 | 4-NHCOCH₂NHAc |
| 364 | Et | =C(Et)₂ | 0 | C=0 | 4-N(Me)COCH₂NHCOOMe |
| 365 | Et | =C(Et)₂ | 0 | C=0 | 4-NHCOCH₂N(Me)Ac |
| 366 | Et | =C(Et)₂ | 0 | C=0 | 4-NHCOC(Me)₂NHCOOMe |
| 367 | Et | =C(Et)₂ | 0 | C=0 | 4-NHCOCH₂CH₂NHCOOMe |
| 368 | Et | =C(Et)₂ | 0 | C=0 | 4-NHCO(1-COOMe-2-Pyrd) |
| 369 | Et | =C(Et)₂ | 0 | C=0 | 4-NHCOOMe |
| 370 | Et | =C(Et)₂ | 0 | C=0 | 4-NHCOOEt |
| 371 | Et | =C(Et)₂ | 0 | C=0 | 4-NHCOOiBu |
| 372 | Et | =C(Et)₂ | 0 | C=0 | 4-NHCONHMe |
| 373 | Et | =C(Et)₂ | 0 | C=0 | 4-NHCONHEt |
| 374 | Et | =C(Et)₂ | 0 | C=0 | 4-NHCONHPr |
| 375 | Et | =C(Et)₂ | 0 | C=0 | 4-NHCONHBu |
| 376 | Et | =C(Et)₂ | 0 | C=0 | 4-NHCONHtBu |
| 377 | Et | =C(Et)₂ | 0 | C=0 | 4-NHCONHcHx |
| 378 | Et | =C(Et)₂ | 0 | C=0 | 4-NHCONHPh |
| 379 | Et | =C(Et)₂ | 0 | C=0 | 4-NHCSNHMe |
| 380 | Et | =C(Et)₂ | 0 | C=0 | 4-NHSO₂Me |
| 381 | Et | =C(Et)₂ | 0 | C=0 | 4-N(Me)SO₂Me |
| 382 | Et | =C(Et)₂ | 0 | C=0 | 4-NHSO₂(4-MePh) |
| 383 | Et | =C(Et)₂ | 0 | C=0 | 4-(2-oxo-1-Azt) |
| 384 | Et | =C(Et)₂ | 0 | C=0 | 4-(2-oxo-1-Pip) |
| 385 | Et | =C(Et)₂ | 0 | C=0 | 4-(2-oxo-1-Pyrd) |
| 386 | Et | =C(Et)₂ | 0 | C=0 | 4-(2-oxo-1,3-oxazolin-3-yl) |
| 387 | Et | =C(CH₂)₂ | 0 | C=0 | 4-NO₂ |
| 388 | Et | =C(CH₂)₂ | 0 | C=0 | 4-NH₂ |
| 389 | Et | =C(CH₂)₂ | 0 | C=0 | 4-NHMe |
| 390 | Et | =C(CH₂)₂ | 0 | C=0 | 4-NMe₂ |
| 391 | Et | =C(CH₂)₂ | 0 | C=0 | 4-MeO |
| 392 | Et | =C(CH₂)₂ | 0 | C=0 | 4-NHAc |
| 393 | Et | =C(CH₂)₂ | 0 | C=0 | 4-N(Me)Ac |
| 394 | Et | =C(CH₂)₂ | 0 | C=0 | 4-NHCOEt |
| 395 | Et | =C(CH₂)₂ | 0 | C=0 | 4-NHCOPr |
| 396 | Et | =C(CH₂)₂ | 0 | C=0 | 4-NHCOtBu |
| 397 | Et | =C(CH₂)₂ | 0 | C=0 | 4-NHCOcPr |
| 398 | Et | =C(CH₂)₂ | 0 | C=0 | 4-NHCOcBu |
| 399 | Et | =C(CH₂)₂ | 0 | C=0 | 4-NHCOcHx |
| 400 | Et | =C(CH₂)₂ | 0 | C=0 | 4-NHCOCF₃ |
| 401 | Et | =C(CH₂)₂ | 0 | C=0 | 4-NHCOCH₂CN |
| 402 | Et | =C(CH₂)₂ | 0 | C=0 | 4-NHCOCH₂Br |
| 403 | Et | =C(CH₂)₂ | 0 | C=0 | 4-NHCOCH₂OEt |
| 404 | Et | =C(CH₂)₂ | 0 | C=0 | 4-NHCOCH₂OAc |
| 405 | Et | =C(CH₂)₂ | 0 | C=0 | 4-NHCOCH₂SMe |
| 406 | Et | =C(CH₂)₂ | 0 | C=0 | 4-NHCOCH₂S(2-Pym) |
| 407 | Et | =C(CH₂)₂ | 0 | C=0 | 4-NHCOCH₂S(2-Pyr) |
| 408 | Et | =C(CH₂)₂ | 0 | C=0 | 4-NHCOCH₂S(2-Thdn) |
| 409 | Et | =C(CH₂)₂ | 0 | C=0 | 4-NHCOCH=CHMe |
| 410 | Et | =C(CH₂)₂ | 0 | C=0 | 4-NHCOPh |
| 411 | Et | =C(CH₂)₂ | 0 | C=0 | 4-NHCO(2-FPh) |
| 412 | Et | =C(CH₂)₂ | 0 | C=0 | 4-NHCO(3-FPh) |
| 413 | Et | =C(CH₂)₂ | 0 | C=0 | 4-NHCO(4-FPh) |
| 414 | Et | =C(CH₂)₂ | 0 | C=0 | 4-NHCO(4-MeOPh) |

TABLE 1-continued

| Cpd. No. | R¹ | Z | n | X | R³ |
|---|---|---|---|---|---|
| 415 | Et | =C(CH$_2$)$_2$ | 0 | C = 0 | 4-NHCO(3,4-di-MeOPh) |
| 416 | Et | =C(CH$_2$)$_2$ | 0 | C = 0 | 4-NHCO(4-NO$_2$Ph) |
| 417 | Et | =C(CH$_2$)$_2$ | 0 | C = 0 | 4-NHCO(4-tBuPh) |
| 418 | Et | =C(CH$_2$)$_2$ | 0 | C = 0 | 4-NHCO(3-Pyr) |
| 419 | Et | =C(CH$_2$)$_2$ | 0 | C = 0 | 4-NHCO(4-Pyr) |
| 420 | Et | =C(CH$_2$)$_2$ | 0 | C = 0 | 4-NHCO(2-Fur) |
| 421 | Et | =C(CH$_2$)$_2$ | 0 | C = 0 | 4-NHCO(2-Thi) |
| 422 | Et | =C(CH$_2$)$_2$ | 0 | C = 0 | 4-NHCOCH$_2$NHCOOMe |
| 423 | Et | =C(CH$_2$)$_2$ | 0 | C = 0 | 4-NHCOCH$_2$NHAc |
| 424 | Et | =C(CH$_2$)$_2$ | 0 | C = 0 | 4-N(Me)COCH$_2$NHCOOMe |
| 425 | Et | =C(CH$_2$)$_2$ | 0 | C = 0 | 4-NHCOCH$_2$N(Me)Ac |
| 426 | Et | =C(CH$_2$)$_2$ | 0 | C = 0 | 4-NHCOC(Me)$_2$NHCOOMe |
| 427 | Et | =C(CH$_2$)$_2$ | 0 | C = 0 | 4-NHCOCH$_2$CH$_2$NHCOOMe |
| 428 | Et | =C(CH$_2$)$_2$ | 0 | C = 0 | 4-NHCO(1-COOMe-2-Pyrd) |
| 429 | Et | =C(CH$_2$)$_2$ | 0 | C = 0 | 4-NHCOOMe |
| 430 | Et | =C(CH$_2$)$_2$ | 0 | C = 0 | 4-NHCOOEt |
| 431 | Et | =C(CH$_2$)$_2$ | 0 | C = 0 | 4-NHCOOiBu |
| 432 | Et | =C(CH$_2$)$_2$ | 0 | C = 0 | 4-NHCONHMe |
| 433 | Et | =C(CH$_2$)$_2$ | 0 | C = 0 | 4-NHCONHEt |
| 434 | Et | =C(CH$_2$)$_2$ | 0 | C = 0 | 4-NHCONHPr |
| 435 | Et | =C(CH$_2$)$_2$ | 0 | C = 0 | 4-NHCONHBu |
| 436 | Et | =C(CH$_2$)$_2$ | 0 | C = 0 | 4-NHCONHcHx |
| 437 | Et | =C(CH$_2$)$_2$ | 0 | C = 0 | 4-NHCO(1-Pyrd) |
| 438 | Et | =C(CH$_2$)$_2$ | 0 | C = 0 | 4-NHCONHPh |
| 439 | Et | =C(CH$_2$)$_2$ | 0 | C = 0 | 4-NHCSNHMe |
| 440 | Et | =C(CH$_2$)$_2$ | 1 | C = 0 | 4-NHSO$_2$Me |
| 441 | Et | =C(CH$_2$)$_2$ | 0 | C = 0 | 4-NHSO$_2$Me |
| 442 | Et | =C(CH$_2$)$_2$ | 0 | C = 0 | 4-N(Me)SO$_2$Me |
| 443 | Et | =C(CH$_2$)$_2$ | 0 | C = 0 | 4-N(Bu)SO$_2$Me |
| 444 | Et | =C(CH$_2$)$_2$ | 0 | C = 0 | 4-NHSO$_2$(4-MePh) |
| 445 | Et | =C(CH$_2$)$_2$ | 0 | C = 0 | 4-(2-oxo-1-Azt) |
| 446 | Et | =C(CH$_2$)$_2$ | 0 | C = 0 | 4-(2-oxo-1-Pip) |
| 447 | Et | =C(CH$_2$)$_2$ | 0 | C = 0 | 4-(2,6-dioxo-1-Pip) |
| 448 | Et | =C(CH$_2$)$_2$ | 0 | C = 0 | 4-(2-oxo-1-Pyrd) |
| 449 | Et | =C(CH$_2$)$_2$ | 0 | C = 0 | 4-(2,5-dioxo-1-Pyrd) |
| 450 | Et | =C(CH$_2$)$_2$ | 0 | C = 0 | 4-(2-oxo-1,3-oxazolin-3-yl) |
| 451 | Et | =C(CH$_2$)$_3$ | 0 | C = 0 | 4-NO$_2$ |
| 452 | Et | =C(CH$_2$)$_3$ | 0 | C = 0 | 4-NH$_2$ |
| 453 | Et | =C(CH$_2$)$_3$ | 0 | C = 0 | 4-NHMe |
| 454 | Et | =C(CH$_2$)$_3$ | 0 | C = 0 | 4-NMe$_2$ |
| 455 | Et | =C(CH$_2$)$_3$ | 0 | C = 0 | 4-MeO |
| 456 | Et | =C(CH$_2$)$_3$ | 0 | C = 0 | 4-OEt |
| 457 | Et | =C(CH$_2$)$_3$ | 0 | C = 0 | 4-NHAc |
| 458 | Et | =C(CH$_2$)$_3$ | 0 | C = 0 | 4-N(Me)Ac |
| 459 | Et | =C(CH$_2$)$_3$ | 0 | C = 0 | 4-NHCOEt |
| 460 | Et | =C(CH$_2$)$_3$ | 0 | C = 0 | 4-NHCOPr |
| 461 | Et | =C(CH$_2$)$_3$ | 0 | C = 0 | 4-NHCOBu |
| 462 | Et | =C(CH$_2$)$_3$ | 0 | C = 0 | 4-NHCOtBu |
| 463 | Et | =C(CH$_2$)$_3$ | 0 | C = 0 | 4-NHCOcBu |
| 464 | Et | =C(CH$_2$)$_3$ | 0 | C = 0 | 4-NHCOcHx |
| 465 | Et | =C(CH$_2$)$_3$ | 0 | C = 0 | 4-NHCOCF$_3$ |
| 466 | Et | =C(CH$_2$)$_3$ | 0 | C = 0 | 4-NHCOCH$_2$CN |
| 467 | Et | =C(CH$_2$)$_3$ | 0 | C = 0 | 4-NHCOCH$_2$OMe |
| 468 | Et | =C(CH$_2$)$_3$ | 0 | C = 0 | 4-NHCOCH$_2$OEt |
| 469 | Et | =C(CH$_2$)$_3$ | 0 | C = 0 | 4-NHCOCH$_2$OAc |
| 470 | Et | =C(CH$_2$)$_3$ | 0 | C = 0 | 4-NHCOCH$_2$SMe |
| 471 | Et | =C(CH$_2$)$_3$ | 0 | C = 0 | 4-NHCOCH=CHMe |
| 472 | Et | =C(CH$_2$)$_3$ | 0 | C = 0 | 4-NHCOPh |
| 473 | Et | =C(CH$_2$)$_3$ | 0 | C = 0 | 4-NHCO(2-FPh) |
| 474 | Et | =C(CH$_2$)$_3$ | 0 | C = 0 | 4-NHCO(3-FPh) |
| 475 | Et | =C(CH$_2$)$_3$ | 0 | C = 0 | 4-NHCO(4-FPh) |
| 476 | Et | =C(CH$_2$)$_3$ | 0 | C = 0 | 4-NHCO(4-MeOPh) |
| 477 | Et | =C(CH$_2$)$_3$ | 0 | C = 0 | 4-NHCO(4-ClPh) |
| 478 | Et | =C(CH$_2$)$_3$ | 0 | C = 0 | 4-NHCO(4-NO$_2$Ph) |
| 479 | Et | =C(CH$_2$)$_3$ | 0 | C = 0 | 4-NHCO(4-tBuPh) |
| 480 | Et | =C(CH$_2$)$_3$ | 0 | C = 0 | 4-NHCO(3-Pyr) |
| 481 | Et | =C(CH$_2$)$_3$ | 0 | C = 0 | 4-NHCO(4-Pyr) |
| 482 | Et | =C(CH$_2$)$_3$ | 0 | C = 0 | 4-NHCO(2-Fur) |
| 483 | Et | =C(CH$_2$)$_3$ | 0 | C = 0 | 4-NHCO(2-Thi) |
| 484 | Et | =C(CH$_2$)$_3$ | 0 | C = 0 | 4-NHCOCH$_2$NHCOOMe |
| 485 | Et | =C(CH$_2$)$_3$ | 0 | C = 0 | 4-NHCOCH$_2$NHAc |
| 486 | Et | =C(CH$_2$)$_3$ | 0 | C = 0 | 4-N(Me)COCH$_2$NHCOOMe |
| 487 | Et | =C(CH$_2$)$_3$ | 0 | C = 0 | 4-NHCOCH$_2$N(Me)Ac |
| 488 | Et | =C(CH$_2$)$_3$ | 0 | C = 0 | 4-NHCOC(Me)$_2$NHCOOMe |
| 489 | Et | =C(CH$_2$)$_3$ | 0 | C = 0 | 4-NHCOCH$_2$CH$_2$NHCOOMe |
| 490 | Et | =C(CH$_2$)$_3$ | 0 | C = 0 | 4-NHCO(1-COOMe-2-Pyrd) |
| 491 | Et | =C(CH$_2$)$_3$ | 0 | C = 0 | 4-NHCOOMe |

TABLE 1-continued

| Cpd. No. | R¹ | Z | n | X | R³ |
|---|---|---|---|---|---|
| 492 | Et | =C(CH$_2$)$_3$ | 0 | C=O | 4-NHCOOEt |
| 493 | Et | =C(CH$_2$)$_3$ | 0 | C=O | 4-NHCOOiBu |
| 494 | Et | =C(CH$_2$)$_3$ | 0 | C=O | 4-NHCONHMe |
| 495 | Et | =C(CH$_2$)$_3$ | 0 | C=O | 4-NHCONHEt |
| 496 | Et | =C(CH$_2$)$_3$ | 0 | C=O | 4-NHCONHPr |
| 497 | Et | =C(CH$_2$)$_3$ | 0 | C=O | 4-NHCONHBu |
| 498 | Et | =C(CH$_2$)$_3$ | 0 | C=O | 4-NHCONHcHx |
| 499 | Et | =C(CH$_2$)$_3$ | 0 | C=O | 4-NHCO(1-Pyrd) |
| 500 | Et | =C(CH$_2$)$_3$ | 0 | C=O | 4-NHCONHPh |
| 501 | Et | =C(CH$_2$)$_3$ | 0 | C=O | 4-NHCSNHMe |
| 502 | Et | =C(CH$_2$)$_3$ | 1 | C=O | 4-NHSO$_2$Me |
| 503 | Et | =C(CH$_2$)$_3$ | 0 | C=O | 4-NHSO$_2$Me |
| 504 | Et | =C(CH$_2$)$_3$ | 0 | C=O | 4-N(Me)SO$_2$Me |
| 505 | Et | =C(CH$_2$)$_3$ | 0 | C=O | 4-N(Bu)SO$_2$Me |
| 506 | Et | =C(CH$_2$)$_3$ | 0 | C=O | 4-NHSO$_2$(4-MePh) |
| 507 | Et | =C(CH$_2$)$_3$ | 0 | C=O | 4-(2-oxo-1-Azt) |
| 508 | Et | =C(CH$_2$)$_3$ | 0 | C=O | 4-(2-oxo-1-Pip) |
| 509 | Et | =C(CH$_2$)$_3$ | 0 | C=O | 4-(2,6-dioxo-1-Pip) |
| 510 | Et | =C(CH$_2$)$_3$ | 0 | C=O | 4-(2-oxo-1-Pyrd) |
| 511 | Et | =C(CH$_2$)$_3$ | 0 | C=O | 4-(2,5-dioxo-1-Pyrd) |
| 512 | Et | =C(CH$_2$)$_3$ | 0 | C=O | 4-(2-oxo-1,3-oxazolin-3-yl) |
| 513 | Et | =C(Me)$_2$ | 0 | CH$_2$ | 4-NO$_2$ |
| 514 | Et | =C(Me)$_2$ | 0 | CH$_2$ | 4-NH$_2$ |
| 515 | Et | =C(Me)$_2$ | 0 | CH$_2$ | 4-NHMe |
| 516 | Et | =C(Me)$_2$ | 0 | CH$_2$ | 4-NMe$_2$ |
| 517 | Et | =C(Me)$_2$ | 0 | CH$_2$ | 4-MeO |
| 518 | Et | =C(Me)$_2$ | 0 | CH$_2$ | 4-OEt |
| 519 | Et | =C(Me)$_2$ | 0 | CH$_2$ | 4-NHAc |
| 520 | Et | =C(Me)$_2$ | 0 | CH$_2$ | 4-N(Me)Ac |
| 521 | Et | =C(Me)$_2$ | 0 | CH$_2$ | 4-NHCOEt |
| 522 | Et | =C(Me)$_2$ | 0 | CH$_2$ | 4-NHCOPr |
| 523 | Et | =C(Me)$_2$ | 0 | CH$_2$ | 4-NHCOcPr |
| 524 | Et | =C(Me)$_2$ | 0 | CH$_2$ | 4-NHCOcBu |
| 525 | Et | =C(Me)$_2$ | 0 | CH$_2$ | 4-NHCOcPn |
| 526 | Et | =C(Me)$_2$ | 0 | CH$_2$ | 4-NHCOCF$_3$ |
| 527 | Et | =C(Me)$_2$ | 0 | CH$_2$ | 4-NHCOCH$_2$CN |
| 528 | Et | =C(Me)$_2$ | 0 | CH$_2$ | 4-NHCOCH$_2$OMe |
| 529 | Et | =C(Me)$_2$ | 0 | CH$_2$ | 4-NHCOCH$_2$OEt |
| 530 | Et | =C(Me)$_2$ | 0 | CH$_2$ | 4-NHCOCH$_2$OAc |
| 531 | Et | =C(Me)$_2$ | 0 | CH$_2$ | 4-NHCOCH$_2$OCOPr |
| 532 | Et | =C(Me)$_2$ | 0 | CH$_2$ | 4-NHCOCH$_2$SMe |
| 533 | Et | =C(Me)$_2$ | 0 | CH$_2$ | 4-NHCOCH=CHMe |
| 534 | Et | =C(Me)$_2$ | 0 | CH$_2$ | 4-NHCOPh |
| 535 | Et | =C(Me)$_2$ | 0 | CH$_2$ | 4-NHCO(2-FPh) |
| 536 | Et | =C(Me)$_2$ | 0 | CH$_2$ | 4-NHCO(3-FPh) |
| 537 | Et | =C(Me)$_2$ | 0 | CH$_2$ | 4-NHCO(4-FPh) |
| 538 | Et | =C(Me)$_2$ | 0 | CH$_2$ | 4-NHCO(4-MeOPh) |
| 539 | Et | =C(Me)$_2$ | 0 | CH$_2$ | 4-NHCO(3-MeOPh) |
| 540 | Et | =C(Me)$_2$ | 0 | CH$_2$ | 4-NHCO(3,4-di-MeOPh) |
| 541 | Et | =C(Me)$_2$ | 0 | CH$_2$ | 4-NHCO(4-NO$_2$Ph) |
| 542 | Et | =C(Me)$_2$ | 0 | CH$_2$ | 4-NHCO(3-NO$_2$Ph) |
| 543 | Et | =C(Me)$_2$ | 0 | CH$_2$ | 4-NHCO(3-Pyr) |
| 544 | Et | =C(Me)$_2$ | 0 | CH$_2$ | 4-NHCO(4-Pyr) |
| 545 | Et | =C(Me)$_2$ | 0 | CH$_2$ | 4-NHCO(2-Fur) |
| 546 | Et | =C(Me)$_2$ | 0 | CH$_2$ | 4-NHCO(2-Thi) |
| 547 | Et | =C(Me)$_2$ | 0 | CH$_2$ | 4-NHCOCH$_2$NHCOOMe |
| 548 | Et | =C(Me)$_2$ | 0 | CH$_2$ | 4-NHCOCH$_2$NHAc |
| 549 | Et | =C(Me)$_2$ | 0 | CH$_2$ | 4-N(Me)COCH$_2$NHCOOMe |
| 550 | Et | =C(Me)$_2$ | 0 | CH$_2$ | 4-NHCOCH$_2$N(Me)COOMe |
| 551 | Et | =C(Me)$_2$ | 0 | CH$_2$ | 4-NHCOC(Me)$_2$NHCOOMe |
| 552 | Et | =C(Me)$_2$ | 0 | CH$_2$ | 4-NHCOCH$_2$CH$_2$NHCOOMe |
| 553 | Et | =C(Me)$_2$ | 0 | CH$_2$ | 4-NHCO(1-COOMe-2-Pyrd) |
| 554 | Et | =C(Me)$_2$ | 0 | CH$_2$ | 4-NHCOOMe |
| 555 | Et | =C(Me)$_2$ | 0 | CH$_2$ | 4-NHCOOEt |
| 556 | Et | =C(Me)$_2$ | 0 | CH$_2$ | 4-NHCOOiBu |
| 557 | Et | =C(Me)$_2$ | 0 | CH$_2$ | 4-NHCOOPh |
| 557 | Et | =C(Me)$_2$ | 0 | CH$_2$ | 4-NHCONHMe |
| 559 | Et | =C(Me)$_2$ | 0 | CH$_2$ | 3-NHCONHMe |
| 560 | Et | =C(Me)$_2$ | 0 | CH$_2$ | 4-NHCONHcHx |
| 561 | Et | =C(Me)$_2$ | 0 | CH$_2$ | 4-NHCO(1-Pyrd) |
| 562 | Et | =C(Me)$_2$ | 0 | CH$_2$ | 4-NHCONHPh |
| 563 | Et | =C(Me)$_2$ | 0 | CH$_2$ | 4-NHCSNHMe |
| 564 | Et | =C(Me)$_2$ | 1 | CH$_2$ | 4-NHSO$_2$Me |
| 565 | Et | =C(Me)$_2$ | 0 | CH$_2$ | 4-NHSO$_2$Me |
| 566 | Et | =C(Me)$_2$ | 0 | CH$_2$ | 4-N(Me)SO$_2$Me |
| 567 | Et | =C(Me)$_2$ | 0 | CH$_2$ | 4-N(Bu)SO$_2$Me |
| 568 | Et | =C(Me)$_2$ | 0 | CH$_2$ | 4-NHSO$_2$(4-MePh) |

TABLE 1-continued

| Cpd. No. | R¹ | Z | n | X | R³ |
|---|---|---|---|---|---|
| 569 | Et | =C(Me)₂ | 0 | CH₂ | 4-(2-oxo-1-Azt) |
| 570 | Et | =C(Me)₂ | 0 | CH₂ | 4-(2-oxo-1-Pip) |
| 571 | Et | =C(Me)₂ | 0 | CH₂ | 4-(2,6-dioxo-1-Pip) |
| 572 | Et | =C(Me)₂ | 0 | CH₂ | 4-(2-oxo-1-Pyrd) |
| 573 | Et | =C(Me)₂ | 0 | CH₂ | 4-(2,5-dioxo-1-Pyrd) |
| 574 | Et | =C(Me)₂ | 0 | CH₂ | 4-(2-oxo-1,3-oxazolin-3-yl) |
| 575 | Et | =C(CH₂)₂ | 0 | CH₂ | 4-NO₂ |
| 576 | Et | =C(CH₂)₂ | 0 | CH₂ | 4-NH₂ |
| 577 | Et | =C(CH₂)₂ | 0 | CH₂ | 4-NHMe |
| 578 | Et | =C(CH₂)₂ | 0 | CH₂ | 4-MeO |
| 579 | Et | =C(CH₂)₂ | 0 | CH₂ | 4-NHAc |
| 580 | Et | =C(CH₂)₂ | 0 | CH₂ | 4-N(Me)Ac |
| 581 | Et | =C(CH₂)₂ | 0 | CH₂ | 4-NHCOEt |
| 582 | Et | =C(CH₂)₂ | 0 | CH₂ | 4-NHCOCF₃ |
| 583 | Et | =C(CH₂)₂ | 0 | CH₂ | 4-NHCOCH₂CN |
| 584 | Et | =C(CH₂)₂ | 0 | CH₂ | 4-NHCOCH₂OMe |
| 585 | Et | =C(CH₂)₂ | 0 | CH₂ | 4-NHCOCH₂OAc |
| 586 | Et | =C(CH₂)₂ | 0 | CH₂ | 4-NHCO(4-FPh) |
| 587 | Et | =C(CH₂)₂ | 0 | CH₂ | 4-NHCOCH₂NHCOOMe |
| 588 | Et | =C(CH₂)₂ | 0 | CH₂ | 4-NHCO(1-COOMe-2-Pyrd) |
| 589 | Et | =C(CH₂)₂ | 0 | CH₂ | 4-NHCOOMe |
| 590 | Et | =C(CH₂)₂ | 0 | CH₂ | 4-NHCONHMe |
| 591 | Et | =C(CH₂)₂ | 0 | CH₂ | 4-NHSO₂Me |
| 592 | Et | =C(CH₂)₃ | 0 | CH₂ | 4-NO₂ |
| 593 | Et | =C(CH₂)₃ | 0 | CH₂ | 4-NH₂ |
| 594 | Et | =C(CH₂)₃ | 0 | CH₂ | 4-NHMe |
| 595 | Et | =C(CH₂)₃ | 0 | CH₂ | 4-MeO |
| 596 | Et | =C(CH₂)₃ | 0 | CH₂ | 4-NHAc |
| 597 | Et | =C(CH₂)₃ | 0 | CH₂ | 4-N(Me)Ac |
| 598 | Et | =C(CH₂)₃ | 0 | CH₂ | 4-NHCOEt |
| 599 | Et | =C(CH₂)₃ | 0 | CH₂ | 4-NHCOCF₃ |
| 600 | Et | =C(CH₂)₃ | 0 | CH₂ | 4-NHCOCH₂CN |
| 601 | Et | =C(CH₂)₃ | 0 | CH₂ | 4-NHCOCH₂OMe |
| 602 | Et | =C(CH₂)₃ | 0 | CH₂ | 4-NHCOCH₂OAc |
| 603 | Et | =C(CH₂)₃ | 0 | CH₂ | 4-NHCO(4-FPh) |
| 604 | Et | =C(CH₂)₃ | 0 | CH₂ | 4-NHCOCH₂NHCOOMe |
| 605 | Et | =C(CH₂)₃ | 0 | CH₂ | 4-NHCO(1-COOMe-2-Pyrd) |
| 606 | Et | =C(CH₂)₃ | 0 | CH₂ | 4-NHCOOMe |
| 607 | Et | =C(CH₂)₃ | 0 | CH₂ | 4-NHCONHMe |
| 608 | Et | =C(CH₂)₃ | 0 | CH₂ | 4-NHSO₂Me |
| 609 | Et | =C(CH₂)₄ | 0 | CH₂ | 4-NO₂ |
| 610 | Et | =C(CH₂)₄ | 0 | CH₂ | 4-NH₂ |
| 611 | Et | =C(CH₂)₄ | 0 | CH₂ | 4-NHMe |
| 612 | Et | =C(CH₂)₄ | 0 | CH₂ | 4-MeO |
| 613 | Et | =C(CH₂)₄ | 0 | CH₂ | 4-NHAc |
| 614 | Et | =C(CH₂)₄ | 0 | CH₂ | 4-N(Me)Ac |
| 615 | Et | =C(CH₂)₄ | 0 | CH₂ | 4-NHCOEt |
| 616 | Et | =C(CH₂)₄ | 0 | CH₂ | 4-NHCOCF₃ |
| 617 | Et | =C(CH₂)₄ | 0 | CH₂ | 4-NHCOCH₂CN |
| 618 | Et | =C(CH₂)₄ | 0 | CH₂ | 4-NHCOCH₂OMe |
| 619 | Et | =C(CH₂)₄ | 0 | CH₂ | 4-NHCOCH₂OAc |
| 620 | Et | =C(CH₂)₄ | 0 | CH₂ | 4-NHCO(4-FPh) |
| 621 | Et | =C(CH₂)₄ | 0 | CH₂ | 4-NHCOCH₂NHCOOMe |
| 622 | Et | =C(CH₂)₄ | 0 | CH₂ | 4-NHCO(1-COOMe-2-Pyrd) |
| 623 | Et | =C(CH₂)₄ | 0 | CH₂ | 4-NHCOOMe |
| 624 | Et | =C(CH₂)₄ | 0 | CH₂ | 4-NHCONHMe |
| 625 | Et | =C(CH₂)₄ | 0 | CH₂ | 4-NHSO₂Me |
| 626 | Et | =C(CH₂)₄ | 0 | C=O | 4-NHCOCH₂(3-OH-4-Isox) |
| 627 | Et | =C(Me)₂ | 0 | C=O | 4-NHCOCH₂(3-OH-4-Isox) |

Of the compounds listed above, preferred compounds are as follows, that is to say Compounds No.: 9, 16, 26, 28, 33, 34, 35, 36, 37, 38, 39, 40, 41, 42, 43, 44, 46, 47, 48, 49, 51, 63, 64, 65, 66, 69, 74, 75, 76, 77, 78, 81, 89, 91, 95, 96, 107, 110, 112, 121, 132, 138, 139, 140, 144, 145, 148, 151, 160, 161, 164, 165, 171, 174, 181, 191, 193, 198, 199, 200, 201, 202, 205, 209, 211, 212, 213, 214, 218, 228, 229, 230, 231, 234, 240, 241, 242, 243, 246, 256, 272, 277, 286, 289, 297, 309, 310, 313, 316, 320, 325, 326, 329, 330, 332, 333, 335, 336, 337, 339, 346, 347, 348, 349, 350, 351, 352, 353, 354, 355, 362, 363, 366, 367, 369, 372, 380, 381, 392, 399, 429, 431, 452, 453, 455, 457, 458, 461, 465, 466, 467, 468, 469, 470, 472, 473, 474, 475, 476, 484, 485, 488, 489, 490, 491, 494, 500, 501, 503, 504, 547, 548, 551, 552, and 553.

More preferred compounds are as follows, that is to say Compounds No.: 9, 26, 42, 46, 63, 64, 65, 91, 96, 121, 144, 165, 171, 191, 209, 213, 214, 313, 320, 336, 457, 547, 548, and 553.

The most preferred compounds are Compounds No.:

46. 13-[2-(4-Cyanoacetylaminophenyl)-2-methylpropionyloxy]-5-hydroxyimino-milbemycin A₄ [(I): R¹=Et, X=CO, Z=>C(Me)₂, R³=4-NHCOCH₂CN, n=0)];

91. 13-{2-[4-(N-Acetylglycyl)aminophenyl]-2-methylpropionyloxy}-5-hydroxyimino-milbemycin A₄ [(I): R¹=Et, X=CO, Z=>C(Me)₂, R³=4-NHCOCH₂NHAc, n=0)];

96. 13-{2-[4-(N-Methoxycarbonylglycyl)methylaminophenyl]-2-methylpropionyloxy}-5-hydroxyimino-milbemycin A$_4$ [(I): R$^1$=Et, X=CO, Z=>C(Me)$_2$, R$^3$=4-N(Me)COCH$_2$NHCOOMe, n=0)];

121. 13-[2-(4-Methoxycarbonylaminophenyl)-2-methylpropionyloxy]-5-hydroxyimino-milbemycin A$_4$ [(I): R$^1$=Et, X=CO, Z=>C(Me)$_2$, R$^3$=4-NHCOOMe, n=0)];

144. 13-{2-[4-(N-Phenhylcarbamoylamino)phenyl]-2-methylpropionyloxy}-5-hydroxyimino-milbemycin A$_4$ [(I): R$^1$=Et, X=CO, Z=>C(Me)$_2$, R$^3$=4-NHCONHPh, n=0)];

165. 13-{2-[4-(2-Oxooxazolin-3-yl)phenyl]-2-methylpropionyloxy}-5-hydroxyimino-milbemycin A$_4$ [(I): R$^1$=Et, X=CO, Z=>C(Me)$_2$, R$^3$=4-(2-oxo-1,3-oxazolin-3-yl, n=0)];

171. 13-[1-(4-Aminophenyl)cyclopentanecarbonyloxy]-5-hydroxyimino-milbemycin A$_4$ [(I): R$^1$=Et, X=CO, Z=>C(CH$_2$)$_4$, R$^3$=4-NH$_2$, n=0)];

191. 13-[1-(4-Acetylaminophenyl)cyclopentanecarbonyloxy]-5-hydroxyimino-milbemycin A$_4$ [(I): R$^1$=Et, X=CO, Z=>C(CH$_2$)$_4$, R$^3$=4-NHAc, n=0)];

214. 13-[1-(4-Acetoxyacetylaminophenyl)cyclopentanecarbonyloxy]-5-hydroxyimino-milbemycin A$_4$ [(I):R$^1$=Et, X=CO, Z=>C(CH$_2$)$_4$, R$^3$=4-NHCOCH$_2$OAc, n=0)];

313. 13-[1-(4-Methanesulfonylaminophenyl)cyclopentanecarbonyloxy]-5-hydroxyimino-milbemycin A$_4$ [(I): R$^1$=Et, X=CO, Z=>C(CH$_2$)$_4$, R$^3$=4-NHSO$_2$Me, n=0)];

336. 13-[1-(4-Acetylaminophenyl)-1-ethylbutyryloxy]-5-hydroxyimino-milbemycin A$_4$ [(I): R$^1$=Et, X=CO, Z=>C(Et)$_2$, R$^3$=4-NHAc, n=0)]; and 457. 13-[1-(4-Acetylaminophenyl)cyclobutanecarbonyloxy]-5-hydroxyimino-milbemycin A$_4$ [(1):R$^1$=Et, X=CO, Z=>C(CH$_2$)$_3$, R$^3$=4-NHAc, n=0)].

The compounds of the present invention can be prepared by well known methods conventional for the preparation of compounds of this type, for example, as described below.

For example, the compounds of the present invention can be prepared by the following Reaction Schemes A and B.

Reaction Scheme A:

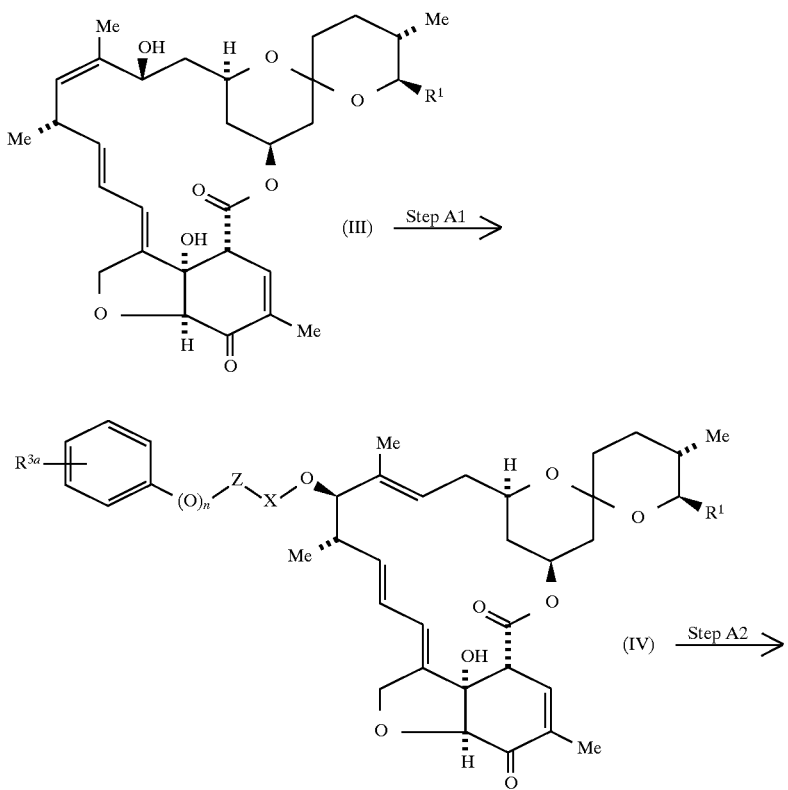

-continued
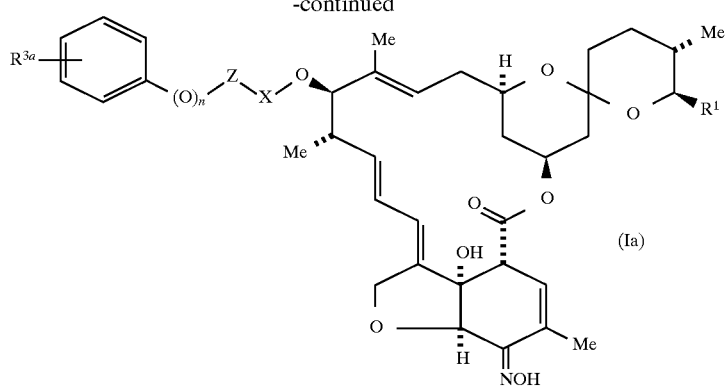
(Ia)
Reaction Scheme B:
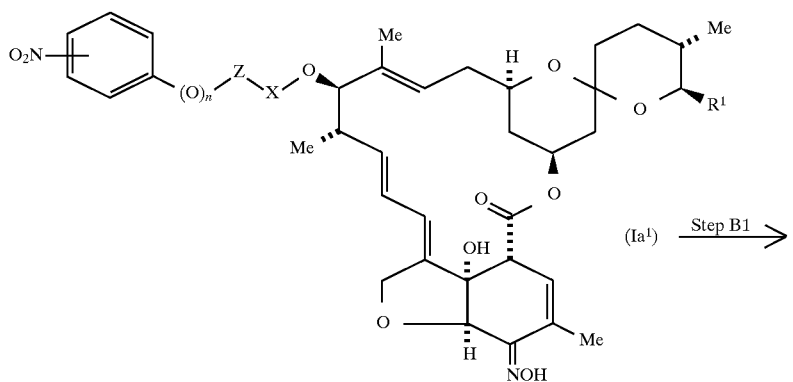
(Ia¹) $\xrightarrow{\text{Step B1}}$
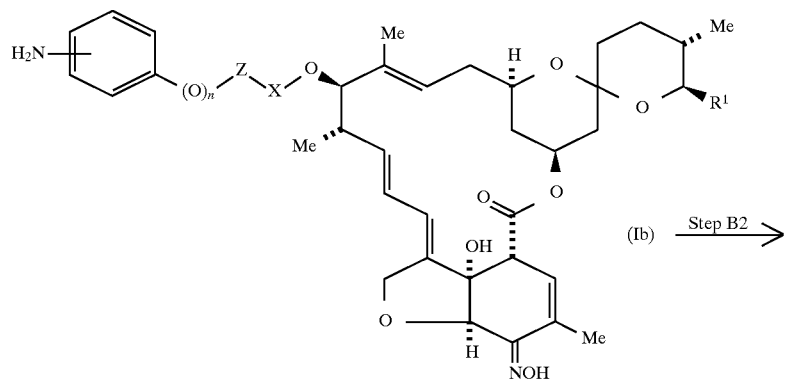
(Ib) $\xrightarrow{\text{Step B2}}$ -continued

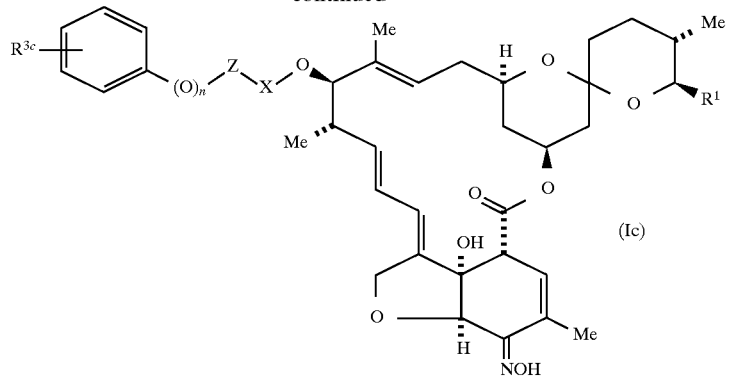

In the above formulae:

$R^1$, X, Z, n and Me are as defined above;

$R^{3a}$ represents any of the groups defined as $R^3$ except an amino group or a substituted amino group; the compound of formula (Ia) is included in the compounds of formula (I) but has a group $R^{3a}$ on its phenyl ring instead of the group $R^3$; the compound of formula (Ia$^1$) is included in the compounds of formula (I) but has a nitro group on its phenyl ring instead of the group $R^3$; the compound of formula (Ib) is included in the compounds of formula (I) but has an amino group on its phenyl ring instead of the group $R^3$;

$R^{3c}$ represents a substituted amino group which is included in the definitions for $R^3$; the compound of formula (Ic) is includedin the compounds of formula (I) but has a group $R^{3c}$ on its phenyl ring instead of the group $R^3$.

The 15-hydroxymilbemycin derivatives of formula (III), which are used as the starting materials in this process are known compounds which are disclosed, for example, in Japanese Patent Kokai Application Sho 60-18191.

Step A1

In this Step, a compound of formula (IV) is prepared by reacting a compound of formula (III) with a carboxylic acid or an alcohol of formula (V):

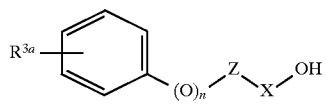 (V)

in the presence of a strong organic acid, such as trifluoromethanesulfonic acid.

The strong organic acid, for example trifluoromethanesulfonic acid, acts as a catalyst, and thus the amount of acid employed need, in principle, be no more than a catalytic amount. However, the amount required may vary widely depending upon the reactivity of the carboxylic acid or alcohol of formula (V) employed. In general, the amount of trifluoromethanesulfonic acid required need be no more than equimolar with respect to the compound of formula (V).

Addition of a powdery inorganic compound to the reaction mixture may, in some cases, accelerate the reaction. Examples of suitable inorganic compounds having such a property, include: metal salts, such as copper trifluoromethanesulfonate, cuprous iodide, stannic iodide, cobalt iodide or nickel iodide; Celite (trade mark) filter aid; silica gel or alumina. Of these, we prefer a copper salt, such as copper trifluoromethanesulfonate or cuprous iodide, and most prefer cuprous iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, 1,2-dichloroethane or chloroform; esters, such as ethyl acetate or propyl acetate; ethers, such as diethyl ether, tetrahydrofuran, dioxane or dimethoxyethane; amides, such as dimethylformamide, dimethylacetamide or hexamethylphosphoric triamide; sulfoxides, such as dimethyl sulfoxide; and nitriles, such as acetonitrile.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 6 hours, more preferably from 10 minutes to 2 hours, will usually suffice.

Step A2

In this Step, a compound of formula (Ia) is prepared by reacting a compound of formula (IV) with hydroxylamine or a salt thereof to change the carbonyl group at the 5-position into a hydroxyimino group.

For this reaction, various kinds of hydroxylamine salts can be used. Examples of salts which may be employed include: salts with inorganic acids, such as the hydrochloride or sulfate; and salts with organic acids, such as the acetate or oxalate. Of these, we prefer the hydrochloride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: lower alcohols which are freely miscible with water, such as methanol, ethanol or propanol; or a mixture of an ether, such as tetrahydrofuran or dioxane, with water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 1 hour to 10 hours will usually suffice.

Step B1

Prior to Step B1, the hydroxyimino group in the compound (Ia$^1$) may be protected by an acid-labile protecting group, such as a t-butyldimethylsilyl group. Introduction of the protecting group may be carried out by conventional means, for example as described in"Protective Group in Organic Synthesis", 2nd edition, T. W. Greene & P. G. M. Wut; John Wiley and Sons Inc., New York (1991), the disclosure of which is incorporated herein by reference.

In this Step B1, a compound of formula (Ib), which contains an amino group, is prepared by reduction of the nitro group in a compound of formula (Ia$^1$), that is a compound of formula (Ia) in which $R^{3a}$ represents a nitro group.

Reduction of the nitro group may be achieved by conventional means. An example of a suitable reduction process is catalytic reduction using a precious metal catalyst, such as palladium-on-carbon, palladium-on-barium sulfate or platinum oxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; and esters, such as ethyl acetate.

The reaction can take place over a wide range of temperatures, and the precise reaction temperature is not critical to the invention. The preferred reaction temperature will depend upon such factors as the nature of the solvent, and the starting material or reagent used. However, in general, we fmd it convenient to carry out the reaction at a temperature of from 10° C. to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 5 hours will usually suffice.

Another preferred reductive method is reduction with zinc powder in a solvent of acetic acid.

This reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to room temperature. The time required for the reaction may also vary widely, depending on many factors, notably the reaction temperature and the nature of the reagents and solvent employed. However, provided that the reaction is effected under the preferred conditions outlined above, a period of from 30 minutes to 12 hours will usually suffice.

A more preferred reductive method is reduction with sodium borohydride in the presence of a nickel catalyst. Suitable nickel catalysts include: nickel salts, such as nickel chloride or nickel bromide; and triphenylphosphine complexes of these nickel salts. The triphenylphosphine complexes are preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and ethers, such as tetrahydrofuran or dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to room temperature. The time required for the reaction may also vary widely, depending on many factors, notably the reaction temperature and the nature of the reagents and solvent employed. However, provided that the reaction is effected under the preferred conditions outlined above, aperiod of from 10 minutes to 120 minutes will usually suffice.

Step B2

In this Step, a compound of formula (Ic) which contains a substituted amino group (A—NH) is prepared by reaction of the amino group in a compound of formula (Ib) with an acid or with a reactive derivative thereof having the formula A—OH (A is as defined below) or with an isocyanate or isothiocyanate, as defined below.

A represents one of the following groups of formula:

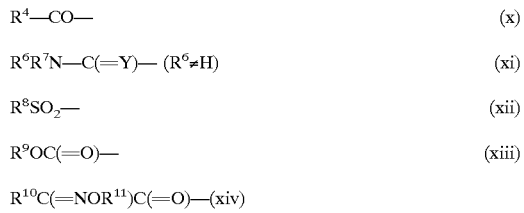

$R^4$—CO— (x)

$R^6R^7N$—C(=Y)— ($R^6{\neq}H$) (xi)

$R^8SO_2$— (xii)

$R^9OC(=O)$— (xiii)

$R^{10}C(=NOR^{11})C(=O)$—(xiv)

The isocyanates and isothiocyanates referred to above have the following formula:

$R^7N=C=Y$ (xv)

In the above formulae, $R^4$, $R^6$, $R^7$, $R^8$, $R^9$, $R^{10}$, $R^{11}$ and Y are as defined above.

There is no particular restriction on the nature of the acid reactive derivatives used, and any acid reactive derivative commonly used in condensation reactions of this type may equally be used here. Examples of such acid reactive derivatives include: acid halides, such as the acid chloride or acid bromide; an acid anhydride, a mixed acid anhydride, an active ester or an active amide.

When the acid itself of formula A—OH is used, a dehydrating agent, such as dicyclohexylcarbodiimide (DCC), 2-chloro-1-methylpyridinium iodide, p-toluenesulfonic acid or sulfuric acid, preferably 2-chloro-1-methylpyridinium iodide, is employed. The amount of dehydrating agent employed is preferably from 1 to 5 moles, preferably from 1 to 2 moles, per mole of the acid (A—OH) employed.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, petroleum ether, benzene or toluene; halogenated hydrocarbons, such as chloroform, methylene chloride or 1,2-dichloroethane; amides, such as dimethylformamide; sulfoxides, such as dimethyl. sulfoxide; nitrites, such as acetonitrile; or a mixture of any two or more thereof; more preferably methylene chloride or 1,2-dichloroethane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −70° C. to 90° C., more preferably from 0° C. to 60° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 30 minutes to 6 hours, will usually suffice.

When a halide of an acid of formula A—OH is used, the reaction is preferably carried out in the presence of a base. There is no particular restriction on the nature of the bases used, and any base commonly used in reactions of this type may equally be used here. Examples of such bases include: organic bases, such as triethylamine, dimethylaniline, pyridine, 4-dimethylaminopyridine, 1,5-diazabicyclo[4.3.0]nonene-5 (DBN) and 1,8-diazabicyclo[5.4.0]undecene-7 (DBU).

The amount of the halide of the acid of formula A—OH is preferably from 1 to 10 moles, and that of the base employed is preferably from 2 to 8 moles, per mole of the compound of formula (Ib).

The preferred solvents are the same as those when the corresponding carboxylic acid is used.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 2 hours will usually suffice.

When an isocyanate or isothiocyanate is used, the reaction is carried out in the presence of a solvent. The preferred solvents are the same as those recommended above for when a carboxylic acid is used. The reaction conditions, such as the reaction temperature and reaction time, are also the same as those recommended above for when a carboxylic acid is used.

Compounds in which $R^3$ represents a group of formula (v) or (vi) may be produced without using a compound of formula A—OH or an isocyanate or isothiocyanate.

If the hydroxyimino group is protected by the silyl group, the protecting group is removed by treatment with an acid in a solvent at the final step.

There is no particular restriction on the nature of the acid catalysts used, and any acid catalyst commonly used in reactions of this type may equally be used here. Examples of such acid catalysts include: hydrochloric acid, hydrobromic acid, hydroiodic acid, sulfuric acid, methanesulfonic acid or toluenesulfonic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 6 hours, more preferably from 10 minutes to 2 hours, will usually suffice.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: lower alcohols which are freely miscible with water, such as methanol, ethanol or propanol; or a mixture of an ether, such as tetrahydrofuran or dioxane, with water.

The milbemycins and analogous natural products, which may be used as the starting materials for the synthesis of the compounds of formula (III), are generally obtained as mixtures at various ratios of related compounds, and they may be reacted after being separated into the various fractions or they may be used in the above reactions as mixtures, whether the natural mixture or an artificially produced mixture. Therefore, the compound used in each step of the above reactions may be either a single compound or a mixture of compounds. Accordingly, the compound of formula (I) may be prepared as a single compound or as a mixture of compounds, and, if prepared as a mixture of compounds, may be used as such or may be separated into the individual compounds prior to use.

After completion of each step, each target compound, the compounds of formula (IV), (Ia), (Ia¹), (Ib) or (Ic), can be isolated from the reaction mixture by conventional means, and, if necessary, purified by any known method, such as column chromatography.

The compound of formula (V), the other starting material of this process, exists as a variety of compounds which differ in the nature of the groups Z and X attached via an optional oxygen atom to the phenyl ring, and these can be represented by the following formulae (Va), (Vb), (Vc) and (Vd):

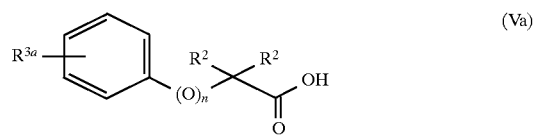

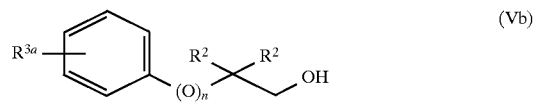

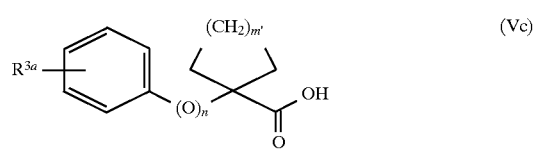

-continued

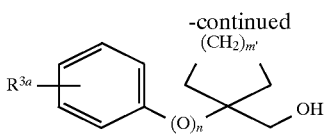

(Vd)

In these formulae, X and Z are as defined above; and m represents 0 or an integer of from 1 to 3.

These can be prepared by a combination of conventional synthetic methods and by the use of commercially available reagents, as briefly mentioned in (1) and (2) below.

(1) When n=1:

An α-alkyl-α-halogenoalkanoate, which is either commercially available or prepared by α-alkylation of a corresponding commercially available alkanoate with a base and an alkyl halide followed by α-halogenation, is allowed to react with phenol in the presence of a base to obtain an α-(phenoxy)-α-alkyl-alkanoate. Hydrolysis of this ester gives a carboxylic acid represented by the formula (Va). When a dihaloalkane, such as 1,2-dibromoethane, 1,3-dibromopropane or 1,4-dibromopentane, is used as the alkyl halide, a cycloalkane carboxylic acid represented by the formula (Vc) can be obtained. The carboxylic acid thus obtained is reduced with a metal hydride, such as lithium aluminum hydride, to obtain an alcohol represented by the formula (Vb) or (Vd).

(2) When n=0:

An α-phenyl-α,α-dialkyl acetate, which is obtained by α-alkylation of a commercially available phenyl acetate with a corresponding base and an alkyl halide, is hydrolysed to give a carboxylic acid represented by the formula (VIIa). When a dihaloalkane, such as 1,2-dibromoethane, 1,3-dibromopropane or 1,4-dibromopentane, is used as the alkyl halide, a cycloalkane carboxylic acid represented by the formula (Vc) can be obtained. The carboxylic acid thus obtained is reduced with a metal hydride, such as lithium aluminum hydride, to obtain an alcohol represented by the formula (Vb) or (Vd).

The compounds of the invention have a strong acaricidal activity. Further, they are active against resistant mites, which are difficult to control with known acaricides and which have recently caused much trouble.

The compounds of the invention also have a strong insecticidal activity, especially against fleas, which are relatively resistant to other milbemycin compounds, and can therefore be used as insecticides. The active compounds of the invention exhibit preventive effects against noxious insects but have no phytotoxicity, and so agricultural plants are never damaged by these compounds. The compounds of the invention can be used to exterminate a variety of noxious insects, including noxious insects which damage plants by sucking or eating them, noxious insects parasitic to plants, noxious insects which damage materials in store, noxious insects for sanitary reasons and the like. The compounds are also effective against various nematodes which affect animals of agricultural importance.

Where the compounds of the invention are used as anthelmintics in animals, whether human or non-human, they can be administered orally in the form of a liquid drink. The drink may comprise a solution, suspension or dispersion of the active compound in an appropriate non-toxic solvent or water and in admixture with a suspending agent, such as bentonite, a wetting agent or other excipients. The drink, in general, may also contain an anti-foaming agent. The active compound is normally present in the drink in an amount of from about 0.01 to 0.5% by weight, more preferably from 0.01 to 0.1% by weight.

Alternatively, compositions can be administered orally in the form of dry solids, preferably in unit dosage form, such as capsules, pills or tablets, containing the desired amount of the active compound. These compositions can be prepared by mixing the active compound uniformly with suitable pulverised diluents, fillers, disintegrators and/or binding agents, for example starch, lactose, talc, magnesium stearate and vegetable gum. The weight and contents of the preparation may vary widely, depending upon the nature of the animal to be treated, the degree of infection, the nature of the parasite and the body weight of the animal to be treated.

The compounds can also be administered as an additive to animal feedstuffs, in which case they can be dispersed uniformly in the feedstuffs, used as a top dressing or used in the form of pellets. The content of active compound in the feedstuff is preferably from 0.0001 to 0.02%, in order to achieve the desired anthelmintic activity.

The compounds of the invention, when dissolved or dispersed in a liquid vehicle, can be administered parenterally to animals by injection into the proventriculus, a muscle or the trachea or by subcutaneous injection. For parenteral administration, the active compound is preferably mixed with a suitable vegetable oil, such as peanut oil or cottonseed oil. The content of the active compound in the formulation is generally from 0.05 to 50% by weight.

The compounds of the invention can also be administered topically in admixture with a suitable carrier, such as dimethyl sulfoxide or a hydrocarbon solvent. Such preparations are applied directly to the outside of the animal by spraying or by dipping.

The dose of the active compound may vary, depending upon the nature of the animal to be treated, and the nature and degree of parasitic infection. However, best results for oral administration are achieved when the dose is from about 0.01 to 100 mg, more preferably from 0.5 to 50 mg, per 1 kg body weight of the animal. The compound can be administered in a single dose or in divided doses for a relatively short period, such as from 1 to 5 days.

Where the composition of the invention is intended for agricultural or horticultural use, a variety of forms and formulations are possible. For example, it can be formulated as dusts, coarse dusts, soluble powders, microgranules, fine microgranules, wettable powders, dilute emulsions, emusifiable concentrates, aqueous or oily suspensions or aqueous or oily solutions (which can be directly sprayable or can be used for dilution), aerosols or capsules in polymeric substances. The carrier used can be natural or synthetic and organic or inorganic, and it is generally employed to assist the active compound to reach the substrate to be treated, and to make it easier to store, transport or handle the active compound. Solid, liquid and gaseous carriers can be chosen from carriers well known in the art for use with composition of this type.

Such formulations may be prepared by conventional means, e.g. by intimate mixing and/or grinding of the active ingredient(s) with a carrier or diluent (solvent) or, optionally, surface-active agent, after which the mixture can, if required, be subjected to such further steps as pulverisation, granulation, tabletting, coating or absorption.

Examples of carriers which may be used, for example, in dusts, coarse dusts, soluble powders, microgranules, fine microgranules, wettable powders and dispersible powders include: clay of the kaolinite group or the pyrophyllite group; talc; calcium carbonate; clay of the montmorillonite group, such as bentonite or Japanese acid clay; powder or granules of a natural mineral, such as attapulgite, sepiolite, diatomaceous earth, pumice stone or silica sand; fine powder of an inorganic compound, such as aqueous or anhydrous synthetic amorphous silicon dioxide, calcium silicate or magnesium carbonate; a sugar, such as sucrose, lactose or glucose; an organic substance, such as starch, dextrin, fine crystalline cellulose, wood powder, coffee bean powder, chaff powder, wheat flour or thumb powder; or an inorganic salt, such as sodium sulfate, sodium carbonate, sodium hydrogencarbonate, sodium phosphate, calcium sulfate or ammorium sulfate; or urea.

Examples of suitable solvents include: aromatic solvents having a high boiling point, such as xylene, methylnaphthalene, alkylbenzenes or phenylxylylethane; solvents of the paraffinic or naphthene group having a high boiling point; esters of various carboxylic acids, such as oleic acid, adipic acid, lauric acid, coconut oil fatty acid, maleic acid and phthalic acid; various phosphates; ketones, such as cyclohexanone or methyl isobutyl ketone; polar solvents, such as N-alkylpyrrolidones or dimethyl sulfoxide; glycols, such as ethylene glycol, propylene glycol, butanediol or hexylene glycol, polymers thereof, ethers thereof or esters thereof; alcohols, such as methanol, ethanol, propanol, butanol, hexanol, octanol or lauryl alcohol, esters thereof or ethers thereof; optionally epoxidated vegetable oils, such as coconut oil or soybean oil; or water.

The surface-active agents can be cationic, anionic or non-ionic compounds having good emulsifying, dispersing and wetting properties, such as are conventionally used in compositions of this type. A single such agent or a mixture of two or more such agents can also be used.

Suitable non-ionic surfactants which may be employed include: polyoxyethylenealkyl ethers; polyoxyethylenealkyl esters; a polyoxyethylenealkyl aryl ethers; polyoxyethylenearyl aryl ethers; polyoxyethylenesorbitan alkyl esters; sorbitan alkyl esters; fatty acid esters of sugar; fatty acid esters of glycerin or pentaerythritol; surfactants of the Pluronic type; acetylene alcohol or acetylenediol or ethylene oxide additives thereof; surfactants of the silicon group, and alkylglucosides.

Suitable anionic surfactants which may be employed include: salts of alkylbenzenesulfonic acid; salts of dialkylsulfosuccinic acid; salt of alkyl sulfates; salts of alkylmethyltauride; anionic surfactants which are prepared by esterification of the aforementioned ethylene dioxide-added non-ionic surfactant with sulfuric acid or phosphoric acid, followed by, if necessary, neutralisation with a suitable alkali; salts of ligninsulfonic acid; salts of (alkyl)-naphthalenesulfonic acid or condensates thereof; salts of phenolsulfonic acid or condensates thereof; polysoaps of the polycarboxylic acid or polysulfonic acid type consisting of a salt of a condensate product of, for example, acrylic acid, maleic acid, stylenesulfonic acid or vinyl radical; surfactants of the starch type consisting of an additive of starch or dextrin with 1-(2-octenoyl)-sodium succinate, salts of carboxymethylcellulose; soaps, such as the sodium or potassium salt of a higher fatty acid; and salts of α-olefinsulfonic acids.

Suitable cationic surfactants which may be employed include: surfactants of the amine salt type or quaternary ammonium type, and ethylene dioxide-additives of a higher aliphatic amine or fatty acid amide.

Suitable amphoteric surfactants which may be employed include: surfactants of the amino acid type or betaine type, or lecithin.

In the molecule of each of aforementioned surfactants, a derivative surfactant where one or all of the hydrogen atoms is substituted by fluorine atoms exhibits a strong surface tension lowering effect, and can be used effectively.

Compositions can also contain one or more additives selected from the group consisting of stabilisers, antifoaming agents, viscosity regulators, binders and adhesives or any combination thereof, as well as fertilisers and other active substances to achieve special effects.

Insecticidal and acaricidal compositions generally contain: from 0.01 to 99%, more preferably from 0.1 to 95%, of the active compound; from 1 to 99.99% of a solid or liquid additive; and from 0 to 25%, more preferably from 0.1 to 25%, of a surface-active agent. Where commercial products are generally sold as concentrated compositions, they are generally diluted by the end-user to a concentration of from 0.001 to 0.0001% by weight (from 10 to 1 ppm).

In the above, percentages are by weight.

The compounds of the present invention can be formulated in admixture with or used in association with other active compounds, for example, insecticides, poisonous feeds, bactericides, acaricides, nematocides, flngicides, plant growth regulators or herbicides. Examples of the said insecticides include: organic phosphorus chemicals, carbamate chemicals, carboxylate chemicals, chlorinated hydrocarbon chemicals and insecticidal substances produced by microorganism.

The compounds of the invention can also be formulated in admixture with or used in association with synergists. It is required that preparations of such chemicals and the form of the intended use are commercially useful. The synergist is, independently of the activity, in itself a compound capable of enhancing the effect of the active compounds.

BIOLOGICAL ACTIVITY

The biological test examples-shown below will further explain the effect of the compounds of the present invention.

In Table 2 below, Comparative Compound 1 is 5-hydroxyimino-milbemycin $A_4$ (Milbemycin $A_4$ oxime) which has been described in the Examples of Japanese Patent Kokai Application Sho 60-142991; Comparative Compound 2 is one of the compounds which has been described in the Examples of Japanese Patent Kokai Application Hei 5-255343; and Comparative Compound 3 is one of the compounds which has been described in the Examples of Japanese Patent Kokai Application Sho 63-10791, the structures of which are shown below [In these formulae, Me means methyl]:

Comparative Compound 1:

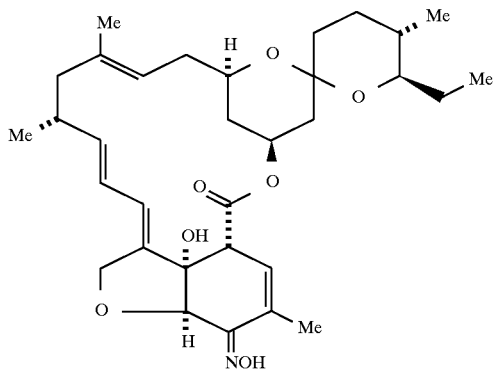

Comparative Compound 2:

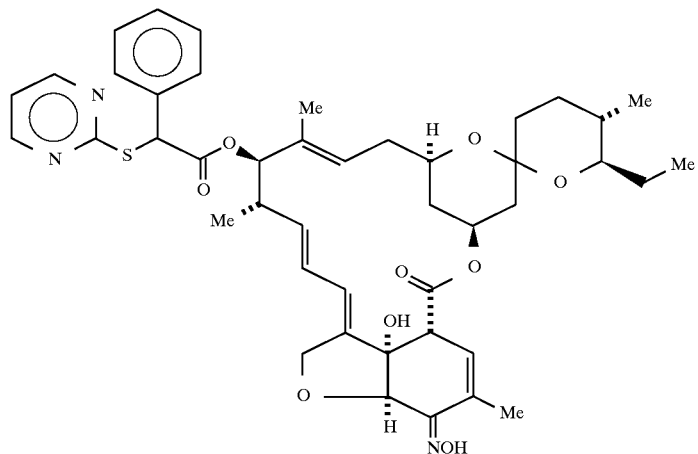

Comparative Compound 3:

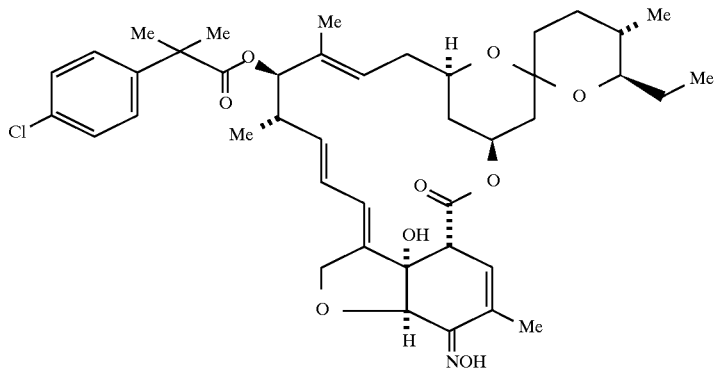

TEST EXAMPLE

Test of insecticidal effect against cat fleas

A container where the living space of fleas was isolated from bovine serum by use of parafilm (which is usually used as an artificial skin) was prepared. A compound to be tested was added to the bovine serum in an amount sufficient for its concentration to be 1 ppm, and fleas were allowed to suck the serum sample through the parafilm at 37° C. Each group contained 20 fleas. After 48 hours, the dead fleas were counted, which allowed the insecticidal effect of the drug sample against fleas to be evaluated. By counting the dead fleas in the control group without the drug sample, the mortality was corrected. Table 2 shows the results.

TABLE 2

| Example No. | Mortality (%) |
|---|---|
| 3 | 97.5 |
| 14 | 97.5 |
| 15 | 92.6 |
| 16 | 100.0 |
| 17 | 90.2 |
| 19 | 90.0 |
| 20 | 94.6 |
| 21 | 92.7 |

TABLE 2-continued

| Example No. | Mortality (%) |
|---|---|
| 24 | 92.5 |
| 25 | 97.5 |
| 26 | 90.0 |
| 27 | 97.6 |
| 28 | 94.7 |
| 30 | 97.5 |
| 39 | 92.7 |
| 40 | 97.5 |
| 42 | 90.2 |
| 43 | 95.3 |
| 44 | 90.5 |
| 46 | 97.5 |
| 47 | 97.4 |
| 49 | 97.5 |
| 50 | 92.3 |
| 55 | 92.1 |
| 57 | 97.5 |
| 58 | 95.0 |
| 59 | 100.0 |
| 60 | 100.0 |
| 64 | 90.2 |
| 66 | 95.0 |
| 67 | 90.0 |
| 68 | 95.0 |
| 70 | 97.5 |
| 74 | 90.0 |
| 85 | 100.0 |
| 91 | 97.5 |
| 93 | 90.0 |
| 101 | 97.5 |
| 105 | 95.2 |
| 109 | 100.0 |
| 110 | 100.0 |
| 111 | 91.1 |
| 112 | 95.5 |
| 114 | 94.7 |
| 115 | 92.3 |
| 116 | 97.3 |
| 118 | 95.1 |
| 123 | 95.0 |
| 124 | 97.3 |
| 130 | 100.0 |
| 137 | 97.4 |
| Comparative Compound 1 | 20.9 |
| Comparative Compound 2 | 31.4 |
| Comparative Compound 3 | 26.8 |

EXAMPLE 1

13-[2-(4-Nitrophenyl)-2-methylpropionyloxy]-5-hydroxyimino-milbemycin $A_4$ [(I): $R^1$=Et, X=CO, Z=>C(Me)$_2$, $R^3$=4-NO$_2$, n=0 (Compound No. 2)]

1(a) 13-[2-(4-Nitrophenyl)-2-methylpropionyl]-5-oxo-milbemycin $A_4$ [(IV): $R^1$=Et, X=CO, Z=>C(Me)$_2$, $R^3$=4-NO$_2$, n=0).

212 mg (1.01 mmol) of 2-(4-nitrophenyl)-2-methylpropionic acid and 15 ml of trifluoromethanesulfonic acid were added in a stream of argon gas to a solution of 188 mg (0.34 mmol) of 15-hydroxy-5-oxo-milbemycin $A_4$ in 8 ml of methylene chloride, whilst cooling with ice, and then the mixture was stirred for 30 minutes at room temperature. At the end of this time, the reaction solution was poured into water and extracted with ethyl acetate. The extract was washed with a 5% w/v aqueous solution of sodium hydrogencarbonaate and then with a saturated aqueous. solution of sodium chloride. The solution was then dried over anhydrous magnesium sulfate, after which the solvent was removed by distillation under reduced pressure. The residue was purified by column chromatography through silica gel, using a 4:6 by volume mixture of ethyl acetate and hexane as the eluent, to give 502 mg (yield 58%) of the title compound.

Nuclear Magnetic Resonance Spectrum (270 MHz) δ ppm:
8.16 (2H, doublet, J=9.8 Hz);
6.54 (1H, triplet, J=1.8 Hz);
5.92–5.69 (2H, multiplet);
5.47–5.29 (3H, multiplet);
4.91 (1H, doublet, J=10.5 Hz);
4.70 (2H, broad singlet);
3.84 (1H, singlet);
1.63 (6H, singlet).

1(b) 13-[2-(4-Nitrophenyl)-2-methylpropioaloxy]-5-hydroxyimino-milbemycin $A_4$ 186 mg (0.25 mmol) of 13-[2-(4-nitrophenyl)-2-methylpropionyl]-5-oxo-milbemycin $A_4$ [prepared as described in step (a) above] was dissolved in 1.5 ml of dioxane. 0.75 ml of water, 1.5 ml of methanol and 165 mg of hydroxylamine hydrochloride were added to the resulting solution, and the mixture was stirred for 3 hours at 40° C. At the end of this time, the reaction solution was diluted with 20 ml of ethyl acetate, and washed 3 times with water. The solution was then dried over anhydrous magnesium sulfate, after which the solvent was removed by distillation under reduced pressure. The resulting residue was purified by column chromatography through silica gel, using a 5:5 by volume mixture of ethyl acetate and hexane as the eluent, to give 170 mg (yield 89.2%) of the title compound.

Nuclear Magnetic Resonance Spectrum (270 MHz) δ ppm:
8.17 (2H, doublet, J=8.7 Hz);
8.00 (1H, broad singlet);
7.47 (2H, doublet, J=8.7 Hz);
5.90–5.71 (3H, multiplet);
5.48–5.27 (3H, multiplet);
4.91 (1H, doublet, J=10.6 Hz);
4.70 & 4.68 (2H, AB-quartet, J=15.0 Hz);
4.65 (1H, singlet);
3.97 (1H, singlet);
3.57 (1H, multiplet);
3.36 (1H, multiplet);
3.04 (1H, doublet of triplets, J=2.3 & 9.3 Hz);
1.93 (3H, singlet),
1.63 (3H singlet);
1.60 (3H, singlet);
1.29 (3H, singlet);
0.99 (3H, triplet, J=7.3 Hz);
0.82 (6H, doublet, J=6.5 Hz).

EXAMPLES 2 TO 8

Following a similar procedure to that described in Example 1, the compounds of Examples 2 to 8 were synthesized. The yields given are calculated as an aggregate of the yields of steps (a) and (b).

EXAMPLE 2

13-[2-(3-Nitropheyl)-2-methylpropionyloxy]-5-hydroxyimino-milbemycin $A_4$ [(I):$R^1$=Et, X=CO, Z=>C(Me)$_2$, $R^3$=3-NO$_2$, n=0 (Compound No. 3)]

Yield: 64.3%.

Nuclear Magnetic Resonance Spectrum (270 MHz) δ ppm:
8.19 (1H, doublet of doublets, J=1.9 & 1.9 Hz);
8.12 (1H, doublet of doublets, J=1.9 & 7.9 Hz);
7.63 (1H, doublet of doublets, J=1.9 & 7.9 Hz);

7.49 (1H, doublet of doublets, J=7.9 & 7.9 Hz);
5.90–5.70 (3H, multiplet);
5.47–5.29 (3H, multiplet);
4.92 (1H, doublet, J=10.6 Hz);
4.73 & 4.68 (2H, AB-quartet, J=14.4 Hz);
4.66 (1H, singlet);
3.97 (1H, singlet);
3.57 (1H, multiplet);
3.36 (1H, multiplet);
3.04 (1H, doublet of triplets, J=2.1 & 9.1 Hz);
1.93 (3H, singlet);
1.66 (3H singlet);
1.61 (3H, singlet);
1.29 (3H, singlet);
0.96 (3H, triplet, J=7.3 Hz);
0.84 (3H, doublet, J=6.5 Hz);
0.83 (3H, doublet, J=6.4 Hz).

EXAMPLE 3

13-[2-(4-Methoxyphenyl)-2-methylpropionyloxy]-5-hdroxyimino-milbemycin $A_4$ [(I): $R^1$=Et, X=CO, Z=>C(Me)$_2$, $R^3$=4-MeO, n=0 (Compound No. 16)]

Mass spectrum (FAB-MS) m/z:748 (M+H$^+$, M=$C_{43}H_{57}NO_{10}$).

(FAB-MS is Fast Atomic Bombardment Mass Spectrum)

Nuclear Magnetic Resonance Spectrum (CDCl$_3$) δ ppm:
7.95 (1H, broad singlet);
7.22 (2H, doublet, J=8.8 Hz);
6.83 (2H, doublet, J=8.8 Hz);
4.86 (1H, doublet, J=10.5 Hz);
4.73 & 4.68 (2H, doublet of AB-quartets, J=1.8 & 14.4 Hz);
4.65 (1H, singlet);
3.96 (1H, singlet);
3.79 (3H, singlet);
3.56 (1H, multiplet);
3.36 (1H, multiplet);
3.04 (1H, doublet of doublets, J=2.2 & 9.2 Hz);
1.93 (3H, singlet);
1.56 (3H, singlet);
1.53 (3H, singlet);
1.30 (3H, singlet);
0.98 (3H, triplet, J=7.3 Hz);
0.83 (3H, doublet, J=6.4 Hz);
0.82 (3H, doublet, J=6.4 Hz).

EXAMPLE 4

13-[1-(4-Methoxyphenyl)cyclopentanecarbonyloxy-5-hydroxyimino-milbemycin $A_4$ [(I): $R^1$=Et, X=CO, Z=>C(CH$_2$)$_4$, $R^3$=4-MeO, n=0 (Compound No. 181)]

Mass spectrum (FAB-MS) m/z:774 (M+H$^+$, M=$C_{45}H_{59}NO_{10}$).

Nuclear Magnetic Resonance Spectrum (CDCl$_3$) δ ppm:
7.25 (2H, doublet, J=8.6 Hz);
6.81 (2H, doublet, J=8.6 Hz);
4.80 (1H, doublet, J=10.6 Hz);
4.72 & 4.70 (2H, AB-quartet, J=14.4 Hz);
4.65 (1H, singlet);
3.96 (1H, singlet);
3.78 (3H, singlet);
3.56 (1H, multiplet);
3.36 (1H, multiplet);
3.02 (1H, doublet of doublets, J=2.2 & 9.2 Hz);
2.66–2.54 (2H, multiplet);
1.93 (3H, singlet);
1.29 (3H, singlet);
0.97 (3H, triplet, J=7.3 Hz);
0.82 (3H, doublet, J=6.6 Hz);
0.77 (3H, doublet, J=5.9 Hz).

EXAMPLE 5

13-[2-(4-Isobutoxyphenyl)-2-methylpropionyloxy]-5-hydroxyimino-milbemycin $A_4$ [(I): $R^1$=Et, X=CO, Z=>C(Me)$_2$, $R^3$=4-OiBu, n=0 (Compound No. 23)]

Mass spectrum (FAB-MS) m/z:790 (M+H$^+$, M=$C_{46}H_{60}NO_{10}$).

Nuclear Magnetic Resonance Spectrum (CDCl$_3$) δ ppm:
7.85 (1H, broad singlet);
7.20 (2H, doublet, J=8.6 Hz);
6.81 (2H, doublet, J=8.6 Hz);
4.86 (1H, doublet, J=10.0 Hz);
4.75 & 4.66 (2H, AB-quartet, J=14.5 Hz);
4.65 (1H, singlet);
3.96 (1H, singlet);
3.71 (2H, singlet);
3.57 (1H, multiplet);
3.36 (1H, multiplet);
3.04 (1H, multiplet);
1.93 (3H, singlet);
1.55 (3H, singlet);
1.53 (3H, singlet);
1.31 (3H, singlet);
0.98 (3H, triplet, J=7.3 Hz);
0.88–0.80 (6H, m).

EXAMPLE 6

13-[1-(4-Nitrophenyl)cyclopropanecarbonyloxy]-5-hydroxyimino-milbemycin $A_4$ [(I): $R^1$=Et, X=CO, Z=>C(CH$_2$)$_2$, $R^3$=4-NO$_2$, n=0 (Compound No. 387)]

Nuclear Magnetic Resonance Spectrum (270 MHz) δ ppm:
8.18 (2H, doublet, J=8.7 Hz);
7.51 (2H, doublet, J=8.7 Hz);
5.82 (1H, singlet);
5.90–5.71 (3H, multiplet);
5.46–5.27 (3H, multiplet);
4.91 (1H, doublet, J=10.6 Hz);
4.72 & 4.66 (2H, AB-quartet, J=14.4 Hz);
4.65 (1H, singlet);
3.93 (1H, singlet);
3.55 (1H, multiplet);
3.35 (1H, multiplet);
3.03 (1H, doublet of triplets, J=2.2 & 9.2 Hz);
1.93 (3H, singlet);
1.36 (3H, singlet);

0.97 (3H, triplet, J=7.3 Hz);
0.91 (3H, doublet, J=6.5 Hz);
0.82 (3H, doublet, J=6.5 Hz).

EXAMPLE 7

13-[1-(4-Nitrophenyl)cyclobutanecarbonyloxy]-5-hydroxyimino-milbemycin $A_4$ [(I): $R^1$=Et, X=CO, Z=>C(CH$_2$)$_3$, $R^3$=4-NO$_2$, n=0 (Compound No. 451)]

Yield: 66.1%
Nuclear Magnetic Resonance Spectrum (270 MHz) δ ppm:
8.18 (2H, doublet, J=8.9 Hz);
7.42 (2H, doublet, J=8.9 Hz);
5.89–5.72 (3H, multiplet);
5.46–5.27 (3H, multiplet);
4.88 (1H, doublet, J=10.5 Hz);
4.73 & 4.67 (2H, AB-quartet, J=14.4 Hz);
4.66 (1H, singlet);
3.95 (1H, singlet);
3.56 (1H, multiplet);
3.36 (1H, multiplet);
3.03 (1H, doublet of triplets, J=2.3 & 9.2 Hz);
1.93 (3H, singlet);
1.35 (3H, singlet);
0.98 (3H, triplet, J=7.3 Hz);
0.82 (3H, doublet, J=6.4 Hz);
0.78 (3H, doublet, J=6.6 Hz).

EXAMPLE 8

13-[2-(4-Nitrophenyl)-2-methylproploxy]-5-hydroxyimino-milbemycin $A_4$ [(I): $R^1$=Et, X=CH$_2$, Z=>C(Me)$_2$, $R^3$=4-NO$_2$, n=0 (Compound No. 513)]

Yield: 65.3%
Nuclear Magnetic Resonance Spectrum (270 MHz) δ ppm:
8.14 (2H, doublet, J=8.9 Hz);
7.51 (2H, doublet, J=8.9 Hz);
5.90–5.71 (3H, multiplet);
5.46–5.27 (3H, multiplet);
4.65 (1H, singlet);
3.94 (1H, singlet);
3.31 (1H, doublet, J=9.0 Hz);
3.13 (2H, doublet, J=9.0 Hz);
1.87 (6H, singlet).

EXAMPLE 9

13-[2-(4-Aminophenyl)-2-methylpropionyloxy]-5-hydroxyimino-milbemycin $A_4$ [(I): $R^1$=Et, X=CO, Z=>C(Me)$_2$, $R^3$=4-NH$_2$, n=0 (Compound No. 6)]

1.0 g (1.31 mmol) of 13-[2-(4-nitrophenyl)-2-methylpropionyloxy]-5-hydroxyimino-milbemycin $A_4$ (prepared as described in Example 1) was dissolved in a mixture of 13 ml of methanol and 7 ml of tetrahydrofuran. 85 mg (0.13 mmol) of nickel (II) chloride triphenylphosphine complex and 100 mg (2.6 mmol) of sodium borohydride were added to the solution, whilst cooling with ice. The reaction mixture was stirred for 30 minutes, after which it was diluted with ethyl acetate, washed 3 times with water, and dried over anhydrous sodium sulfate. The solvent was then removed by distillation under reduced pressure. The resulting residue was purified by column chromatography through silica gel, using a 5:5 by volume mixture of ethyl acetate and hexane as the eluent, to give 802 mg (yield 83.8%) of the title compound.

Nuclear Magnetic Resonance Spectrum (270 MHz) δ ppm:
8.00 (1H, broad singlet);
7.09 (2H, doublet, J=8.5 Hz);
6.62 (2H, doublet, J=8.5 Hz);
5.95–5.71 (3H, multiplet);
5.50–5.25 (3H, multiplet);
4.86 (1H, doublet, J=10.5 Hz);
4.75 & 4.68 (2H, AB-quartet, J=15.0 Hz);
4.66 (1H, singlet);
3.57 (1H, multiplet);
3.36 (1H, multiplet);
3.04 (1H, doublet of triplets, J=2.1 & 9.0 Hz);
1.93 (3H, singlet);
1.54 (3H, singlet);
1.51 (3H, singlet);
1.32 (3H, singlet);
0.98 (3H, triplet, J=7.2 Hz);
0.82 (6H, doublet, J=6.4 Hz).

EXAMPLES 10 TO 13

Following a similar procedure to that described in Example 9, the compounds of Examples 10 to 13 were synthesized.

EXAMPLE 10

13-[2-(3-Aminophenyl)-2-methylpropionyloxy]-5-hydroxyimino-milbemycin $A_4$ [(I): $R^1$=Et, X=CO, Z=>C(Me)$_2$, $R^3$=3-NH$_2$, n=0 (Compound No. 7)]

Nuclear Magnetic Resonance Spectrum (270 MHz) δ ppm:
7.42 (1H, multiplet);
7.21 (1H, multiplet);
6.90 (1H, multiplet);
5.90–5.70 (3H, multiplet);
5.48–5.29 (3H, multiplet);
4.89 (1H, doublet, J=10.6 Hz);
4.73 & 4.68 (2H, AB-quartet, J=14.4 Hz);
4.65 (1H, singlet);
3.97 (1H, broad singlet);
3.57 (1H, multiplet);
3.36 (1H, multiplet);
3.04 (1H, multiplet);
1.93 (3H, singlet);
1.65 (3H, singlet);
1.62 (3H, singlet);
1.29 (3H, singlet);
0.97 (3H, triplet, J=7.3 Hz);
0.84 (3H, doublet, J=6.5 Hz);
0.83 (3H, doublet, J=6.4 Hz).

EXAMPLE 11

13-[1-(4-Aminophenol)cyclopropanecarbonyloxy]-5-hydroxyimino-milbemycin $A_4$ [(I): $R^1$=Et, X=CO, Z=>C(CH$_2$)$_2$, $R^3$=4-NH$_2$, n=0 (Compound No. 388)]

Mass spectrum (FAB-MS) m/z: 731 (M+H$^+$, M=C$_{42}$H$_{54}$N$_2$O$_9$).

Nuclear Magnetic Resonance Spectrum (270 MHz) δ ppm:
7.11 (2H, doublet, J=8.2 Hz);
6.63 (2H, doublet, J=8.2 Hz);
4.85 (1H, doublet, J=10.6 Hz);
4.74 & 4.67 (2H, AB-quartet, J=14.8 Hz);
4.65 (1H, singlet);
3.92 (1H, singlet);
3.68 (2H, broad singlet);
3.55 (1H, multiplet);
3.36 (1H, multiplet);
3.03 (1H, doublet oftriplets, J=2.2 & 9.2 Hz);
1.93 (3H, singlet);
1.39 (3H, singlet);
1.12 (2H, multiplet);
0.97 (3H, triplet, J=7.3 Hz);
0.91 (3H, doublet, J=6.5 Hz);
0.83 (3H, doublet, J=6.4 Hz).

EXAMPLE 12

13-[1-(4-Aminophenyl)cyclobutanecarbonyloxy]-5-hydroxyimino-milbemycin $A_4$ [(I): $R^1$=Et, X=CO, Z=>C(CH$_2$)$_3$, $R^3$=4-NH$_2$, n=0 (Compound No. 452)]

Nuclear Magnetic Resonance Spectrum (270 MHz) δ ppm:
7.19 (2H, doublet, J=8.1 Hz);
7.01 (2H, doublet, J=8.1 Hz);
5.96–5.71 (3H, multiplet);
5.50–5.25 (3H, multiplet);
4.82 (1H, doublet, J=10.5 Hz);
4.66 (1H, singlet);
3.57 (1H, multiplet);
3.36 (1H, multiplet);
3.03 (1H, doublet of triplets, J=2.2 & 9.2 Hz);
1.96 (3H, singlet);
1.40 (3H, singlet);
0.98 (3H, triplet, J=7.2 Hz);
0.89 (3H, doublet, J=6.5 Hz);
0.82 (3H, doublet, J=6.5 Hz).

EXAMPLE 13

13-[2-(4-Aminophenyl)-2-methylpropionyl-5-hydroxyimino-milbemycin $A_4$ [(I): $R^1$=Et, X=CH$_2$, Z=>C(Me)$_2$, $R_3$=4-NH$_2$, n=0 (Compound No. 514)]

Nuclear Magnetic Resonance Spectrum (270 MHz) δ ppm:
7.14 (2H, doublet, J=8.5 Hz);
6.63 (2H, doublet, J=8.5 Hz);
5.90–5.71 (3H, multiplet);
5.46–5.27 (3H, multiplet);
4.65 (1H, singlet);
3.94 (1H, singlet);
3.22 (1H, doublet, J=8.9 Hz).

EXAMPLE 14

13-[2-(4-Methoxycarbonylaminoacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCH$_2$NHCOOMe, n=0 (Compound No. 81)]

3.61 g (5.0 mmol) of 13-[2-(4-aminophenyl)-2-methylpropionyloxy]-5-hydroxyimino-milbemycin $A_4$, 1.012 g (10.0 mmol) of triethylamine and 2.56 g (10.0 mmol) of 2-chloro-1-methylpyridinium iodide were added to a solution of 2.0 g (15.0 mmol) of N-methoxycarbonylglycine in 20 ml of methylene chloride, in that order. The mixture was then stirred for 1.5 hours at room temperature. At the end of this time, the reaction mixture was poured into water and extracted with ethyl acetate. The extract was dried over anhydrous magnesium sulfate and condensed by evaporation under reduced pressure. The resulting residue was purified by column chromatography through silica gel, using a 6:4 by volume mixture of ethyl acetate and hexane as the eluent, to give 3.53 g (yield 84.4%) of the title compound.

Nuclear MagneticResonance Spectrum (270 MHz) δ ppm:
8.30 (1H, broad singlet);
7.9 (1H, broad singlet);
7.45 (2H, doublet, J=8.5 Hz);
7.24 (2H, doublet, J=8.5 Hz);
5.89–5.71 (3H, multiplet);
5.51–5.26 (4H, multiplet);
4.86 (1H, doublet, J=10.8 Hz);
4.73 & 4.65 (2H, AB-quartet, J=15.0 Hz);
3.99 (1H, doublet, J=5.6 Hz);
3.97 (3H, singlet);
3.36 (1H, multiplet);
3.75 (3H, singlet).

EXAMPLES 15 AND 16

Following a similar procedure to that described in Example 14, the compounds of Examples 15 and 16 were synthesized by using 13-[2-(4-aminophenyl)-2-methylpropyloxy]-5-hydroxyimino-milbemycin $A_4$ (prepared as described in Example 13) as a starting material.

EXAMPLE 15

13-[2-(4-Methoxycarbonlyaminoacetylaminophenyl)-2-methylpropyloxy]-5-hydroxyimino-milbemycin $A_4$ [(I): $R^1$=Et, X=CH$_2$, Z=>C(Me)$_2$, $R^3$=4-NHCOCH$_2$NHCOOMe, n=0 (Compound No. 547)]

Mass spectrum (FAB-MS) m/z:983 (M+H$^+$+triethanolamine=833+1+149).

Nuclear Magnetic Resonance Spectrum (270 MHz) δ ppm:
7.88 (1H, broad singlet);
7.80 (1H, broad singlet);
7.42 (2H, doublet, J=8.9 Hz);
7.31 (2H, doublet, J=8.9 Hz);
5.85–5.69 (3H, multiplet);
5.45–5.26 (3H, multiplet);
5.12 (1H, multiplet);
4.70 (2H, multiplet);
4.66 (1H, singlet);
3.98 (2H, doublet, J=5.9 Hz);
3.90 (1H, singlet);
3.74 (3H, singlet);
3.57 (1H, broad singlet);
3.36 (1H, triplet, J=2.4 Hz);
3.25 (1H, doublet, J=8.9 Hz);
3.13–3.04 (3H, multiplet).

EXAMPLE 16

13-{2-[4-(1-Methoxycarbonylpyrrolidine-2-carbonylamino)phenyl]-2-methylpropoxy}-5-hydroxyimino-milbemycin $A_4$ [(I): $R^1$=Et, X=CH$_2$, Z=>C(Me)$_2$, $R^3$=4-NHCO(1-COOMe-2-Pyrd), n=0 (Compound No. 553)]

Mass spectrum (FAB-MS) m/z:1023 (M+H$^+$+triethanolamine=873+1+149).

Nuclear Magnetic Resonance Spectrum (270 MHz) δ ppm:
  7.89 (1H, broad singlet);
  7.44 (2H, doublet, J=8.5 Hz);
  7.30 (2H, doublet, J=8.5 Hz);
  5.85–5.69 (3H, multiplet);
  5.44–5.27 (3H, multiplet);
  5.14 (1H, multiplet);
  4.75 (2H, multiplet);
  4.66 (1H, singlet);
  4.47 (1H, broad singlet);
  3.91 (1H, singlet);
  3.77 (3H, singlet);
  3.73–3.38 (5H, multiplet);
  3.37 (1H, triplet, J=2.4 Hz);
  3.25 (1H, doublet, J=8.7 Hz);
  3.14–3.04 (3H, multiplet).

EXAMPLE 17

13-[1-(4-Acetylaminophenyl) cyclopropanecarbonyloxy]-5-hydroxyimino-milbemycin $A_4$ [(I): $R^1$=Et, X=CO, Z=>C(CH$_2$)$_2$, $R^3$=4-NHAc, n=0 (Compound No. 392)]

A solution of 0.0121 ml (0.15 mmol) of pyridine in 1.0 ml of methylene chloride and a solution of 0.0142 ml (0.15 mmol) of acetic anhydride in 1.0 ml of methylene chloride were added to a solution of 98.0 mg (0.134 mmol) of 13-[1-(4-aminophenyl)-cyclopropanecarbonyloxy]-5-hydroxyimino-milbemycin $A_4$ (prepared as described in Example 11) in 1.0 ml of methylene chloride at 4° C. The mixture was stirred for 30 minutes at that temperature and then for 10 minutes at room temperature. At the end of this time, the reaction solution was diluted with 15 ml of ethyl acetate, washed 3 times with water and dried over anhydrous sodium sulfate. The solvent was then removed by distillation under reduced pressure. The resulting residue was purified by column chromatography through silica gel, using a 6:4 by volume mixture of ethyl acetate and hexane as the eluent, to give 70.0 mg (yield 67.6%) of the title compound.
Mass spectrum (FAB-MS) m/z:773 (M+H$^+$, M=C$_{44}$H$_{56}$N$_2$O$_{10}$).
Nuclear Magnetic Resonance Spectrum (270 MHz) δ ppm:
  8.26 (1H, singlet);
  7.43 (2H, doublet, J=8.4 Hz);
  7.28 (2H, doublet, J=8.4 Hz);
  5.90–5.73 (3H, multiplet);
  5.44–5.27 (3H, multiplet);
  4.87 (1H, doublet, J=10.6 Hz);
  4.73 & 4.67(2H, AB-quartet, J=14.4 Hz);
  4.65 (1H, singlet);
  3.93 (1H, singlet);
  3.56 (1H, multiplet);
  3.35 (1H, multiplet);
  3.04 (1H, doublet of doublets, J=2.2 & 9.2 Hz);
  2.18 (3H, singlet);
  1.93 (3H, singlet);
  25 1.37 (3H, singlet);
  0.97 (1H, triplet, J=7.3 Hz);
  0.91 (3H, doublet, J=6.5 Hz);
  0.83 (3H, doublet, J=6.5 Hz).

EXAMPLE 18

13-[2-(4-Methanesulfonylaminophenyl)-2-methylpropionyloxy]-5-hydroxyimino-milbemycin $A_4$ [(I): $R^1$=Et, X=CO, Z=>C(Me)$_2$, $R^3$=4-NHSO$_2$Me, n=0 (Compound No. 148)]

18(a) 13-[2-(4-Nitrophenyl)-2-methylpropionyloxy]-5-t-butyldimethylsilyloxyimino-milbemycin $A_4$ 245 mg (3.6 mmol) of imidazole, 543 mg (3.6 mmol) of t-butyldimethylsilyl chloride, and 20 mg of 4-dimethylaminopyridine were added to a solution of 2.289 g (3.0 mmol) of 13-[2-(4-nitrophenyl)-2-methylpropionyloxy]-5-hydroxyimino-milbemycin $A_4$ (prepared as described in Example 1) in 25 ml of methylene chloride, and the mixture was stirred at 40° C. for 2 hours. At the end of this time, the reaction mixture was diluted with 100 ml of ethyl acetate, washed with 0.2M aqueous citric acid, with water, with a 4% w/v aqueous solution of sodium hydrogencarbonate, and with water, in that order, after which it was dried over anhydrous sodium sulfate, and the solvent was removed by evaporation under reduced pressure. The resulting residue was purified by column chromatography through silica gel, using a 1:9 by volume mixture of ethyl acetate and hexane as the eluent, to give 2.542 g (yield 96.6%) of the title compound as an amorphous solid.

18(b) 13-[2-(4-Aminophenyl)-2-methylpropionyloxy]-5-t-butyldimethylsilyloxyimino-milbemycin $A_4$ 2.45 g (2.71 mmol) of 13-[2-(4-nitrophenyl)-2-methylpropionyloxy]-5-t-butyldimethylsilyloxyimino-milbemycin $A_4$ [prepared as described in step (a) above] were dissolved in 15 ml of methanol and 253 mg of bis(triphenylphosphine)-nickel (II) chloride were added to the resulting solution. 170 mg of sodium borohydride were added to the mixture over a period of 10 minutes, whilst stirring, and the stirring was continued for a further 7 minutes. The reaction mixture was then poured into 200 ml of 1% w/v aqueous acetic acid, and extracted with 200 ml and then 50 ml of ethyl acetate. The extract was washed with water, with a 4% aqueous solution of sodium hydrogencarbonate, and with water, in that order, after which it was dried over anhydrous sodium sulfate, and and the solvent as removed by evaporation under reduced pressure. The resulting residue was purified by column chromatography through silica gel, using a 3:7 by volume mixture of ethyl acetate and hexane as the eluent, to give 2.101 g (yield 91.5%) of the title compound as an amorphous solid.

18(c) 13-[2-(4-Methanesulfonylaminophenyl)-2-methyl propionyloxy]-5-hydroxyimino-milbemycin $A_4$ 0.177 ml (2.20 mmol) of pyridine and 252 mg (2.20 mmol) of methanesulfonyl chloride were added to a solution of 169 mg (0.20 mmol) of 13-[2-(4-aminophenyl)-2-methylpropionyloxy]-5-t-butyldimethylsilyloxyimino-milbemycin $A_4$ [prepared as described in step (b) above] in 2.0 ml of methylene chloride, and the mixture was stirred at room temperature for 2 hours. At the end of this time, the reaction mixture was diluted with 20 ml of ethyl acetate, washed with 0.2M aqueous citric acid, with water, with a 4% w/v aqueous solution of sodium hydrogencarbonate, and with water, in that order, after which it was dried over anhydrous sodium sulfate, and the solvent was removed by evaporation under reduced pressure. The resulting residue was dissolved in 3.0 ml of methanol, and 0.3 ml of 1M aqueous hydrochloric acid was added to the solution. The mixture was them stirred at room temperature for 20 minutes. At the end of this time, the reaction mixture was diluted with 20 ml of ethyl acetate, washed with water, with a 4% w/v aqueous solution of sodium hydrogencarbonate, and with water, in that order, after which it was dried over anhydrous sodium sulfate. The solvent was then removed by evaporation under reduced pressure. The resulting residue was purified by column chromatography through silica gel, using a 6:4 by volume mixture of ethyl acetate and hexane as the eluent, to give 717 mg (yield 94.5%) of the title compound as an amorphous solid.

Mass spectrum (FAB-MS) m/z:811 (M+H$^+$, M=C$_{43}$H$_{58}$N$_2$O$_{11}$S).

Nuclear Magnetic Resonance Spectrum (CDCl$_3$) δ ppm:
8.14 (1H, broad singlet);
7.26 (2H, doublet, J=8.6 Hz);
7.20 (2H, doublet, J=8.6 Hz);
6.35 (1H, broad singlet);
4.87 (1H, doublet, J=9.9 Hz);
4.71 & 4.69 (2H, AB-quartet, J=14.5 Hz);
4.65 (1H, singlet);
3.95 (1H, singlet);
3.56 (1H, multiplet);
3.36 (1H, multiplet);
3.04 (1H, multiplet);
2.98 (3H, singlet);
1.93 (3H, singlet);
1.58 (3H, singlet);
1.55 (3H, singlet);
1.31 (3H, singlet);
0.98 (3H, triplet, J=7.3 Hz);
0.84–0.80 (6H, multiplet).

EXAMPLES 19 TO 56

Following a similar procedure to that described in Example 18, the compounds of Examples 19 to 56 were prepared.

EXAMPLE 19

13-[2-(4-Benzoylaminophenyl)-2-methylpropionyloxy]-5-hydroxyimino-milbemycin A$_4$ [(I): R$^1$=Et, X=CO, Z=>C(Me)$_2$, R$^3$=4-NHCOPh, n=0 (Compound No. 63)]

Mass spectrum (FAB-MS) m/z:837 (M+H$^+$, M=C$_{49}$H$_{60}$N$_2$O$_{10}$).

Nuclear Magnetic Resonance Spectrum (CDCl$_3$) δ ppm:
7.89–7.31 (2H, multiplet);
7.77 (1H, broad singlet);
7.60–7.47 (5H, multiplet);
7.31 (2H, doublet, J=8.6 Hz);
4.89 (1H, doublet, J=10.6 Hz);
4.71 & 4.69 (2H, AB-quartet, J=15.2 Hz);
4.65 (1H, singlet);
3.95 (1H, singlet);
3.56 (1H, multiplet);
3.36 (1H, multiplet);
3.04 (1H, multiplet);
1.93 (3H, singlet);
1.59 (3H, singlet);
1.56 (3H, singlet);
1.33 (3H, singlet);
0.98 (3H, triplet, J=7.3 Hz);
0.85–0.82 (6H, multiplet).

EXAMPLE 20

13-[2-(4-Methoxycarbonylaminophenyl)-2-methylpropionyloxy]-5-hydroxyimino-milbemycin A$_4$ [(I): R$^1$=Et, X=CO, Z=>C(Me)$_2$, R$^3$=4-NHCOOMe, n=0 (Compound No. 121)]

Mass spectrum (FAB-MS) m/z:791 (M+H$^+$, M=C$_{44}$H$_{58}$N$_2$O$_{11}$).

NuclearMagnetic Resonance Spectrum (CDCl$_3$) δ ppm:
7.82 (1H, broad singlet);
7.31 (2H, doublet, J=8.6 Hz);
7.23 (2H, doublet, J=8.6 Hz);
6.56 (1H, broad singlet);
4.87 (1H, doublet, J=10.6 Hz);
4.71 & 4.69 (2H, AB-quartet, J=14.5 Hz);
4.65 (1H, singlet);
3.96 (1H, singlet);
3.78 (3H, singlet);
3.56 (1H, multiplet);
3.36 (1H, multiplet);
3.04 (1H, doublet of triplets, J=2.6 & 9.2 Hz);
1.93 (3H, singlet);
1.56 (3H, singlet);
1.53 (3H, singlet);
1.30 (3H, singlet);
0.98 (3H, triplet, J=7.3 Hz);
0.84–0.81 (6H, multiplet).

EXAMPLE 21

13-{2-[4-Acetylaminophenyl]-2-methylpropionyloxy}-5-hydroxyimino-milbemycin A$_4$ [(I): R$^1$=Et, X=CO, Z=>C(Me)$_2$, R$^3$=4-NHAc, n=0 (Compound No. 26)]

Mass spectrum (FAB-MS) m/z:775 (M+H$^+$, M=C$_{44}$H$_{58}$N$_2$O$_{10}$).

Nuclear Magnetic Resonance Spectrum (CDCl$_3$) δ ppm:
7.83 (1H, broad singlet);
7.42 (2H, doublet, J=8.6 Hz);
7.25 (2H, doublet, J=8.6 Hz);
7.11 (1H, broad singlet);
4.87 (1H, doublet, J=10.6 Hz);
4.71 & 4.69(2H, AB-quartet, J=14.5 Hz);
4.65 (1H, singlet);
3.95 (1H, singlet);
3.56 (1H, multiplet);
3.36 (1H, multiplet);
3.04 (1H, doublet of triplets, J=2.3 & 9.2 Hz);
2.18 (3H, singlet);
1.93 (3H, singlet);
1.57 (3H, singlet);
1.53 (3H, singlet);
1.30 (3H, singlet);
0.98 (3H, triplet, J=7.3 Hz);
0.84–0.80 (6H, multiplet).

EXAMPLE 22

13-[2-(4-Phenoxycarbonylaminophenyl)-2-methylpropionyloxy]-5-hydroxyimino-milbemycin A$_4$ [(I): R$^1$=Et, X=CO, Z=>C(Me)$_2$, R$^3$=4-NHCOOPh, n=0 (Compound No. 131)]

Mass spectrum (FAB-MS) m/z:853 (M+H$^+$, M=C$_{49}$H$_{60}$N$_2$O$_{11}$).

Nuclear Magnetic Resonance Spectrum (CDCl$_3$) δ ppm:
7.89 (1H, broad singlet);
7.43–7.37 (4H, multiplet);
7.29–7.24 (2H, multiplet);

7.19 (2H, doublet, J=7.3 Hz);
6.91 (1H, broad singlet);
4.88 (1H, doublet, J=10.6 Hz);
4.72 & 4.69 (2H, AB-quartet, J=14.5 Hz);
4.65 (1H, singlet);
3.96 (1H, singlet);
3.56 (1H, multiplet);
3.36 (1H, multiplet);
3.04 (1H, multiplet);
1.93 (3H, singlet);
1.57 (3H, singlet);
1.55 (3H, singlet);
1.31 (3H, singlet);
0.98 (3H, triplet, J=7.3 Hz);
0.83 (6H, doublet, J=6.6 Hz).

EXAMPLE 23

13-[2-(4-Crotonylaminophenyl)-2-methylpropionyloxy]-5-hydroxyimino-milbemycin $A_4$ [(I): $R^1$=Et, X=CO, Z=>C(Me)$_2$, $R^3$=4-NHCO=CHMe (trans), n=0 (Compound No. 59)]
Mass spectrum (FAB-MS) m/z:801 (M+H$^+$, M=$C_{46}H_{60}N_2O_{10}$).
Nuclear Magnetic Resonance Spectrum (CDCl$_3$) δ ppm:
8.16 (1H, singlet);
7.48 (2H, doublet, J=8.5 Hz);
7.26 (2H, doublet, J=8.5 Hz);
7.11 (1H, singlet);
7.00 (1H, multiplet);
5.93 (1H, doublet of doublets, J=1.4 & 15.2 Hz);
5.84 (1H, doubled doublet of doublets, J=2.0, 2.0 & 11.5 Hz);
4.87 (1H, doublet, J=10.6 Hz);
4.73 & 4.66 (2H, doublet of AB-quartets, J=1.9Hz & 14.6 Hz);
4.65 (1H, singlet);
3.97 (1H, singlet);
3.56 (1H, multiplet);
3.36 (1H, multiplet);
3.04 (1H, doublet of triplets, J=2.0 & 9.4 Hz);
1.93 (3H, singlet);
1.57 (3H, singlet);
1.54 (3H, singlet);
1.30 (3H, singlet);
0.98 (3H, triplet, J=7.3 Hz);
0.83 (3H, doublet, J=6.3 Hz);
0.81 (3H, doublet, J=6.3 Hz).

EXAMPLE 24

13-[2-(4-Pivaloylaminophenyl)-2-methylpropionyloxy]-5-hydroxyimino-milbemycin $A_4$ [(I): $R^1$=Et, X=CO, Z=>C(Me)$_2$, $R^3$=4-NHCOtBu, n=0 (Compound No. 38)]
Mass spectrum (FAB-MS) m/z:817 (M+H$^+$, M=$C_{47}H64N_2O_{10}$).
Nuclear Magnetic Resonance Spectrum (CDCl$_3$) δ ppm:
7.81 (1H, singlet);
4.88 (1H, doublet, J=10.6 Hz);
4.72 & 4.69 (2H, AB-quartet, J=13.9 Hz);
4.65 (1H, singlet);
3.96 (1H, singlet);
3.56 (1H, multiplet);
3.36 (1H, multiplet);
3.04 (1H, doublet of triplets, J=2.6 & 9.2 Hz);
1.93 (3H, singlet);
1.57 (3H, singlet);
1.53 (3H, singlet);
1.32 (12H, singlet);
0.98 (3H, triplet, J=7.3 Hz);
0.83 (6H, doublet, J=6.3 Hz).

EXAMPLE 25

13-[2-(4-Valerylaminophenyl)-2-methylpropionyloxy]-5-hydroxyimino-milbemycin $A_4$ [(I): $R^1$=Et, X=CO, Z=>C(Me)$_2$, $R^3$=4-NHCOBu, n=0 (Compound No. 36)]
Mass spectrum (FAB-MS) m/z:817 (M+H$^+$, M=$C_{47}H_{64}N_2O_{10}$).
Nuclear Magnetic Resonance Spectrum (CDCl$_3$) δ ppm:
7.90 (1H, broad singlet);
7.44 (2H, doublet, J=8.6 Hz);
7.24 (2H, doublet, J=8.6 Hz);
7.08 (1H, singlet);
4.87 (1H, doublet, J=10.6 Hz);
4.72 & 4.69 (2H, AB-quartet, J=15.8 Hz);
4.65 (1H, singlet);
3.96 (1H, singlet);
3.56 (1H, multiplet);
3.36 (1H, multiplet);
3.04 (1H, multiplet);
1.93 (3H, singlet);
1.57 (3H, singlet);
1.53 (3H, singlet);
1.31 (3H, singlet);
0.98 (3H, triplet, J=7.3 Hz);
0.95 (3H, triplet, J=7.6 Hz);
0.84–0.81 (6H, multiplet).

EXAMPLE 26

13-{2-[4-(3-Fluorobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(3-FPh), n=0 (Compound No. 65)]
Mass spectrum (FAB-MS) m/z:855 (M+H$^+$, M=$C_{49}H_{59}FN_2O_{10}$).
Nuclear Magnetic Resonance Spectrum (CDCl$_3$) δ ppm:
9.05 (1H, broad singlet);
7.97 (1H, singlet);
7.65–7.56 (2H, multiplet);
7.57 (2H, doublet, J=8.6 Hz);
7.32–7.20 (1H, multiplet);
7.29 (2H, doublet, J=8.6 Hz);
4.88 (1H, doublet, J=10.5 Hz);
4.70 & 4.68 (2H, AB-quartet, J=15.2 Hz);
4.65 (1H, singlet);
4.00 (1H, singlet);

3.56 (1H, multiplet);
3.36 (1H, multiplet);
3.05 (1H, multiplet);
1.91 (3H, singlet);
1.58 (3H, singlet);
1.56 (3H, singlet);
1.33 (3H, singlet);
0.98 (3H, triplet, J=7.2 Hz);
0.83 (6H, doublet, J=6.6 Hz).

EXAMPLE 27

13-[2-(4-Methylthioacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCH$_2$SMe, n=0 (Compound No. 51)]
Mass spectrum (FAB-MS) m/z:821 (M+H$^+$, M=C$_{45}$H$_{60}$N$_2$O$_{10}$S).
Nuclear Magnetic Resonance Spectrum (CDCl$_3$) δ ppm:
  8.67 (1H, singlet);
  8.30 (1H, broad singlet);
  7.50 (2H, doublet, J=8.6 Hz);
  7.28 (2H, doublet, J=8.6 Hz);
  4.88 (1H, doublet, J=10.5 Hz);
  4.72 & 4.69 (2H, AB-quartet, J=14.6 Hz);
  4.66 (1H, singlet);
  3.97 (1H, singlet);
  3.56 (1H, multiplet);
  3.36 (1H, multiplet);
  3.35 (2H, singlet);
  3.04 (1H, multiplet);
  2.05 (3H, singlet);
  1.93 (3H, singlet);
  1.57 (3H, singlet);
  1.55 (3H, singlet);
  1.32 (3H, singlet);
  0.98 (3H, triplet, J=7.2 Hz);
  0.83 (6H, doublet, J=6.4 Hz).

EXAMPLE 28

13-[2-(4-Methoxyacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCH$_2$OMe, n=0 (Compound No. 47)]ps Mass spectrum (FAB-MS) m/z:805 (M+H$^+$, M=C$_{45}$H$_{60}$N$_2$O$_{11}$).
Nuclear Magnetic Resonance Spectrum (CDCl$_3$) δ ppm:
  9.01 (1H, broad singlet);
  8.24 (1H, singlet);
  7.51 (2H, doublet, J=8.6 Hz);
  7.28 (2H, doublet, J=8.6 Hz);
  4.87 (1H, doublet, J=10.5 Hz);
  4.71 & 4.68 (2H, AB-quartet, J=15.2 Hz);
  4.66 (1H, singlet);
  3.97 (3H, singlet);
  3.58 (1H, multiplet);
  3.51 (3H, singlet);
  3.36 (1H, multiplet);
  3.04 (1H, multiplet);
  1.92 (3H, singlet);
  1.57 (3H, singlet);
  1.54 (3H, singlet);
  1.30 (3H, singlet);
  0.98 (3H, triplet, J=7.2 Hz);
  0.83 (3H, doublet, J=6.4 Hz);
  0.82 (3H, doublet, J=6.4 Hz).

EXAMPLE 29

13-[2-(4-Cyclopropylcarbonylaminophenyl)-2-methylpropionyloxy]-5-hydroxyimino-milbemycin $A_4$ [(I): $R^1$=Et, X=CO, Z=>C(Me)$_2$, $R^3$=4-NHCOcPr, n=0 (Compound No. 39)]
Mass spectrum (FAB-MS) m/z:801 (M+H$^+$, M=C$_{46}$H$_{60}$N$_2$O$_{10}$).
Nuclear Magnetic Resonance Spectrum (CDCl$_3$) δ ppm:
  8.80 (1H, broad singlet);
  7.49 (1H, singlet);
  7.44 (2H, doublet, J=8.6 Hz);
  7.24 (2H, doublet, J=8.6 Hz);
  4.87 (1H, doublet, J=10.6 Hz);
  4.72 & 4.69 (2H, AB-quartet, J=14.8 Hz);
  4.66 (1H, singlet);
  3.57 (1H, multiplet);
  3.36 (1H, multiplet);
  3.04 (1H, multiplet);
  1.92 (3H, singlet);
  1.56 (3H, singlet);
  1.53 (3H, singlet);
  1.30 (3H, singlet);
  1.09 (2H, multiplet);
  0.98 (3H, triplet, J=7.3 Hz);
  0.83 (3H, doublet, J=6.3 Hz);
  0.82 (3H, doublet, J=6.5 Hz).

EXAMPLE 30

13-[2-(4-Cyclohexanecarbonylaminophenyl)-2-methylpropionyloxy]-5-hydroxyimino-milbemycin $A_4$ [(I): $R^1$=Et, X=CO, Z=>C(Me)$_2$, $R^3$=4-NHCOcHx, n=0 (Compound No. 42)]
Mass spectrum (FAB-MS) m/z:843 (M+H$^+$, M=C$_{49}$H$_{66}$N$_2$O$_{10}$).
Nuclear Magnetic Resonance Spectrum (CDCl$_3$) δ ppm:
  7.99 (1H, broad singlet);
  7.45 (2H, doublet, J=8.6 Hz);
  7.24 (2H, doublet, J=8.6 Hz);
  7.10 (1H, broad singlet);
  4.87 (1H, doublet, J=10.6 Hz);
  4.72 & 4.70 (2H4, AB-quartet, J=14.5 Hz);
  4.65 (1H, singlet);
  3.96 (1H, singlet);
  3.57 (1H, multiplet);
  3.36 (1H, multiplet);
  3.04 (1H, multiplet);
  1.93 (3H, singlet);
  1.56 (3H, singlet);
  1.53 (3H, singlet);
  1.31 (3H, singlet);

0.98 (3H, triplet, J=7.3 Hz);
0.83 (3H, doublet, J=6.3 Hz);
0.82 (3H, doublet, J=6.5 Hz).

EXAMPLE 31

13-{2-[4-(4-Methoxyphenyl)acetylaminophenyl]-2-methylpropionyloxy}-5-hydroxyimino-milbemycin $A_4$ [(I): $R^1$=Et, X=CO, Z=>C(Me)$_2$, $R^3$=4-NHCOCH$_2$(4-MeOPh), n=0 (Compound No. 62)]
Mass spectrum (FAB-MS) m/z:881 (M+H$^+$, M=C$_{51}$H$_{64}$N$_2$O$_{11}$).
Nuclear Magnetic Resonance Spectrum (CDCl$_3$) δ ppm:
7.91 (1H, broad singlet);
7.34 (2H, doublet, J=8.6 Hz);
7.25 (2H, doublet, J=8.6 Hz);
7.21 (2H, doublet, J=8.6 Hz);
7.01 (1H, broad singlet);
6.94 (2H, doublet, J=8.6 Hz);
4.86 (1H, doublet, J=10.5 Hz);
4.72 & 4.70 (2H, AB-quartet, J=14.3 Hz);
4.66 (1H, singlet);
3.96 (1H, singlet);
3.84 (3H, singlet);
3.69 (2H, singlet);
3.58 (1H, multiplet);
3.36 (1H, multiplet);
3.04 (1H, multiplet);
1.94 (3H, singlet);
1.54 (3H, singlet);
1.51 (3H, singlet);
1.29 (3H, singlet);
0.98 (3H, triplet, J=7.2 Hz);
0.82 (6H, doublet, J=6.6 Hz).

EXAMPLE 32

13-{2-[4-(4-Nitrobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(4-NO$_2$Ph), n=0 (Compound No. 73)]
Mass spectrum (FAB-MS) m/z:882 (M+H$^+$, M=C$_{49}$H$_{60}$N$_3$O$_{12}$).
Nuclear Magnetic Resonance Spectrum (CDCl$_3$) δ ppm:
9.10 (1H, broad singlet);
8.35 (2H, doublet, J=8.6 Hz);
8.05 (2H, doublet, J=8.6 Hz);
7.82 (1H, singlet);
7.58 (2H, doublet, J=8.6 Hz);
7.34 (2H, doublet, J=8.6 Hz);
4.89 (1H, doublet, J=10.6 Hz);
4.74 & 4.66 (2H, AB-quartet, J=15.0 Hz);
4.65 (1H, singlet);
3.97 (1H, singlet);
3.57 (1H, multiplet);
3.35 (1H, multiplet);
3.04 (1H, multiplet);
1.93 (3H, singlet);
1.60 (3H, singlet);
1.57 (3H, singlet);
1.33 (3H, singlet);
0.98 (3H, triplet, J=7.3 Hz);
0.90–0.80 (4H, multiplet).

EXAMPLE 33

13-{2-[4-(2-Furoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(2-Furyl), n=0 (Compound No. 77)]
Mass spectrum (FAB-MS) m/z:827 (M+H$^+$, M=C$_{47}$H$_{58}$N$_2$O$_{11}$).
Nuclear Magnetic Resonance Spectrum (CDCl$_3$) δ ppm:
8.08 (1H, singlet);
7.59 (2H, doublet, J=8.6 Hz);
7.51 (1H, doublet, J=2.0 Hz);
7.30 (2H, doublet, J=8.6 Hz);
7.26 (1H, doublet, J=3.7 Hz);
6.56 (1H, doublet of doublets, J=2.0 & 3.7 Hz);
4.88 (1H, doublet, J=10.5 Hz);
4.71 & 4.68 (2H, AB-quartet, J=14.3 Hz);
4.66 (1H, singlet);
3.97 (1H, singlet);
3.57 (1H, multiplet);
3.36 (1H, multiplet);
3.04 (1H, multiplet);
1.92 (3H, singlet);
1.58 (3H, singlet);
1.56 (3H, singlet);
1.31 (3H, singlet);
0.98 (3H, triplet, J=7.3 Hz);
0.83 (6H, doublet, J=6.4 Hz).

EXAMPLE 34

13-[2-(4-Propioloylaminophenyl)-2-methylpropionyloxy]-5-hydroxyimino-milbemycin $A_4$ [(I): $R^1$=Et, X=CO, Z=>C(Me)$_2$, $R^3$=4-NHCOC≡CH, n=0 (Compound No. 60)]
Mass spectrum (FAB-MS) m/z:785 (M+H$^+$, M=C$_{45}$H$_{56}$N$_2$O$_{10}$).
Nuclear Magnetic Resonance Spectrum (CDCl$_3$) δ ppm:
7.61 (1H, broad singlet);
7.62 (1H, singlet);
7.45 (2H, doublet, J=8.6 Hz);
7.27 (2H, doublet, J=8.6 Hz);
4.87 (1H, doublet, J=10.5 Hz);
4.71 & 4.69 (2H, AB-quartet, J=14.4 Hz);
4.66 (1H, singlet);
3.98 (1H, broad singlet);
3.57 (1H, multiplet);
3.36 (1H, multiplet);
3.04 (1H, multiplet);
2.93 (1H, singlet);
1.92 (3H, singlet);
1.57 (3H, singlet);
1.54 (3H, singlet);
1.30 (3H, singlet);
0.98 (3H, triplet, J=7.3 Hz);
0.84 (3H, doublet, J=6.4 Hz);

0.83 (3H, doublet, J=6.5 Hz).

EXAMPLE 35

13-{2-[4-(4-Nitrophenyl)acetylaminophenyl]-2-methylpropionyloxy}-5-hydroxyimino-milbemycin $A_4$ [(I): $R^1$=Et, X=CO, Z=>C(Me)$_2$, $R^3$=4-NHCOCH$_2$(4-NO$_2$Ph), n=0 (Compound No. 61)]
Mass spectrum (FAB-MS) m/z:896 (M+H$^+$, M=C$_{50}$H$_{61}$N$_3$O$_{12}$).
Nuclear Magnetic Resonance Spectrum (CDCl$_3$) δ ppm:
  8.25 (2H, doublet, J=8.6 Hz);
  7.80 (1H, broad singlet);
  7.54 (2H, doublet, J=8.6 Hz);
  7.39 (2H, doublet, J=8.6 Hz);
  7.24 (2H, doublet, J=8.6 Hz);
  7.11 (1H, broad singlet);
  4.87 (1H, doublet, J=10.6 Hz);
  4.71 & 4.69 (2H, AB-quartet, J=14.1 Hz);
  4.65 (1H, singlet);
  3.96 (1H, singlet);
  3.82 (2H, singlet);
  3.58 (1H, multiplet);
  3.36 (1H, multiplet);
  3.03 (1H, doublet of triplets, J=2.2 & 7.1 Hz);
  1.93 (3H, singlet);
  1.56 (3H, singlet);
  1.52 (3H, singlet);
  1.29 (3H, singlet);
  0.98 (3H, triplet, J=7.3 Hz);
  0.84–0.80 (6H, multiplet).

EXAMPLE 36

13-{2-[4-(4-Methoxybenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(4-MeOPh), n=0 (Compound No. 69)]
Mass spectrum (FAB-MS) m/z:867 (M+H$^+$, M=C$_{50}$H$_{62}$N$_2$O$_{11}$).
Nuclear Magnetic Resonance Spectrum (CDCl$_3$) δ ppm:
  7.85 (2H, doublet, J=8.8 Hz);
  7.70 (1H, broad singlet);
  7.57 (2H, doublet, J=8.7 Hz);
  7.30 (2H, doublet, J=8.7 Hz);
  6.98 (2H, doublet, J=8.8 Hz);
  4.88 (1H, doublet, J=10.4 Hz);
  4.72 & 4.70 (2H, AB-quartet, J=14.6 Hz);
  4.65 (1H, singlet);
  3.96 (1H, singlet);
  3.88 (3H, singlet);
  3.57 (1H, multiplet);
  3.35 (1H, multiplet);
  3.04 (1H, doublet of triplets, J=2.4 & 9.1 Hz);
  1.93 (3H, singlet);
  1.59 (3H, singlet);
  1.56 (3H, singlet);
  1.32 (3H, singlet);
  0.98 (3H, triplet, J=7.3 Hz);
  0.83 (6H, doublet, J=6.3 Hz).

EXAMPLE 37

13-{2-[4-(4-t-Butylbenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(4-tBuPh), n=0 (Compound No. 72)]
Mass spectrum (FAB-MS) m/z:893 (M+H$^+$, M=C$_{53}$H$_{68}$N$_2$O$_{10}$).
Nuclear Magnetic Resonance Spectrum (CDCl$_3$) δ ppm:
  7.81 (2H, doublet, J=8.4 Hz);
  7.76 (1H, broad singlet);
  7.58 (2H, doublet, J=8.6 Hz);
  7.51 (2H, doublet, J=8.4 Hz);
  7.31 (2H, doublet, J=8.6 Hz);
  4.89 (1H, doublet, J=10.4 Hz);
  4.72 & 4.70 (2H, AB-quartet, J=14.8 Hz);
  4.65 (1H, singlet);
  3.97 (1H, singlet);
  3.56 (1H, multiplet);
  3.35 (1H, multiple t);
  3.04 (1H, multiplet);
  1.93 (3H, singlet);
  1.58 (3H, singlet);
  1.56 (3H, singlet);
  1.36 (9.H, singlet);
  1.33 (3H, sin,-let);
  0.99 (3H, triplet, J=7.2 Hz);
  0.78 (6H, doublet, J=6.3 Hz).

EXAMPLE 38

13-{2-[4-(4-Chlorobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(4-ClPh), n=0 (Compound No. 67)]
Mass spectrum (FAB-MS) m/z:801 (M+H$^+$, M=C$_{49}$H$_{59}$ClN$_2$O$_{10}$).
Nuclear Magnetic Resonance Spectrum (CDCl$_3$) δ ppm:
  7.94 (1H, broad singlet);
  7.83 (2H, doublet, J=8.5 Hz);
  7.74 (1H, broad singlet);
  7.57 (2H, doublet, J=8.6 Hz);
  7.48 (2H, doublet, J=8.5 Hz);
  7.32 (2H, doublet, J=8.6 Hz);
  4.89 (1H, doublet, J=10.5 Hz);
  4.72 & 4.69 (2H, AB-quartet, J=14.4 Hz);
  4.65 (1H, singlet);
  3.97 (1H, singlet);
  3.56 (1H, multiplet);
  3.35 (1H, multiplet);
  3.04 (1H, multiplet);
  1.93 (3H, singlet);
  1.59 (3H, singlet);
  1.56 (3H, singlet);
  1.32 (3H, singlet);
  0.99 (3H, triplet, J=7.3 Hz);
  0.83 (6H, doublet, J=6.4 Hz).

EXAMPLE 39

13-[2-(4-Cyclobutanecarbonylaminophenyl)-2-methylpropionyloxy]-5-hydroxyimino-milbemycin $A_4$ [(I): $R^1$=Et, X=CO, Z=>C(Me)$_2$, $R^3$=4-NHCOcBu, n=0 (Compound No. 40)]
Mass spectrum (FAB-MS) m/z:815 (M+H$^+$, M=C$_{47}$H$_{62}$N$_2$O$_{10}$).

Nuclear Magnetic Resonance Spectrum (CDCl$_3$) δ ppm:
  9.24 (1H, broad singlet);
  7.46 (2H, doublet, J=8.6 Hz);
  7.24 (2H, doublet, J=8.6 Hz);
  7.20 (1H, singlet);
  4.87 (1H, doublet, J=9.9 Hz);
  4.71 & 4.67 (2H, AB-quartet, J=14.9 Hz);
  4.66 (1H, singlet);
  3.99 (1H, broad singlet);
  3.57 (1H, multiplet);
  3.36 (1H, multiplet);
  3.15 (1H, multiplet);
  3.04 (1H, multiplet);
  1.91 (3H, singlet);
  1.56 (3H, singlet);
  1.53 (3H, singlet);
  1.30 (3H, singlet);
  0.98 (3H, triplet, J=7.3 Hz);
  0.83 (3H, doublet, J=6.3 Hz);
  0.82 (3H, doublet, J=6.4 Hz).

EXAMPLE 40

13-[2-(4-Cyclopentanecarbonylaminophenyl)-2-methylpropionyloxy]-5-hydroxyimino-milbemycin A$_4$ [(I): R$^1$=Et, X=CO, Z=>C(Me)$_2$, R$^3$=4-NHCOcPn, n=0 (Compound No. 41)]
Mass spectrum (FAB-MS) m/z:829 (M+H$^+$, M=C$_{48}$H$_{64}$N$_2$O$_{10}$).
Nuclear Magnetic Resonance Spectrum (CDCl$_3$) δ ppm:
  7.46 (2H, doublet, J=8.6 Hz);
  7.24 (2H, doublet, J=8.6 Hz);
  7.21 (1H, singlet);
  4.87 (1H, doublet, J=10.5 Hz);
  4.72 & 4.69 (2H, AB-quartet, J=15.3 Hz);
  4.66 (1H, singlet);
  3.57 (1.H, multiplet);
  3.36 (1H, multiplet);
  3.04 (1H, multiplet);
  2.67 (1H, multiplet);
  1.92 (3H, singlet);
  1.56 (3H, singlet);
  1.53 (3H, singlet);
  1.31 (3H, singlet);
  0.98 (3H, triplet, J=7.3 Hz);
  0.83 (3H, doublet, J=6.3 Hz);
  0.82 (3H, doublet, J=6.5 Hz).

EXAMPLE 41

13-[2-(4-Propionylaminophenyl)-2-methylpropionyloxy]-5-hydroxyimino-milbemycin A$_4$ [(I): R$^1$=Et, X=CO, Z=>C(Me)$_2$, R$^3$=4-NHCOEt, n=0 (Compound No. 33)]
Mass spectrum (FAB-MS) m/z:789 (M+H$^+$, M=C$_{45}$H$_{60}$N$_2$O$_{10}$).
Nuclear Magnetic Resonance Spectrum (CDCl$_3$) δ ppm:
  9.09 (1H, broad singlet);
  7.45 (2H, doublet, J=8.6 Hz);
  7.24 (2H, doublet, J=8.6 Hz);
  4.87 (1H, doublet, J=10.6 Hz);
  4.71 & 4.69 (2H, AB-quartet, J=14.5 Hz);
  4.66 (1H, singlet);
  3.98 (1H, broad singlet);
  3.57 (1H, multiplet);
  3.36 (1H, multiplet);
  3.04 (1H, multiplet);
  2.38 (1H, quartet, J=7.6 Hz);
  1.92 (3H, singlet);
  1.56 (3H, singlet);
  1.53 (3H, singlet);
  1.30 (3H, singlet);
  0.98 (3H, triplet, J=7.3 Hz);
  0.83 (3H, doublet, J=6.4 Hz);
  0.82 (3H, doublet, J=6.5 Hz).

EXAMPLE 42

13-[2-(4-Isovalerylaminophenyl)-2-methylpropionyloxy]-5-hydroxyimino-milbemycin A$_4$ [(I): R$^1$=Et, X=CO, Z=>C(Me)$_2$, R$^3$=4-NHCOiBu, n=0 (Compound No. 37)]
Mass spectrum (FAB-MS) m/z:817 (M+H$^+$, M=C$_{47}$H$_{64}$N$_2$O$_{10}$).
Nuclear Magnetic Resonance Spectrum (CDCl$_3$) δ ppm:
  8.70 (1H, broad singlet);
  7.45 (2H, doublet, J=8.6 Hz);
  7.25 (2H, doublet, J=8.6 Hz);
  7.16 (1H, singlet);
  4.87 (1H, doublet, J=10.5 Hz);
  4.71 & 4.68 (2H, AB-quartet, J=15.0 Hz);
  4.66 (1H, singlet);
  3.88 (1H, broad singlet);
  3.57 (1H, multiplet);
  3.36 (1H, multiplet);
  3.04 (1H, multiplet);
  2.21 (2H, doublet, J=2.3 Hz);
  1.92 (3H, singlet);
  1.56 (3H, singlet);
  1.53 (3H, singlet);
  1.31 (3H, singlet);
  1.02–0.92 (9H, multiplet);
  0.83 (3H, doublet, J=6.6 Hz);
  0.82 (3H, doublet, J=6.3 Hz).

EXAMPLE 43

13-[2-(4-Isobutyrylaminophenyl)-2-methylpropionyloxy]-5-hydroxyimino-milbemycin A$_4$ [(I): R$^1$=Et, X=CO, Z=>C(Me)$_2$, R$^3$=4-NHCOiPr, n=0 (Compound No. 35)]
Mass spectrum (FAB-MS) m/z:803 (M+H$^+$, M=C$_{46}$H$_{62}$N$_2$O$_{10}$).
Nuclear Magnetic Resonance Spectrum (CDCl$_3$) δ ppm:
  9.20 (1H, broad singlet);
  7.45 (2H, doublet, J=8.6 Hz);
  7.31 (1H, singlet);
  7.24 (2H, doublet, J=8.6 Hz);
  4.87 (1H, doublet, J=10.5 Hz);
  4.71 & 4.69 (2H, AB-quartet, J=15.3 Hz);

4.66 (1H, singlet);
4.01 (1H, broad singlet);
3.57 (1H, multiplet);
3.36 (1H, multiplet);
3.04 (1H, multiplet);
2.33 (1H, multiplet);
1.92 (3H, singlet);
1.56 (3H, singlet);
1.53 (3H, singlet);
1.31 (3H, singlet);
1.03–0.95 (9H, multiplet);
0.83 (3H, doublet, J=6.2 Hz);
0.82 (3H, doublet, J=6.4 Hz).

EXAMPLE 44

13-[2-(4-Butyrylaminophenyl)-2-methylpropionyloxy]-5-hydroxyimino-milbemycin $A_4$ [(I): $R^1$=Et, X=CO, Z=>C(Me)$_2$, $R^3$=4-NHCOPr, n=0 (Compound No. 34)]

Mass spectrum (FAB-MS) m/z:803 (M+H$^+$, M=C$_{46}$H$_{62}$N$_2$O$_{10}$).

Nuclear Magnetic Resonance Spectrum (CDCl$_3$) δ ppm:
9.35 (1H, broad singlet);
7.45 (2H, doublet, J=8.6 Hz);
7.35 (1H, singlet);
7.24 (2H, doublet, J=8.6 Hz);
4.87 (1H, doublet, J=10.5 Hz);
4.72 & 4.69 (2H, AB-quartet, J=15.0 Hz);
4.66 (1H, singlet);
3.99 (1H, broad singlet);
3.57 (1H, multiplet);
3.36 (1H, multiplet);
3.04 (1H, multiplet);
2.51 (1H, triplet, J=6.8 Hz);
1.91 (3H, singlet);
1.56 (3H, singlet);
1.53 (3H, singlet);
1.31 (3H, singlet);
0.98 (3H, triplet, J=7.2 Hz);
0.83 (3H, doublet, J=6.3 Hz);
0.82 (3H, doublet, J=6.5 Hz).

EXAMPLE 45

13-[2-(4-Bromoacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCH$_2$Br, n=0 (Compound No. 43)]

Mass spectrum (FAB-MS) m/z:853 (M+H$^+$, M=C$_{44}$H$_{57}$BrN$_2$O$_{10}$).

Nuclear Magnetic Resonance Spectrum (CDCl$_3$) δ ppm:
8.09 (1H, broad singlet);
7.47 (2H, doublet, J=8.6 Hz);
7.30 (2H, doublet, J=8.6 Hz);
4.88 (1H, doublet, J=10.7 Hz);
4.72 & 4.69 (2H, AB-quartet, J=14.6 Hz);
4.65 (1H, singlet);
4.03 (2H, singlet);
3.56 (1H, multiplet);
3.37 (1H, multiplet);
3.04 (1H, doublet of triplets, J=2.0 & 8.9 Hz);
1.93 (3H, singlet);
1.58 (3H, singlet);
1.56 (3H, singlet);
1.31 (3H, singlet);
0.98 (3H, triplet, J=7.2 Hz);
0.83–0.74 (6H, multiplet).

EXAMPLE 46

13-[2-(4-Cyanoacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCH$_2$CN, n=0 (Compound No. 46)]

Mass spectrum (FAB-MS) m/z:853 (M+H$^+$, M=C$_{45}$H$_{57}$N$_3$O$_{10}$).

Nuclear Magnetic Resonance Spectrum (CDCl$_3$) δ ppm:
7.69 (1H, broad singlet);
7.44 (2H, doublet, J=8.6 Hz);
7.30 (2H, doublet, J=8.6 Hz);
4.88 (1H, doublet, J=10.5 Hz);
4.72 & 4.70 (2H, AB-quartet, J=14.8 Hz);
4.66 (1H, singlet);
3.57 (1H, multiplet);
3.56 (2H, singlet);
3.36 (1H, multiplet);
3.04 (1H, multiplet);
1.93 (3H, singlet);
1.58 (3H, singlet);
1.55 (3H, singlet);
1.31 (3H, singlet);
0.98 (3H, triplet, J=7.2 Hz);
0.84–0.74 (6H, multiplet).

EXAMPLE 47

13-{2-[4-(3-Nitrobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(3-NO$_2$Ph), n=0 (Compound No. 74)]

Mass spectrum (FAB-MS) m/z:871 (M+H$^+$, M=C$_{49}$H$_{59}$N$_3$O$_{12}$).

Nuclear Magnetic Resonance Spectrum (CDCl$_3$) δ ppm:
8.71 (1H, singlet);
8.43 (1H, doublet of doublets, J=1.4 & 8.0 Hz);
8.27 (1H, doublet, J=8.0 Hz);
7.88 (1H, broad singlet);
7.73 (1H, doublet of doublets, J=8.0 & 8.0 Hz);
7.60 (2H, doublet, J=8.6 Hz);
7.35 (2H, doublet, J=8.6 Hz);
4.90 (1H, doublet, J=10.5 Hz);
4.72 & 4.69 (2H, AB-quartet, J=14.4 Hz);
4.65 (1H, singlet);
3.56 (1H, multiplet);
3.36 (1H, multiplet);
3.04 (1H, doublet of triplets, J=2.2 & 9.7 Hz);
1.93 (3H, singlet);
1.60 (3H, singlet);
1.57 (3H, singlet);

1.33 (3H, singlet);
0.99 (3H, triplet, J=7.2 Hz);
0.88–0.79 (6H, multiplet).

EXAMPLE 48

13-{2-[4-(3-Chlorobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(3-ClPh), n=0 (Compound No. 68)]

Mass spectrum (FAB-MS) m/z:871 (M+H$^+$, M=$C_{49}H_{59}ClN_2O_{10}$).
Nuclear Magnetic Resonance Spectrum (CDCl$_3$) δ ppm:
7.87–7.85 (1H, multiplet);
7.76–7.70 (2H, multiplet);
7.57 (2H, doublet, J=8.6 Hz);
7.44 (1H, doublet of doublets, J=7.8 & 7.8 Hz);
7.32 (2H, doublet, J=8.6 Hz);
4.89 (1H, doublet, J=10.5 Hz);
4.71 & 4.69 (2H, AB-quartet, J=14.2 Hz);
4.65 (1H, singlet);
3.56 (1H, multiplet);
3.36 (1H, multiplet);
3.04 (1H, multiplet);
1.93 (3H, singlet);
1.59 (3H, singlet);
1.56 (3H, singlet);
1.32 (3H, singlet);
0.98 (3H, triplet, J=7.3 Hz);
0.84–0.77 (6H, multiplet).

EXAMPLE 49

13-{2-[4-(4-Fluorobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(4-FPh), n=0 (Compound No. 66)]

Mass spectrum (FAB-MS) m/z:855 (M+H$^+$, M=$C_{49}H_{59}FN_2O_{10}$).
Nuclear Magnetic Resonance Spectrum (CDCl$_3$) δ ppm:
7.90 (2H, doublet, J=8.5 Hz);
7.72 (1H, broad singlet);
7.57 (2H, doublet, J=8.6 Hz);
7.32 (1H, doublet, J=7.6 Hz);
7.18 (2H, doublet, J=8.5 Hz);
4.89 (1H, doublet, J=10.5 Hz);
4.72 & 4.69 (2H, AB-quartet, J=14.4 Hz);
4.65 (1H, singlet);
3.56 (1H, multiplet);
3.36 (1H, multiplet);
3.04 (1H, doublet of triplets, J=1.9 & 8.9 Hz);
1.93 (3H, singlet);
1.59 (3H, singlet);
1.56 (3H, singlet);
1.32 (3H, singlet);
0.98 (3H, triplet, J=7.2 Hz);
0.83 (6H, doublet, J=6.3 Hz).

EXAMPLE 50

13-{2-[4-(2-Fluorobenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(2-FPh), n=0 (Compound No. 64)]

Mass spectrum (FAB-MS) m/z:855 (M+H$^+$, M=$C_{49}H_{59}FN_2O_{10}$).
Nuclear Magnetic Resonance Spectrum (CDCl$_3$) δ ppm:
7.61 (2H, doublet, J=8.6 Hz);
7.31 (1H, doublet, J=7.6 Hz);
4.89 (1H, doublet, J=10.5 Hz);
4.72 & 4.69 (2H, AB-quartet, J=14.4 Hz);
4.65 (1H, singlet);
3.56 (1H, multiplet);
3.36 (1H, multiplet);
3.04 (1H, multiplet);
1.93 (3H, singlet);
1.59 (3H, singlet);
1.56 (3H, singlet);
1.32 (3H, singlet);
0.98 (3H, triplet, J=7.3 Hz);
0.83 (6H, doublet, J=6.3 Hz).

EXAMPLE 51

13-[2-(4-Trifluoroacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCF$_3$, n=0 (Compound No. 44)]

Mass spectrum (FAB-MS) m/z:871 (M+H$^+$, M=$C_{44}H_{55}F_3N_2O_{10}$).
Nuclear Magnetic Resonance Spectrum (CDCl$_3$) δ ppm:
8.81 (1H, broad singlet);
8.03 (1H, singlet);
7.51 (2H, doublet, J=8.7 Hz);
7.33 (2H, doublet, J=8.7 Hz);
4.88 (1H, doublet, J=10.5 Hz);
4.71 & 4.68 (2H, AB-quartet, J=14.2 Hz);
4.65 (1H, singlet);
3.98 (1H, broad singlet);
3.57 (1H, multiplet);
3.36 (1H, multiplet);
3.04 (1H, multiplet);
1.92 (3H, singlet);
1.58 (3H, singlet);
1.56 (3H, singlet);
1.31 (3H, singlet);
0.98 (3H, triplet, J=7.3 Hz);
0.83 (6H, doublet, J=6.4 Hz).

EXAMPLE 52

13-[2-(4-Difluoroacetylaminophenyl)-2-methylpropionyloxy]-5-hydroxyimino-milbemycin $A_4$ [(I): $R^1$=Et, X=CO, Z=>C(Me)$_2$, $R^3$=4-NHCOCF$_2$, n=0 (Compound No. 45)]

Mass spectrum (FAB-MS) m/z:811 (M+H$^+$, M=$C_{44}H_{56}F_2N_2O_{10}$).
Nuclear Magnetic Resonance Spectrum (CDCl$_3$) δ ppm:
8.72 (1H, broad singlet);
7.93 (1H, singlet);
7.52 (2H, doublet, J=8.7 Hz);
7.31 (2H, doublet, J=8.7 Hz);
6.02 (1H, triplet, J=54.6 Hz);
4.88 (1H, doublet, J=10.5 Hz);
4.71 & 4.69 (2H, AB-quartet, J=15.2 Hz);
4.65 (1H, singlet);

3.98 (1H, broad singlet);
3.57 (1H, multiplet);
3.36 (1H, multiplet);
3.04 (1H, multiplet);
1.92 (3H, singlet);
1.58 (3H, singlet);
1.55 (3H, singlet);
1.30 (3H, singlet);
0.98 (3H, triplet, J - 7.3 Hz);
0.83 (3H, doublet, J=6.4 Hz);
0.82 (3H, doublet, J=6.5 Hz).

EXAMPLE 53

13-{2-[4-(3-Methoxybenzoyl)aminophenyl]-2-methylpropionyloxy}-5-hydroxyimino-milbemycin $A_4$ [(I): $R^1$=Et, X=CO, Z=>C(Me)$_2$, $R^3$=4-NHCOC(3-MeOPh), n=0 (Compound No. 70)]

Mass spectrum (FAB-MS) m/z:867 (M+H$^+$, M=$C_{50}H_{62}N_2O_{11}$).

Nuclear Magnetic Resonance Spectrum (CDCl$_3$) δ ppm:
8.05 (1H, broad singlet);
7.78 (1H, singlet);
7.58 (2H, doublet, J=8.6 Hz);
7.44 (1H, doublet, J=1.4 Hz);
7.34–7.41 (2H, multiplet);
7.31 (2H, doublet, J=8.6 Hz);
7.09 (1H, multiplet);
4.88 (1H, doublet, J=10.5 Hz);
4.72 & 4.69 (2H, AB-quartet, J=14.5 Hz);
4.65 (1H, singlet);
3.96 (1H, singlet);
3.88 (3H, singlet);
3.57 (1H, multiplet);
3.35 (1H, multiplet);
3.04 (1H, doublet of triplets, J=2.0 & 9.3 Hz);
1.93 (3H, singlet);
1.59 (3H, singlet);
1.56 (3H, singlet);
1.32 (3H, singlet);
0.98 (3H, triplet, J=7.3 Hz);
0.83 (6H, doublet, J=5.8 Hz).

EXAMPLE 54

13-[2-(4-Thenoylaminophenyl)-2-methylpropionyloxy]-5-hydroxyimino-milbemycin $A_4$ [(I): $R^1$=Et, X=CO, Z=>C(Me)$_2$, $R^3$=4-NHCO(2-Thienyl), n=0 (Compound No. 78)]

Mass spectrum (FAB-MS) m/z:843 (M+H$^+$, M=$C_{47}H_{58}N_2O_{10}S$).

Nuclear Magnetic Resonance Spectrum (CDCl$_3$) δ ppm:
8.09 (1H, singlet);
7.66 (1H, singlet);
7.62 (1H, multiplet);
7.55 (2H, doublet, J=8.7 Hz);
7.55 (1H, doublet of doublets, J=2.0 & 4.2 Hz);
7.30 (2H, doublet, J=8.7 Hz);
7.14 (1H, doublet of doublets, J=4.2 & 4.2 Hz);
5.84 (1H, doubled doublet of doublets, J=2.1, 2.1, & 11.5 Hz);
5.78 (1H, multiplet);
4.88 (1H, doublet, J=10.4 Hz);
4.73 & 4.67 (2H, doublet of AB-quartets, J=2.0 & 14.5 Hz);
4.65 (1H, singlet);
3.97 (1H, singlet);
3.56 (1H, multiplet);
3.36 (1H, multiplet);
3.04 (1H, doublet of triplets, J=2.3 & 9.3 Hz);
1.93 (3H, doublet, J=1.4 Hz);
1.59 (3H, singlet);
1.56 (3H, singlet);
1.31 (3H, singlet);
0.98 (3H, triplet, J=7.2 Hz);
0.83 (6H, doublet, J=6.5 Hz).

EXAMPLE 55

13-[2-(4-Nicotinoylaminophenyl)-2-methylpropionyloxy]-5-hydroxyimino-milbemycin $A_4$ [(I): $R^1$=Et, X=CO, Z=>C(Me)$_2$, $R^3$=4-NHCO(3-Pyr), n=0 (Compound No. 75)]

Mass spectrum (FAB-MS) m/z:838 (M+H$^+$, M=$C_{48}H_{59}N_3O_{10}$).

Nuclear Magnetic Resonance Spectrum (CDCl$_3$) δ ppm:
9.09 (1H, singlet);
8.78 (1H, doublet, J=4.8 Hz);
8.61 (1H, singlet);
8.23 (1H, doublet, J=7.9 Hz);
7.91 (1H, singlet);
7.58 (2H, doublet, J=8.6 Hz);
7.46 (1H, doublet of doublets, J=4.8 & 7.9 Hz);
7.33 (2H, doublet, J=8.6 Hz);
4.89 (1H, doublet, J=10.6 Hz);
4.73 & 4.67 (2H, doublet of AB-quartets, J=2.0 & 14.7 Hz);
4.66 (1H, singlet);
4.02 (1H, singlet);
3.57 (1H, multiplet);
3.36 (1H, multiplet);
3.04 (1H, doublet of triplets, J=2.2 & 9.3 Hz);
1.92 (3H, doublet, J=1.5 Hz);
1.59 (3H, singlet);
1.56 (3H, singlet);
1.33 (3H, singlet);
0.98 (3H, triplet, J=7.3 Hz);
0.83 (6H, doublet, J=6.6 Hz).

EXAMPLE 56

13-[2-(4-Isonicotinoylaminophenyl)-2-methylpropionyloxy]-5-hydroxyimino-milbemycin $A_4$ [(I): $R^1$=Et, X=CO, Z=>C(Me)$_2$, $R^3$=4-NHCO(4Pyr), n=0 (Compound No. 44)]

Mass spectrum (FAB-MS) m/z:838 (M+H$^+$, M=$C_{48}H_{59}N_3O_{10}$).

Nuclear Magnetic Resonance Spectrum (CDCl$_3$) δ ppm:
8.81 (2H, doublet, J=5.7 Hz);
8.52 (1H, singlet);
7.88 (1H, singlet);

7.72 (2H, doublet, J=5.7 Hz);
7.58 (2H, doublet, J=8.6 Hz);
7.33 (2H, doublet, J=8.6 Hz);
4.89 (1H, doublet, J=10.5 Hz);
4.73 & 4.67 (2H, doublet of AB-quartets, J=2.0 & 13.5 Hz);
4.66 (1H, singlet);
3.99 (1H, singlet);
3.57 (1H, multiplet);
3.36 (1H, multiplet);
3.04 (1H, doublet of triplets, J=2.2 & 9.3 Hz);
1.93 (3H, singlet);
1.59 (3H, singlet);
1.57 (3H, singlet);
1.32 (3H, singlet);
0.98 (3H, triplet, J=7.3 Hz);
0.83 (6H, doublet, J=6.5 Hz).

EXAMPLE 57

13-[1-(4-Aminophenyl)cyclopentanecarbonyloxy]-5-hydroxyimino-milbemycin $A_4$ [(I): $R^1$=Et, X=CO, Z=>C(Me)$_4$, $R^3$=4-NH$_2$, n=0 (Compound No. 171)]

57(a) 13-[1-(4-Nitrophenyl)cyclopentanecarbonyloxy]-5-oxo-milbemycin $A_4$ 4.11 g (17.5 mmol) of 1-(4-nitrophenyl)cyclopentanecarboxylic acid, 2.0 g of anhydrous copper (II) sulfate, and 8 drops of trifluoromethanesulfonic acid were added to a solution of 1.95 g (3.50 mmol) of 15-hydroxy-5-oxo-milbemycin $A_4$ in 50 ml of methylene chloride, and the mixture was stirred at room temperature for 20 minutes under a nitrogen atmosphere. At the end of this time, the reaction mixture was filtered to remove insoluble materials, and the filtrate was poured into a mixture of a 4% w/v aqueous solution of sodium hydrogencarbonate and ethyl acetate, whilst stirring. The ethyl acetate layer was separated from the mixture, and the aqueous layer was extracted with small amount of ethyl acetate. The separated ethyl acetate layer was combined with the ethyl acetate extract, and the mixture wa washed with a 4% w/v aqueous solution of sodium hydrogencarbonate and then with water. It was then dried over anhydrous sodium sulfate, and the solvent was removed by evaporation under reduced pressure. The resulting residue was used for the next step without further purification.

57(b) 13-[1-(4-Nitrophenyl)cyclopentanecarbonyloxy]-5-hydroxyimino-milbemycin $A_4$ The crude 13-[1-(4-nitrophenyl)cyclopentanecarbonyloxy]-5-oxo-milbemycin $A_4$ [prepared as described in step (a) above] was dissolved in 20 ml of dioxane, and 10 ml of water, 20 ml of methanol, and 3.0 g of hydroxylamine hydrochloride were added to the resulting solution. The mixture was stirred at 55° C. for 1 hours, after which it was diluted with ethyl acetate and washed twice with water. The solvent was then removed by evaporation under reduced pressure. The resulting residue was used for the next step without further purification.

57(c) 13-[1-(4-Nitrophenyl)cyclopentanecarbonyloxy]-5-t-butyldimethylsilyloxyimino-milbemycin $A_4$ The crude 13-[1-(4-nitrophenyl)cyclopentanecarbonyloxy]-5-hydroxyiminomilbemycin $A_4$ [prepared as described in step (b) above] was dissolved in 30 ml of methylene chloride, and 286 mg (4.2 mmol) of imidazole, 634 mg (4.2 nmnol) of t-butyldimethylsilyl chloride, and 20 mg of 4-dimethylaminopyridine were added to the resulting solution. The mixture was then stirred at 40° C. for 2 hours. At the end of this time, the reaction mixture was diluted with 200 ml of ethyl acetate, washed with 0.2M aqueous citric acid, with water, with a 4% w/v aqueous solution of sodium hydrogencarbonate, and with water, in that order, after which it was dried over anhydrous sodium sulfate. The solvent was then removed by evaporation under reduced pressure. The resulting residue was purified by column chromatography through silica gel, using a 1:9 by volume mixture of ethyl acetate and hexane as the eluent, to give 2.327 g (yield 73.6%) of the title compound as an amorphous solid.

57(d) 13-[1-(4-Aminophenyl)cyclopentanecarbonyloxy]-5-t-butyldimethylsilyloxyimino-milbemycin $A_4$ The 13-[1-(4-nitrophenyl)cyclopentanecarbonyloxy]-5-t-butyldimethylsilyloxyimino-milbemycin $A_4$ [prepared as described in step (c) above] was dissolved in 15 ml of methanol, and 327 mg of bis(triphenylphosphine)-nickel(II) chloride were added to the resulting solution. 230 mg of sodium borohydride were then added to the mixture over a period of 10 minutes, whilst stirring, and the stirring was then continued for a further 7 minutes. At the end of this time, the reaction mixture was poured into 200 ml of 1% w/v aqueous acetic acid, and extracted with 200 ml and then 50 ml of ethyl acetate. The extract was washed with water, with a 4% w/v aqueous solution of sodium hydrogencarbonate, and with water, in that order, after which it was dried over anhydrous sodium sulfate, and the solvent was removed by evaporation under reduced pressure. The resulting residue was purified by column chromatography through silica gel, using a 3:7 by volume mixture of ethyl acetate and hexane as the eluent, to give 1.834 g (yield 81.5%) of the title compound as an amorphous solid.

57(e) 13-[1-(4-Aminophenyl)cyclopentanecarbonyloxy]-5-hydroxyimino-milbemycin $A_4$ 873 mg (1.0 mmol) of 13-[1-(4-aminophenyl)cyclopentanecarbonyloxy]-5-t-butyldimethylsilyloxyimino-milbemycin $A_4$ [prepared as described in step (d) above] was dissolved in 20 ml of methanol, and 2.0 ml of 1M aqueous hydrochloric acid were added to the resulting solution. The mixture was then stirred at room temperature for 20 minutes. At the end of this time, the reaction mixture was diluted with ethyl acetate, and washed with water, with a 4% w/v aqueous solution of sodium hydrogencarbonate, and with water, in that order. It was then dried over anhydrous sodium sulfate, and the solvent was removed by evaporation under reduced pressure. The resulting residue was purified by column chromatography through silica gel, using a 6:4 by volume mixture of ethyl acetate and hexane as the eluent, to give 717 mg (yield 94.5%) of the title compound as an amorphous solid.

Mass spectrum (FAB-MS) m/z:759 (M+H$^+$, M=C$_{44}$H$_{58}$N$_2$O$_9$).

Nuclear Magnetic Resonance Spectrum (CDCl$_3$) δ ppm:
8.59 (1H, broad singlet);
7.11 (2H, doublet, J=8.5 Hz);
6.60 (2H, doublet, J=8.5 Hz);
4.80 (1H, doublet, J=10.5 Hz);
4.65 (1H, singlet);
3.90 (2H, broad singlet);
3.55 (1H, multiplet);
3.36 (1H, multiplet);
3.02 (1H, doublet of triplets, J=2.1 & 9.3 Hz);
2.60 (2H, multiplet);
1.93 (3H, singlet);

1.31 (3H, singlet);
0.97 (3H, triplet, J=7.3 Hz);
0.82 (3H, doublet, J=6.4 Hz);
0.77 (3H, doublet, J=6.5 Hz).

EXAMPLE 58

13-[2-(4-Methylaminophenyl)-2-methylpropionyloxy]-5-hydroxyimino-milbemycin $A_4$ [(I): $R^1$=Et, X=CO, Z=>C(Me)$_2$, $R^3$=4-NHMe, n=0 (Compound No. 9)]

The title compound was prepared by a method similar to that described in Example 57 except that 2-[4-(N-(4-nitrobenzyloxycarbonyl)methyaminophenyl]-2-methylpropionic acid was used in place of 1-(4-nitrophenyl)cyclopentanecarboxylic acid.
Mass spectrum (FAB-MS) m/z:747 (M+H$^+$, M=$C_{43}H_{58}N_2O_9$).
Nuclear Magnetic Resonance Spectrum (CDCl$_3$) δ ppm:
8.13 (1H, broad singlet);
7.12 (2H, doublet, J=8.6 Hz);
7.54 (2H, doublet, J=8.6 Hz);
5.86 (1H, doubled doublet of doublets, J=2.1, 2.1 & 11.2 Hz);
5.79 (1H, multiplet);
5.77 (1H, doublet of doublets, J=11.2 & 14.0 Hz);
4.86 (1H, doublet, J=10.4 Hz);
4.74 & 4.71 (2H, doublet of AB-quartets, 2.1 & 14.5 Hz);
4.65 (1H, singlet);
3.97 (1H, broad singlet);
3.57 (1H, multiplet);
3.36 (1H, multiplet);
3.04 (1H, doublet of triplets, J=2.3 & 9.4 Hz);
2.82 (3H, singlet);
1.93 (3H, doublet, J=1.4 Hz);
1.54 (3H, singlet);
1.51 (3H, singlet);
1.32 (3H, singlet);
0.98 (3H, triplet, J=7.2 Hz);
0.83 (6H, doublet, J=6.5 Hz).

EXAMPLE 59

13-[1-(4-Acetylaminophenal)cyclopentanecarbonyloxy]-5-hydroxyimino-milbemycin $A_4$ [(I): $R^1$=Et, X=CO, Z=>C(CH$_2$)$_4$, $R^3$=4-NHAc, n=0 (Compound No. 191)]

1.31 g (1.50 mmol) of 13-[1-(4-aminophenyl)cyclopentanecarbonyl]-5-t-butyldimethylsilyloxyimino-milbemycin $A_4$ [prepared as described in Example 57(c)] were dissolved in 15 ml of methylene chloride, and 0.137 ml (1.70 rnmol) of pyridine and 0.161 ml (1.70 mmol) of acetic anhydride were added to the resulting solution. The mixture was then stirred at room temperature for 20 minutes. At the end of this time, the reaction mixture was diluted with 100 ml of ethyl acetate, and washed with 0.2M aqueous citric acid, with water, a with 4% w/v aqueous solution of sodium hydrogencarbonate, and with water, in that order. It was then dried over anhydrous sodium sulfate, and the solvent was removed by evaporation under reduced pressure. The resulting residue was dissolved in 30 ml of methanol, and 3.0 ml of 1M aqueous hydrochloric acid was added to the resulting solution. The reaction mixture was stirred at room temperature for 20 minutes and then diluted with ethyl acetate, after which it was washed with water, with a 4% w/v aqueous solution of sodium hydrogencarbonate, and with water, in that order. It was then dried over anhydrous sodium sulfate, and the solvent was removed by evaporation under reduced pressure. The resulting residue was purified by column chromatography through silica gel, using a 6:4 by volume mixture of ethyl acetate and hexane as the eluent, to give 717 mg (yield 94.5%) of the title compound as an amorphous solid.
Mass spectrum (FAB-MS) m/z:801 (M+H$^+$, M=$C_{46}H_{60}N_2O_{10}$).
Nuclear Magnetic Resonance Spectrum (CDCl$_3$) δ ppm:
8.34 (1H, singlet);
7.41 (2H, doublet, J=8.5 Hz);
7.28 (2H, doublet, J=8.5 Hz);
7.17 (1H, singlet);
5.83 (1H, multiplet);
5.78 (1H, multiplet);
5.77 (1H, multiplet);
4.80 (1H, doublet, J=10.5 Hz);
4.74 & 4.60 (2H, doublet of AB-quartets, J=1.9 & 14.6 Hz);
4.65 (1H, singlet);
3.97 (1H, singlet);
3.54 (1H, multiplet);
3.36 (1H, multiplet);
3.02 (1H, doublet of triplets, J=2.2 & 9.3 Hz);
2.61 (2H, multiplet),;
2.17 (3H, singlet);
1.93 (3H, singlet);
1.29 (3H, singlet);
0.97 (3H, triplet, J=7.3 Hz);
0.82 (3H, doublet, J=6.5 Hz);
0.76 (3H, doublet, J=6.5 Hz).

EXAMPLES 60 TO 71

The compounds of Examples 60 to 71 were prepared using the same procedures as described in Example 59.

13-[1-(4-Methanesulfonylaminophenyl)cyclopentanecarbonyloxy]-5-hydroxyimino-milbemycin $A_4$ [(I): $R^1$=Et, X=CO, Z=>C(CH$_2$)$_4$, $R^3$=4-NHSO$_2$Me, n=0 (Compound No. 313)]
Mass spectrum (FAB-MS) m/z:837 (M+H$^+$, M=$C_{45}H_{60}N_2O_{11}S$).
Nuclear Magnetic Resonance Spectrum (CDCl$_3$) δ ppm:
8.74 (1H, broad singlet);
7.32 (2H, doublet, J=8.6 Hz);
7.14 (2H, doublet, J=8.6 Hz);
6.72 (1H, broad singlet);
4.80 (1H, doublet, J=10.6 Hz);
4.73 & 4.60 (2H, AB-quartet, J=14.5 Hz);
4.65 (1H, singlet);
3.99 (1H, singlet);
3.54 (1H, multiplet);
3.36 (1H, multiplet);
3.01 (1H, doublet of triplets, J=2.2 & 9.3 Hz);
2.96 (3H, singlet);

2.61 (2H, multiplet);
1.91 (3H, singlet);
1.28 (3H, singlet);
0.96 (3H, triplet, J=7.2 Hz);
0.81 (3H, doublet, J=6.3 Hz);
0.74 (3H, doublet, J=6.5 Hz).

EXAMPLE 61

13-[1-(4-Pivaloylaminophenyl)cyclopentanecarbonyloxy]-5-hydroxyimino-milbemycin $A_4$ [(I): $R^1$=Et, X=CO, Z=>C(CH$_2$)$_4$, $R^3$=4-NHCOtBu, n=0 (Compound No. 203)]

Mass spectrum (FAB-MS) m/z :843 (M+H$^+$, M=C$_{49}$H$_{66}$N$_2$O$_{10}$).
Nuclear Magnetic Resonance Spectrum (CDCl$_3$) δ ppm:
8.50 (1H, broad singlet);
7.44 (2H, doublet, J=8.7 Hz);
7.20–7.30 (3H, multiplet);
4.81 (1H, doublet, J=10.5 Hz);
4.75 & 4.67 (2H, AB-quartet, J=14.5 Hz);
4.65 (1H, singlet);
3.96 (1H, broad singlet);
3.55 (1H, multiplet);
3.36 (1H, multiplet);
2.59 (2H, multiplet);
1.92 (3H, singlet);
1.31 (3H, singlet);
1.14 (3H, doublet, J=5.9 Hz);
1.02 (3H, doublet, J=6.4 Hz);
0.82 (3H, doublet, J=6.4 Hz).

EXAMPLE 62

13-[1-(4-Cyclohexanecarbonylaminophenyl)cyclopentanecarbonyloxy]-5-hydroxyimino-milbemycin $A_4$ [(I): $R^1$=Et, X=CO, Z=>C(CH$_2$)$_4$, $R^3$=4-NHCO-cHx, n=0 (Compound No. 207)]

Mass spectrum (FAB-MS) m/z:869 (M+H$^+$, M=C$_{51}$H$_{68}$N$_2$O$_{10}$).
Nuclear Magnetic Resonance Spectrum (CDCl$_3$) δ ppm:
8.75 (1H, broad singlet);
7.44 (2H, doublet, J=8.6 Hz);
7.27 (2H, doublet, J=8.6 Hz);
7.17 (1H, singlet);
4.81 (1H, doublet, J=10.6 Hz);
4.74 & 4.66 (2H, AB-quartet, J=15.2 Hz);
4.66 (1H, singlet);
4.00 (1H, broad singlet);
3.55 (1H, multiplet);
3.36 (1H, multiplet);
3.02 (1H, multiplet);
2.59 (2H, multiplet);
1.92 (3H, singlet);
1.30 (3H, singlet);
0.97 (3H, triplet, J=7.3 Hz);
0.82 (3H, doublet, J=6.4 Hz);
0.76 (3H, doublet, J=6.5 Hz).

EXAMPLE 63

13-[1-(4-Valerylaminophenyl)cyclopentanecarbonyloxy]-5-hydroxyimino-milbemycin $A_4$ [(I): $R^1$=Et, X=CO, Z=>C(CH$_2$)$_4$, $R^3$=4-NHCOBu, n=0 (Compound No. 201)]

Mass spectrum (FAB-MS) m/z:843 (M+H$^+$, M=C$_{49}$H$_{66}$N$_2$O$_{10}$).
Nuclear Magnetic Resonance Spectrum (CDCl$_3$) δ ppm:
8.30 (1H, broad singlet);
7.43 (2H, doublet, J=8.5 Hz);
7.27 (2H, doublet, J=8.5 Hz);
7.08 (1H, singlet);
4.81 (1H, doublet, J=10.6 Hz);
4.75 & 4.67 (2H, AB-quartet, J=15.0 Hz);
4.66 (1H, singlet);
3.95 (1H, broad singlet);
3.55 (1H, multiplet);
3.36 (1H, multiplet);
3.02 (1H, multiplet);
2.60 (2H, multiplet);
1.93 (3H, singlet),
1.31 (3H, singlet);
1.00–0.90 (4H, multiplet);
0.82 (3H, doublet, J=6.4 Hz);
0.76 (3H, doublet, J=6.5 Hz).

EXAMPLE 64

13-[1-(4-Propionylaminophenyl)cyclopentanecarbonyloxy]-5-hydroxyimino-milbemycin $A_4$ [(I): $R^1$=Et X=CO, Z=>C(CH$_2$)$_4$, $R^3$=4-NHCOEt, n=0 (Compound No. 198)]

Mass spectrum (FAB-MS) m/z:815 (M+H$^+$, M=C$_{47}$H$_{62}$N$_2$O$_{10}$).
Nuclear Magnetic Resonance Spectrum (CDCl$_3$) δ ppm:
8.50 (1H, broad singlet);
7.43 (2H, doublet, J=8.5 Hz);
7.27 (2H, doublet, J=8.5 Hz);
7.12 (1H, broad singlet);
4.81 (1H, doublet, J=10.5 Hz);
4.74 & 4.66 (2H, AB-quartet, J=15.2 Hz);
4.65 (1H, singlet);
3.95 (1H, broad singlet);
3.55 (1H, multiplet);
3.36 (1H, multiplet);
3.02 (1H, multiplet);
2.60 (2H, multiplet);
1.92 (3H, singlet);
1.30 (3H, singlet);
0.97 (3H, triplet, J=7.2 Hz);
0.82 (3H, doublet, J=6.3 Hz);
0.76 (3H, doublet, J=6.5 Hz).

EXAMPLE 65

13-[1-(4-Cyclopropanecarbonylaminophenyl)cyclopentanecarbonyloxy]-5-hydroxyimino-milbemycin $A_4$ [(I): $R^1$=Et, X=CO, Z=>C(CH$_2$)$_4$, $R^3$=4-NHCOcPr, n=0 (Compound No. 204)]

Mass spectrum (FAB-MS) m/z:827 (M+H$^+$, M=C$_{48}$H$_{62}$N$_2$O$_{10}$).
Nuclear Magnetic Resonance Spectrum (CDCl$_3$) δ ppm:
8.11 (1H, broad singlet);
7.52–7.28 (5H, multiplet);
4.80 (1H, doublet, J=10.4 Hz);
4.75 & 4.68 (2H, doublet of AB-quartets, J=1.8 & 14.9 Hz);

4.65 (1H, singlet);
3.97 (1H, broad singlet);
3.55 (1H, multiplet);
3.36 (1H, multiplet);
3.03 (1H, multiplet);
2.62 (2H, multiplet);
1.93 (3H, singlet);
1.29 (3H, singlet);
0.97 (3H, triplet, J=7.2 Hz);
0.82 (3H, doublet, J=6.4 Hz);
0.76 (3H, doublet, J=6.5 Hz).

EXAMPLE 66

13-{1-[4-(Cyclobutanecarbonylamino)phenyl] cyclopentanecarbonyloxy}-5-hydroxyimino-milbemycin $A_4$ [(I): $R^1$=Et, X=CO, Z=>C(CH$_2$)$_4$, $R^3$=4-NHCOcBu, n=0 (Compound No. 205)]

Mass spectrum (FAB-MS) m/z:843 (M+H$^+$, M=$C_{49}H_{64}N_2O_{10}$).

Nuclear Magnetic Resonance Spectrum (CDCl$_3$) δ ppm:
  8.13 (1H, singlet);
  7.44 (2H, doublet, J=8.7 Hz);
  7.27 (2H, doublet, J=8.7 Hz);
  6.97 (1H, singlet);
  4.81 (1H, doublet, J=10.4 Hz);
  4.74 & 4.68 (2H, AB-quartet, J=14.4 Hz);
  4.65 (1H, singlet);
  3.97 (1H, singlet);
  3.55 (2H, multiplet);
  3.36 (2H, multiplet);
  3.02 (1H, multiplet);
  2.58 (2H, multiplet);
  1.93 (3H, singlet);
  1.30 (3H, singlet);
  0.97 (3H, triplet, J=7.2 Hz);
  0.82 (3H, doublet, J=6.4 Hz);
  0.76 (3H, doublet, J=6.5 Hz).

EXAMPLE 67

13-[1-(4-Cyanoacetylaminophenyl) cyclopentanecarbonyloxy]-5-hydroxyimino-milbemycin $A_4$ [(I): $R^1$=Et, X=CO, Z=>C(CH$_2$)$_4$, $R^3$=4-NHCOCH$_2$CN, n=0 (Compound No. 211)]

Mass spectrum (FAB-MS) m/z:826 (M+H$^+$, M=$C_{47}H_{59}N_3O_{10}$).

Nuclear Magnetic Resonance Spectrum (CDCl$_3$) δ ppm:
  8.07 (1H, singlet);
  7.70 (1H, singlet);
  7.42 (2H, doublet, J=8.7 Hz);
  7.33 (2H, doublet, J=8.7 Hz);
  4.81 (1H, doublet, J=10.4 Hz);
  4.74 & 4.68 (2H, AB-quartet, J=14.4 Hz);
  4.65 (1H, singlet);
  3.97 (1H, singlet);
  3.55 (2H, singlet);
  3.54 (1H, multiplet);
  3.36 (1H, multiplet);
  3.02 (1H, multiplet);
  2.61 (2H, multiplet);
  1.93 (3H, doublet, J=1.6 Hz);
  1.30 (3H, singlet);
  0.97 (3H, triplet, J=7.2 Hz);
  0.82 (3H, doublet, J=6.5 Hz);
  0.76 (3H, doublet, J=6.5 Hz).

EXAMPLE 68

13-[1-(4-Butyrylaminophenyl) cyclopentanecarbonyloxy]-5-hydroxyimino-milbemycin $A_4$ [(I): $R^1$=Et, X=CO, Z=>C(CH$_2$)$_4$, $R^3$=4-NHCOPr, n=0 (Compound No. 199)]

Mass spectrum (FAB-MS) m/z:829 (M+H$^+$, M=$C_{48}H_{64}N_2O_{10}$).

Nuclear Magnetic Resonance Spectrum (CDCl$_3$) δ ppm:
  8.12 (1H, singlet);
  7.43 (2H, doublet, J=8.6 Hz);
  7.28 (2H, doublet, J=8.6 Hz);
  7.09 (1H, singlet);
  4.81 (1H, doublet, J=10.4 Hz);
  4.74 & 4.67 (2H, doublet of AB-quartets, J=2.0 & 14.4 Hz);
  4.65 (1H, singlet);
  3.97 (1H, singlet);
  3.54 (1H, multiplet);
  3.36 (1H, multiplet);
  3.02 (1H, multiplet);
  2.61 (2H, multiplet);
  1.93 (3H, doublet, J=1.6 Hz);
  1.30 (3H, singlet);
  1.03–0.95 (6H, multiplet);
  0.82 (3H, doublet, J=6.4 Hz);
  0.76 (3H, doublet, J=6.4 Hz).

EXAMPLE 69

13-[1-(4-Isobutyrylaminophenyl) cyclopentanecarbonyloxy]-5-hydroxyimino-milbemycin $A_4$ [(I): $R^1$=Et, X=CO, Z=>C(CH$_2$)$_4$, $R^3$=4-NHCOiPr, n=0 (Compound No. 200)]

Mass spectrum (FAB-MS) m/z:829 (M+H$^+$, M=$C_{48}H_{64}N_2O_{10}$).

Nuclear Magnetic Resonance Spectrum (CDCl$_3$) δ ppm:
  8.11 (1H, singlet);
  7.44 (2H, doublet, J=8.6 Hz);
  7.28 (2H, doublet, J=8.6 Hz);
  7.10 (1H, singlet);
  4.81 (1H, doublet, J=10.4 Hz);
  4.75 & 4.68 (2H, doublet of AB-quartets, J=2.0 & 14.4 Hz);
  4.65 (1H, singlet);
  3.97 (1H, singlet);
  3.54 (1H, multiplet);
  3.36 (1H, multiplet);
  3.02 (1H, multiplet);
  2.60 (2H, multiplet);
  1.93 (3H, doublet, J=1.6 Hz);
  1.30 (3H, singlet);
  1.26 (6H, doublet, J=6.8 Hz);

0.97 (3H, triplet, J=7.2 Hz);
0.82 (3H, doublet, J=6.4 Hz);
0.77 (3H, doublet, J=6.4 Hz).

EXAMPLE 70

13-[1-(4-Isovalerylaminophenyl)
cyclopentanecarbonyloxy]-5-hydroxyimino-
milbemycin $A_4$ [(I): $R^1$=Et, X=CO, Z =>C(CH$_2$)$_4$,
$R^3$=4-NHCOiBu, n=0 (Compound No. 202)]

Mass spectrum (FAB-MS) m/z:843 (M+H$^+$, M=$C_{49}H_{66}N_2O_{10}$).
Nuclear Magnetic Resonance Spectrum (CDCl$_3$) δ ppm:
  8.14 (1H, broad singlet);
  7.43 (2H, doublet, J=8.6 Hz);
  7.28 (2H, doublet, J=8.6 Hz);
  7.07 (1H, singlet);
  4.81 (1H, doublet, J=10.4 Hz);
  4.74 & 4.68 (2H, doublet of AB-quartets, J=1.8 & 14.2 Hz);
  4.65 (1H, singlet);
  3.97 (1H, singlet);
  3.54 (1H, multiplet);
  3.36 (1H, multiplet);
  3.02 (1H, multiplet);
  2.60 (2H, multiplet);
  1.93 (3H, doublet, J=1.4 Hz);
  1.30 (3H, singlet);
  1.02 (6H, doublet, J=7.2 Hz);
  0.97 (3H, triplet, J=7.2 Hz);
  0.82 (3H, doublet, J=6.4 Hz);
  0.76 (3H, doublet, J=6.4 Hz).

EXAMPLE 71

13-{1-[4-(Cyclopentanecarbonylamino)phenyl]
cyclopentanecarbonyloxy}-5-hydroxyimino-
milbemycin $A_4$ [(I): $R^1$=Et, X=CO, Z=>C(CH$_2$)$_4$,
$R^3$=4-NHCOcPn, n=0 (Compound No. 206)]

Mass spectrum (FAB-MS) m/z:855 (M+H$^+$, M=$C_{50}H_{66}N_2O_{10}$).
Nuclear Magnetic Resonance Spectrum (CDCl$_3$) δ ppm:
  8.16 (1H, broad singlet);
  7.44 (2H, doublet, J=8.4 Hz);
  7.27 (2H, doublet, J=8.4 Hz);
  7.12 (1H, singlet);
  4.81 (1H, doublet, J=10.8 Hz);
  4.74 & 4.68 (2H, doublet of AB-quartets, J=1.8 & 14.2 Hz);
  4.65 (1H, singlet);
  3.97 (1H, singlet);
  3.54 (1H, multiplet);
  3.36 (1H, multiplet);
  3.03 (1H, multiplet);
  2.66 (1H, multiplet);
  2.61 (2H, multiplet);
  1.93 (3H, doublet, J=1.4 Hz);
  1.30 (3H, singlet);
  0.97 (3H, triplet, J=7.3 Hz);
  0.82 (3H, doublet, J=6.4 Hz);
  0.76 (3H, doublet, J=6.4 Hz).

EXAMPLE 72

13-{2-[4-(N-Methylmethanesulfonylamino)phenyl]-
2-methylpropionyloxy-}5-hydroxyimino-
milbemycin $A_4$ [(I): $R^1$=Et, X=CO, Z=>C(Me)$_2$,
$R^3$=4-N(Me)SO$_2$Me, n=0 (Compound No. 151)]

Mass spectrum (FAB-MS) m/z:825 (M+H$^+$, M=$C_{44}H_{60}N_2O_{11}S$).
Nuclear Magnetic Resonance Spectrum (CDCl$_3$) δ ppm:
  8.05 (1H, singlet);
  7.31 (4H, singlet);
  4.87 (1H, doublet, J=10.7 Hz);
  4.73 & 4.67 (2H, doublet of AB-quartets, J=2.0 & 14.3 Hz);
  4.65 (1H, singlet);
  3.96 (1H, singlet);
  3.57 (1H, multiplet);
  3.36 (1H, multiplet);
  3.30 (3H, singlet);
  3.03 (1H, doublet of doublets, J=2.3 & 9.3 Hz);
  2.81 (3H, singlet);
  1.93 (3H, singlet);
  1.59 (3H, singlet);
  1.56 (3H, singlet);
  1.29 (3H, singlet);
  0.98 (3H, triplet, J=7.3 Hz);
  0.83 (3H, doublet, J=6.6 Hz);
  0.81 (3H, doublet, J=6.6 Hz).

EXAMPLE 73

13-{2-[4-(N-Methlmethoxycarbonylamino)phenyl]-
2-methylpropionyloxy}-5-hydroxyimino-
milbemycin $A_4$ [(I): $R^1$=Et, X=CO, Z=>C(Me)$_2$,
$R^3$=4-N(Me)COOMe, n=0 (Compound No. 123)]

Mass spectrum (FAB-MS) m/z:805 (M+H$^+$, M=$C_{45}H_{60}N_2O_1$).
Nuclear Magnetic Resonance Spectrum (CDCl$_3$) δ ppm:
  8.10 (1H, singlet);
  7.27 (2H, doublet, J=8.5 Hz);
  7.16 (2H, doublet, J=8.5 Hz);
  4.87 (1H, doublet, J=10.6 Hz);
  4.73 & 4.67 (2H, doublet of AB-quartets, J=2.0 & 14.5 Hz);
  4.65 (1H, singlet);
  3.97 (1H, singlet);
  3.71 (3H, singlet);
  3.57 (1H, multiplet);
  3.36 (1H, multiplet);
  3.27 (3H, singlet);
  3.03 (1H, doublet of doublets, J=2.2 & 9.3 Hz);
  1.93 (3H, singlet);
  1.59 (3H, singlet);
  1.56 (3H, singlet);
  1.29 (3H, singlet);
  0.98 (3H, triplet, J=7.3 Hz);
  0.83 (3H, doublet, J=6.5 Hz);
  0.81 (3H, doublet, J=6.5 Hz).

EXAMPLES 74 TO 83

The compounds of Examples 74 to 83 were prepared from 13-[1-(4-nitrophenyl)cyclobutanecarbonyloxy]-5-hydroxyimino-milbemycin $A_4$ (prepared as described in Example 7) using the same procedures as described in Example 18.

EXAMPLE 74

13-[1-(4-Acetylaminophenyl)cyclobutanecarbonyloxy]-5-hydroxyimino-milbemycin $A_4$ [(I): $R^1$=Et, X=CO, Z=>C(CH$_2$)$_3$, $R^3$=4-NHAc, n=0 (Compound No. 457)]

Mass spectrum (FAB-MS) m/z:787 (M+H$^+$, M=$C_{45}H_{58}N_2O_{10}$).

Nuclear Magnetic Resonance Spectrum (CDCl$_3$) δ ppm:
8.34 (1H, singlet);
7.41 (2H, doublet, J=8.5 Hz);
7.28 (2H, doublet, J=8.5 Hz);
7.17 (1H, singlet);
5.83 (1H, multiplet);
5.78 (1H, multiplet);
5.77 (1H, multiplet);
4.80 (1H, doublet, J=10.5 Hz);
4.74 & 4.60 (2H, doublet of AB-quartets, J=1.9 & 14.6 Hz);
4.65 (1H, singlet);
3.97 (1H, singlet);
3.54 (1H, multiplet);
3.36 (1H, multiplet);
3.02 (1H, doublet of triplets, J=2.2 & 9.3 Hz);
2.61 (2H, multiplet);
2.17 (3H, singlet);
1.93 (3H, singlet);
1.29 (3H, singlet);
0.97 (3H, triplet, J=7.3 Hz);
0.82 (3H, doublet, J=6.5 Hz);
0.76 (3H, doublet, J=6.5 Hz).

EXAMPLE 75

13-[1-(4-Methoxycarbonylaminophenyl)cyclobutanecarbonyloxy]-5-hydroxyimino-milbemycin $A_4$ [(I): $R^1$=Et, X=CO, Z=>C(CH$_2$)$_3$, $R^3$=4-NHCOOMe, n=0 (Compound No. 491)]

Mass spectrum (FAB-MS) m/z:803 (M+H$^+$, M=$C_{45}H_{58}N_2O_{11}$).

Nuclear Magnetic Resonance Spectrum (CDCl$_3$) δ ppm:
7.82 (1H, broad singlet);
7.32 (2H, doublet, J=8.6 Hz);
7.21 (2H, doublet, J=8.6 Hz);
6.57 (1H, broad singlet);
4.84 (1H, doublet, J=10.6 Hz);
4.72 & 4.70 (2H, AB-quartet, J=14.5 Hz);
4.65 (1H, singlet);
3.95 (1H, singlet);
3.78 (3H, singlet);
3.54 (1H, multiplet);
3.36 (1H, multiplet);
3.03 (1H, doublet of triplets, J=2.3 & 9.2 Hz);
2.86–2.70 (2H, multiplet);
2.52–2.41 (3H, multiplet);
1.93 (3H, singlet);
1.34 (3H, singlet);
0.98 (3H, triplet, J=7.3 Hz);
0.82 (3H, doublet, J=6.6 Hz);
0.76 (3H, doublet, J=6.6 Hz).

EXAMPLE 76

13-[1-(4-Methanesulfonylaminophenyl)cyclobutanecarbonyloxy]-5-hydroxyimino-milbemycin $A_4$ [(I): $R^3$32 Et , X=CO, Z=>C(CH$_2$)$_3$, $R^3$=4-NHSO$_2$Me, n=0 (Compound No. 503)]

Mass spectrum (FAB-MS) ml/z:823 (M+H$^+$, M=C44H$_{58}$N$_2$O0IS).

Nuclear Magnetic Resonance Spectrum (CDCl$_3$) δ ppm:
7.85 (1H, broad singlet);
7.27 (2H, doublet, J=8.6 Hz);
7.17 (2H, doublet, J=8.6 Hz);
6.35 (1H, broad singlet);
4.85 (1H, doublet, J=10.6 Hz);
4.73 & 4.70 (2H, AB-quartet, J=14.5 Hz);
4.66 (1H, singlet);
3.96 (1H, singlet);
3.54 (1H, multiplet);
3.36 (1H, multiplet);
3.03 (1H, multiplet);
2.98 (3H, singlet);
2.88–2.73 (2H, multiplet);
2.53–2.42 (3H, multiplet);
1.93 (3H, singlet);
1.34 (3H, singlet);
0.97 (3H, triplet, J=7.3 Hz);
0.82 (3H, doublet, J=6.4 Hz);
0.76 (3H, doublet, J=6.6 Hz).

EXAMPLE 77

13-{1-[4-(4-Nitrobenzoylamino)phenyl]cyclobutanecarbonyloxy}-5-hydroxyimino-milbemycin $A_4$ [(I): $R^1$=Et, X=CO, Z=>C(CH$_2$)$_3$, $R^3$=4-NHCO(4-NO$_2$Ph), n=0 (Compound No. 478)]

Mass spectrum (FAB-MS) m/z:894 (M+H$^+$, M=$C_{50}H_{59}N_3O_{12}$).

Nuclear Magnetic Resonance Spectrum (CDCl$_3$) δ ppm:
8.60 (1H, broad singlet);
8.35 (2H, doublet, J=8.8 Hz);
8.05 (2H, doublet, J=8.4 Hz);
7.85 (1H, singlet);
7.59 (2H, doublet, J=8.4 Hz);
7.31 (2H, doublet, J=8.8 Hz);
4.87 (1H, doublet, J=10.4 Hz);
4.74 & 4.68 (2H, doublet of AB-quartets, J=1.6 & 14.4 Hz);
4.65 (1H, singlet);
3.96 (1H, singlet);
3.54 (1H, multiplet);
3.36 (1H, multiplet);
3.03 (1H, multiplet);
2.88–2.75 (2H, multiplet);

1.93 (3H, singlet);
1.36 (3H, singlet);
0.98 (3H, triplet, J=7.3 Hz);
0.82 (3H, doublet, J=6.4 Hz);
0.79 (3H, doublet, J=6.4 Hz).

EXAMPLE 78

13-{1-[4-(4-t-Butylbenzoylamino)phenyl]
cyclobutanecarbonyloxy}-5-hydroxyimino-
milbemycin $A_4$ [(I): $R^1$=Et, X=CO, Z=>C(CH$_2$)$_3$,
$R^3$=4-NHCO(4-tBuPh), n=0 (Compound No. 479)]

Mass spectrum (FAB-MS) m/z:905 (M+H, M=$C_{54}H_{68}N_2O_{10}$).

Nuclear Magnetic Resonance Spectrum (CDCl$_3$) δ ppm:
 8.02 (1H, broad singlet);
 7.81 (2H, doublet, J=8.4 Hz);
 7.77 (1H, singlet);
 7.59 (2H, doublet, J=8.4 Hz);
 7.50 (2H, doublet, J=8.4 Hz);
 7.29 (1H, singlet);
 4.86 (1H, doublet, J=10.4 Hz);
 4.75 & 4.68 (2H, AB-quartet, J=14.7 Hz);
 4.66 (1H, singlet);
 3.95 (1H, singlet);
 3.55 (1H, multiplet);
 3.36 (1H, multiplet);
 3.03 (1H, multiplet);
 2.87–2.74 (2H, multiplet);
 1.93 (3H, singlet);
 1.36 (12H, multiplet);
 0.98 (3H, triplet, J=7.4 Hz);
 0.82 (3H, doublet, J=6.4 Hz);
 0.78 (3H, doublet, J=6.8 Hz).

EXAMPLE 79

13-{1-[4-(4-Methoxybenzoylamino)phenyl]
cyclobutanecarbonyloxy}-5-hydroxyimino-
milbemycin $A_4$ [(I): $R^1$=Et, X=CO Z=>C(CH$_2$)$_3$,
$R^3$=4-NHCO(4-MeOPh), n=0
(Compound No. 476)]

Mass spectrum (FAB-MS) m/z:867 (M H+, M=$C_{50}H_{62}N_2O_{11}$).

Nuclear Magnetic Resonance Spectrum (CDCl$_3$) δ ppm:
 8.23 (1H, broad singlet);
 7.85 (2H, doublet, J=8.8 Hz);
 7.73 (1H, singlet);
 7.58 (2H, doublet, J=8.6 Hz);
 7.28 (1H, singlet);
 6.98 (2H, doublet, J=8.8 Hz);
 4.86 (1H, doublet, J=10.4 Hz);
 4.75 & 4.68 (2H, doublet of AB-quartets, J=1.8 & 14.6 Hz);
 4.66 (1H, singlet);
 3.95 (1H, singlet);
 3.88 (3H, singlet);
 3.54 (1H, multiplet);
 3.36 (1H, multiplet);
 3.03 (1H, multiplet);
 2.87–2.74 (2H, multiplet);
 1.93 (3H, singlet);
 1.36 (3H, multiplet);
 0.98 (3H, triplet, J=7.4 Hz);
 0.82 (3H, doublet, J=6.6 Hz);
 0.78 (3H, doublet, J=6.4 Hz).

EXAMPLE 80

13-{1-[4-(4-Chlorobenzoylamino)phenyl]
cyclobutanecarbonyloxy}-5-hydroxyimino-
milbemycin $A_4$ [(I): $R^1$=Et, X=CO, Z=>C(CH$_2$)$_3$,
$R^3$=4-NHCO(4-ClPh), n=0 (Compound No. 477)]

Mass spectrum (FAB-MS) m/z:883 (M+H$^+$, M=$C_{50}H_{59}ClN_2O_{10}$).

Nuclear Magnetic Resonance Spectrum (CDCl$_3$) δ ppm:
 8.04 (1H, broad singlet);
 7.82 (2H, doublet, J=8.8 Hz);
 7.76 (1H, singlet);
 7.57 (2H, doublet, J=8.4 Hz);
 7.47 (2H, doublet, J=8.4 Hz);
 7.28 (2H, doublet, J=8.8 Hz);
 4.86 (1H, doublet, J=10.4 Hz);
 4.75 & 4.68 (2H, doublet of AB-quartets, J=1.8 & 14.6 Hz);
 4.66 (1H, singlet);
 3.96 (1H, singlet);
 3.54 (1H, multiplet);
 3.36 (1H, multiplet);
 3.03 (1H, multiplet);
 2.87–2.74 (2H, multiplet);
 1.93 (3H, singlet);
 1.36 (3H, singlet);
 0.98 (3H, triplet, J=7.2 Hz);
 0.82 (3H, doublet, J=6.4 Hz);
 0.78 (3H, doublet, J=6.4 Hz).

EXAMPLE 81

13-[1-(4-Valerylaminophenyl)
cyclobutanecarbonyloxy]-5-hydroxyimino-
milbemycin $A_4$ [(I): $R^1$=Et, X=CO, Z=>C(CH$_2$)$_3$,
$R^3$=4-NHCOBu. n=0 (Compound No. 461)]

Mass spectrum (FAB-MS) m/z:829 (M+H$^+$, M=$C_{48}H_{64}N_2O_{10}$).

Nuclear Magnetic Resonance Spectrum (CDCl$_3$) δ ppm:
 8.48 (1H, broad singlet);
 7.46 (2H, doublet, J=8.6 Hz);
 7.22 (2H, doublet, J=8.6 Hz);
 7.11 (1H, singlet);
 4.85 (1H, doublet, J=10.4 Hz);
 4.75 & 4.68 (2H, doublet of AB-quartets, J=1.6 & 14.4 Hz);
 4.66 (1H, singlet);
 3.96 (1H, singlet);
 3.54 (1H, multiplet);
 3.36 (1H, multiplet);
 3.03 (1H, multiplet);
 2.84–2.72 (2H, multiplet);
 1.93 (3H, singlet);

1.34 (3H, singlet);
0.99–0.93 (6H, multiplet);
0.82 (3H, doublet, J=6.4 Hz);
0.77 (3H, doublet, J=6.4 Hz).

EXAMPLE 82

13-[1-(4-Pivaloylaminophenyl)
cyclobutanecarbonyloxy]-5-hydroxyimino-
milbemycin $A_4$ [(I): $R^1$=Et, X=CO, Z=>C(CH$_2$)$_3$,
$R^3$=4-NHCOtBu, n=0 (Compound No. 462)]

Mass spectrum (FAB-MS) m/z:829 (M+H$^+$, M=C$_{48}$H$_{64}$N$_2$O$_{10}$).

Nuclear Magnetic Resonance Spectrum (CDCl$_3$) δ ppm:
  8.09 (1H, broad singlet);
  7.47 (2H, doublet, J=8.8 Hz);
  7.29 (1H, singlet);
  7.23 (2H, doublet, J=8.8 Hz);
  4.85 (1H, doublet, J=10.8 Hz);
  4.75 & 4.68 (2H, doublet of AB-quartets, J=1.8 & 14.2 Hz);
  4.66 (1H, singlet);
  3.95 (1H, singlet);
  3.54 (1H, multiplet);
  3.36 (1H, multiplet);
  3.03 (1H, multiplet);
  2.85–2.72 (2H, multiplet);
  1.93 (3H, singlet);
  1.34 (3H, singlet);
  1.32 (9H, singlet);
  0.98 (3H, triplet, J=7.4 Hz);
  0.82 (3H, doublet, J=6.8 Hz);
  0.78 (3H, doublet, J=6.4 Hz).

EXAMPLE 83

13-{1-[4-(Cyclohexanecarbonylamino)phenyl]
cyclobutanecarbonyloxy}-5-hydroxyimino-
milbemycin $A_4$ [(I): $R^1$=Et, X=CO, Z=>C(CH$_2$)$_3$,
$R^3$=4-NHCOcHx, n=0 (Compound No. 464)]

Mass spectrum (FAB-MS) m/z:855 (M+H$^+$, M=C$_{50}$H$_{66}$N$_2$O$_{10}$).

Nuclear Magnetic Resonance Spectrum (CDCl$_3$) δ ppm:
  8.20 (1H, broad singlet);
  7.47 (2H, doublet, J=8.6 Hz);
  7.22 (2H, doublet, J=8.6 Hz);
  7.12 (1H, singlet);
  4.85 (1H, doublet, J=10.4 Hz);
  4.75 & 4.68 (2H, doublet of AB-quartets, J=1.8 & 14.2 Hz);
  4.66 (1H, singlet);
  3.95 (1H, singlet);
  3.54 (1H, multiplet);
  3.36 (1H, multiplet);
  3.05 (1H, multiplet);
  2.85–2.71 (2H, multiplet);
  1.93 (3H, singlet);
  1.34 (3H, singlet);
  0.97 (3H, triplet, J=7.2 Hz);
  0.82 (3H, doublet, J=6.4 Hz);
  0.77 (3H, doublet, J=6.4 Hz).

EXAMPLE 84

13-[1-(4-Aminophenyl)-1-ethylbutyryloxy-]5-
hydroxyimino-milbemycin $A_4$ [(I): $R^1$=Et, X=CO,
Z=>C(Et)$_2$, $R^3$=4-NH$_2$, n=0 (Compound No. 332)]

84(a) 13-[1-(4-Aminophenyl)-1-ethylbutyryloxy]-5-t-butyldimethylsilyloxyimino-milbemycin $A_4$ 15-Hydroxy-5-oxo-milbemycin was treated with 1-(4-nitrophenyl)-1-ethylbutyric acid under the conditions described in Example 57(a), and the product was treated in the same manner as described in Example 57(b), (c) and (d), to give the title compound in a yield of 46.9% as an amorphous solid 84(b) 13-[1-(4-Aminophenyl)-1-ethylbutyrloxy]-5-hydroxyimino-milbemycin $A_4$ The title compound was prepared from 13-[1-(4-aminophenyl)-1-ethyl-butyryloxy]-5-t-butyldimethylsilyloxyimino-milbemycin $A_4$ [prepared as described in step (a) above] using the same procedures as described in Example 57(e).

Mass spectrum (FAB-MS) m/z:761 (M+H$^+$, M=C$_{44}$H$_{60}$N$_2$O$_9$).

Nuclear Magnetic Resonance Spectrum (CDCl$_3$) δ ppm:
  7.84 (1H, singlet);
  6.99 (2H, doublet, J=8.6 Hz);
  6.61 (2H, doublet, J=8.6 Hz);
  4.88 (1H, doublet, J=10.7 Hz);
  4.73 & 4.67 (2H, doublet of AB-quartets, J=2.2 & 14.4 Hz);
  4.65 (1H, singlet);
  3.99 (1H, singlet);
  3.65–3.50 (3H, multiplet);
  3.36 (1H, multiplet);
  3.04 (1H, doublet of doublets, J=2.2 & 9.4 Hz);
  1.93 (3H, doublet, J=1.8 Hz);
  1.27 (3H, singlet);
  0.98 (3H, triplet, J=7.3 Hz);
  0.83 (3H, doublet, J=6.1 Hz);
  0.82 (3H, doublet, J=6.4 Hz);
  0.72 (3H, triplet, J=7.4 Hz);
  0.67 (3H, triplet, J=7.4 Hz).

EXAMPLE 85

13-[1-(4-Acetylaminophenyl)-1-ethylbutyryloxy]-5-
hydroxyimino-milbemycin $A_4$ [(I): $R^1$=Et, X=CO,
Z=>C(Et)$_2$, $R^1$=4-NHAc, n=0
(Compound No. 336)]

172 mg (0.20 mmol) of 13-[1-(4-aminophenyl)-1-ethylbutyryloxy]-5-t-butyl-dimethylsilyloxyimino-milbemycin $A_4$ [prepared as described in Example 84(a)] was dissolved in 2.0 ml of methylene chloride, and 0.018 ml (0.22 mmol) of pyridine and 0.021 ml (0.22 mmol) of acetic anhydride were added to the solution. The resulting mixture was then stirred at room temperature for 20 minutes. At the end of this time, the reaction mixture was diluted with 20 ml of ethyl acetate, and washed with 0.2M aqueous citric acid, with water, with a 4% w/v aqueous solution of sodium hydrogencarbonate, and with water, in that order. It was then dried over anhydrous sodium sulfate, and the solvent was removed by evaporation under reduced pressure. The resulting residue was dissolved in 4.0 ml of methanol, and 0.4 ml of 1M aqueous hydrochloric acid was added to the resulting solution. The reaction mixture was stirred at room temperature for 20 minutes, after which it was diluted with 20 ml of ethyl acetate, and washed with water, with a 4% w/v aqueous solution of sodium hydrogencarbonate, and with water, in that order. It was then dried over anhydrous sodium sulfate, and the solvent was removed by evaporation under reduced pressure. The resulting residue was purified by column chromatography through silica gel, using a 6:4 by volume mixture of ethyl acetate and hexane as the eluent, to give 149 mg (yield 92.7%) of the title compound as an amorphous solid.

Mass spectrum (FAB-MS) m/z:803 (M+H$^+$, M=$C_{46}H_{62}N_2O_{10}$).

Nuclear Magnetic Resonance Spectrum (CDCl$_3$) δ ppm:
  8.30 (1H, singlet);
  7.42 (2H, doublet, J=8.6 Hz);
  7.17 (2H, doublet, J=8.6 Hz);
  7.15 (1H, broad singlet);
  4.89 (1H, doublet, J=10.6 Hz);
  4.73 & 4.65 (2H, AB-quartet, J=14.3 Hz);
  4.65 (1H, singlet);
  3.99 (1H, singlet);
  3.58 (1H, multiplet);
  3.37 (1H, multiplet);
  3.03 (1H, multiplet);
  2.17 (3H, singlet);
  1.93 (3H, singlet);
  1.25 (3H, singlet);
  0.98 (3H, triplet, J=7.1 Hz);
  0.84–0.79 (6H, multiplet);
  0.72–0.65 (6H, multiplet).

EXAMPLES 86 TO 89

The compounds of Examples 86 to 89 were prepared using the same procedures as described in Example 85.

EXAMPLE 86

13-[1-(4-Methanesulfonylaminophenyl)-1-ethylbutyryloxyl-5-hydroxyimino-milbemycin A$_4$ (I) : R$^1$=Et, X=CO, Z=>C(Et)$_2$, R$^3$=4-NHSO$_2$Me, n=0 (Compound No. 380)]

Mass spectrum (FAB-MS) m/z:839 (M+H$^+$, M=$C_{45}H_{62}N_2O_{11}S$).

Nuclear Magnetic Resonance Spectrum (CDCl$_3$) δ ppm:
  8.15 (1H, singlet);
  7.23 (2H, doublet, J=8.6 Hz);
  7.14 (2H, doublet, J=8.6 Hz);
  6.43 (1H, singlet);
  4.89 (1H, doublet, J=10.6 Hz);
  4.73 & 4.65 (2H, AB-quartet, J=15.4 Hz);
  4.65 (1H, singlet);
  4.00 (1H, singlet);
  3.57 (1H, multiplet);
  3.36 (1H, multiplet);
  3.04 (1H, multiplet);
  2.98 (3H, singlet);
  1.93 (3H, singlet);
  1.27 (3H, singlet);
  0.98 (3H, triplet, J=7.3 Hz);
  0.83 (3H, doublet, J=6.6 Hz);
  0.79 (3H, doublet, J=6.0 Hz);
  0.75–0.66 (6H, multiplet).

EXAMPLE 87

13-{1-[4-(4-Chlorobenzoylamio)phenyl]-1-ethylbutyryloxy}-5-hydroxyimino-milbemycin A$_4$ [ (I): R$^1$=Et, X=CO, Z=>C(Et)$_2$, R$^3$=4-NHCO(4-ClPh), n=0 (Compound No. 356)]

Mass spectrum (FAB-MS) m/z:899 (M+H$^+$, M=$C_{51}H_{64}ClN_2O_{10}$).

Nuclear Magnetic Resonance Spectrum (CDCl$_3$) δ ppm:
  8.65 (1H, singlet);
  7.82 (2H, doublet, J=8.5 Hz);
  7.73 (1H, singlet);
  7.56 (2H, doublet, J=8.6 Hz);
  7.48 (2H, doublet, J=8.5 Hz);
  7.24 (2H, doublet, J=8.7 Hz);
  4.91 (1H, doublet, J=10.5 Hz);
  4.74 & 4.66 (2H, AB-quartet, J=14.4 Hz);
  4.65 (1H, singlet);
  4.00 (1H, singlet);
  3.58 (1H, multiplet);
  3.35 (1H, multiplet);
  3.05 (1H, multiplet);
  1.93 (3H, singlet);
  1.28 (3H, singlet);
  0.99 (3H, triplet, J=7.3 Hz);
  0.81–0.84 (6H, multiplet);
  0.76–0.66 (6H, multiplet).

EXAMPLE 88

13-[1-(4-Valerylaminophenyl)-1-ethylbutyryloxy]-5-hydroxyimino-milbemycin A$_4$ [(I): R$^1$=Et, X=CO, Z=>C(Et)$_2$, R$^3$=4-NHCOBu, n=0 (Compound No. 342)]

Mass spectrum (FAB-MS) m/z:845 (M+H$^+$, M=$C_{49}H_{68}N_2O_{10}$).

Nuclear Magnetic Resonance Spectrum (CDCl$_3$) δ ppm:
  8.34 (1H, broad singlet);
  7.43 (2H, doublet, J=8.6 Hz);
  7.17 (2H, doublet, J=8.6 Hz);
  7.09 (1H, singlet);
  4.90 (1H, doublet, J=10.8 Hz);
  4.73 & 4.65 (2H, doublet of AB-quartets, J=2.2 & 14.6 Hz);
  4.65 (1H, singlet);
  3.99 (1H, singlet);
  3.57 (1H, multiplet);
  3.36 (1H, multiplet);
  3.04 (1H, multiplet);
  2.20 (1H, doublet of doublets, J=11.6 & 24.0 Hz);
  1.93 (3H, singlet);
  1.26 (3H, singlet);
  1.00–0.88 (6H, multiplet);
  0.86–0.77 (6H, multiplet);
  0.73–0.66 (6H, multiplet).

EXAMPLE 89

13-{1-[4-(Cyclohexanecarbonylamino)phenyl]-1-ethylbutyryloxy}-5-hydroxyimino-milbemycin A$_4$ [ (I): R$^1$=Et, X=CO, Z=>C(Et)$_2$, R$^3$=4-NHCOcHx, n=0 (Compound No. 345)]

Mass spectrum (FAB-MS) m/z:871 (M+H$^+$, M=$C_{51}H_{70}N_2O_{10}$).

Nuclear Magnetic Resonance Spectrum (CDCl$_3$) δ ppm:
    8.05 (1H, broad singlet);
    7.45 (2H, doublet, J=8.6 Hz);
    7.16 (2H, doublet, J=8.6 Hz);
    7.11 (1H, singlet);
    4.90 (1H, doublet, J=10.8 Hz);
    4.73 & 4.65 (2H, doublet of AB-quartets, J=2.0 & 14.4 Hz);
    4.65 (1H, singlet);
    3.99 (1H, singlet);
    3.57 (1H, multiplet);
    3.36 (1H, multiplet);
    3.04 (1H, multiplet);
    1.93 (3H, singlet);
    1.27 (3H, singlet);
    0.98 (3H, triplet, J=7.2 Hz);
    0.84–0.80 (6H, multiplet);
    0.73–0.67 (6H, multiplet).

EXAMPLES 90 TO 97

The compounds of Examples 90 to 97 were prepared from 13-[1-(4-nitrophenyl)cyclopropanecarbonyloxy]-5-hydroxyimino-milbemycin A$_4$ (prepared as described in Example 6) using the same procedures as described in Example 18.

EXAMPLE 90

13-[1-(4-Methanesulfonylaminophenyl)cyclopropanecarbonyloxy]-5-hydroxyimino-milbemycin A$_4$ [(I): R$^1$=Et, X=CO, Z=>C(CH$_2$)$_2$, R$^3$=4-NHSO$_2$Me, n=0 (Compound No. 441)]

Mass spectrum (FAB-MS) m/z:809 (M+H$^+$, M=C$_{43}$H$_{56}$N$_2$O$_{11}$S).
Nuclear Magnetic Resonance Spectrum (CDCl$_3$) δ ppm:
    8.13 (1H, singlet);
    7.32 (2H, doublet, J=8.5 Hz);
    7.15 (2H, doublet, J=8.5 Hz);
    6.50 (1H, singlet);
    4.88 (1H, doublet, J=10.4 Hz);
    4.73 & 4.70 (2H, doublet of AB-quartets, J=2.0 & 14.5 Hz);
    4.65 (1H, singlet);
    3.93 (1H, singlet);
    3.55 (1H, multiplet);
    3.36 (1H, multiplet);
    3.03 (1H, multiplet);
    3.01 (3H, singlet);
    1.93 (3H, doublet, J=1.4 Hz);
    1.38 (3H, singlet);
    1.17 (2H, multiplet);
    0.97 (3H, triplet, J=7.3 Hz);
    0.92 (3H, doublet, J=6.5 Hz);
    0.82 (3H, doublet, J=6.5 Hz).

EXAMPLE 91

13-[1-(4-Methoxycarbonylaminophenyl)cyclopropanecarbonyloxy]-5-hydroxyimino-milbemycin A$_4$ [(I): R$^1$=Et, X=CO, Z=>C(CH$_2$)$_2$, R$^3$=4-NHCOOMe, n=0 (Compound No. 429)]

Mass spectrum (FAB-MS) m/z:789 (M+H$^+$, M=C$_{44}$H$_{56}$N$_2$O$_{11}$).
Nuclear Magnetic Resonance Spectrum (CDCl$_3$) δ ppm:
    8.11 (1H, singlet);
    7.31 (2H, doublet, J=8.4 Hz);
    7.26 (2H, doublet, J=8.4 Hz);
    6.61 (1H, singlet);
    4.86 (1H, doublet, J=10.4 Hz);
    4.73 & 4.65 (2H, doublet of AB-quartets, J=2.1 & 14.5 Hz);
    4.65 (1H, singlet);
    3.92 (1H, singlet);
    3.78 (3H, singlet);
    3.55 (1H, multiplet);
    3.36 (1H, multiplet);
    3.03 (1H, doublet of triplets, J=2.2 & 9.3 Hz);
    1.93 (3H, singlet);
    1.37 (3H, singlet);
    1.15 (2H, multiplet);
    0.97 (3H, triplet, J=7.3 Hz);
    0.91 (3H, doublet, J=6.5 Hz);
    0.82 (3H, doublet, J=6.5 Hz).

EXAMPLE 92

13-[1-(4-Bromoacetylaminophenyl)cyclopropanecarbonyloxy]-5-hydroxyimino-milbemycin A$_4$ [(I): R$^1$=Et, X=CO, Z=>C(CH$_2$)$_2$, R$^3$=4-NHCOCH$_2$Br, n=0 (Compound No. 402)]

Mass spectrum (FAB-MS) m/z:851 (M+H$^+$, M=C$_{44}$H$_{55}$BrN$_2$O$_{10}$).
Nuclear Magnetic Resonance Spectrum (CDCl$_3$) δ ppm:
    8.14 (1H, singlet);
    8.13 (1H, singlet);
    7.47 (2H, doublet, J=8.4 Hz);
    7.32 (2H, doublet, J=8.4 Hz);
    4.87 (1H, doublet, J=10.5 Hz);
    4.73 & 4.66 (2H, doublet of AB-quartets, J=2.0 & 15.3 Hz);
    4.65 (1H, singlet);
    4.04 (2H, singlet);
    3.93 (1H, singlet);
    3.55 (1H, multiplet);
    3.36 (1H, multiplet);
    3.03 (1H, doublet of triplets, J=2.2 & 9.4 Hz);
    1.93 (3H, doublet of doublets, J=1.5 & 1.5 Hz);
    1.37 (3H, singlet);
    1.15 (2H, multiplet);
    0.97 (3H, triplet, J=7.3 Hz);
    0.91 (3H, doublet, J=6.5 Hz);
    0.83 (3H, doublet, J=6.5 Hz).

EXAMPLE 93

13-[1-(4-Isobutoxycarbonylaminophenyl)cyclopropanecarbonyloxy]-5-hydroxyimino-milbemycin A$_4$ [(I): R$^1$=Et, X=CO, Z=>C(CH$_2$)$_2$, R$^3$=4-NHCOOiBu, n=0 (Compound No. 431)]

Mass spectrum (FAB-MS) m/z:831 (M+H$^+$, M=C$_{47}$H$_{62}$N$_2$O$_{11}$).
Nuclear Magnetic Resonance Spectrum (CDCl$_3$) δ ppm:
    8.01 (1H, singlet);

7.32 (2H, doublet, J=8.6 Hz);
7.26 (2H, doublet, J=8.6 Hz);
6.60 (1H, singlet);
4.86 (1H, doublet, J=10.5 Hz);
4.73 & 4.67 (2H, doublet of AB-quartets, J=2.0 & 14.6 Hz);
4.65 (1H, singlet);
3.96 (2H, doublet, J=6.7 Hz);
3.92 (1H, singlet);
3.55 (1H, multiplet);
3.36 (1H, multiplet);
3.03 (1H, doublet of triplets, J=2.2 & 9.4 Hz);
1.93 (3H, singlet);
1.37 (3H, singlet);
1.15 (2H, multiplet);
0.97 (6H, doublet, J=6.9 Hz);
0.97 (3H, triplet, J=7.2 Hz);
0.91 (3H, doublet, J=6.5 Hz);
0.83 (3H, doublet, J=6.5 Hz).

EXAMPLE 94

13-[1-(4-Cyanoacetylaminophenyl) cyclopropanecarbonyloxy]-5-hydroxyimino-milbemycin $A_4$ [(I): $R^1$=Et, X=CO, Z=>C(CH$_2$)$_2$, $R^3$=4-NHCOCH$_2$CN, n=0 (Compound No. 401)]

Mass spectrum (FAB-MS) m/z:798 (M+H$^+$, M=C$_{45}$H$_{55}$N$_3$O$_{10}$).

Nuclear Magnetic Resonance Spectrum (CDCl$_3$) δ ppm:
8.24 (1H, singlet);
7.80 (1H, singlet);
7.42 (2H, doublet, J=8.6 Hz);
7.32 (2H, doublet, J=8.6 Hz);
4.88 (1H, doublet, J=10.5 Hz);
4.73 & 4.67 (2H, doublet of AB-quartets, J=1.9 & 14.6 Hz);
4.65 (1H, singlet);
3.94 (1H, singlet);
3.55 (1H, multiplet);
3.54 (2H, singlet);
3.36 (1H, multiplet);
3.03 (1H, doublet of triplets, J=2.1 & 9.5 Hz);
1.93 (3H, doublet, J=1.5 Hz);
1.38 (3H, singlet);
1.18 (2H, multiplet);
0.97 (3H, triplet, J=7.3 Hz);
0.92 (3H, doublet, J=6.6 Hz);
0.83 (3H, doublet, J=6.5 Hz).

EXAMPLE 95

13-{1-[4-(4-Nitrobenzoylamino)phenyl] cyclopropanecarbonyloxy}-5-hydroxyimino-milbemycin $A_4$ [(I): $R^1$=Et, X=CO, Z=>C(CH$_2$)$_2$, $R^3$=4-NHCO(4-NO$_2$Ph), n=0 (Compound No. 416)]

Mass spectrum (FAB-MS) m/z:880 (M+H$^+$, M=C$_{49}$H$_{58}$N$_3$O$_{12}$).

Nuclear Magnetic Resonance Spectrum (CDCl$_3$) δ ppm:
8.35 (2H, doublet, J=8.8 Hz);
8.07 (1H, singlet);
8.05 (2H, doublet, J=8.8 Hz);
7.88 (1H, singlet);
7.58 (2H, doublet, J=8.4 Hz);
7.37 (2H, doublet, J=8.4 Hz);
4.90 (1H, doublet, J=10.4 Hz);
4.73 & 4.66 (2H, doublet of AB-quartets, J=1.9 & 14.4 Hz);
4.64 (1H, singlet);
3.94 (1H, singlet);
3.55 (1H, multiplet);
3.54 (2H, singlet);
3.36 (1H, multiplet);
3.03 (1H, multiplet);
1.93 (3H, singlet);
1.39 (3H, singlet);
1.18 (2H, multiplet);
0.97 (3H, triplet, J=7.2 Hz);
0.93 (3H, doublet, J=6.4 Hz);
0.83 (3H, doublet, J=6.4 Hz).

EXAMPLE 96

13-{1-[4-(4-t-Butylbenzoylamino)phenyl] cyclopropanecarbonyloxy}-5-hydroxyimino-milbemycin $A_4$ [(I): $R^1$=Et, X=CO, Z=>C(CH$_2$)$_2$, $R^3$=4-NHCO(4-tBuPh), n=0 (Compound No. 417)]

Mass spectrum (FAB-MS) m/z:913 (M+Na$^+$, M=C$_{53}$H$_{67}$N$_2$O$_{10}$).

Nuclear Magnetic Resonance Spectrum (CDCl$_3$) δ ppm:
8.08 (1H, broad singlet);
7.81 (2H, doublet, J=8.8 Hz);
7.79 (1H, singlet);
7.58 (2H, doublet, J=8.4 Hz);
7.51 (2H, doublet, J=8.8 Hz);
7.33 (2H, doublet, J=8.4 Hz);
4.88 (1H, doublet, J=10.4 Hz);
4.73 & 4.66 (2H, doublet of AB-quartets, J=1.9 & 14.6 Hz);
4.65 (1H, singlet);
3.92 (1H, singlet);
3.55 (1H, multiplet);
3.36 (1H, multiplet);
3.03 (1H, multiplet);
1.93 (3H, singlet);
1.38 (3H, singlet);
1.18 (2H, multiplet);
0.97 (3H, triplet, J=7.2 Hz);
0.92 (3H, doublet, J=6.4 Hz);
0.83 (3H, doublet, J=6.4 Hz).

EXAMPLE 97

13-{1-[4-(3,4-Dimethoxybenzoylamino)phenyl] cyclopropanecarbonyloxy}-5-hydroxyimino-milbemycin $A_4$ [(I): $R^1$=Et, X=CO, Z=>C(CH$_{2)2}$, $R^3$=4-NHCO(3,4-di-MeOPh), n=0 (Compound No. 415)]

Mass spectrum (FAB-MS) m/z:895 (M+H$^+$, M=C$_{51}$H$_{62}$N$_2$O$_{12}$).

Nuclear Magnetic Resonance Spectrum (CDCl$_3$) δ ppm:
7.76 (1H, doublet, J=7.5 Hz);

7.59 (1H, singlet);
7.11 (2H, doublet, J=7.9 Hz);
6.91 (1H, doublet, J=8.6 Hz);
6.63 (2H, doublet, J=8.6 Hz);
4.85 (1H, doublet, J=10.8 Hz);
4.78-4.64 (2H, multiplet);
4.68 (1H, singlet);
3.96 (3H, singlet);
3.95 (3H, singlet);
3.55 (1H, multiplet);
3.37 (1H, multiplet);
3.03 (1H, multiplet);
1.95 (3H, singlet);
1.39 (3H, singlet);
1.18 (2H, multiplet);
1.00–0.92 (6H, multiplet);
0.83 (3H, doublet, J=6.6 Hz).

EXAMPLE 98

13-{2-[4-(3-Methoxycarbonylaminopropionyl) aminophenyl]-2-methylpropionyl-oxy}-5-hydroxyimino-milbemycin $A_4$ [(I): $R^1$=Et, X=CO, Z=>C(Me)$_2$, $R^3$=4-NHCOCH$_2$CH$_2$NHCOOMe, n=0 (Compound No. 110)]

0.032 ml (0.30 mmol) of triethylamine and 41 mg (0.30 mmol) of isobutyl chloroformate were added at 4° C. to a solution of 44 mg (0.30 mmol) of 3-methoxycarbonylaminopropionic acid in 2.0 ml of methylene chloride, and the mixture was stirred for 5 minutes. 101 mg (0.12 mmol) of 13-[2-(4-aminophenyl)-2-methylpropionyloxy]-5-t-butyldimethylsilyloxyimino-milbemycin $A_4$ [prepared as described in Example 18(a) and (b)] were then added to the mixture, and the mixture was stirred at room temperature for 2 hours. At the end of this time, the reaction mixture was diluted with 20 ml of ethyl acetate, and washed with 0.2M aqueous citric acid, with water, with a 4% w/v aqueous solution of sodium hydrogencarbonate, and with water, in that order. It was then dried over anhydrous sodium sulfate, and the solvent was removed by evaporation under reduced pressure. The resulting residue was dissolved in 2.0 ml of methanol, and 0.2 ml of 1M aqueous hydrochloric acid was added. The reaction mixture was then stirred at room temperature for 20 minutes, after which it was diluted with 20 ml of ethyl acetate, and washed with water, with a 4% w/v aqueous solution of sodium hydrogencarbonate, and with water, in that order. It was then dried over anhydrous sodium sulfate, after which the solvent was removed by evaporation under reduced pressure. The resulting residue was purified by column chromatography through silica gel, using a 6:4 by volume mixture of ethyl acetate and hexane as the eluent, to give 96 mg (yield 92.8%) of the title compound as an amorphous solid.

Mass spectrum (FAB-MS) m/z:862 (M+H$^+$, M=C$_{47}$H$_{63}$N$_3$O$_{12}$).

Nuclear Magnetic Resonance Spectrum (CDCl$_3$) δ ppm:
8.39 (1H, singlet);
7.50 (1H, singlet);
7.44 (2H, doublet, J=8.6 Hz);
7.26 (2H, doublet, J=8.6 Hz);
4.87 (1H, doublet, J=10.6 Hz);
4.73 & 4.67 (2H, doublet of AB-quartets, J=2.0 & 14.7 Hz);
4.66 (1H, singlet);
3.98 (1H, singlet);
3.78 (3H, singlet);
3.55 (1H, multiplet);
3.36 (1H, multiplet);
3.04 (1H, doublet of triplets, J=2.2 & 9.3 Hz);
1.93 (3H, singlet);
1.56 (3H, singlet);
1.54 (3H, singlet);
1.31 (3H, singlet);
0.98 (3H, triplet, J=7.3 Hz);
0.83 (3H, doublet, J=6.0 Hz);
0.82 (3H, doublet, J=6.3 Hz).

EXAMPLES 99 TO 109

The compounds of Examples 99 to 109 were prepared using the same procedures as described in Example 98.

EXAMPLE 99

13-{2-[4-(N-Methyl-N-methoxycarbonylglycyl) aminophenyl]-2-methylpropionyloxy}-5-hydroxyimino-milbemycin $A_4$ [(I): $R^1$=Et, X=CO, Z=>C(Me)$_2$, $R^3$=4-NHCOCH$_2$N(Me)COOMe, n=0 (Compound No. 95)]

Mass spectrum (FAB-MS) m/z:862 (M+H$^+$, M=C$_{47}$H$_{63}$N$_3$O$_{12}$).

Nuclear Magnetic Resonance Spectrum (CDCl$_3$) δ ppm:
8.22 (1H, singlet);
7.45 (2H, doublet, J=8.6 Hz);
7.26 (2H, doublet, J=8.6 Hz);
4.87 (1H, doublet, J=10.4 Hz);
4.74 & 4.67 (2H, doublet of AB-quartets, J=2.0 & 14.5 Hz);
4.66 (1H, singlet);
4.03 (2H, singlet);
3.97 (1H, singlet);
3.78 (3H, singlet);
3.57 (1H, multiplet);
3.36 (1H, multiplet);
3.06 (3H, singlet);
3.04 (1H, doublet of triplets, J=2.3 & 9.4 Hz);
1.93 (3H, doublet, J=1.4 Hz);
1.56 (3H, singlet);
1.53 (3H, singlet);
1.31 (3H, singlet);
0.98 (3H, triplet, J=7.3 Hz);
0.83 (3H, doublet, J=6.5 Hz);
0.82 (3H, doublet, J=6.5 Hz).

EXAMPLE 100

13-{2-[4-(N-Methoxycarbonylprolyl)aminophenyl]-2-methylpropionyloxy}-5-hydroxyimino-milbemycin $A_4$ [(I): $R^1$=Et, X=CO, Z=>C(Me)$_2$, $R^3$=4-NHCO(1-COOMe-2-Pyrd), n=0 (Compound No. 112)]

Mass spectrum (FAB-MS) m/z:888 (M+H$^+$, M=C$_{49}$H$_{65}$N$_3$O$_{12}$).

Nuclear Magnetic Resonance Spectrum (CDCl$_3$) δ ppm:
8.13 (1H, singlet);

7.46 (2H, doublet, J=8.6 Hz);
7.24 (2H, doublet, J=8.6 Hz);
4.88 (1H, doublet, J=10.6 Hz);
4.74 & 4.68 (2H, doublet of AB-quartets, J=2.0 & 14.4 Hz);
4.66 (1H, singlet);
3.97 (1H, singlet);
3.78 (3H, singlet);
3.73 (1H, multiplet);
3.57 (1H, multiplet);
3.36 (1H, multiplet);
3.04 (1H, doublet of triplets, J=2.3 & 9.3 Hz);
1.93 (3H, doublet, J=1.5 Hz);
1.56 (3H, singlet);
1.53 (3H, singlet);
1.32 (3H, singlet);
0.98 (3H, triplet, J=7.3 Hz);
0.83 (6H, doublet, J=6.5 Hz).

EXAMPLE 101

13-{2-[4-(N-Methoxycarbonylglycl) methylaminophenyl]-2-methylpropionyloxy}-5-hydroxyimino-milbemycin $A_4$ [(I): $R^1$=Et, X=CO, Z=>C(Me)$_2$, $R^3$=4-N(Me)COCH$_2$NHCOOMe, n=0 (Compound No. 96)]

Mass spectrum (FAB-MS) m/z: 862 (M+H$^+$, M=$C_{47}H_{63}N_3O_{12}$).
Nuclear Magnetic Resonance Spectrum (CDCl$_3$) δ ppm:
8.12 (1H, singlet);
7.38 (2H, doublet, J=8.5 Hz);
7.14 (2H, doublet, J=8.5 Hz);
4.88 (1H, doublet, J=10.4 Hz);
4.73 & 4.68 (2H, doublet of AB-quartets, J=1.9 & 14.7 Hz);
4.65 (1H, singlet);
3.97 (1H, singlet);
3.64 (3H, singlet);
3.57 (1H, multiplet);
3.36 (1H, multiplet);
3.23 (3H, singlet);
3.04 (1H, doublet of triplets, J=2.2 & 9.4 Hz);
1.93 (3H, doublet, J=1.5 Hz);
1.61 (3H, singlet);
1.58 (3H, singlet);
1.31 (3H, singlet);
0.98 (3H, triplet, J=7.2 Hz);
0.83 (3H, doublet, J=6.4 Hz);
0.82 (3H, doublet, J=6.3 Hz).

EXAMPLE 102

13-{2-[4-(N-t-Butoxycarbonylglycyl)aminophenyl]-2-methylpropionyloxy}-5-hydroxyimino-milbemycin $A_4$ [(I): $R^1$=Et, X=CO, Z=>C(Me)$_2$, $R^3$=4-NHCOCH$_2$NHCOOtBu, n=0 (Compound No. 89)]

Mass spectrum (FAB-MS) m/z: 890 (M+H$^+$, M=$C_{49}H_{67}N_3O_{12}$).
Nuclear Magnetic Resonance Spectrum (CDCl$_3$) δ ppm:
8.19 (1H, singlet);
8.07 (1H, broad singlet);
7.36 (2H, doublet, J=8.4 Hz);
7.26 (2H, doublet, J=8.4 Hz);
4.87 (1H, doublet, J=10.4 Hz);
4.74 & 4.67 (2H, doublet of AB-quartets, J=1.7 & 14.6 Hz);
4.65 (1H, singlet);
3.97 (1H, singlet);
3.92 (2H, doublet, J=6.0 Hz);
3.57 (1H, multiplet);
3.36 (1H, multiplet);
3.04 (1H, multiplet);
1.93 (3H, singlet);
1.60 (3H, singlet);
1.56 (3H, singlet);
1.53 (3H, singlet);
1.48 (9H, singlet);
0.98 (3H, triplet, J=7.4 Hz);
0.83 (6H, doublet, J=6.5 Hz).

EXAMPLE 103

13-{2-[4-(N-Methoxycarbonyl-2,2-dimethylglycyl) aminophenyl]-2-methyl-propionyloxy}-5-hydroxyimino-milbemycin $A_4$ [(I): $R^1$=Et, X=CO, Z=>C(Me)$_2$, $R^3$=4-NHCOC(Me)$_2$NHCOOMe, n=0 (Compound No. 107)]

Mass spectrum (FAB-MS) m/z: 874 (M+H$^+$, M=$C_{48}H_{63}N_3O_{12}$).
Nuclear Magnetic Resonance Spectrum (CDCl$_3$) δ ppm:
8.67 (1H, broad singlet);
8.17 (1H, singlet);
7.47 (2H, doublet, J=8.6 Hz);
7.28 (2H, doublet, J=8.6 Hz);
5.13 (1H, singlet);
4.87 (1H, doublet, J=10.4 Hz);
4.74 & 4.67 (2H, doublet of AB-quartets, J=1.8 & 14.6 Hz);
4.65 (1H, singlet);
3.92 (1H, singlet);
3.71 (3H, singlet);
3.56 (1H, multiplet);
3.36 (1H, multiplet);
3.04 (1H, multiplet);
1.93 (3H, singlet);
1.61 (6H, singlet);
1.38 (3H singlet);
0.98 (3H, triplet, J=7.4 Hz);
0.83 (6H, doublet, J=6.5 Hz).

EXAMPLE 104

13-{1-[4-(N-Methoxycarbonylglycyl)aminophenyl] cyclopropanecarbonyloxy}-5-hydroxyimino-milbemycin $A_4$ [(I): $R^1$=Et, X=CO, Z=>C(CH$_2$)$_2$, $R^3$=4-NHCOCH$_2$NHCOOMe, n=0 (Compound No. 422)]

Mass spectrum (FAB-MS) m/z: 846 (M+H$^+$, M=$C_{46}H_{59}N_3O_{12}$).
Nuclear Magnetic Resonance Spectrum (CDCl$_3$) δ ppm:
8.43 (1H, singlet);

8.00 (1H, broad singlet);
7.46 (2H, doublet, J=8.5 Hz);
7.29 (2H, doublet, J=8.5 Hz);
4.87 (1H, doublet, J=10.4 Hz);
4.73 & 4.67 (2H, doublet of AB-quartets, J=2.0 & 14.7 Hz);
4.66 (1H, singlet);
4.00 (2H, doublet, J=5.9 Hz);
3.94 (1H, singlet);
3.75 (3H, singlet);
3.55 (1H, multiplet);
3.36 (1H, multiplet);
3.03 (1H, doublet of triplets, J=2.0 & 9.3 Hz);
1.93 (3H, doublet, J=1.6 Hz);
1.36 (3H, singlet);
1.15 (2H, multiplet);
0.97 (3H, triplet, J=7.2 Hz);
0.91 (3H, doublet, J=6.5 Hz);
0.83 (3H, doublet, J=6.4 Hz).

EXAMPLE 105

13-{1-[4-(N-Methoxycarbonylglycyl)aminophenyl]cyclobutanecarbonyloxy}-5-hydroxyimino-milbemycin $A_4$ [(I): $R^1$=Et, X=CO, Z=>C(CH$_2$)$_3$, $R^3$=4-NHCOCH$_2$NHCOOMe, n=0 (Compound No. 484)]

Mass spectrum (FAB-MS) m/z: 860 (M+H$^+$, M=C$_{47}$H$_{61}$N$_3$O$_{12}$).
Nuclear Magnetic Resonance Spectrum (CDCl$_3$) δ ppm:
  8.23 (1H, singlet);
  7.94 (1H, broad singlet);
  7.46 (2H, doublet, J=8.4 Hz);
  7.23 (2H, doublet, J=8.4 Hz);
  5.47 (1H, multiplet);
  4.84 (1H, doublet, J=10.4 Hz);
  4.75 & 4.68 (2H, doublet of AB-quartets, J=1.9 & 14.6 Hz);
  4.66 (1H, singlet);
  4.00 (2H, doublet, J=6.0 Hz);
  3.96 (1H, singlet);
  3.75 (3H, singlet);
  3.55 (1H, multiplet);
  3.36 (1H, multiplet);
  3.03 (1H, multiplet);
  2.84–2.73 (2H, multiplet);
  1.93 (3H, singlet);
  1.33 (3H, singlet);
  0.97 (3H, triplet, J=7.2 Hz);
  0.82 (3H, doublet, J=6.4 Hz);
  0.77 (3H, doublet, J=6.4 Hz).

EXAMPLE 106

13-{1-[4-(N-Methoxycarbonylglycyl)aminophenyl]cyclopentanecarbonyloxy}-5-hydroxyimino-milbemycin $A_4$ [(I): $R^1$=Et, X=CO, Z=>C(CH$_2$)$_4$, $R^3$=4-NHCOCH$_2$NHCOOMe, n=0 (Compound No. 246)]

Mass spectrum (FAB-MS) m/z: 874 (M+H$^+$, M=C$_{48}$H$_{63}$N$_3$O$_{12}$).
Nuclear Magnetic Resonance Spectrum (CDCl$_3$) δ ppm:
  8.34 (1H, singlet);
  7.96 (1H, broad singlet);
  7.43 (2H, doublet, J=8.4 Hz);
  7.29 (2H, doublet, J=8.4 Hz);
  5.50 (1H, broad singlet);
  4.81 (1H, doublet, J=10.4 Hz);
  4.74 & 4.67 (2H, doublet of AB-quartets, J=1.8 & 14.4 Hz);
  4.66 (1H, singlet);
  3.99 (2H, doublet, J=6.0 Hz);
  3.98 (1H, singlet);
  3.75 (3H, singlet);
  3.55 (1H, multiplet);
  3.36 (1H, multiplet);
  3.03 (1H, multiplet);
  2.64–2.56 (2H, multiplet);
  2.17 (1H, doublet of doublets, J 11.6 & 24.0 Hz);
  1.93 (3H, singlet);
  1.29 (3H, singlet);
  0.97 (3H, triplet, J=7.2 Hz);
  0.82 (3H, doublet, J=6.4 Hz);
  0.76 (3H, doublet, J=6.4 Hz).

EXAMPLE 107

13-{1-[4-(N-Methoxycarbonyl-2,2-dimethylglycyl)aminophenyl]cyclopentane-carbonyloxyl-}5-hydroxyimino-milbemycin $A_4$ [(I): $R^1$=Et, X=CO, Z=>C(CH$_2$)$_4$, $R^3$=4-NHCOC(Me)$_2$NHCOOMe, n=0 (Compound No. 272)]

Mass spectrum (FAB-MS) m/z: 902 (M+H$^+$, M=C$_{50}$H$_{67}$N$_3$O$_{12}$).
Nuclear Magnetic Resonance Spectrum (CDCl$_3$) δ ppm:
  8.64 (1H, broad singlet);
  7.45 (2H, doublet, J=8.4 Hz);
  7.28 (2H, doublet, J=8.4 Hz);
  5.20 (1H, broad singlet);
  4.82 (1H, doublet, J=10.4 Hz);
  4.75 & 4.68 (2H, doublet of AB-quartets, J=1.8 & 14.2 Hz);
  4.66 (1H, singlet);
  3.67 (3H, singlet);
  3.55 (1H, multiplet);
  3.36 (1H, multiplet);
  3.03 (1H, multiplet);
  2.65–2.52 (2H, multiplet);
  2.18 (1H, doublet of doublets, J=11.6 & 24.0 Hz);
  1.93 (3H, singlet);
  1.60 (3H, singlet);
  1.58 (3H, singlet);
  1.32 (3H, singlet);
  0.97 (3H, triplet, J=7.2 Hz);
  0.82 (3H, doublet, J=6.4 Hz);
  0.78 (3H, doublet, J=6.4 Hz).

EXAMPLE 108

13-{1-[4-(N-Acetylglycyl)aminophenyl]cyclopentanecarbonyloxy}-5-hydroxyimino-milbemycin $A_4$ [(I): $R^1$=Et, X=CO, Z=>C(CH$_2$)$_4$, $R^3$=4-NHCOCH$_2$NHAc, n=0 (Compound No. 256)]

Mass spectrum (FAB-MS) m/z: 858 (M+H$^+$, M=C$_{48}$H$_{63}$N$_3$O$_{11}$).

Nuclear Magnetic Resonance Spectrum (CDCl$_3$) δ ppm:
- 8.50 (1H, singlet);
- 8.45 (1H, broad singlet);
- 7.45 (2H, doublet, J=8.6 Hz);
- 7.28 (2H, doublet, J=8.6 Hz);
- 6.56 (1H, multiplet);
- 4.80 (1H, doublet, J=10.4 Hz);
- 4.74 & 4.67 (2H, doublet of AB-quartets, J=1.8 & 14.6 Hz);
- 4.10 (2H, doublet, J=5.2 Hz);
- 4.00 (1H, singlet);
- 3.55 (1H, multiplet);
- 3.36 (1H, multiplet);
- 3.03 (1H, multiplet);
- 2.64–2.56 (2H, multiplet);
- 2.17 (1H, doublet of doublets, J=11.6 & 24.0 Hz);
- 2.09 (3H, singlet);
- 1.93 (3H, singlet);
- 1.29 (3H, singlet);
- 0.97 (3H, triplet, J=7.4 Hz);
- 0.82 (3H, doublet, J=6.4 Hz);
- 0.75 (3H, doublet, J=6.4 Hz).

EXAMPLE 109

13-{2-[4-(N-Acetylglycyl)aminophenyl]-2-methylpropionyloxy}-5-hydroxyimino-milbemycin A$_1$ [(I): R$^1$=Et, X=CO, Z=>C(Me)$_2$, R$^3$=4-NHCOCH$_2$NHAc, n=0 (Compound No. 91)]

Mass spectrum (FAB-MS) m/z:832 (M+H$^+$, M=C$_{46}$H$_{61}$N$_3$O$_{11}$).

Nuclear Magnetic Resonance Spectrum (CDCl$_3$) δ ppm:
- 8.34 (1H, broad singlet);
- 7.46 (2H, doublet, J=8.4 Hz);
- 7.26 (2H, doublet, J=8.4 Hz);
- 6.48 (1H, broad singlet);
- 4.87 (1H, doublet, J=10.5 Hz);
- 4.72 & 4.70 (2H, AB-quartet, J=14.4 Hz);
- 4.66 (1H, singlet);
- 4.09 (2H, doublet, J=4.4 Hz);
- 3.55 (1H, multiplet);
- 3.36 (1H, multiplet);
- 3.04 (4H, doublet of triplets, J=2.1 & 8.9 Hz);
- 2.10 (3H, singlet);
- 1.93 (3H, singlet);
- 1.57 (3H, singlet);
- 1.54 (3H, singlet);
- 1.30 (3H, singlet);
- 0.98 (3H, triplet, J=7.3 Hz);
- 0.84–0.76 (6H, multiplet).

EXAMPLE 110

13-[1-(4-Acetoxyacetylaminophenyl)cyclopentanecarbonyloxy]-5-hydroxyimino-milbemycin A$_4$ [(I): R$^1$=Et, X=CO, Z=>C(CH$_2$)$_4$, R$^3$=4-NHCOCH$_2$OAc, n=0 (Compound No. 214)]

47.2 mg (0.40 mmol) of 3-acetoxyacetic acid, 0.028 ml (0.20 mmol) of triethylamine and 51.1 mg (0.20 numol) of 2-chloro-1-methylpyridinium iodide were added to a solution of 87.3 mg (0.10 mmol) of 13-[2-(4-aminophenyl)-2-methylpropionyloxy]-5-t-butyldimethylsilyloxyimino-milbemycin A$_4$ [prepared as described in Example 57(a)–(d)] in 2.0 ml of methylene chloride, and the mixture was stirred for 1.5 hours. At the end of this time, the reaction mixture was diluted with 20 ml of ethyl acetate, and washed with 0.2M aqueous citric acid, with water, with a 4% w/v aqueous solution of sodium hydrogencarbonate and with water, in that order. It was then dried over anhydrous sodium sulfate, and the solvent was removed by evaporation under reduced pressure. The resulting residue was dissolved in 2.0 ml of methanol, and 0.2 ml of 1M aqueous hydrochloric acid was added. The reaction mixture was then stirred at room temperature for 20 minutes, after which it was diluted with 20 ml of ethyl acetate, and washed with water, with a 4% w/v aqueous solution of sodium hydrogencarbonate and with water, in that order. It was then dried over anhydrous sodium sulfate, and the solvent was removed by evaporation under reduced pressure. The resulting residue was purified by column chromatography through silica gel, using a 3:97 by volume mixture of ethanol and methylene chloride as the eluent, to give 66.4 mg (yield 77.4%) of the title compound as an amorphous solid.

Mass spectrum (FAB-MS) m/z:859 (M+H$^+$, M=C$_{48}$H$_{62}$N$_2$O$_{12}$).

Nuclear Magnetic Resonance Spectrum (CDCl$_3$) δ ppm:
- 8.00 (1H, singlet);
- 7.74 (1H, singlet);
- 7.46 (2H, doublet, J=8.6 Hz);
- 7.31 (2H, doublet, J=8.6 Hz);
- 4.81 (1H, doublet, J=10.4 Hz);
- 4.74 & 4.68 (2H, doublet of AB-quartets, J=1.9 & 14.6 Hz);
- 4.69 (2H, singlet);
- 4.65 (1H, singlet);
- 3.97 (1H, singlet);
- 3.55 (1H, multiplet);
- 3.36 (1H, multiplet);
- 3.03 (1H, doublet of triplets, J=2.2 & 9.3 Hz);
- 2.62 (2H, multiplet);
- 2.25 (3H, singlet);
- 1.93 (3H, singlet);
- 1.29 (3H, singlet);
- 0.97 (3H, triplet, J=7.4 Hz);
- 0.82 (3H, doublet, J=6.4 Hz);
- 0.77 (3H, doublet, J=6.4 Hz).

EXAMPLES 111 TO 113

The compounds of Examples 111 to 113 were prepared using the same procedures as described in Example 110.

EXAMPLE 111

13-[1-(4-Ethoxyacetylaminophenyl)cyclopentanecarbonyloxy]-5-hydroxyimino-milbemycin A$_4$ [(I): R$^1$=Et, X=CO, Z=>C(CH$_2$)$_4$, R$^3$=4-NHCOCH$_2$OEt, n=0 (Compound No. 213)]

Mass spectrum (FAB-MS) m/z:845 (M+H$^+$, M=C$_{48}$H$_{64}$N$_2$O$_{11}$).

Nuclear Magnetic Resonance Spectrum (CDCl$_3$) δ ppm:
- 8.27 (1H, singlet);
- 8.13 (1H, singlet);
- 7.49 (2H, doublet, J=8.4 Hz);

7.30 (2H, doublet, J=8.4 Hz);
4.81 (1H, doublet, J=10.4 Hz);
4.74 & 4.67 (2H, doublet of AB-quartets, J=1.8 & 14.6 Hz);
4.65 (1H, singlet);
4.05 (2H, singlet);
3.97 (1H, singlet);
3.66 (2H, quartet, J=7.2 Hz);
3.54 (1H, multiplet);
3.36 (1H, multiplet);
3.02 (1H, doublet of triplets,=2.1 & 9.4 Hz);
2.61 (2H, multiplet);
1.93 (3H, singlet);
1.31 (3H, triplet, J=7.2 Hz);
1.29 (3H, singlet);
0.97 (3H, triplet, J=7.4 Hz);
0.82 (3H, doublet, J=6.4 Hz);
0.76 (3H, doublet , J=6.4 Hz).

EXAMPLE 112

13-[1-(4-Phenylthioacetylaminophenyl)cyclopentanecarbonyloxy]-5-hydroxyimino-milbemycin $A_4$ [(I): $R^1$=Et, X=CO, Z=>$(CH_2)_4$, $R^3$=4-NHCOCH$_2$SPh, n=0 (Compound No. 218)]

Mass spectrum (FAB-MS) m/z:909 (M+H$^+$, M=$C_{52}H_{64}N_2O_{10}S$).

Nuclear Magnetic Resonance Spectrum (CDCl$_3$) δ ppm:
8.54 (1H, singlet);
8.09 (1H, singlet);
7.40–7.21 (9H, multiplet);
4.80 (1H, doublet, J=10.4 Hz);
4.75 & 4.6 8 (2H, doublet of AB-quartets, J=1.8 & 14.6 Hz);
4.66 (1H, singlet);
3.97 (1H, singlet);
3.77 (2H, singlet);
3.54 (1H, multiplet);
3.36 (1H, multiplet);
3.02 (1H, doublet of triplets, J=2.2 & 9.3 Hz);
2.60 (2H, multiplet);
1.93 (3H, doublet, J=1.4 Hz);
1.29 (3H, singlet);
0.97 (3H, triplet, J=7.2 Hz);
0.82 (3H, doublet, J=6.5 Hz);
0.76 (3H, doublet, J=6.4 Hz).

EXAMPLE 113

13-[1-(4-Benzenesulfonylacetylaminophenyl)cyclopentanecarbonyloxy]-5-hydroxyimino-milbemycin $A_4$ [(I): $R^1$=Et, X=CO, Z=>$C(CH_2)_4$, $R^3$=4-NHCOCH$_2$SO$_2$, Ph, n=0 (Compound No. 217)]

Mass spectrum (FAB-MS) m/z:941 (M+H$^+$, M=$C_{52}H_{64}N_2O_{12}S$).

Nuclear Magnetic Resonance Spectrum (CDCl$_3$) δ ppm:
8.46 (1H, singlet);
8.06 (1H, singlet);
7.92 (2H, doublet, J=7.3 Hz);
7.70 (1H, doublet of doublets, J=7.4 & 7.4 Hz);
7.58 (2H, doublet of doublets, J=7.3 & 7.4 Hz);
7.42 (2H, doublet, J=8.7 Hz);
7.31 (2H, doublet, J=8.7 Hz);
4.82 (1H, doublet, J=10.5 Hz);
4.75 & 4.68 (2H, doublet of AB-quartets, J=1.8 & 14.5 Hz);
4.65 (1H, singlet);
4.15 (2H, singlet);
3.97 (1H, singlet);
3.55 (1H, multiplet);
3.36 (1H, multiplet);
3.02 (1H, doublet of triplets, J=2.2 & 9.4 Hz);
2.62 (2H, multiplet);
1.93 (3H, doublet, J=1.6 Hz);
1.31 (3H, singlet);
0.97 (3H, triplet, J=7.3 Hz);
0.82 (3H, doublet, J=6.5 Hz);
0.76 (3H, doublet, J=6.5 Hz).

EXAMPLE 114

13-{2-[4-(N-Methylcarbamoylamino)phenyl]-2-methylpropionyloxy}-5-hydroxyimino-milbemycin $A_4$ [(I): $R^1$=Et, X=CO, Z=>C(Me)$_2$, $R^3$=4-NHCONHMe, n=0 (Compound No. 132)]

11.4 mg (0.20 mmol) of methyl isocyanate was added to a solution of 101 mg (0.12 mmol) of 13-[2-(4-aminophenyl)-2-methylpropionyloxy]-5-t-butyldimethylsilyloxyimino-milbemycin $A_4$ [prepared as described in Example 18(a) and (b) ] in 2.0 ml of methylene chloride, and the mixture was stirred at room temperature for 5 hours. At the end of this time, the solvent was removed from the reaction mixture by evaporation under reduced pressure. The resulting residue was dissolved in 2.0 ml of methanol, and 0.2 ml of 1M aqueous hydrochloric acid was added to the solution. The reaction mixture was then stirred at room temperature for 20 minutes, after which it was diluted with 20 ml of ethyl acetate, washed with water, with a 4% w/v aqueous solution of sodium hydrogencarbonate and with water, in that order. It was then dried over anhydrous sodium sulfate, and the solvent was removed by evaporation under reduced pressure. The resulting residue was purified by column chromatography through silica gel, using a 6:4 by volume mixture of ethyl acetate and hexane as the eluent, to give 87 mg (yield 91%) of the title compound as an amorphous solid.

Mass spectrum (FAB-MS) m/z:790 (M+H$^+$, M=$C_{44}H_{59}N_3O_{10}$).

Nuclear Magnetic Resonance Spectrum (CDCl$_3$) δ ppm:
8.14 (1H, broad singlet);
7.26 (2H, doublet, J=8.6 Hz);
7.20 (2H, doublet, J=8.6 Hz);
6.27 (1H, broad singlet);
4.87 (1H, doublet, J=10.6 Hz);
4.72 & 4.69 (2H, AB-quartet, J=15.2 Hz);
4.66 (1H, singlet);
3.95 (1H, singlet);
3.55 (1H, multiplet);
3.36 (1H, multiplet);
3.04 (1H, multiplet);
2.84 (3H, doublet, J=4.7 Hz);
1.93 (3H, singlet);

1.58 (3H, singlet);
1.54 (3H, singlet);
1.31 (3H, singlet);
0.98 (3H, triplet, J=7.3 Hz);
0.83–0.81 (6H, multiplet).

EXAMPLES 115 TO 119

The compounds of Examples 115 to 119 were prepared using the same procedures as described in Example 114.

EXAMPLE 115

13-{2-[4-(N-Phenylcarbamoylamino)phenyl]-2-methylpropionyloxy}-5-hydroxyimino-milbemycin $A_4$ [(I): $R^1$=Et, X=CO, Z=>C(Me)$_2$, $R^3$=4-NHCONHPh, n=0 (Compound No. 144)]

Mass spectrum (FAB-MS) m/z:852 (M+H$^+$, M=$C_{49}H_{61}N_3O_{10}$).
Nuclear Magnetic Resonance Spectrum (CDCl$_3$) δ ppm:
8.22 (1H, broad singlet);
6.69 (1H, broad singlet);
6.64 (1H, broad singlet);
4.87 (1H, doublet, J=10.6 Hz);
4.72 & 4.70 (2H, AB-quartet, J=14.5 Hz);
4.66 (1H, singlet);
3.95 (1H, singlet);
3.55 (1H, multiplet);
3.36 (1H, multiplet);
3.04 (1H, multiplet);
1.92 (3H, singlet);
1.58 (3H, singlet);
1.54 (3H, singlet);
1.32 (3H, singlet);
0.98 (3H, triplet, J=7.3 Hz);
0.83 (6H, doublet, J=6.6 Hz).

EXAMPLE 116

13-{2-[4-(N-Methylthiocarbamoylamino)phenyl]-2-methylpropionyloxy}-5-hydroxyimino-milbemycin $A_4$ [(I): $R^1$=Et, X=CO, Z=>C(Me)$_2$, $R^3$=4-NHCSNHMe, n=0 (Compound No. 145)]

Mass spectrum (FAB-MS) m/z:806 (M+H$^+$, M=$C_{44}H_{59}N_3O_9S$).
Nuclear Magnetic Resonance Spectrum (CDCl$_3$) δ ppm:
7.94 (1H, broad singlet);
7.61 (1H, broad singlet);
7.37 (2H, doublet, J=8.6 Hz);
7.14 (2H, doublet, J=8.6 Hz);
5.97 (1H, broad singlet);
4.89 (1H, doublet, J=10.6 Hz);
4.72 & 4.70 (2H, AB-quartet, J=14.5 Hz);
4.66 (1H, singlet);
3.96 (1H, singlet);
3.55 (1H, multiplet);
3.36 (1H, multiplet);
3.14 (3H, doublet, J=4.6 Hz);
3.03 (1H, doublet of doublets, J=2.0 & 9.2 Hz);
1.93 (3H, singlet);
1.59 (3H, singlet);
1.57 (3H, singlet);
1.34 (3H, singlet);
0.98 (3H, triplet, J=7.3 Hz);
0.83 (6H, doublet, J=6.5 Hz).

EXAMPLE 117

13-{1-[4-(N-Methylcarbamoylamino)phenyl]cyclobutanecarbonyloxy}-5-hydroxyimino-milbemycin $A_4$ [(I): $R^1$=Et, X=CO, Z=>C (CH$_2$)$_3$, $R^3$=4-NHCONHMe, n=0 (Compound No. 494)]

Mass spectrum (FAB-MS) m/z:802 (M+H$^+$, M=$C_{45}H_{59}N_3O_{10}$).
Nuclear Magnetic Resonance Spectrum (CDCl$_3$) δ ppm:
8.30 (1H, broad singlet);
7.22 (4H, singlet);
6.31 (1H, broad singlet);
4.85 (1H, doublet, J=10.6 Hz);
4.73 & 4.70 (2H, AB-quartet, J=14.5 Hz);
4.66 (1H, singlet);
3.95 (1H, singlet);
3.55 (1H, multiplet);
3.36 (1H, multiplet);
3.03 (1H, doublet of doublets, J=2.3 & 9.2 Hz);
2.84 (3H, doublet, J=4.6 Hz);
2.53–2.42 (3H, multiplet);
1.93 (3H, singlet);
1.35 (3H, singlet);
0.97 (3H, triplet, J=7.3 Hz);
0.82 (3H, doublet, J=6.6 Hz);
0.77 (3H, doublet, J=6.3 Hz).

EXAMPLE 118

13-{1-[4-(N-Phenylcarbamoylamino)phenyl]cyclobutanecarbonyloxy}-5-hydroxyimino-milbemycin $A_4$ [(I): $R^1$=Et, X=CO, Z=>C(CH$_2$)$_3$, $R^3$=4-NHCONHPh, n=0 (Compound No. 500)]

Mass spectrum (FAB-MS) m/z:864 (M+H$^+$, M=$C_{50}H_{61}N_3O_{10}$).
Nuclear Magnetic Resonance Spectrum (CDCl$_3$) δ ppm:
8.56 (1H, singlet);
7.35–7.30 (4H, multiplet);
7.25–7.19 (4H, multiplet);
7.15–7.10 (1H, multiplet);
6.89 (1H, singlet);
6.75 (1H, singlet);
4.86 (1H, doublet, J=10.4 Hz);
4.75 & 4.68 (2H, doublet of AB-quartets, J=1.6 & 14.8 Hz);
4.67 (1H, singlet);
3.95 (1H, singlet);
3.55 (1H, multiplet);
3.36 (1H, multiplet);
3.04 (1H, multiplet);
2.84–2.72 (2H, multiplet);
1.91 (3H, singlet);
1.36 (3H, singlet);
0.96 (3H, triplet, J=7.4 Hz);
0.82 (3H, doublet, J=6.5 Hz);

0.79 (3H, doublet, J=6.5 Hz).

EXAMPLE 119

13-{1-[4-(N-Phenylcarbamoylamino)phenyl]
cyclopentanecarbonyloxy}-5-hydroxyimino-
milbemycin $A_4$ [(I): $R^1$=Et, X=CO, Z=>C(CH$_2$)$_4$,
$R^3$=4-NHCONHPh, n=0 (Compound No. 309)]

Mass spectrum (FAB-MS) m/z:878 (M+H$^+$, M=$C_{51}H_{63}N_3O_{10}$).

Nuclear Magnetic Resonance Spectrum (CDCl$_3$) δ ppm:
8.80 (1H, broad singlet);
7.40–7.00 (10H, multiplet);
4.86 (1H, doublet, J=10.3 Hz);
4.74 & 4.66 (2H, AB-quartet, J=15.5 Hz);
4.66 (1H, singlet);
3.95 (1H, singlet);
3.53 (1H, multiplet);
3.36 (1H, multiplet);
3.01 (1H, multiplet);
2.60 (2H, multiplet);
1.88 (3H, singlet);
1.34 (3H, singlet);
0.95 (3H, triplet, J=7.2 Hz);
0.81 (3H, doublet, J=6.3 Hz);
0.76 (3H, doublet, J=6.4 Hz).

EXAMPLE 120

13-{1-[4-(N-Methylcarbamoylamino)phenyl]
cyclopropanecarbonyloxy}-5-hydroxyimino-
milbemycin $A_4$ [(I): $R^1$=Et, X=CO, Z=>C(CH$_2$)$_2$,
$R^3$=4-NHCONHMe, n=0 (Compound No. 432)]

120(a) 13-{1-[4-(1,2,4-triazolo[4,3-a]pyridine-3-one-2-carbonyl)aminophenyl]-cyclopropanecarbonyloxy}-5-t-butyldimethylsilyloxyimino-milbemycin $A_4$ 13-[1-(4-Nitrophenyl)-cyclopropanecarbonyloxy]-5-hydroxyimino-milbemycin $A_4$ (prepared as described in Example 6) was converted to 13-[1-(4-aminophenyl)cyclopropanecarbonyloxy]-5-t-butyldimethylsilyloxyimino-milbemycin $A_4$ using the same procedures as described in Example 18(a) and (b).

845 mg (1.0 mmol) of this amino derivative were dissolved in 10 ml of methylene chloride, and 0.081 ml (1.0 mmol) of pyridine and 198 mg (1.0 mmol) of 2-chloroformyl-1,2,4-triazolo[4,3-a]pyridine-3-one were added at 4° C. The reaction mixture was then stirred at room temperature for 20 minutes, after which it was diluted with 100 ml of ethyl acetate, washed with 0.2M aqueous citric acid, with water, with a 4% w/v aqueous solution of sodium hydrogencarbonate and with water, in that order. It was then dried over anhydrous sodium sulfate, and the solvent was removed by evaporation under reduced pressure. The resulting residue was purified by column chromatography through silica gel, using a 1:1 by volume mixture of ethyl acetate and hexane as the eluent, to give 995 mg (yield 97.4%) of the title compound as an amorphous solid.

120(b) 13-{1-[4-(N-Methylcarbamoylamino)phenyl]cyclopropanecarbonyloxy}-5-hydroxyimino-milbemycin $A_4$ 153 mg (0.15 numol) of 13-{1-[4-(1,2,4-triazolo[4,3-a]pyridine-3-one-2-carbonyl)aminophenyl]cyclopropanecarbonyloxy}-5-t-butyldimethylsilyloxyimino-milbemycin $A_4$ [prepared as described in step (a) above] was dissolved in 1.0 ml of N-methylpyrrolidone. 19.4 mg (0.25 mmol) of 40% v/v methylamine in H$_2$O, was added to the resulting solution, and the mixture was stirred at room temperature for 1 hour. The reaction mixture was then diluted with 20 ml of ethyl acetate, and washed with water, with 0.2M aqueous citric acid, with water, with a 4% w/v aqueous solution of sodium hydrogencarbonate, and with water, in that order. It was then dried over anhydrous sodium sulfate, and the solvent was removed by evaporation under reduced pressure. The resulting residue was dissolved in 2.0 ml of methanol, and 0.2 ml of 1M aqueous hydrochloric acid was added to the solution. The reaction mixture was then stirred at room temperature for 20 minutes, after which it was diluted with 20 ml of ethyl acetate, washed with water, with a 4% w/v aqueous solution of sodium hydrogencarbonate, and with water, in that order. It was then dried over anhydrous sodium sulfate, and the solvent was removed by evaporation under reduced pressure. The resulting residue was purified by column chromatography through silica gel, using a 5:95 by volume mixture of ethanol and methylene chloride as the eluent, to give 109 mg (yield 92.4%) of the title compound as an amorphous solid.

Mass spectrum (FAB-MS) m/z:788 (M+H$^+$, M=$C_{44}H_{57}N_3O_{10}$).

Nuclear Magnetic Resonance Spectrum (CDCl$_3$) δ ppm:
8.86 (1H, singlet);
7.27 (2H, doublet, J=8.4 Hz);
7.21 (2H, doublet, J=8.4 Hz);
6.53 (1H, singlet);
4.87 (1H, doublet, J=10.4 Hz);
4.81 (1H, multiplet);
4.73 & 4.67 (2H, doublet of AB-quartets, J=1.8 & 14.6 Hz);
4.67 (1H, singlet);
3.93 (1H, singlet);
3.55 (1H, multiplet);
3.36 (1H, multiplet);
3.03 (s H, doublet of doublets, a 2.1 & 9.4 Hz);
2.83 (3H, doublet, J=4.9 Hz);
1.93 (3H, singlet);
1.38 (3H, singlet);
1.16 (2H, multiplet);
0.97 (3H, triplet, J=7.3 Hz);
0.92 (3H, doublet, J=6.5 Hz);
0.82 (3H, doublet, J=6.5 Hz).

EXAMPLES 121 TO 124

The compounds of Examples 121 to 124 were prepared using the same procedures as described in Example 120

EXAMPLE 121

13-{1-[4-(1-Pyrrolidinylcarbonylamino)phenyl]
cyclopropanecarbonyloxy}-5-hydroxyimino-
milbemycin $A_4$ [(I): $R^1$=Et, X=CO, Z=>C(CH$_2$)$_2$,
$R^3$=4-NHCO(1-Pyrd), n=0 (Compound No. 437)]

Mass spectrum (FAB-MS) m/z:828 (M+H$^+$, M=$C_{47}H_{61}N_3O_{10}$).

Nuclear Magnetic Resonance Spectrum (CDCl$_3$) δ ppm:
8.37 (1H, singlet);
7.35 (2H, doublet, J=8.6 Hz);
7.23 (2H, doublet, J=8.6 Hz);
6.15 (1H, singlet);
4.86 (1H, doublet, J=10.4 Hz);

4.73 & 4.67 (2H, doublet of AB-quartets, J=1.9 & 14.7 Hz);
4.66 (1H, singlet);
3.92 (1H, singlet);
3.55 (1H, multiplet);
3.47 (4H, multiplet);
3.36 (1H, multiplet);
3.03 (1H, doublet of doublets, J=2.2 & 9.4 Hz);
1.98 (4H, multiplet);
1.93 (3H, doublet, J=1.5 Hz);
1.36 (3H, singlet);
1.15 (2H, multiplet);
0.97 (3H, triplet, J=7.3 Hz);
0.90 (3H, doublet, J=6.5 Hz);
0.83 (3H, doublet, J=6.5 Hz).

EXAMPLE 122

13-{1-[4-(N-Butylcarbamoylamino)phenyl] cyclopropanecarbonyloxy}-5-hydroxyimino-milbemycin $A_4$ [(I): $R^1$=Et, X=CO, Z=>C(Me)$_2$, $R^3$=4-NHCONHBu, n=0 (Compound No. 138)]

Mass spectrum (FAB-MS) m/z:832 (M+H$^+$, M=$C_{47}H_{65}N_3O_{10}$).
Nuclear Magnetic Resonance Spectrum (CDCl$_3$) δ ppm:
8.24 (1H, broad singlet);
7.25 (2H, doublet, J=8.6 Hz);
7.20 (2H, doublet, J=8.6 Hz);
6.28 (1H, broad singlet);
4.87 (1H, doublet, J=10.6 Hz);
4.72 & 4.69 (2H, AB-quartet, J=14.5 Hz);
4.66 (1H, singlet);
3.95 (1H, singlet);
3.56 (1H, multiplet);
3.36 (1H, multiplet);
3.25 (2H, quartet, J=6.6 Hz);
3.03 (1H, multiplet);
1.93 (3H, singlet);
1.57 (3H, singlet);
1.54 (3H, singlet);
1.31 (3H, singlet);
0.98 (3H, triplet, J=7.3 Hz);
0.84–0.81 (6H, multiplet).

EXAMPLE 123

13-{1-[4-(N-t-Butylcarbamoylamino)phenyl] cyclopropanecarbonyloxy}-5-hydroxyimino-milbemycin $A_4$ [(I): $R^1$=Et, X=CO, Z=>C(Me)$_2$, $R^3$=4-NHCONHtBu, n=0 (Compound No. 139)]

Mass spectrum (FAB-MS) m/z:832 (M+H$^+$, M=$C_{47}H_{65}N_3O_{10}$).
Nuclear Magnetic Resonance Spectrum (CDCl$_3$) δ ppm:
8.22 (1H, broad singlet);
7.23 (2H, doublet, J=8.6 Hz);
7.17 (2H, doublet, J=8.6 Hz);
6.13 (1H, broad singlet);
4.87 (1H, doublet, J=10.6 Hz);
4.72 & 4.69 (2H, AB-quartet, J=14.5 Hz);
4.66 (1H, singlet);
3.95 (1H, singlet);
3.56 (1H, multiplet);
3.36 (1H, multiplet);
3.03 (1H, doublet of triplets, J=1.7 & 8.9 Hz);
1.93 (3H, singlet);
1.56 (3H, singlet);
1.53 (3H, singlet);
1.37 (9H, singlet);
1.32 (3H, singlet);
0.98 (3H, triplet, J=7.3 Hz);
0.84–0.80 (6H, multiplet).

EXAMPLE 124

13-{1-[4-(N-cyclohexylcarbamoylamino)phenyl] cyclopropanecarbonyloxy}-5-hydroxyimino-milbemycin $A_4$ [(I): $R^1$=Et, X=CO, Z=>C(Me)$_2$, $R^3$=4-NHCONH-cHx, n=0 (Compound No. 140)]

Mass spectrum (FAB-MS) m/z:858 (M+H$^+$, M=$C_{49}H_{67}N_3O_{10}$).
Nuclear Magnetic Resonance Spectrum (CDCl$_3$) δ ppm:
8.17 (1H, broad singlet);
7.25 (2H, doublet, J=8.6 Hz);
7.19 (2H, doublet, J=8.6 Hz);
6.18 (1H, broad singlet);
4.87 (1H, doublet, J=10.5 Hz);
4.72 & 4.69 (2H, AB-quartet, J=14.5 Hz);
4.66 (1H, singlet);
3.95 (1H, singlet);
3.56 (1H, multiplet);
3.36 (1H, multiplet);
3.04 (1H, doublet of triplets, J=1.9 & 9.2 Hz);
1.93 (3H, singlet);
1.57 (3H, singlet);
1.54 (3H, singlet);
1.31 (3H, singlet);
0.98 (3H, triplet, J=7.3 Hz);
0.84–0.81 (6H, multiplet).

EXAMPLE 125

13-{1-[4-(Pyrimidine-2-ylthioacetylamino)phenyl] cyclopropanecarbonyloxy}-5-hydroxyimino-milbemycin $A_4$ [(I): $R^1$=Et, X=CO, Z=>C(CH$_2$)$_2$, $R^3$=4-NHCOCH$_2$S-(2-Pym), n=0 (Compound No. 406)]

13-[1-(4-Nitrophenyl)-cyclopropanecarbonyloxy]-5-hydroxyimino-milbemycin $A_4$ (prepared as described in Example 6) was converted to 13-[1-(4-bromoacetylaminophenyl)cyclopropanecarbonyloxy]-5-t-butyldimethylsilyloxyimino-milbemycin $A_4$ using the same procedures as described in Example 18.

115 mg (0.12 mmol) of this bromoacetyl derivative were dissolved in 2.0 ml of N-methylpyrrolidone, and 22.4 mg (0.20 mmol) of 2-mercaptopyrimidine and 6.5 mg (0.15 mmol) of sodium hydride (as a 55% w/v suspension in mineral oil) were added. The reaction mixture was then stirred at room temperature for 30 minutes, after which it was diluted with 20 ml of ethyl acetate, and washed with 0.2M aqueous citric acid, with water, with a 4% w/v aqueous solution of sodium hydrogencarbonate, and with water, in that order. It was then dried over anhydrous sodium sulfate, and the solvent was removed by evaporation under reduced pressure. The resulting residue was dissolved in 2.0 ml of methanol, and 0.2 ml of 1M aqueous hydrochloric acid was added. The reaction mixture was then stirred at room temperature for 20 minutes, after which it was diluted with 20 ml of ethyl acetate, washed with water, with a 4% w/v aqueous solution of sodium hydrogencarbonate, and with water, in that order. It was then dried over anhydrous sodium sulfate, and the solvent was removed by evaporation under reduced pressure. The resulting residue was purified by column chromatography through silica gel, using a 2.5:97.5 by volume mixture of ethanol and methylene chloride as the eluent, to give 105 mg (yield 99.1%) of the title compound as an amorphous solid.

Mass spectrum (FAB-MS) m/z:883 (M+H$^+$, M=$C_{48}H_{58}N_4O_{10}S$).

Nuclear Magnetic Resonance Spectrum (CDCl$_3$) δ ppm:
9.13 (1H, singlet);
8.63 (2H, doublet, J=5.1 Hz);
8.28 (1H, singlet);
7.40 (2H, doublet, J=8.4 Hz);
7.25 (2H, doublet, J=8.4 Hz);
7.13 (1H, triplet, J=5.1 Hz);
4.85 (1H, doublet, J=10.5 Hz);
4.73 & 4.66 (2H, doublet of AB-quartets, J=2.0 & 14.5 Hz);
4.65 (1H, singlet);
3.93 (3H, singlet);
3.54 (1H, multiplet);
3.36 (1H, multiplet);
3.02 (1H, doublet of doublets, J=2.2 & 9.4 Hz);
1.93 (3H, doublet, J=1.5 Hz);
1.36 (3H, singlet);
1.13 (2H, multiplet);
0.97 (3H, triplet, J=7.3 Hz);
0.89 (3H, doublet, J=6.5 Hz);
0.82 (3H, doublet, J=6.5 Hz).

EXAMPLES 126 TO 127

The compounds of Examples 126 to 127 were prepared using the same procedures as described in Example 125.

EXAMPLE 126

13-{1-[4-(Thiazolidine-2-ylthioacetylamino)phenyl]cyclopropanecarbonyloxy}-5-hydroxyimino-milbemycin A$_4$ [(I): R$^1$=Et, X=CO, Z=>C(CH$_2$)$_2$, R$^3$=4-NHCOCH$_2$S-(2-Thdn), n=0 (Compound No. 408)]

Mass spectrum (FAB-MS) m/z:890 (M+H$^+$, M=$C_{47}H_{59}N_3O_{10}S_2$).

Nuclear Magnetic Resonance Spectrum (CDCl$_3$) δ ppm:
8.21 (1H, singlet);
7.41 (2H, doublet, J=8.5 Hz);
7.27 (2H, doublet, J=8.5 Hz);
4.87 (1H, doublet, J=10.5 Hz);
4.73 & 4.66 (2H, doublet of AB-quartets, J=2.0 & 14.5 Hz);
4.65 (1H, singlet);
4.31 (2H, triplet, J=8.0 Hz);
3.92 (3H, singlet);
3.79 (2H, singlet);
3.56 (1H, multiplet);
3.54 (2H, triplet, J=8.0 Hz);
3.36 (1H, multiplet);
3.03 (1H, doublet of doublets, J=2.2 & 9.4 Hz);
1.93 (3H, doublet, J=1.4 Hz);
1.37 (3H, singlet);
1.14 (2H, multiplet);
0.97 (3H, triplet, J=7.3 Hz);
0.91 (3H, doublet, J=6.5 Hz);
0.82 (3H, doublet, J=6.5 Hz).

EXAMPLE 127

13-{1-[4-(Pyridine-2-ylthioacetylamino)phenyl]cyclopropanecarbonyloxy}-5-hydroxyimino-milbemycin A$_4$ [(I): R$^1$=Et, X=CO, Z=>C(CH$_2$)$_2$, R$^3$=4-NHCOCH$_2$S-(2-Pyr), n=0 (Compound No. 407)]

Mass spectrum (FAB-MS) m/z:882 (M+H$^+$, M=$C_{49}H_{59}N_3O_{10}S$).

Nuclear Magnetic Resonance Spectrum (CDCl$_3$) δ ppm:
8.55 (1H, doublet, J=5.2 Hz);
8.18 (1H, singlet);
7.60 (1H, multiplet);
7.42 (2H, doublet, J=8.6 Hz);
7.32 (1H, doublet, J=8.0 Hz);
7.25 (2H, doublet, J=8.6 Hz);
7.16 (1H, doublet of doublets, J=5.2 & 7.2 Hz);
4.85 (1H, doublet, J=10.5 Hz);
4.73 & 4.66 (2H, doublet of AB-quartets, J=2.0 & 14.6 Hz);
4.65 (1H, singlet);
3.92 (1H, singlet);
3.89 (2H, singlet);
3.54 (1H, multiplet);
3.36 (1H, multiplet);
3.03 (1H, doublet of doublets, J=2.2 & 9.4 Hz);
1.93 (3H, multiplet);
1.36 (3H, singlet);
1.13 (2H, multiplet);
0.97 (3H, triplet, J=7.3 Hz);
0.89 (3H, doublet, J=6.4 Hz);
0.82 (3H, doublet, J=6.5 Hz).

EXAMPLES 128 TO 137

The compounds of Examples 128 to 137 were prepared using the same procedures as described in Example 1.

EXAMPLE 128

13-{1-[4-(N-Methylacetylamino)phenyl]cyclopentanecarbonyloxy}-5-hydroxyimino-milbemycin A$_4$ [(I): R$^1$=Et, X=CO, Z=>C(CH$_2$)$_4$, R$^3$=4-N(Me)Ac, n=0 (Compound No. 193)]

Mass spectrum (FAB-MS) m/z:815 (M+H$^+$, M=$C_{47}H_{62}N_2O_{10}$).

Nuclear Magnetic Resonance Spectrum (CDCl$_3$) δ ppm:
8.70 (1H, broad singlet);
7.38 (2H, doublet, J=8.3 Hz);
7.11 (2H, doublet, J=8.3 Hz);
4.81 (1H, doublet, J=10.5 Hz);

4.74 & 4.66 (2H, AB-quartet, J=14.9 Hz);
4.65 (1H, singlet);
3.95 (1H, broad singlet);
3.55 (1H, multiplet);
3.35 (1H, multiplet);
3.23 (3H, singlet);
3.02 (1H, multiplet);
2.65 (2H, multiplet);
1.92 (3H, singlet);
1.84 (3H, singlet);
1.30 (3H, singlet);
0.97 (3H, triplet, J=7.2 Hz);
0.82 (3H, doublet, J=6.3 Hz);
0.76 (3H, doublet, J=6.5 Hz).

EXAMPLE 129

13-{1-[4-(N-Butylacetylamino)phenyl]
cyclopentanecarbonyloxy}-5-hydroxyimino-
milbemycin $A_4$ [(I): $R^1$=Et, X=CO, Z=>C(CH$_2$)$_4$,
$R^3$=4-N(Bu)Ac, n=0 (Compound No. 196)]

Mass spectrum (FAB-MS) m/z:857 (M+H$^+$, M=C$_{50}$H$_{68}$N$_2$O$_{10}$).

Nuclear Magnetic Resonance Spectrum (CDCl$_3$) δ ppm:
8.11 (1H, singlet);
7.38 (2H, doublet, J=8.6 Hz);
7.07 (2H, doublet, J=8.6 Hz);
4.80 (1H, doublet, J=10.4 Hz);
4.74 & 4.67 (2H, AB-quartet, J=14.4 Hz);
4.65 (1H, singlet);
3.97 (1H, singlet);
3.66 (2H, triplet, J=7.6 Hz);
3.55 (1H, multiplet);
3.36 (1H, multiplet);
3.03 (1H, multiplet);
2.65 (2H, multiplet);
1.93 (3H, singlet);
1.78 (3H, singlet);
1.28 (3H, singlet);
0.97 (3H, triplet, J=7.3 Hz);
0.87 (3H, triplet, J=7.2 Hz);
0.82 (3H, doublet, J=6.4 Hz);
0.72 (3H, doublet, J=6.4 Hz).

EXAMPLE 130

13-{1-[4-(N-Methylmethanesulfonylamino)phenyl]
cyclopentanecarbonyloxy}-5-hydroxyimino-
milbemycin $A_4$ [(I): $R^1$=Et, X=CO, Z=>C(CH$_2$)$_4$,
$R^3$=4-N(Me)SO$_2$Me, n=0 (Compound No. 316)]

Mass spectrum (FAB-MS) m/z:851 (M+H$^+$, M=C$_{46}$H$_{62}$N$_2$O$_{11}$S).

Nuclear Magnetic Resonance Spectrum (CDCl$_3$) δ ppm:
8.13 (1H, singlet);
7.35 (2H, doublet, J=8.7 Hz);
7.29 (2H, doublet, J=8.7 Hz);
4.80 (1H, doublet, J=10.4 Hz);
4.74 & 4.67 (2H, doublet of AB-quartets, J=1.8 & 14.2 Hz);
4.65 (1H, singlet);
3.97 (1H, singlet);
3.55 (1H, multiplet);
3.36 (1H, multiplet);
3.29 (3H, singlet);
3.02 (1H, multiplet);
2.80 (3H, singlet);
2.62 (2H, multiplet);
1.93 (3H, singlet);
1.27 (3H, singlet);
0.97 (3H, triplet, J=7.2 Hz);
0.82 (3H, doublet, J=6.4 Hz);
0.75 (3H, doublet, J=6.4 Hz).

EXAMPLE 131

13-{1-[4-(N-Butylmethanesulfonylamino)phenyl]
cyclopentanecarbonyloxy}-5-hydroxyimino-
milbemycin $A_4$ [(I): $R^1$=Et, X=CO, Z=>C(CH$_2$)$_4$,
$R^3$=4-N(Bu)SO$_2$Me, n=0 (Compound No. 319)]

Mass spectrum (FAB-MS) m/z:893 (M+H$^+$, M=C$_{49}$H$_{68}$N$_2$O$_{11}$S).

Nuclear Magnetic Resonance Spectrum (CDCl$_3$) δ ppm:
8.03 (1H, singlet);
7.36 (2H, doublet, J=8.7 Hz);
7.25 (2H, doublet, J=8.7 Hz);
4.79 (1H, doublet, J=10.8 Hz);
4.74 & 4.67 (2H, doublet of AB-quartets, J=1.8 & 14.6 Hz);
4.65 (1H, singlet);
3.97 (1H, singlet);
3.64 ((2H, triplet, J=6.8 Hz);
3.55 (1H, multiplet);
3.36 (1H, multiplet);
3.03 (1H, multiplet);
2.83 (3H, singlet);
2.65 (2H, multiplet);
1.93 (3H, singlet);
1.27 (3H, singlet);
0.97 (3H, triplet, J=7.3 Hz);
0.86 (3H, triplet, J=7.2 Hz);
0.82 (3H, doublet, J=6.4 Hz);
0.72 (3H, doublet, J=6.4 Hz).

EXAMPLE 132

13-{2-[4-(2-Oxopiperidino)phenyl]-2-
methylpropionyloxy}-5-hydroxyimino-milbemycin
$A_4$ [(I): $R^1$=Et, X=CO, Z=>C(Me)$_2$, $R^3$=4-(2-oxo-1-
Pip), n=0 (Compound No. 161)]

Mass spectrum (FAB-MS) m/z:815 (M+H$^+$, M=C$_{47}$H$_{62}$N$_2$O$_{10}$).

Nuclear Magnetic Resonance Spectrum (CDCl$_3$) δ ppm:
8.18 (1H, singlet);
7.31 (2H, doublet, J=8.5 Hz);
7.18 (2H, doublet, J=8.5 Hz);
4.87 (1H, doublet, J=10.8 Hz);
4.73 & 4.66 (2H, doublet of AB-quartets, J=1.8 & 14.6 Hz);
4.65 (1H, singlet);
3.96 (1H, broad singlet);

3.62–3.52 (3H, multiplet);
3.36 (1H, multiplet);
3.03 (1H, multiplet);
2.57 (2H, multiplet);
1.92 (3H, singlet);
1.58 (3H, singlet);
1.55 (3H, singlet);
1.29 (3H, singlet);
0.98 (3H, triplet, J=7.4 Hz);
0.84–0.82 (6H, multiplet).

EXAMPLE 133

13-{2-[4-(2-Oxo-1-pyrrolidinyl)phenyl]-2-methylpropionyloxy}-5-hydroxyimino-milbemycin $A_4$ [(I): $R^1$=Et, X=CO, Z=>C(Me)$_2$, $R^3$=4-(2-oxo-1-Pyrd), n=0)] (Compound No. 163)]

Mass spectrum (FAB-MS) m/z:801 (M+H$^+$, M=$C_{46}H_{60}N_2O_{10}$).

Nuclear Magnetic Resonance Spectrum (CDCl$_3$) δ ppm:
8.80 (1H, broad singlet);
7.55 (2H, doublet, J=8.6 Hz);
7.30 (2H, doublet, J=8.6 Hz);
4.88 (1H, doublet, J=10.6 Hz);
4.74 & 4.65 (2H, AB-quartet, J=14.5 Hz);
4.65 (1H, singlet);
3.96 (1H, singlet);
3.71 (2H, singlet);
3.57 (1H, multiplet);
3.38 (1H, multiplet);
3.04 (1H, multiplet);
2.62 (2H, triplet, J=8.2 Hz);
2.17 (2H, triplet, J=7.5 Hz);
1.93 (3H, singlet);
1.57 (3H, singlet);
1.54 (3H, singlet);
1.32 (3H, singlet);
0.98 (3H, triplet, J=7.2 Hz);
0.85–0.82 (6H, multiplet).

EXAMPLE 134

13-{2-[4-(2-Oxoazetidin-1-yl)phenyl]-2-methylpropionyloxy}-5-hydroxyimino-milbemycin $A_4$ [(I): $R^1$=Et, X=CO, Z=>C(Me)$_2$, $R^3$=4-(2-oxo-1-Azt), n=0 (Compound No. 160)]

Mass spectrum (FAB-MS) m/z:787 (M+H$^+$, M=$C_{45}H_{58}N_2O_{10}$).

Nuclear Magnetic Resonance Spectrum (CDCl$_3$) δ ppm:
7.99 (1H, singlet);
7.28–7.26 (4H, multiplet);
4.87 (1H, doublet, J=10.8 Hz);
4.74 & 4.67 (2H, doublet of AB-quartets, J=2.0 & 14.4 Hz);
4.66 (1H, singlet);
3.97 (1H, singlet);
3.63–3.60 (2H, multiplet);
3.57 (1H, multiplet);
3.38 (1H, multiplet);
3.13–3.10 (2H, multiplet);
3.03 (1H, multiplet);
1.93 (3H, singlet);
1.58 (3H, singlet);
1.54 (3H, singlet);
1.32 (3H, singlet);
0.98 (3H, triplet, J=7.2 Hz);
0.84–0.81 (6H, multiplet).

EXAMPLE 135

13-{2-[4-(2,6-Dioxopiperidino)phenyl]-2-methylpropionyloxy}-5-hydroxyimino-milbemycin $A_4$ [(I): $R^1$=Et, X=CO, Z=>C(Me)$_2$, $R^3$=4-(2,6-dioxo-1-Pip), n=0 (Compound No. 162)]

Mass spectrum (FAB-MS) m/z:829 (M+H$^+$, M=$C_{47}H_{60}N_2O_{11}$).

Nuclear Magnetic Resonance Spectrum (CDCl$_3$) δ ppm:
8.12 (1H, singlet);
7.36 (2H, doublet, J=8.6 Hz);
7.01 (2H, doublet, J=8.6 Hz);
4.86 (1H, doublet, J=10.4 Hz);
4.72 & 4.66 (2H, doublet of AB-quartets, J=2.1 & 14.5 Hz);
4.65 (1H, singlet);
3.96 (1H, singlet);
3.56 (1H, multiplet);
3.35 (1H, multiplet);
3.04 (1H, multiplet);
2.81 (4H, triplet, J=6.6 Hz);
2.11 (2H, multiplet);
1.93 (3H, singlet);
1.61 (3H, singlet);
1.56 (3H, singlet);
1.23 (3H, singlet);
0.98 (3H, triplet, J=7.2 Hz);
0.84 (3H, doublet, J=6.5 Hz);
0.83 (3H, doublet, J=6.4 Hz).

EXAMPLE 136

13-{2-[4-(2,5-Dioxo-1-pyrrolidinyl)phenyl]-2-methylpropionyloxy}-5-hydroxyimino-milbemycin $A_4$ [(I): $R^1$=Et, X=CO, Z=>C(Me)$_2$, $R^3$=4-(2,5-dioxo-1-Pyrd), n=0 (Compound No. 164)]

Mass spectrum (FAB-MS) m/z:815 (M+H$^+$, M=$C_{46}H_{58}N_2O_{11}$).

Nuclear Magnetic Resonance Spectrum (CDCl$_3$) δ ppm:
8.25 (1H, singlet);
7.39 (2H, doublet, J=8.5 Hz);
7.23 (2H, doublet, J=8.5 Hz);
4.88 (1H, doublet, J=10.6 Hz);
4.73 & 4.67 (2H, doublet of AB-quartets, J=2.0 & 14.5 Hz);
4.65 (1H, singlet);
3.97 (1H, singlet);
3.56 (1H, multiplet);
3.36 (1H, multiplet);
3.04 (1H, doublet of doublets, J=2.2 & 9.5 Hz);
2.90 (4H, singlet);
1.93 (3H, doublet, J=1.5 Hz);

1.60 (3H, singlet);
1.56 (3H, singlet);
1.27 (3H, singlet);
0.98 (3H, triplet, J=7.3 Hz);
0.84 (3H, doublet, J=6.5 Hz);
0.83 (3H, doublet, J=8.5 Hz).

EXAMPLE 137

13-{2-[4-(2-Oxooxazolin-3-yl)phenyl]-2-methylpropionyloxy}-5-hydroxyimino-milbemycin $A_4$[(I): $R^1$=Et, X=CO, Z=>C(Me)$_2$, $R^3$=4-(2-oxo-3-Oxazoline), n=0 (Compound No. 165)]

Mass spectrum (FAB-MS) m/z:803 (M+H$^+$, M=$C_{45}H_{58}N_2O_{11}$).

Nuclear Magnetic Resonance Spectrum (CDCl$_3$) δ ppm:
8.19 (1H, broad singlet);
7.48 (2H, doublet, J=9.0 Hz);
7.30 (2H, doublet, J=9.0 Hz);
4.88 (1H, doublet, J=10.5 Hz);
4.74 & 4.66 (2H, doublet of AB-quartets, J=2.0 & 14.5 Hz);
4.65 (1H, singlet);
4.49 (2H, multiplet);
4.05 (2H, multiplet);
3.97 (1H, singlet);
3.57 (1H, multiplet);
3.36 (1H, multiplet);
3.04 (1H, doublet of doublets, J=2.2 & 9.4 Hz),
1.93 (3H, doublet, J=1.4 Hz);
1.58 (3H, singlet);
1.55 (3H, singlet);
1.32 (3H, singlet);
0.98 (3H, triplet, J=7.3 Hz);
0.83 (3H, doublet, J=6.5 Hz);
0.82 (3H, doublet, J=6.5 Hz).

EXAMPLES 138 TO 139

The compounds of Examples 138 to 139 were obtained from 13-[2-(3-nitrophenyl)-2-methylpropionyloxy]-5-hydroxyimino-milbemycin $A_4$ (prepared as described in Example 2) using the same procedures as described in Example 18.

EXAMPLE 138

13-[2-(3-Acetylaminophenyl)-2-methylpropionyloxy]-5-hydroxyimino-milbemycin $A_4$ [(I): $R^1$=Et, X=CO, Z=>C(Me)$_2$, $R^3$=3-NHAc, n=0 (Compound No. 32)]

Mass spectrum (FAB-MS) m/z:775 (M+H$^+$, M=$C_{44}H_{58}N_2O_{10}$).

Nuclear Magnetic Resonance Spectrum (CDCl$_3$) δ ppm:
7.87 (1H, broad singlet);
7.50 (1H, doublet, J=8.6 Hz);
7.39 (1H, singlet);
7.22 (1H, doublet, J=7.9 Hz);
7.10 (1H, broad singlet);
7.02 (1H, doublet, J=7.9 Hz);
4.87 (1H, doublet, J=10.6 Hz);
4.71 & 4.69 (2H, AB-quartet, J=13.9 Hz);
4.65 (1H, singlet);
3.95 (1H, singlet);
3.57 (1H, multiplet);
3.36 (1H, multiplet);
3.04 (1H, multiplet);
2.18 (3H, singlet);
1.93 (3H, singlet);
1.57 (3H, singlet);
1.54 (3H, singlet);
1.28 (3H, singlet);
0.98 (3H, triplet, J=7.3 Hz);
0.84–0.81 (6H, multiplet).

EXAMPLE 139

13-[2-(3-Methanesulfonylaminophenyl)-2-methylpropionyloxy]-5-hydroxyimino-milbemycin $A_4$ [(I): $R^1$=Et, X=CO, Z=>C(Me)$_2$, $R^3$=3-NHSO$_2$Me, n=0 (Compound No. 150)]

Mass spectrum (FAB-MS) m/z:711 (M+H$^+$, M=$C_{43}H_{58}N_2O_{11}S$).

Nuclear Magnetic Resonance Spectrum (CDCl$_3$) δ ppm:
7.76 (1H, broad singlet);
7.50–7.10 (24, multiplet);
6.33 (1H, broad singlet);
4.88 (1H, doublet, J=10.6 Hz);
4.71 & 4.70 (2H, AB-quartet, J=14.5 Hz);
4.65 (1H, singlet);
3.94 (1H, singlet);
3.57 (1H, multiplet);
3.36 (1H, multiplet);
3.04 (1H, multiplet);
2.99 (3H, singlet)
1.93 (3H, singlet);
1.58 (3H, singlet);
1.56 (3H, singlet);
1.31 (3H, singlet);
0.98 (3H, triplet, J=7.3 Hz);
0.84–0.81 (6H, multiplet).

EXAMPLE 140

13-[1-(4-Acetylaminophenyl)cyclopentanecarbonyloxy]-5-hydroxyimino-milbemycin $A_3$[(I): $R^1$=Me, X=CO, Z=>C(CH$_2$)$_4$, $R^3$=4-NHAc, n=0 (Compound No. 192)]

The title compound was prepared from 15-hydroxy-5-oxo-milbemycin $A_3$ using the same method as described in Examples 57 and 59.

Mass spectrum (FAB-MS) m/z:787 (M+H$^+$, M=$C_{45}H_{58}N_2O_{10}$).

Nuclear Magnetic Resonance Spectrum (CDCl$_3$) δ ppm:
8.11 (1H, singlet);
7.41 (2H, doublet, J=8.6 Hz);
7.28 (2H, doublet, J=8.6 Hz);
7.13 (1H, singlet);
4.81 (1H, doublet, J=10.4 Hz);
4.75 & 4.69 (2H, AB-quartet, J=14.7 Hz);
4.65 (1H, singlet);
3.97 (1H, singlet);

3.52 (1H, multiplet);
3.36 (1H, multiplet);
3.21 (1H, multiplet);
2.61 (2H, multiplet);
2.17 (3H, singlet);
1.93 (3H, singlet);
1.29 (3H, singlet);
1.14 (3H, doublet, J=6.4 Hz);
0.83 (3H, doublet, J=6.5 Hz);
0.75 (3H, doublet, J=6.5 Hz).

EXAMPLES 141 TO 142

The compounds of Examples 141 to 142 were obtained from 15-hydroxy-5-oxo-milbemycin $A_4$ using the same procedures as described in Examples 57 and 110.

EXAMPLE 141

13-{2-[4-(1-Methoxycarbonylpyrrolidine-2-carbonylamino)phenyloxy]}-5-hydroxyimino-milbemycin $A_4$ [(I): $R^1$=Et, X=C=O, Z=C(Me)$_2$, $R^3$=4-NHCO(1-COOMe-2-Pyrd), n=1 (Compound No. 111)]

Mass spectrum (FAB-MS) m/z:1053 (M+H$^+$+triethanolamine=903+1+149).
Nuclear Magnetic Resonance Spectrum (270M Hz) δ ppm:
 8.63 (1H, broad singlet);
 7.34 (2H, doublet, J=8.8 Hz);
 6.74 (2H, doublet, J=8.8 Hz);
 5.86–5.79 (3H, multiplet);
 5.45–5.30 (3H, multiplet);
 5.02 (1H, doublet, J=10.9 Hz);
 4.79–4.68 (2H, AB-quartet, J=14.5 Hz);
 4.67 (1H, singlet);
 4.45 (1H, broad singlet);
 4.00 (1H, singlet);
 3.77 (3H, singlet);
 3.73–3.38 (5H, multiplet);
 3.65–3.42 (3H, multiplet);
 3.37 (1H, multiplet);
 3.06 (1H, multiplet).

EXAMPLE 142

13-{2-[4-(N-Methoxycarbonylglycylamino)-2-methylproionyloxyphenyloxy]}-5-hydroxyimino-milbemycin $A_4$ [(I): $R^1$=Et, X=C=O, Z=C(Me)$_2$, $R^3$=4-NHCOCH$_2$NHCOOMe, n=1 (Compound No. 80)]

Mass spectrum (FAB-MS) m/z:1013 (M+H$^+$+triethanolamine=863+1+149).
Nuclear Magnetic Resonance Spectrum (270M Hz) δ ppm:
 8.27 (1H, broad singlet);
 7.83 (1H, broad singlet);
 7.31 (2H, doublet, J=8.9 Hz);
 6.74 (2H, doublet, J=8.9 Hz);
 5.90–5.82 (3H, multiplet);
 5.50–5.31 (4H, multiplet);
 5.00 (1H, doublet, J=10.4 Hz);
 4.73–4.67 (2H, AB-quartet, J=14.4 Hz);
 4.66 (1H, singlet);
 3.98 (2H, singlet);
 3.97 (1H, singlet);
 3.74 (3H, singlet);
 3.66–3.55 (1H, multiplet);
 3.37 (1H, multiplet);
 3.05 (1H, multiplet).

We claim:
1. A compound of formula (I):

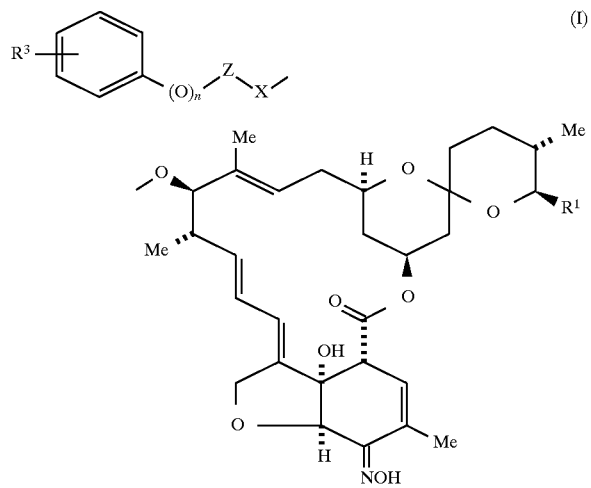

wherein:

$R^1$ represents a methyl group, an ethyl group, an isopropyl group or a sec-butyl group:

X represents a carbonyl group or a methylene group:

Z represents a group of formula (i) or (ii):

in which $R^2$ represents an alkyl group having from 1 to 3 carbon atoms, and m represents an integer of from 2 to 5;

n is 0 or 1;

$R^3$ represents a nitro group, an amino group, a ($C_1$–$C_4$ alkyl)amino group, a di($C_1$–$C_4$ alkyl)amino group, an alkoxy group having from 1 to 4 carbon atoms, a ($C_1$–$C_3$ alkoxy)-($C_2$–$C_3$ alkoxy) group, or a group of formula (iii), (iv), (v), (vi), (vii), (viii) or (ix):

-continued

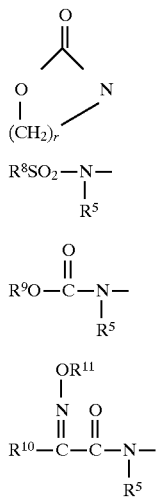

wherein:
R[4] represents: an alkyl group having from 1 to 6 carbon atoms; a substituted alkyl group which has from 1 to 6 carbon atoms and which is substituted by at least one substituent selected from the group consisting of substituents α, defined below; a cycloalkyl group having from 3 to 6 carbon atoms; a cycloalkyl group which has from 3 to 10 carbon atoms and which is substituted by at least one substituent selected from the group consisting of substituents β, defined below; an alkenyl group having from 2 to 6 carbon atoms; an alkynyl group having from 2 to 6 carbon atoms; a carbocyclic aryl group which has from 6 to 14 ring carbon atoms and which is unsubstituted or which is substituted by at least one substituent selected from the group consisting of substituents γ, defined below; or a heterocyclic group having from 3 to 6 ring atoms, of which at least one is a hetero-atom selected from the group consisting of nitrogen, oxygen and sulfur hetero-atoms; said heterocyclic group being unsubstituted or being substituted by at least one substituent selected from the group consisting of substituents γ, defined below, and oxygen atoms;

R[5] represents a hydrogen atom or an alkyl group having from 1 to 4 carbon atoms;

R[6] represents: a hydrogen atom; an alkyl group having from 1 to 6 carbon atoms; or a cycloalkyl group having from 3 to 6 carbon atoms;

R[7] represents: an alkyl group having from 1 to 6 carbon atoms; a cycloalkyl group having from 3 to 6 carbon atoms; a carbocyclic aryl group which has from 6 to 14 ring carbon atoms which is unsubstituted or which is substituted by at least one substituent selected from the group consisting of substituents γ, defined below; or an aralkyl group in which the aryl part is carbocyclic and has from 6 to 10 ring carbon atoms and the alkyl part has from 1 to 4 carbon atoms; or R[6] and R[7], together with the nitrogen atom to which they are attached, are fused to form a heterocyclic ring having from 3 to 6 ring atoms;

Y represents oxygen atom or sulfur atom;

r is 1,2 or 3;

Q represents a methylene group or a carbonyl group;

R[8] represents: an alkyl group having from 1 to 4 carbon atoms or a carbocyclic aryl group which has from 6 to 10 ring carbon atoms which is unsubstituted or which is substituted by at least one substituent selected from the group consisting of substituents γ, defined below;

R[9] represents: an alkyl group having from 1 to 6 carbon atoms; a cycloalkyl group having from 3 to 6 carbon atoms; a carbocyclic aryl group which has from 6 to 10 ring carbon atoms which is unsubstituted or which is substituted by at least one substituent selected from the group consisting of substituents γ, defined below; or an aralkyl group in which the aryl part is carbocyclic and has from 6 to 10 ring carbon atoms and the alkyl part has from 1 to 4 carbon atoms;

R[10] represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents δ, defined below, and oxygen atoms;

R[11] represents an alkyl group having from 1 to 3 carbon atoms;

substituents α are selected from the group consisting of: halogen atoms; cyano groups; alkoxy groups having from 1 to 4 carbon atoms; alkylthio groups having from 1 to 4 carbon atoms; alkylsulfonyl groups having from 1 to 4 carbon atoms; alkanoyloxy groups having from 2 to 5 carbon atoms; alkoxycarbonyl groups having from 2 to 5 carbon atoms; carbocyclic aryloxy groups which have from 6 to 10 ring carbon atoms; carbocyclic arylthio groups which have from 6 to 10 ring carbon atoms; carbocyclic arylsulfonyl groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 5 carbon atoms; alkoxycarbonylamino groups having from 2 to 5 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has from 1 to 4 carbon atoms; carbocyclic aryl groups which have from 6 to 10 ring carbon atoms which are unsubstituted or which are substituted by at least one substituent selected from the group consisting of substituents γ; groups R[h], where R[h] represents a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents γ, defined below, and oxygen atoms; groups of formula R[h]—S—, where R[h] is as defined above; alkanoyl groups having from 2 to 5 carbon atoms; and aralkyloxycarbonylamino groups in which the aryl part is carbocyclic and has from 6 to 10 ring carbon atoms and the alkyl part has from 1 to 4 carbon atoms;

substituents β are selected from the group consisting of halogen atoms, alkoxy groups having from 1 to 4 carbon atoms, and alkanoyloxy groups having from 2 to 5 carbon atoms;

substituents γ are selected from the group consisting of: halogen atoms; hydroxy groups; cyano groups; nitro groups; alkyl groups having from 1 to 4 carbon atoms; alkoxy groups having from 1 to 4 carbon atoms; and alkoxycarbonyl groups having from 2 to 5 carbon atoms;

substituents δ are selected from the group consisting of amino groups, alkanoylamino groups having from 2 to 5 carbon atoms, haloalkanoylamino groups having from 2 to 5 carbon atoms, and alkoxycarbonylamino groups having from 2 to 6 carbon atoms;

and salts thereof.

2. The compound of claim 1, wherein Z represents a group of formula (i) and $R^2$ represents a methyl or ethyl group.

3. The compound of claim 1, wherein Z represents a group of formula (ii) and m is 2, 3 or 4.

4. The compound of claim 1, wherein n is 0.

5. The compound of claim 1, wherein $R^3$ represents an amino group, a $(C_1-C_3$ alkyl)amino group, a di($C_1-C_3$ alkyl)amino group, an alkoxy group having from 1 to 3 carbon atoms, or a group of formula (iii), (iv), (v), (vi) or (vii):

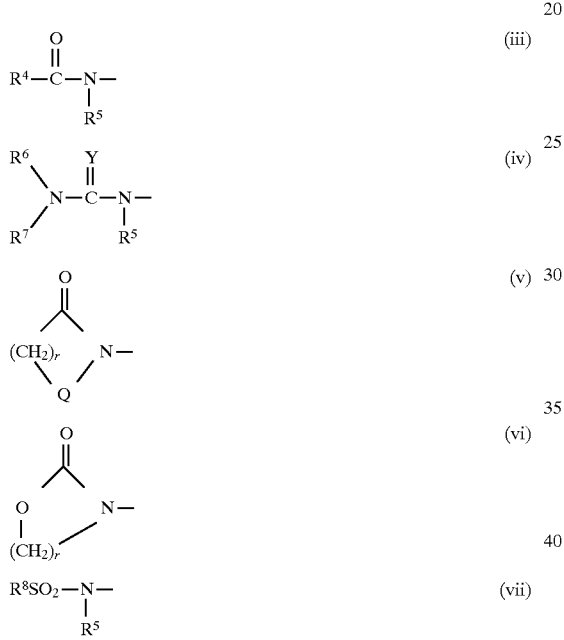

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;

$R^5$ represents a hydrogen atom or an alkyl group having from 1 to 3 carbon atoms;

$R^6$ represents: a hydrogen atom; or an alkyl group having from 1 to 4 carbon atoms;

$R^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the alkyl part has 1 or 2 carbon atoms; or $R^6$ and $R^7$, together with the nitrogen atom to which they are attached, are fused to form a heterocyclic ring having 5 or 6 ring atoms;

Y represents oxygen atom or sulfur atom;

r is 1,2 or 3;

Q represents a methylene group or a carbonyl group;

$R^8$ represents: an alkyl group having from 1 to 4 carbon atoms or a carbocyclic aryl group which has from 6 to 10 ring carbon atoms which is unsubstituted or which is substituted by at least one substituent selected from the group consisting of substituents $\gamma^1$, defined below;

substituents $\alpha^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2-C_5$ alkanoyl)-N-($C_1-C_3$ alkyl)amino groups; haloalkanoylamino groups having from 2 to 4 carbon atoms; alkoxycarbonylamino groups having from 2 to 4 carbon atoms; N-($C_2-C_5$ alkoxycarbonyl)-N-($C_1-C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents $\gamma^1$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms; groups of formula $R^h$—S—, where $R^h$ is as defined above; and alkanoyl groups having from 2 to 5 carbon atoms;

substituents $\gamma^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

6. The compound of claim 1, wherein:

Z represents a group of formula (i) and $R^2$ represents a methyl or ethyl group; and $R^3$ represents an amino group, a $(C_1-C_3$ alkyl)amino group, a di($C_1-C_3$ alkyl)amino group, an alkoxy group having from 1 to 3 carbon atoms, or a group of formula (iii), (iv), (v), (vi) or (vii):

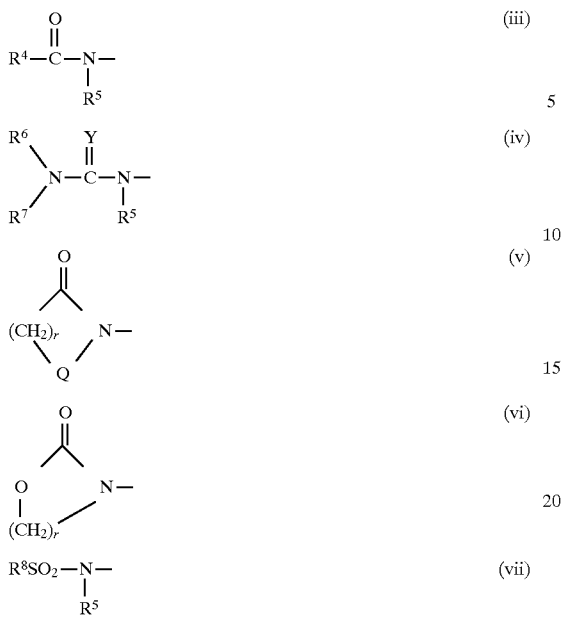

wherein:

R⁴ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms;

R⁵ represents a hydrogen atom or an alkyl group having from 1 to 3 carbon atoms;

R⁶ represents: a hydrogen atom; or an alkyl group having from 1 to 4 carbon atoms;

R⁷ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the alkyl part has 1 or 2 carbon atoms; or R⁶ and R⁷, together with the nitrogen atom to which they are attached, are fused to form a heterocyclic ring having 5 or 6 ring atoms;

Y represents oxygen atom or sulfur atom;

r is 1, 2 or 3;

Q represents a methylene group or a carbonyl group;

R⁸ represents: an alkyl group having from 1 to 4 carbon atoms or a carbocyclic aryl group which has from 6 to 10 ring carbon atoms which is unsubstituted or which is substituted by at least one substituent selected from the group consisting of substituents $\gamma^1$, defined below;

substituents $\alpha^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents $\gamma^1$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms; groups of formula $R^h$—S—, where $R^h$ is as defined above; and alkanoyl groups having from 2 to 5 carbon atoms;

substituents $\gamma^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

7. The compound of claim 6, wherein n is 0.

8. The compound of claim 1, wherein:

Z represents a group of formula (ii) and m is 2, 3 or 4; and

R³ represents an amino group, a ($C_1$–$C_3$ alkyl)amino group, a di($C_1$–$C_3$ alkyl)amino group, an alkoxy group having from 1 to 3 carbon atoms, or a group of formula (iii), (iv), (v), (vi) or (vii):

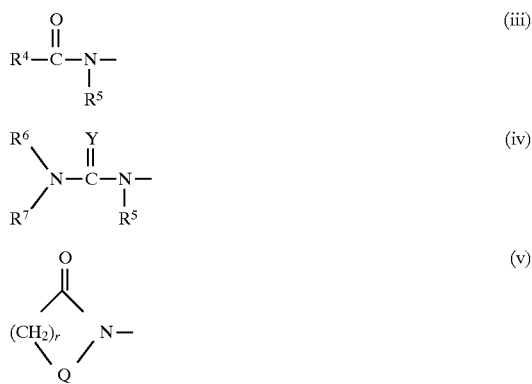

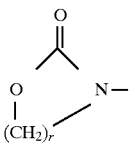
(vi)

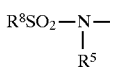
(vii)

wherein:
R$^4$ represents: an alkyl group having from 1 to 4 carbon atoms; a substituted alkyl group which has from 1 to 3 carbon atoms and which is substituted by at least one substituent selected from the group consisting of substituents α$^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ$^1$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ$^1$, defined below, and oxygen atoms;

R$^5$ represents a hydrogen atom or an alkyl group having from 1 to 3 carbon atoms;

R$^6$ represents: a hydrogen atom; or an alkyl group having from 1 to 4 carbon atoms;

R$^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents γ$^1$, defined below; or an aralkyl group in which the aryl part is carbocyclic and has from 6 to 10 ring carbon atoms and the alkyl part has 1 or 2 carbon atoms; or R$^6$ and R$^7$, together with the nitrogen atom to which they are attached, are fused to form a heterocyclic ring having 5 or 6 ring atoms;

Y represents oxygen atom or sulfur atom;

r is 1, 2 or 3;

Q represents a methylene group or a carbonyl group;

R$^8$ represents: an alkyl group having from 1 to 4 carbon atoms or a carbocyclic aryl group which has from 6 to 10 ring carbon atoms which is unsubstituted or which is substituted by at least one substituent selected from the group consisting of substituents γ$^1$, defined below;

substituents α$^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-(C$_2$–C$_5$ alkanoyl)-N-(C$_1$–C$_3$ alkyl)amino groups; haloalkanoylamino groups having from 2 to 4 carbon atoms; alkoxycarbonylamino groups having from 2 to 4 carbon atoms; H-(C$_2$–C$_5$ alkoxycarbonyl)-N-(C$_1$–C$_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents γ$^1$; groups R$^h$, where R$^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ$^1$, defined below, and oxygen atoms; groups of formula R$^h$—S—, where R$^h$ is as defined above; and alkanoyl groups having from 2 to 5 carbon atoms;

substituents γ$^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

9. The compound of claim 8, wherein n is 0.

10. The compound of claim 1, wherein R$^1$ represents a methyl or ethyl group.

11. The compound of claim 1, wherein Z represents a group of formula (i) and R$^2$ represents a methyl group.

12. The compound of claim 1, wherein Z represents a group of formula (ii) and m is 2 or 4.

13. The compound of claim 1, wherein R$^3$ represents an amino group, a methylamino group, an ethylamino group, an alkoxy group having from 1 to 3 carbon atoms, or a group of formula (iii), (v) or (vi):

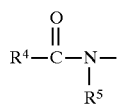
(iii)

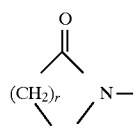
(v)

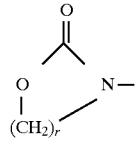
(vi)

wherein:
R$^4$ represents: an alkyl group having from 1 to 4 carbon atoms; a substituted alkyl group which has from 1 to 3 carbon atoms and which is substituted by at least one substituent selected from the group consisting of substituents α$^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ$^1$, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;

r is 1, 2 or 3;

Q represents a methylene group or a carbonyl group;

substituents $\alpha^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms; and groups of formula $R^h$—S—, where $R^h$ is as defined above;

substituents $\gamma^2$ are selected from the group consisting of: halogen atoms; cyano groups; nitro groups; methyl groups; ethyl groups; methoxy groups; and alkoxycarbonyl groups having 2 or 3 carbon atoms.

14. The compound of claim 1, wherein:

$R^1$ represents a methyl or ethyl group;

Z represents a group of formula (i) and $R^2$ represents a methyl group; and $R^3$ represents an amino group, a methylamino group, an ethylamino group, an alkoxy group having from 1 to 3 carbon atoms, or a group of formula (iii), (v) or (vi):

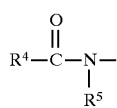
(iii)

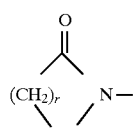
(v)

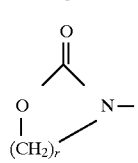
(vi)

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;

r is 1, 2 or 3;

Q represents a methylene group or a carbonyl group;

substituents $\alpha^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms; and groups of formula $R^h$—S—, where $R^h$ is as defined above;

substituents $\gamma^2$ are selected from the group consisting of: halogen atoms; cyano groups; nitro groups; methyl groups; ethyl groups; methoxy groups; and alkoxycarbonyl groups having 2 or 3 carbon atoms.

15. The compound of claim 14, wherein n is 0.

16. The compound of claim 1, wherein:

$R^1$ represents a methyl or ethyl group;

Z represents a group of formula (ii) and m is 2 or 4; and $R^3$ represents an amino group, a methylamino group, an ethylamino group, an alkoxy group having from 1 to 3 carbon atoms, or a group of formula (iii), (v) or (vi):

(iii)

-continued

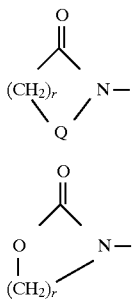

(v)

(vi)

wherein:
R$^4$ represents: an alkyl group having from 1 to 4 carbon atoms; a substituted alkyl group which has from 1 to 3 carbon atoms and which is substituted by at least one substituent selected from the group consisting of substituents α$^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ$^2$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ$^2$, defined below, and oxygen atoms;

r is 1, 2or 3;

Q represents a methylene group or a carbonyl group;

substituents α$^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-(C$_2$–C$_5$ alkanoyl)-N-(C$_1$–C$_3$ alkyl)amino groups; haloalkanoylamino groups having from 2 to 4 carbon atoms; alkoxycarbonylamino groups having from 2 to 4 carbon atoms; N-(C$_2$–C$_5$ alkoxycarbonyl)-N-(C$_1$–C$_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents γ$^2$; groups R$^h$, where R$^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ$^2$, defined below, and oxygen atoms; and groups of formula R$^h$—S—, where R$^h$ is as defined above;

substituents γ$^2$ are selected from the group consisting of: halogen atoms; cyano groups; nitro groups; methyl groups; ethyl groups; methoxy groups; ethoxy groups; and alkoxycarbonyl groups having 2 or 3 carbon atoms.

17. The compound of claim 16, wherein n is 0.

18. The compound of claim 1, wherein R$^1$ represents an ethyl group.

19. The compound of claim 1, wherein R$^3$ represents an amino group, a methylamino group, an ethylamino group, or a group of formula (iii) or (vi):

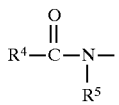

(iii)

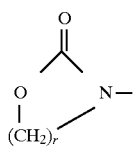

(vi)

wherein:
R$^4$ represents: an alkyl group having from 1 to 4 carbon atoms; a substituted alkyl group which has from 1 to 3 carbon atoms and which is substituted by at least one substituent selected from the group consisting of substituents α$^3$, defined below; a cycloalkyl group having 5 or 6 carbon atoms; a phenyl group which is unsubstituted or which is substituted by at least one substituent selected from the group consisting of substituents γ$^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ$^3$, defined below;

r is 2;

Q represents a methylene group or a carbonyl group;

substituents α$^3$ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents γ$^2$ are selected from the group consisting of: halogen atoms; cyano groups; nitro groups; methyl groups; ethyl groups; methoxy groups; and ethoxy groups.

20. The compound of claim 1, wherein:

R$^1$ represents an ethyl group;

Z represents a group of formula (i) and R$^2$ represents a methyl group; and

R$^3$ represents an amino group, a methylamino group, an ethylamino group, or a group of formula (iii) or (vi):

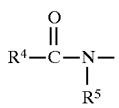

(iii)

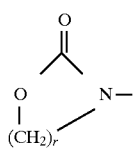

(vi)

wherein:

R⁴ represents: an alkyl group having from 1 to 4 carbon atoms; a substituted alkyl group which has from 1 to 3 carbon atoms and which is substituted by at least one substituent selected from the group consisting of substituents α³, defined below; a cycloalkyl group having 5 or 6 carbon atoms; a phenyl group which is unsubstituted or which is substituted by at least one substituent selected from the group consisting of substituents γ³, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ³, defined below; r is 2;

Q represents a methylene group or a carbonyl group;

substituents α³ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents γ² are selected from the group consisting of: halogen atoms; cyano groups; nitro groups; methyl groups; ethyl groups; methoxy groups; and ethoxy groups.

21. The compound of claim 20, wherein n is 0.
22. The compound of claim 1, wherein:
R¹ represents an ethyl group;
Z represents a group of formula (ii) and m is 2 or 4; and
R³ represents an amino group, a methylamino group, an ethylamino group, or a group of formula (iii) or (vi):

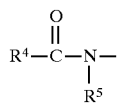

(iii)

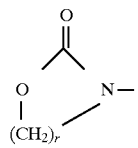

(vi)

wherein:
R⁴ represents: an alkyl group having from 1 to 4 carbon atoms; a substituted alkyl group which has from 1 to 3 carbon atoms and which is substituted by at least one substituent selected from the group consisting of substituents α³, defined below; a cycloalkyl group having 5 or 6 carbon atoms; a phenyl group which is unsubstituted or which is substituted by at least one substituent selected from the group consisting of substituents γ³, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ³, defined below; r is 2;

Q represents a methylene group or a carbonyl group;
substituents α³ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents γ² are selected from the group consisting of: halogen atoms; cyano groups; nitro groups; methyl groups; ethyl groups; methoxy groups; and ethoxy groups.

23. The compound of claim 22, wherein n is 0.
24. The compound of claim 1, which is 13-[2-(4-cyanoacetylaminophenyl)-2-methylpropionyloxy]-5-hydroxyimino-milbemycin A₄.
25. The compound of claim 1, which is 13-{2-[4-(N-acetylglycyl)aminophenyl]-2-methylpropionyloxy}-5-hydroxyimino-milbemycin A₄.
26. The compound of claim 1, which is 13-{2-[4-(N-methoxycarbonylglycyl)-methylaminophenyl]-2-methylpropionyloxy}-5-hydroxyimino-milbemycin A₄.
27. The compound of claim 1, which is 13-[2-(4-methoxycarbonylaminophenyl)-2-methylpropionyloxy]-5-hydroxyimino-milbemycin A₄.
28. The compound of claim 1, which is 13-{2-[4-(N-phenylcarbamoylamino)-phenyl]-2-methylpropionyloxy}-5-hydroxyimino-milbemycin A₄.
29. The compound of claim 1, which is 13-{2-[4-(2-oxooxazolin-3-yl)phenyl]-2-methylpropionyloxy}-5-hydroxyimino-milbemycin A₄.
30. The compound of claim 1, which is 13-[1-(4-aminophenyl)cyclopentane-carbonyloxy]-5-hydroxyimino-milbemycin A₄.
31. The compound of claim 1, which is 13-[1-(4-acetylaminophenyl)cyclopentanecarbonyloxy]-5-hydroxyimino-milbemycin A₄.
32. The compound of claim 1, which is 13-[1-(4-acetoxyacetylaminophenyl)-cyclopentanecarbonyloxy]-5-hydroxyimino-milbemycin A₄.
33. The compound of claim 1, which is 13-[1-(4-methanesulfonylaminophenyl)-cyclopentanecarbonyloxy]-5-hydroxyimino-milbemycin A₄.
34. The compound of claim 1, which is 13-[1-(4-acetylaminophenyl)-1-ethylbutyryloxy]-5-hydroxyimino-milbemycin A₄.
35. The compound of claim 1, which is 13-[1-(4-acetylaminophenyl)cyclobutane-carbonyloxy]-5-hydroxyimino-milbemycin A₄.
36. An anthelmintic, acaricidal and insecticidal composition comprising an anthelmintic, acaricidal and insecticidal compound in admixture with an agriculturally or horticulturally acceptable carrier or diluent, wherein said compound is selected from the group consisting of compounds of formula (I) and salts thereof; as defined in claim 1.
37. The composition of claim 36, wherein Z represents a group of formula (i) and R² represents a methyl or ethyl group.
38. The composition of claim 36, wherein Z represents a group of formula (ii) and m is 2, 3 or 4.
39. The composition of claim 36, wherein n is 0.
40. The composition of claim 36, wherein R³ represents an amino group, a (C₁–C₃ alkyl)amino group, a di(C₁–C₃ alkyl)amino group, an alkoxy group having from 1 to 3 carbon atoms, or a group of formula (iii), (iv), (v), (vi) or (vii):

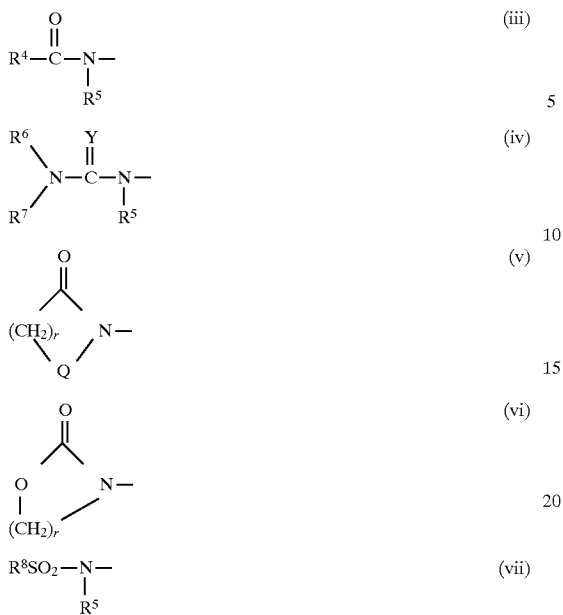

wherein:

R⁴ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms;

R⁵ represents a hydrogen atom or an alkyl group having from 1 to 3 carbon atoms;

R⁶ represents: a hydrogen atom; or an alkyl group having from 1 to 4 carbon atoms;

R⁷ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the alkyl part has 1 or 2 carbon atoms; or R⁶ and R⁷, together with the nitrogen atom to which they are attached, are fused to form a heterocyclic ring having 5 or 6 ring atoms;

Y represents oxygen atom or sulfur atom; r is 1,2 or 3;

Q represents a methylene group or a carbonyl group;

R⁸ represents: an alkyl group having from 1 to 4 carbon atoms or a carbocyclic aryl group which has from 6 to 10 ring carbon atoms which is unsubstituted or which is substituted by at least one substituent selected from the group consisting of substituents $\gamma^1$, defined below;

substituents $\alpha^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents $\gamma^1$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms; groups of formula $R^h$-S-, where $R^h$ is as defined above; and alkanoyl groups having from 2 to 5 carbon atoms;

substituents $\gamma^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

41. The composition of claim 36, wherein:

Z represents a group of formula (i) and R² represents a methyl or ethyl group; and R³ represents an amino group, a ($C_1$–$C_3$ alkyl)amino group, a di($C_1$–$C_3$ alkyl)amino group, an alkoxy group having from 1 to 3 carbon atoms, or a group of formula (iii), (iv), (v), (vi) or (vii):

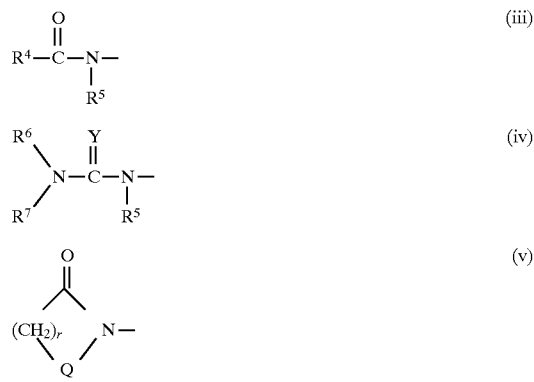

-continued

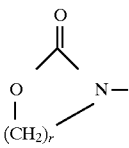
(vi)

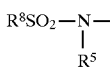
(vii)

wherein:
R⁴ represents: an alkyl group having from 1 to 4 carbon atoms; a substituted alkyl group which has from 1 to 3 carbon atoms and which is substituted by at least one substituent selected from the group consisting of substituents α¹, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ¹, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ¹, defined below, and oxygen atoms;

R⁵ represents a hydrogen atom or an alkyl group having from 1 to 3 carbon atoms;

R⁶ represents a hydrogen atom; or an alkyl group having from 1 to 4 carbon atoms;

R⁷ represents: an alkyl group having from 1 to 6 carbon atoms; a carbocyclic aryl group which has from 6 to 10 ring carbon atoms which is unsubstituted or which is substituted by at least one substituent selected from the group consisting of substituents γ¹, defined below; or an aralkyl group in which the aryl part is carbocyclic and has from 6 to 10 ring carbon atoms and the alkyl part has 1 or 2 carbon atoms; or R⁶ and R⁷, together with the nitrogen atom to which they are attached, are fused to form a heterocyclic ring having 5 or 6 ring atoms;

Y represents oxygen atom or sulfur atom;
r is 1, 2 or 3;
Q represents a methylene group or a carbonyl group;
R⁸ represents: an alkyl group having from 1 to 4 carbon atoms or a carbocyclic aryl group which has from 6 to 10 ring carbon atoms which is unsubstituted or which is substituted by at least one substituent selected from the group consisting of substituents γ¹, defined below;

substituents α¹ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-(C₂–C₅ alkanoyl)-N-(C₁–C₃ alkyl)amino groups; haloalkanoylamino groups having from 2 to 4 carbon atoms; alkoxycarbonylamino groups having from 2 to 4 carbon atoms; N-(C₂–C₅ alkoxycarbonyl)-N-(C₁–C₃ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents γ¹; groups Rʰ, where Rʰ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ¹, defined below, and oxygen atoms; groups of formula Rʰ-S-, where Rʰ is as defined above; and alkanoyl groups having from 2 to 5 carbon atoms;

substituents γ¹ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

42. The composition of claim 41, wherein n is 0.
43. The composition of claim 36, wherein:

Z represents a group of formula (ii) and m is 2, 3 or 4; and
R³ represents an amino group, a (C₁–C₃ alkyl)amino group, a di(C₁–C₃ alkyl)amino group, an alkoxy group having from 1 to 3 carbon atoms, or a group of formula (iii), (iv), (v), (vi) or (vii):

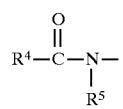
(iii)

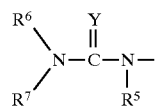
(iv)

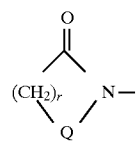
(v)

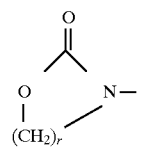
(vi)

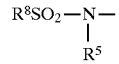
(vii)

wherein:
R⁴ represents: an alkyl group having from 1 to 4 carbon atoms; a substituted alkyl group which has from 1 to 3 carbon atoms and which is substituted by at least one substituent selected from the group consisting of substituents α¹, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ¹, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents γ¹, defined below, and oxygen atoms;

$R^5$ represents a hydrogen atom or an alkyl group having from 1 to 3 carbon atoms;

$R^6$ represents: a hydrogen atom; or an alkyl group having from 1 to 4 carbon atoms;

$R^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents γ¹, defined below; or an aralkyl group in which the aryl part is carbocyclic and has from 6 to 10 ring carbon atoms and the alkyl part has 1 or 2 carbon atoms; or $R^6$ and $R^7$, together with the nitrogen atom to which they are attached, are fused to form a heterocyclic ring having 5 or 6 ring atoms;

Y represents oxygen atom or sulfur atom;

r is 1, 2 or 3;

Q represents a methylene group or a carbonyl group;

$R^8$ represents: an alkyl group having from 1 to 4 carbon atoms or a carbocyclic aryl group which has from 6 to 10 ring carbon atoms which is unsubstituted or which is substituted by at least one substituent selected from the group consisting of substituents γ¹, defined below;

substituents α¹ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents γ¹; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ¹, defined below, and oxygen atoms; groups of formula $R^h$-S-, where $R^h$ is as defined above; and alkanoyl groups having from 2 to 5 carbon atoms;

substituents γ¹ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

44. The composition of claim 43, wherein n is 0.

45. The composition of claim 36, wherein $R^1$ represents a methyl or ethyl group.

46. The composition of claim 36, wherein Z represents a group of formula (i) and $R^2$ represents a methyl group.

47. The composition of claim 36, wherein Z represents a group of formula (ii) and m is 2 or 4.

48. The composition of claim 36, wherein $R^3$ represents an amino group, a methylamino group, an ethylamino group, an alkoxy group having from 1 to 3 carbon atoms, or a group of formula (iii), (v) or (vi):

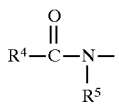

(iii)

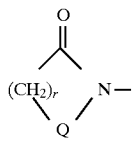

(v)

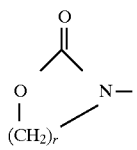

(vi)

wherein:

$R^4$ represents: an alkyl group having from 1 to 4 carbon atoms; a substituted alkyl group which has from 1 to 3 carbon atoms and which is substituted by at least one substituent selected from the group consisting of substituents α², defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ¹, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ¹, defined below, and oxygen atoms;

r is 1, 2 or 3;

Q represents a methylene group or a carbonyl group;

substituents α² are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms;

carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms; and groups of formula $R^h$-S-, where $R^h$ is as defined above;

substituents $\gamma^2$ are selected from the group consisting of: halogen atoms; cyano groups; nitro groups; methyl groups; ethyl groups; methoxy groups; and alkoxycarbonyl groups having 2 or 3 carbon atoms.

49. The composition of claim 36, wherein:

$R^1$ represents a methyl or ethyl group;

Z represents a group of formula (i) and $R^2$ represents a methyl group; and $R^3$ represents an amino group, a methylamino group, an ethylamino group, an alkoxy group having from 1 to 3 carbon atoms, or a group of formula (iii), (v) or (vi):

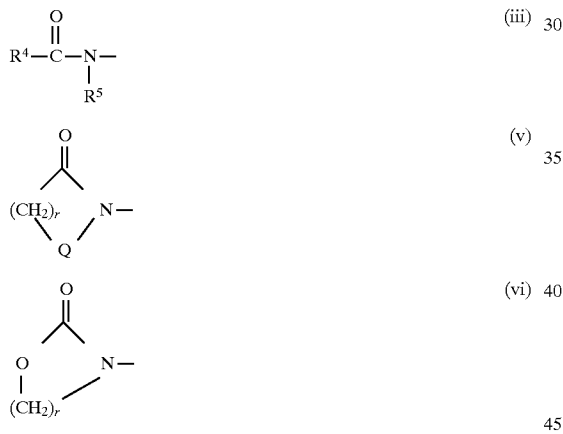

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents y1, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;

r is 1, 2or 3;

Q represents a methylene group or a carbonyl group;

substituents $\alpha^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms; and groups of formula $R^h$-S-, where $R^h$ is as defined above;

substituents $\gamma^2$ are selected from the group consisting of: halogen atoms; cyano groups; nitro groups; methyl groups; ethyl groups; methoxy groups; and alkoxycarbonyl groups having 2 or 3 carbon atoms.

50. The composition of claim 49, wherein n is 0.

51. The composition of claim 36, wherein:

$R^1$ represents a methyl or ethyl group;

Z represents a group of formula (ii) and m is 2 or 4; and $R^3$ represents an amino group, a methylamino group, an ethylamino group, an alkoxy group having from 1 to 3 carbon atoms, or a group of formula (iii), (v) or (vi):

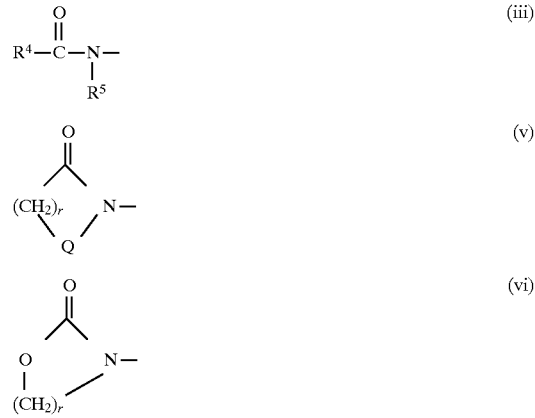

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^2$, defined below; or a heterocyclic group having from 3 to 6 ring atoms, of which at least one is a hetero-atom selected from the group consisting of nitrogen, oxygen and sulfur hetero-atoms, said heterocyclic group being uhsubstituted or being substituted by at least one substituent selected from the group consisting of substituents $\gamma^2$, defined below, and oxygen atoms;

r is 1, 2 or 3;

Q represents a methylene group or a carbonyl group;

substituents $\alpha^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring-carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents 2, defined below, and oxygen atoms; and groups of formula $R^h$-S-, where $R^h$ is as defined above;

substituents $\gamma^2$ are selected from the group consisting of: halogen atoms; cyano groups; nitro groups; methyl groups; ethyl groups; methoxy groups; ethoxy groups; and alkoxycarbonyl groups having 2 or 3 carbon atoms.

52. The composition of claim 51, wherein n is 0.

53. The composition of claim 36, wherein $R^1$ represents an ethyl group.

54. The composition of claim 36, wherein $R^3$ represents an amino group, a methylamino group, an ethylamino group, or a group of formula (iii) or (vi):

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha$, defined below; a cycloalkyl group having 5 or 6 carbon atoms; a phenyl group which is unsubstituted or which is substituted by at least one substituent selected from the group consisting of substituents $\gamma^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^3$, defined below;

r is 2;

Q represents a methylene group or a carbonyl group;

substituents a3 are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents 2 are selected from the group consisting of: halogen atoms; cyano groups; nitro groups; methyl groups; ethyl groups; methoxy groups; and ethoxy groups.

55. The composition of claim 36, wherein:

$R^1$ represents an ethyl group;

Z represents a group of formula (i) and $R^2$ represents a methyl group; and $R^3$ represents an amino group, a methylamino group, an ethylamino group, or a group of formula (iii) or (vi):

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^3$, defined below; a cycloalkyl group having 5 or 6 carbon atoms; a phenyl group which is unsubstituted or which is substituted by at least one substituent selected from the group consisting of substituents $\gamma^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^3$, defined below;

r is 2;

Q represents a methylene group or a carbonyl group;

substituents $\alpha^3$ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents $\gamma^2$ are selected from the group consisting of: halogen atoms; cyano groups; nitro groups; methyl groups; ethyl groups; methoxy groups; and ethoxy groups.

56. The composition of claim 55, wherein n is 0.

57. The composition of claim 36, wherein:

$R^1$ represents an ethyl group;

Z represents a group of formula (ii) and m is 2 or 4; and $R^3$ represents an amino group, a methylamino group, an ethylamino group, or a group of formula (iii) or (vi):

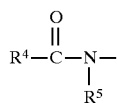

(iii)

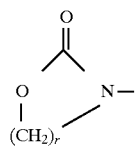

(vi)

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^3$, defined below; a cycloalkyl group having 5 or 6 carbon atoms; a phenyl group which is unsubstituted or which is substituted by at least one substituent selected from the group consisting of substituents $\gamma^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^3$, defined below;

r is 2;

Q represents a methylene group or a carbonyl group;

substituents $\alpha^3$ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents $\gamma^2$ are selected from the group consisting of: halogen atoms; cyano groups; nitro groups; methyl groups; ethyl groups; methoxy groups; and ethoxy groups.

58. The composition of claim 57, wherein n is 0.

59. The composition of claim 36, wherein said anthelmintic, acaricidal and insecticidal compound is selected from the group consisting of:

13-[2-(4-Cyanoacetylaminophenyl)-2-methylpropionyloxy]-5-hydroxyimino-milbemycin $A_4$;

13-{2-[4-(4-Acetylglycyl)aminophenyl]-2-methylpropionyloxy}-5-hydroxyimino-milbemycin $A_4$;

13-{2-[4-(-Methoxycarbonylglycyl)methylaminophenyl]-2-methylpropionyloxy}-5-hydroxyimino-milbemycin $A_4$;

13-[2-(4-Methoxycarbonylaminophenyl)-2-methylpropionyloxy]-5-hydroxyimino-milbemycin $A_4$;

13-{2-[4-(N-Phenylcarbamoylamino)phenyl]-2-methylpropionyloxy}-5-hydroxyimino-milbemycin $A_4$;

13-{2-[4-(2-Oxooxazolin-3-yl)phenyl]-2-methylpropionyloxy}-5-hydroxyimino-milbemycin $A_4$;

13-[1-(4-Aminophenyl)cyclopentanecarbonyloxy]-5-hydroxyimino-milbemycin $A_4$;

13-[1-(4-Acetylaminophenyl)cyclopentanecarbonyloxy]-5-hydroxyimino-milbemycin $A_4$;

13-[1-(4-Acetoxyacetylaminophenyl)cyclopentanecarbonyloxy]-5-hydroxyimino-milbemycin $A_4$;

13-[1-(4-Methanesulfonylaminophenyl)cyclopentanecarbonyloxy]-5-hydroxyimino-milbemycin $A_4$;

13-[1-(4-Acetylaminophenyl)-1-ethylbutyryloxy]-5-hydroxyimino-milbemycin $A_4$; and 13-[1-(4-Acetylaminophenyl)cyclobutanecarbonyloxy]-5-hydroxyimino-milbemycin $A_4$.

60. A method of protecting plants and animals from damage by parasites selected from the group consisting of acarids, helminths and insects, which comprises applying an active compound to said plants or animals or to parts of or reproductive matter of said plants or to a locus including said plants, said animals or parts of said plants or reproductive matter of said plants, wherein the active compound is selected from the group consisting of compounds of formula (I) and salts thereof, as defined in claim 1.

61. The method of claim 60, wherein Z represents a group of formula (i) and $R^2$ represents a methyl or ethyl group.

62. The method of claim 60, wherein Z represents a group of formula (ii) and m is 2, 3 or 4.

63. The method of claim 60, wherein n is 0.

64. The method of claim 60, wherein $R^3$ represents an amino group, a $(C_1-C_3$ alkyl)amino group, a di($C_1-C_3$ alkyl)amino group, an alkoxy group having from 1 to 3 carbon atoms, or a group of formula (iii), (iv), (v), (vi) or (vii):

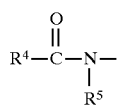

(iii)

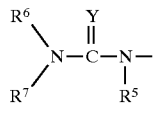

(iv)

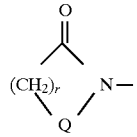

(v)

-continued

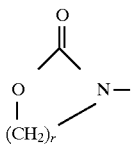(vi)

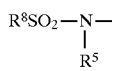(vii)

wherein:
- $R^4$ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;
- $R^5$ represents a hydrogen atom or an alkyl group having from 1 to 3 carbon atoms;
- $R^6$ represents: a hydrogen atom; or an alkyl group having from 1 to 4 carbon atoms;
- $R^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the ail part has 1 or 2 carbon atoms; or
- $R^6$ and $R^7$, together with the nitrogen atom to which they are attached, are fused to form a heterocyclic ring having 5 or 6 ring atoms;
- Y represents oxygen atom or sulfur atom;
- n is 1, 2 or 3;
- Q represents a methylene group or a carbonyl group;
- $R^8$ represents: an alkyl group having from 1 to 4 carbon atoms or a carbocyclic aryl group which has from 6 to 10 ring carbon atoms which is unsubstituted or which is substituted by at least one substituent selected from the group consisting of substituents $\gamma^1$, defined below;
- substituents $\alpha^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents $\gamma^1$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$ defined below, and oxygen atoms; groups of formula $R^h$-S-, where $R^h$ is as defined above; and alkanoyl groups having from 2 to 5 carbon atoms;
- substituents $\gamma^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

65. The method of claim 60, wherein:
- Z represents a group of formula (i) and $R^2$ represents a methyl or ethyl group; and
- $R^3$ represents an amino group, a ($C_1$–$C_3$ alkyl)amino group, a di($C_1$–$C_3$ alkyl)amino group, an alkoxy group having from 1 to 3 carbon atoms, or a group of formula (iii), (iv), (v), (vi) or (vii):

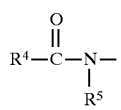(iii)

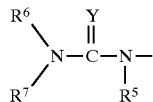(iv)

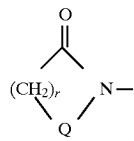(v)

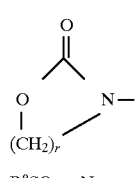(vi)

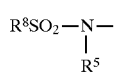(vii)

wherein:
- $R^4$ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;

$R^5$ represents a hydrogen atom or an alkyl group having from 1 to 3 carbon atoms;

$R^6$ represents: a hydrogen atom; or an alkyl group having from 1 to 4 carbon atoms;

$R^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the alkyl part has 1 or 2 carbon atoms; or $R^6$ and $R^7$, together with the nitrogen atom to which they are attached, are fused to form a heterocyclic ring having 5 or 6 ring atoms;

Y represents oxygen atom or sulfur atom;

r is 1, 2 or 3;

Q represents a methylene group or a carbonyl group;

$R^8$ represents: an alkyl group having from 1 to 4 carbon atoms or a carbocyclic aryl group which has from 6 to 10 ring carbon atoms which is unsubstituted or which is substituted by at least one substituent selected from the group consisting of substituents $\gamma^1$, defined below;

substituents $\alpha^1$ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-($C_2$-$C_5$ alkanoyl)-N-($C_1$-$C_3$ alkyl)amino groups; haloalkanoylamino groups having from 2 to 4 carbon atoms; alkoxycarbonylamino groups having from 2 to 4 carbon atoms; N-($C_2$-$C_5$ alkoxycarbonyl)-N-($C_1$-$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents $\gamma^1$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms; groups of formula $R^h$-S-, where $R^h$ is as defined above; and alkanoyl groups having from 2 to 5 carbon atoms;

substituents $\gamma^1$ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

66. The method of claim 65, wherein n is 0.

67. The method of claim 60, wherein:

Z represents a group of formula (ii) and m is 2, 3 or 4; and $R^3$ represents an amino group, a ($C_1$-$C_3$ alkyl)amino group, a di($C_1$-$C_3$ alkyl)amino group, an alkoxy group having from 1 to 3 carbon atoms, or a group of formula (iii), (iv), (v), (vi) or (vii):

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^1$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur heteroatoms, said heterocyclic group being unsubstituted or being substituted by at least one substituent selected from the group consisting of substituents $\gamma^1$, defined below, and oxygen atoms;

$R^5$ represents a hydrogen atom or an alkyl group having from 1 to 3 carbon atoms;

$R^6$ represents: a hydrogen atom; or an alkyl group having from 1 to 4 carbon atoms;

$R^7$ represents: an alkyl group having from 1 to 6 carbon atoms; a carbocyclic aryl group which has from 6 to 10 ring carbon atoms which is unsubstituted or which is substituted by at least one substituent selected from the group consisting of substituents $\gamma^1$, defined below; or an aralkyl group in which the aryl part is carbocyclic and has from 6 to 10 ring carbon atoms and the alkyl part has 1 or 2 carbon atoms; or R⁶ and R⁷, together with the nitrogen atom to which they are attached, are fused to form a heterocyclic ring having 5 or 6 ring atoms;

Y represents oxygen atom or sulfur atom;

r is 1, 2 or 3;

Q represents a methylene group or a carbonyl group;

R⁸ represents: an alkyl group having from 1 to 4 carbon atoms or a carbocyclic aryl group which has from 6 to 10 ring carbon atoms which is unsubstituted or which is substituted by at least one substituent selected from the group consisting of substituents γ¹, defined below;

substituents α¹ are selected from the group consisting of: halogen atoms; cyano groups; alkoxy groups having from 1 to 3 carbon atoms; alkylthio groups having from 1 to 3 carbon atoms; alkanoyloxy groups having from 2 to 5 carbon atoms; alkoxycarbonyl groups having from 2 to 4 carbon atoms; carbocyclic aryloxy groups which have from 6 to 10 ring carbon atoms; carbocyclic arylthio groups which have from 6 to 10 ring carbon atoms; amino groups; alkanoylamino groups having from 2 to 5 carbon atoms; N-(C₂–C₅ alkanoyl)-Nh-(C₁–C₃ alkyl)amino groups; haloalkanoylamino groups having from 2 to 4 carbon atoms; alkoxycarbonylamino groups having from 2 to 4 carbon atoms; N-(C₂–C₅ alkoxycarbonyl)-N-(C₁–C₃ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; carbocyclic aryl groups which have from 6 to 10 ring carbon atoms which are unsubstituted or which are substituted by at least one substituent selected from the group consisting of substituents γ¹; groups Rʰ, where Rʰ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ¹, defined below, and oxygen atoms; groups of formula Rʰ-S-, where Rʰ is as defined above; and alkanoyl groups having from 2 to 5 carbon atoms;

substituents γ¹ are selected from the group consisting of: halogen atoms; cyano groups; nitro groups; alkyl groups having from 1 to 4 carbon atoms; alkoxy groups having from 1 to 4 carbon atoms; and alkoxycarbonyl groups having from 2 to 5 carbon atoms.

68. The method of claim 67, wherein n is 0.

69. The method of claim 60, wherein R¹ represents a methyl or ethyl group.

70. The method of claim 60, wherein Z represents a group of formula (i) and R² represents a methyl group.

71. The method of claim 60, wherein Z represents a group of formula (ii) and m is 2 or 4.

72. The method of claim 60, wherein R³ represents an amino group, a methylamino group, an ethylamino group, an alkoxy group having from 1 to 3 carbon atoms, or a group of formula (iii), (v) or (vi):

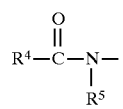

(iii)

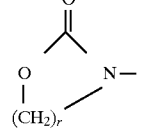

(v)

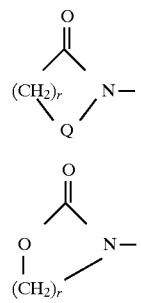

(vi)

wherein:

R⁴ represents: an alkyl group having from 1 to 4 carbon atoms; a substituted alkyl group which has from 1 to 3 carbon atoms and which is substituted by at least one substituent selected from the group consisting of substituents α², defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents γ¹, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ¹, defined below, and oxygen atoms;

r is 1,2or3;

Q represents a methylene group or a carbonyl group;

substituents α² are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-(C₂–C₅ alkanoyl)-N-(C₁–C₃ alkyl)amino groups; haloalkanoylamino groups having from 2 to 4 carbon atoms; alkoxycarbonylamino groups having from 2 to 4 carbon atoms; N-(C₂–C₅ alkoxycarbonyl)-N-(C₁–C₃ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents γ²; groups Rʰ, where Rʰ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ², defined below, and oxygen atoms; and groups of formula Rʰ-S-, where Rʰ is as defined above;

substituents γ² are selected from the group consisting of: halogen atoms; cyano groups; nitro groups; methyl groups; ethyl groups; methoxy groups; and alkoxycarbonyl groups having 2 or 3 carbon atoms.

73. The method of claim 60, wherein:

$R^1$ represents a methyl or ethyl group;

Z represents a group of formula (i) and $R^2$ represents a methyl group; and $R^3$ represents an amino group, a methylamino group, an ethylamino group, an alkoxy group having from 1 to 3 carbon atoms, or a group of formula (iii), (v) or (vi):

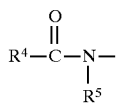

(iii)

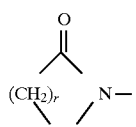

(v)

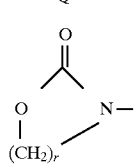

(vi)

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^1$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^1$, defined below, and oxygen atoms;

r is 1, 2 or 3;

Q represents a methylene group or a carbonyl group;

substituents $\alpha^1$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoylamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms; and groups of formula $R^h$-S-, where $R^h$ is as defined above;

substituents $\gamma^2$ are selected from the group consisting of: halogen atoms; cyano groups; nitro groups; methyl groups; ethyl groups; methoxy groups; and alkoxycarbonyl groups having 2 or 3 carbon atoms.

74. The method of claim 73, wherein n is 0.

75. The method of claim 60, wherein:

$R^1$ represents a methyl or ethyl group;

Z represents a group of formula (ii) and m is 2 or 4; and $R^3$ represents an amino gro up, a methylamino group, an ethylamino group, an alkoxy group having from 1 to 3 carbon atoms, or a group of formula (iii), (v) or (vi):

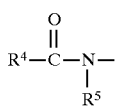

(iii)

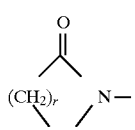

(v)

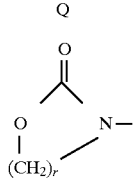

(vi)

wherein:

$R^4$ represents: an alkyl group having from 1 to 4 carbon atoms; a substituted alkyl group which has from 1 to 3 carbon atoms and which is substituted by at least one substituent selected from the group consisting of substituents $\alpha^2$, defined below; a cycloalkyl group having from 3 to 6 carbon atoms; an alkenyl group having 3 or 4 carbon atoms; an alkynyl group having 3 or 4 carbon atoms; a carbocyclic aryl group which has from 6 to 10 ring carbon atoms and which is unsubstituted or which is substituted by at least one substituent selected from the group consisting of substituents $\gamma^2$, defined below; or a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms;

r is 1, 2 or 3;

Q represents a methylene group or a carbonyl group;

substituents $\alpha^2$ are selected from the group consisting of: halogen atoms; cyano groups; methoxy groups; ethoxy groups; methylthio groups; ethylthio groups; alkanoyloxy groups having 2 or 3 carbon atoms; alkoxycarbonyl groups having 2 or 3 carbon atoms; phenoxy groups; phenylthio groups; amino groups; alkanoyllamino groups having from 2 to 5 carbon atoms; N-($C_2$–$C_5$ alkanoyl)-N-($C_1$–$C_3$ alkyl)amino groups; haloalkanoylamino groups having from 2 to 4 carbon atoms; alkoxycarbonylamino groups having from 2 to 4 carbon atoms; N-($C_2$–$C_5$ alkoxycarbonyl)-N-($C_1$–$C_3$ alkyl)amino groups; haloalkoxycarbonylamino groups having from 2 to 5 carbon atoms; carbocyclic arylcarbonylamino groups in which the aryl part has from 6 to 10 ring carbon atoms; aralkylcarbonylamino groups in which the aryl part is carbocyclic and has from 6 to 10 ring carbon atoms and the alkyl part has 1 or 2 carbon atoms; phenyl groups which are unsubstituted or which are substituted by at least one substituent selected from the group consisting of substituents $\gamma^2$; groups $R^h$, where $R^h$ represents a heterocyclic group having from 3 to 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^2$, defined below, and oxygen atoms; and groups of formula $R^h$-S-, where $R^h$ is as defined above;

substituents $\gamma^2$ are selected from the group consisting of: halogen atoms; cyano groups; nitro groups; methyl groups; ethyl groups; methoxy groups; ethoxy groups; and alkoxycarbonyl groups having 2 or 3 carbon atoms.

76. The method of claim 75, wherein n is 0.

77. The method of claim 60, wherein $R^1$ represents an ethyl group.

78. The method of claim 60, wherein $R^3$ represents an amino group, a methylamino group, an ethylamino group, or a group of formula (iii) or (vi):

wherein:
- $R^4$ represents: an alkyl group having from 1 to 4 carbon atoms; a substituted alkyl group which has from 1 to 3 carbon atoms and which is substituted by at least one substituent selected from the group consisting of substituents a defined below; a cycloalkyl group having 5 or 6 carbon atoms; a phenyl group which is unsubstituted or which is substituted by at least one substituent selected from the group consisting of substituents $\gamma^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^3$, defined below;
- r is 2;
- Q represents a methylene group or a carbonyl group;
- substituents $\alpha^3$ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;
- substituents $\gamma^2$ are selected from the group consisting of: halogen atoms; cyano groups; nitro groups; methyl groups; ethyl groups; methoxy groups; and ethoxy groups.

79. The method of claim 60, wherein:

$R^1$ represents an ethyl group;

Z represents a group of formula (i) and $R^2$ represents a methyl group; and $R^3$ represents an amino group, a methylamino group, an ethylamino group, or a group of formula (iii) or (vi):

wherein:
- $R^4$ represents: an alkyl group having from 1 to 4 carbon atoms; a substituted alkyl group which has from 1 to 3 carbon atoms and which is substituted by at least one substituent selected from the group consisting of substituents $\alpha^3$, defined below; a cycloalkyl group having 5 or 6 carbon atoms; a phenyl group which is unsubstituted or which is substituted by at least one substituent selected from the group consisting of substituents $\gamma^3$, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents $\gamma^3$, defined below;
- r is 2;
- Q represents a methylene group or a carbonyl group;
- substituents $\alpha^3$ are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;
- substituents $\gamma^2$ are selected from the group consisting of: halogen atoms; cyano groups; nitro groups; methyl groups; ethyl groups; methoxy groups; and ethoxy groups.

80. The method of claim 79, wherein n is 0.

81. The method of claim 60, wherein:

$R^1$ represents an ethyl group;

Z represents a group of formula (ii) and m is 2 or 4; and $R^3$ represents an amino group, a methylamino group, an ethylamino group, or a group of formula (iii) or (vi):

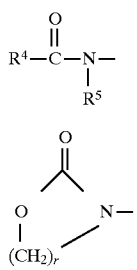

wherein:

R⁴ represents: an alkyl group having from 1 to 4 carbon atoms; a substituted alkyl group which has from 1 to 3 carbon atoms and which is substituted by at least one substituent selected from the group consisting of substituents α³, defined below; a cycloalkyl group having 5 or 6 carbon atoms; a phenyl group which is unsubstituted or which is substituted by at least one substituent selected from the group consisting of substituents γ³, defined below; or a heterocyclic group having 5 or 6 ring atoms, of which at least one is a hetero-atom selected from the group consisting of nitrogen, oxygen and sulfur hetero-atoms, said heterocyclic group being unsubstituted or being substituted by at least one substituent selected from the group consisting of substituents γ³, defined below;

r is 2;

Q represents a methylene group or a carbonyl group;

substituents a are selected from the group consisting of: halogen atoms; cyano groups; methoxy groups; ethoxy groups; alkanoyloxy groups having 2 or 3 carbon atoms; alkoxycarbonyl groups having 2 or 3 carbon atoms; phenoxy groups; amino groups; alkanoylamino groups having 2 or 3 carbon atoms; alkoxycarbonylamino groups having from 2 to 4 carbon atoms; and benzoylcarbonylamino groups;

substituents γ² are selected from the group consisting of: halogen atoms; cyano groups; nitro groups; methyl groups; ethyl groups; methoxy groups; and ethoxy groups.

82. The method of claim 81, wherein n is 0.

83. The method of claim 60, wherein said anthelmintic, acaricidal and insecticidal compound is selected from the group consisting of:

13-[2-(4-Cyanoacetylaminophenyl)-2-methylpropionyloxy]-5-hydroxyimino-milbemycin A₄;

13-{2-[4-(N-Acetylglycyl)aminophenyl]-2-methylpropionyloxy}-5-hydroxyimino-milbemycin A₄;

13-{2-[4-(N-Methoxycarbonylglycyl) methylaminophenyl]-2-methylpropionyloxy}-5-hydroxyimino-milbemycin A₄;

13-[2-(4-Methoxycarbonylaminophenyl)-2-methylpropionyloxy]-5-hydroxyimino-milbemycin A₄;

13-{2-[4-(N-Phenylcarbamoylamino)phenyl]-2-methylpropionyloxy}-5-hydroxyimino-milbemycin A₄;

13-{2-[4-(2-Oxooxazolin-3-yl)phenyl]-2-methylpropionyloxy}-5-hydroxyimino-milbemycin A₄;

13-[1-(4-Aminophenyl)cyclopentanecarbonyloxy]-5-hydroxyimino-milbemycin A₄;

13-[1-(4-Acetylaminophenyl)cyclopentanecarbonyloxy]-5-hydroxyimino-milbemycin A₄;

13-[1-(4-Acetoxyacetylaminophenyl) cyclopentanecarbonyloxy]-5-hydroxyimino-milbemycin A₄;

13-[1-(4-Methanesulfonylaminophenyl) cyclopentanecarbonyloxy]-5-hydroxyimino-milbemycin A₄;

13-[1-(4-Acetylaminophenyl)-1-ethylbutyryloxy]-5-hydroxyimino-milbemycin A₄; and 13-[1-(4-Acetylaminophenyl)cyclobutanecarbonyloxy]-5-hydroxyimino-milbemycin A₄.

* * * * *